United States Patent
Munivar et al.

(10) Patent No.: US 10,702,558 B2
(45) Date of Patent: Jul. 7, 2020

(54) THERAPEUTIC TREATMENT OF SKIN DISEASE WITH RECOMBINANT COMMENSAL SKIN MICROORGANISMS

(71) Applicant: Azitra, Inc., Farmington, CT (US)

(72) Inventors: Azim Momin Munivar, New Haven, CT (US); Travis Michael Whitfill, New Haven, CT (US)

(73) Assignee: Azitra Inc, Farmington, CT (US)

( * ) Notice: Subject to any disclaimer, the term of this patent is extended or adjusted under 35 U.S.C. 154(b) by 63 days.

(21) Appl. No.: 15/312,441

(22) PCT Filed: May 28, 2015

(86) PCT No.: PCT/US2015/032972
§ 371 (c)(1),
(2) Date: Nov. 18, 2016

(87) PCT Pub. No.: WO2015/184134
PCT Pub. Date: Dec. 3, 2015

(65) Prior Publication Data
US 2018/0161380 A1    Jun. 14, 2018

Related U.S. Application Data

(60) Provisional application No. 62/005,558, filed on May 30, 2014, provisional application No. 62/005,652, filed on May 30, 2014.

(51) Int. Cl.
| | |
|---|---|
| *A61K 39/00* | (2006.01) |
| *A61K 39/02* | (2006.01) |
| *A61K 49/00* | (2006.01) |
| *A61K 35/74* | (2015.01) |
| *A61K 38/17* | (2006.01) |
| *A61K 9/00* | (2006.01) |
| *C07K 14/47* | (2006.01) |
| *A61P 17/00* | (2006.01) |
| *C12N 1/20* | (2006.01) |
| *C12N 15/74* | (2006.01) |

(52) U.S. Cl.
CPC ............ *A61K 35/74* (2013.01); *A61K 9/0014* (2013.01); *A61K 38/1709* (2013.01); *A61P 17/00* (2018.01); *C07K 14/4713* (2013.01); *C12N 1/20* (2013.01); *C12N 15/74* (2013.01); *C07K 2319/02* (2013.01); *C07K 2319/10* (2013.01)

(58) Field of Classification Search
CPC ............................... A61K 39/00; A61K 39/02
USPC .................. 424/9.1, 9.2, 184.1, 185.1, 234.1
See application file for complete search history.

(56) References Cited

U.S. PATENT DOCUMENTS

| | | | |
|---|---|---|---|
| 4,659,774 A | 4/1987 | Webb et al. | |
| 2013/0018000 A1 | 1/2013 | Stout | |

FOREIGN PATENT DOCUMENTS

| | | |
|---|---|---|
| JP | H0637384 B2 | 5/1994 |
| KR | 20120091074 A | 8/2012 |
| WO | 1994000098 A1 | 1/1994 |
| WO | 1994000109 A1 | 1/1994 |
| WO | 2014/025938 A1 | 2/2014 |

OTHER PUBLICATIONS

International Search Report for PCT/US2015/032972.
Stout et al., Recombinant filaggrin is internalized and processed to correct filaggrin deficiency, Journal of Investigative Dermatology, vol. 134, No. 2, pp. 423-429.
Kezic et al., Filaggrin loss-of-function mutations are associated with enhanced expression of IL-1 cytokines in the stratum corneum of patients with atopic dermatitis and in a murine model of filaggrin deficiency, Journal of Allergy and Clinical Immunology, vol. 129, No. 4, pp. 1031-1039.
Armengot-Carbo M. et al. (2014) The role of filaggrin in the skin barrier and disease development. Actas Dermosifiliogr Mar.; 106 (2):86-95.
Brachkova M. I. (2011) Alginate films containing Lactobacillus plantarum as wound dressing for prevention of burn infection. J Hosp Infect 79(4): 375-377.
Monk I. et al. (2012) Transforming the Untransformable: Application of Direct Transformation to Manipulate Genetically *Staphylococcus aureus* and *Staphylococcus epidermidis*. mBio.
Grown SJ. et al. (2012) J. Invest. Dermatol. 132, 751-62.
Chen YE. et al. (2013) J. Am. Acad. Dermatol. 69, 143-155.
Cheung AL et al. (2004) Regulation of virulence determinants in vitro and in vivo in *Staphylococcus aureus*. FEMS Immunological Medical Microbiology 40(1):1-9.
Gueniche k et al. (2010) Bifidobacterium longum lysate, a new ingredient for reactive skin. Exp Dermatol 19(8):1-8.
Jeong JG et al. (2011). A Tat-grafted anti-nucleic acid antibody acquires nuclear-localization property and a preference for TAR RNA. Biochem. Biophys Res Commun. Mar. 18;406(3):403-7.

(Continued)

*Primary Examiner* — Rodney P Swartz
(74) *Attorney, Agent, or Firm* — McCarter & English, LLP; Jonathan M. Sparks

(57) ABSTRACT

The invention relates to methods for treating or preventing abnormal skin conditions in a human in need thereof, comprising administering a cell culture composition comprising a living culture of bacteria comprising at least one engineered strain that produces a recombinant polypeptide for therapeutic treatment of the abnormal skin condition. The invention also relates to pharmaceutical compositions containing, as the active principle, engineered microorganisms expressing non-vaccinogenic pharmacologically active recombinant therapeutic polypeptides in order to treat or prevent abnormal skin conditions.

17 Claims, 8 Drawing Sheets
Specification includes a Sequence Listing.

(56) References Cited

OTHER PUBLICATIONS

Kreiswirth BN. et al. (1983) The toxic shock syndrome exotoxin structural gene is not detectably transmitted by a prophage. Nature 305:709-712.
Lauderdale et al. (2010) Biofilm dispersal of community-associated methicillin-resistant *Staphylococcus aureus* on orthopedic implant material. J. Orthop. Research. 28:55-61.
Lee SH. et al. (2006) An update of the defensive bather function of skin. Yonsei Med J 47(3): 293-306.
Lin YT. et al. (2007) Role of bacterial pathogens in atopic dermatitis. Clin Rev Allergy Immunol 33(3): 167-177.
Ma J. et al. (2014) Cell-penetrating peptides mediated protein cross-membrane delivery and its use in bacterial vector vaccine. Fish & Shellfish Immunology 39 8-16.
Mcaleer MA. et al. (2013) J. Allergy Clin. Immunol. 131, 280-91.
Muizzuddin N. et al. (2012) Physiological effect of a probiotic on skin. J Cosmet Sci 63(6): 385-395.
Nakanishi N. et al. (1986). Construction and characterization of new cloning vectors derived from Streptomyces griseobrunneus plasmid pBT1 and containing amikacin and sulfomycin resistance genes. Plasmid 15(3): 217-229.
Nakatsuji T. et al. (2014) Dermatological therapy by topical application of non-pathogenic bacteria. J Invest Dermatol 134(1): 11-14.
Oehike J et al. (1998) Cellular uptake of an alpha-helical amphipathic model peptide with the potential to deliver polar compounds into the cell interior non-endocytically. Biochim Biophys Acta. Nov. 11;1414 (1-2):127-39.
Ostenson CG et al. (1997) Galparan: a powerful insulin-releasing chimeric peptide acting at a novel site. Endocrinology. Aug.;138(8):3308-13.
Otsuka A. el al. (2014) J. Allergy Clin. Immunol. 133, 139-46.e1-10 (2014).
Peral M. C. et al. (2009) Bacteriotherapy with Lactobacillus plantarum in burns. Int Wound J 6(1): 73-81.
Peral M. C. et al. (2010) Interleukin-8 production by polymorphonuclear leukocytes from patients with chronic infected leg ulcers treated with Lactobacillus plantarum. Clin Microbiol Infect 16(3): 281-286.
Powers ME et al. (2011) J Bacteriol., 193:340-348.
Proksch E. et al. (2008) The skin: an indispensable barrier. Exp Dermatol 17(12): 1063-1072.
Simonen M. et al. (1993) Protein secretion in *Bacillus* species. Microbiol Rev 57(1): 109-137.
Volz T. et al. (2014) Nonpathogenic bacteria alleviating atopic dermatitis inflammation induce IL-10-producing dendritic cells and regulatory Trl cells. J Invest Dermatol 134(1): 96-104.
Wyman TB et al. (1997) Design, synthesis, and characterization of a cationic peptide that binds to nucleic acids and permeabilizes bilayers. Biochemistry. Mar. 11;36(10):3008-17.
Zhang YQ. et al. (2003) Genome-based analysis of virulence genes in a non-biofilm-forming *Staphylococcus epidermidis* strain (ATCC12228). Molecular Microbiology 49(6), 1577-1593.
Pusch et al., An anti-HIV microbicide engineered in commensal bacteria: secretion of HIV-1 fusion inhibitors by lactobacilli. AIDS. Oct. 3, 2006;20(15):1917-22.
Japanese Office Action for Application No. 2017-515014, dated May 21, 2019, 10 pages.

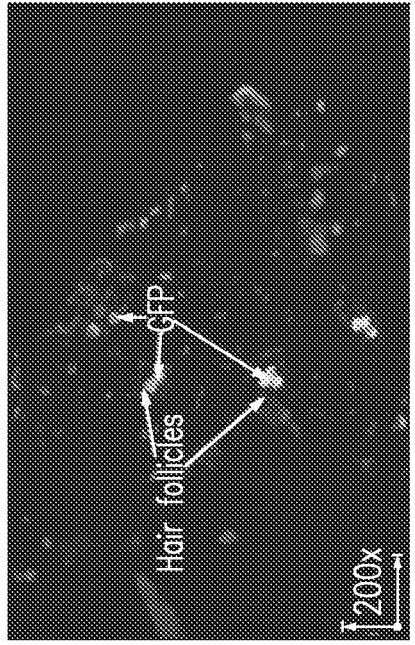
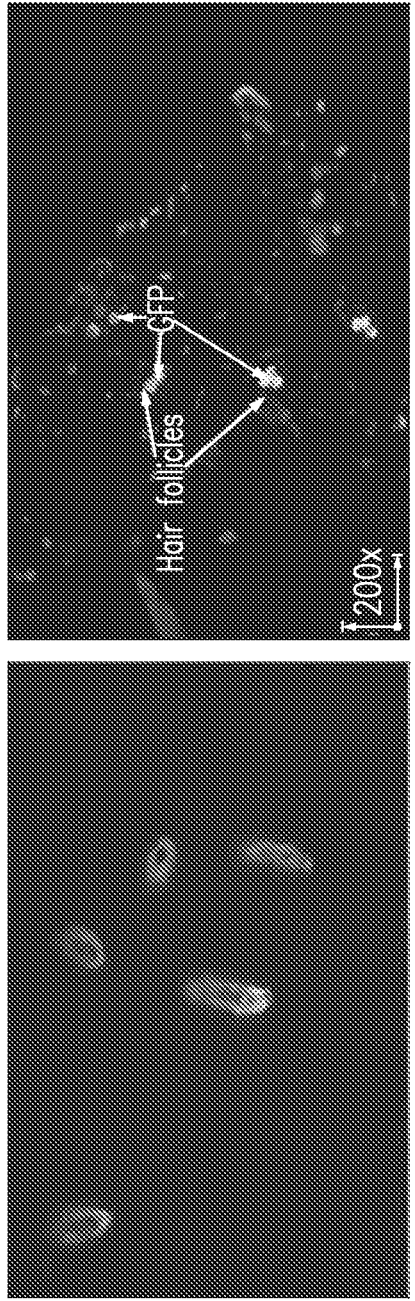
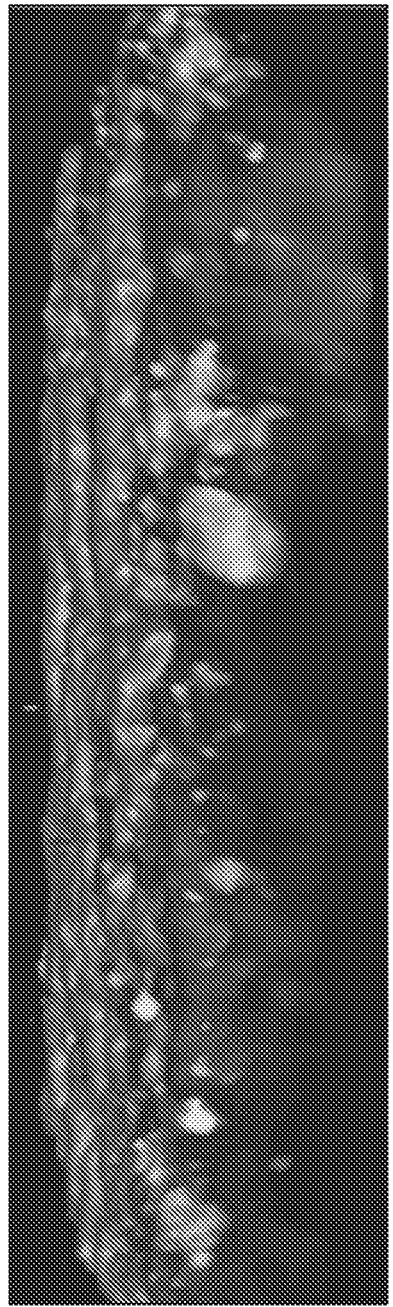
FIG. 8A
FIG. 8B
FIG. 8C

SEQUENCE LISTING

```
<160> NUMBER OF SEQ ID NOS: 35

<210> SEQ ID NO 1
<211> LENGTH: 4061
<212> TYPE: PRT
<213> ORGANISM: Homo sapiens

<400> SEQUENCE: 1

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
            20                  25                  30

Leu Lys Glu Leu Leu Glu Lys Glu Phe Arg Gln Ile Leu Lys Asn Pro
        35                  40                  45

Asp Asp Pro Asp Met Val Asp Val Phe Met Asp His Leu Asp Ile Asp
    50                  55                  60

His Asn Lys Lys Ile Asp Phe Thr Glu Phe Leu Leu Met Val Phe Lys
65                  70                  75                  80

Leu Ala Gln Ala Tyr Tyr Glu Ser Thr Arg Lys Glu Asn Leu Pro Ile
                85                  90                  95

Ser Gly His Lys His Arg Lys His Ser His His Asp Lys His Glu Asp
            100                 105                 110

Asn Lys Gln Glu Glu Asn Lys Glu Asn Arg Lys Arg Pro Ser Ser Leu
        115                 120                 125

Glu Arg Arg Asn Asn Arg Lys Gly Asn Lys Gly Arg Ser Lys Ser Pro
    130                 135                 140

Arg Glu Thr Gly Gly Lys Arg His Glu Ser Ser Ser Glu Lys Lys Glu
145                 150                 155                 160

Arg Lys Gly Tyr Ser Pro Thr His Arg Glu Glu Glu Tyr Gly Lys Asn
                165                 170                 175

His His Asn Ser Ser Lys Lys Glu Lys Asn Lys Thr Glu Asn Thr Arg
            180                 185                 190

Leu Gly Asp Asn Arg Lys Arg Leu Ser Glu Arg Leu Glu Glu Lys Glu
        195                 200                 205

Asp Asn Glu Glu Gly Val Tyr Asp Tyr Glu Asn Thr Gly Arg Met Thr
    210                 215                 220

Gln Lys Trp Ile Gln Ser Gly His Ile Ala Thr Tyr Tyr Thr Ile Gln
225                 230                 235                 240

Asp Glu Ala Tyr Asp Thr Thr Asp Ser Leu Leu Glu Glu Asn Lys Ile
                245                 250                 255

Tyr Glu Arg Ser Arg Ser Ser Asp Gly Lys Ser Ser Ser Gln Val Asn
            260                 265                 270

Arg Ser Arg His Glu Asn Thr Ser Gln Val Pro Leu Gln Glu Ser Arg
```

```
                    275                 280                 285
Thr Arg Lys Arg Arg Gly Ser Arg Val Ser Gln Asp Arg Asp Ser Glu
290                 295                 300
Gly His Ser Glu Asp Ser Glu Arg His Ser Gly Ser Ala Ser Arg Asn
305                 310                 315                 320
His His Gly Ser Ala Trp Glu Gln Ser Asp Gly Ser Arg His Pro
                325                 330                 335
Arg Ser His Asp Glu Asp Arg Ala Ser His Gly His Ser Ala Asp Ser
                340                 345                 350
Ser Arg Gln Ser Gly Thr Arg His Ala Glu Thr Ser Arg Gly Gln
                355                 360                 365
Thr Ala Ser Ser His Glu Gln Ala Arg Ser Ser Pro Gly Glu Arg His
370                 375                 380
Gly Ser Gly His Gln Gln Ser Ala Asp Ser Ser Arg His Ser Ala Thr
385                 390                 395                 400
Gly Arg Gly Gln Ala Ser Ser Ala Val Ser Asp Arg Gly His Arg Gly
                405                 410                 415
Ser Ser Gly Ser Gln Ala Ser Asp Ser Glu Gly His Ser Glu Asn Ser
                420                 425                 430
Asp Thr Gln Ser Val Ser Gly His Gly Lys Ala Gly Leu Arg Gln Gln
                435                 440                 445
Ser His Gln Glu Ser Thr Arg Gly Arg Ser Gly Glu Arg Ser Gly Arg
450                 455                 460
Ser Gly Ser Ser Leu Tyr Gln Val Ser Thr His Glu Gln Pro Asp Ser
465                 470                 475                 480
Ala His Gly Arg Thr Gly Thr Ser Thr Gly Gly Arg Gln Gly Ser His
                485                 490                 495
His Glu Gln Ala Arg Asp Ser Ser Arg His Ser Ala Ser Gln Glu Gly
                500                 505                 510
Gln Asp Thr Ile Arg Gly His Pro Gly Ser Ser Arg Gly Gly Arg Gln
                515                 520                 525
Gly Ser His His Glu Gln Ser Val Asn Arg Gly His Ser Gly Ser
530                 535                 540
His His Ser His Thr Thr Ser Gln Gly Arg Ser Asp Ala Ser His Gly
545                 550                 555                 560
Gln Ser Gly Ser Arg Ser Ala Ser Arg Gln Thr Arg Asn Glu Glu Gln
                565                 570                 575
Ser Gly Asp Gly Thr Arg His Ser Gly Ser Arg His His Glu Ala Ser
                580                 585                 590
Ser Gln Ala Asp Ser Ser Arg His Ser Gln Val Gly Gln Gly Gln Ser
                595                 600                 605
Ser Gly Pro Arg Thr Ser Arg Asn Gln Gly Ser Ser Val Ser Gln Asp
                610                 615                 620
Ser Asp Ser Gln Gly His Ser Glu Asp Ser Glu Arg Trp Ser Gly Ser
625                 630                 635                 640
Ala Ser Arg Asn His His Gly Ser Ala Gln Glu Gln Ser Arg Asp Gly
                645                 650                 655
Ser Arg His Pro Arg Ser His His Glu Asp Arg Ala Gly His Gly His
                660                 665                 670
Ser Ala Asp Ser Ser Arg Lys Ser Gly Thr Arg His Thr Gln Asn Ser
                675                 680                 685
Ser Ser Gly Gln Ala Ala Ser Ser His Glu Gln Ala Arg Ser Ser Ala
                690                 695                 700
```

-continued

Gly Glu Arg His Gly Ser Arg His Gln Leu Gln Ser Ala Asp Ser Ser
705                 710                 715                 720

Arg His Ser Gly Thr Gly His Gly Gln Ala Ser Ser Ala Val Arg Asp
            725                 730                 735

Ser Gly His Arg Gly Ser Gly Ser Gln Ala Thr Asp Ser Glu Gly
        740                 745                 750

His Ser Glu Asp Ser Asp Thr Gln Ser Val Ser Gly His Gly Gln Ala
            755                 760                 765

Gly His His Gln Gln Ser His Gln Glu Ser Ala Arg Asp Arg Ser Gly
    770                 775                 780

Glu Arg Ser Arg Arg Ser Gly Ser Phe Leu Tyr Gln Val Ser Thr His
785                 790                 795                 800

Lys Gln Ser Glu Ser Ser His Gly Trp Thr Gly Pro Ser Thr Gly Val
                805                 810                 815

Arg Gln Gly Ser His His Glu Gln Ala Arg Asp Asn Ser Arg His Ser
            820                 825                 830

Ala Ser Gln Asp Gly Gln Asp Thr Ile Arg Gly His Pro Gly Ser Ser
        835                 840                 845

Arg Arg Gly Arg Gln Gly Ser His His Glu Gln Ser Val Asp Arg Ser
850                 855                 860

Gly His Ser Gly Ser His His Ser His Thr Thr Ser Gln Gly Arg Ser
865                 870                 875                 880

Asp Ala Ser Arg Gly Gln Ser Gly Ser Arg Ser Ala Ser Arg Thr Thr
            885                 890                 895

Arg Asn Glu Glu Gln Ser Arg Asp Gly Ser Arg His Ser Gly Ser Arg
        900                 905                 910

His His Glu Ala Ser Ser His Ala Asp Ile Ser Arg His Ser Gln Ala
            915                 920                 925

Gly Gln Gly Gln Ser Glu Gly Ser Arg Thr Ser Arg Arg Gln Gly Ser
    930                 935                 940

Ser Val Ser Gln Asp Ser Asp Ser Glu Gly His Ser Glu Asp Ser Glu
945                 950                 955                 960

Arg Trp Ser Gly Ser Ala Ser Arg Asn His Arg Gly Ser Ala Gln Glu
                965                 970                 975

Gln Ser Arg His Gly Ser Arg His Pro Arg Ser His His Glu Asp Arg
            980                 985                 990

Ala Gly His Gly His Ser Ala Asp Ser Ser Arg Gln Ser Gly Thr Pro
        995                 1000                1005

His Ala Glu Thr Ser Ser Gly Gly Gln Ala Ala Ser Ser His Glu
    1010                1015                1020

Gln Ala Arg Ser Ser Pro Gly Glu Arg His Gly Ser Arg His Gln
    1025                1030                1035

Gln Ser Ala Asp Ser Ser Arg His Ser Gly Ile Pro Arg Arg Gln
    1040                1045                1050

Ala Ser Ser Ala Val Arg Asp Ser Gly His Trp Gly Ser Ser Gly
    1055                1060                1065

Ser Gln Ala Ser Asp Ser Glu Gly His Ser Glu Glu Ser Asp Thr
    1070                1075                1080

Gln Ser Val Ser Gly His Gly Gln Asp Gly Pro His Gln Gln Ser
    1085                1090                1095

His Gln Glu Ser Ala Arg Asp Trp Ser Gly Gly Arg Ser Gly Arg
    1100                1105                1110

-continued

```
Ser Gly Ser Phe Ile Tyr Gln Val Ser Thr His Glu Gln Ser Glu
1115                1120                1125

Ser Ala His Gly Arg Thr Arg Thr Ser Thr Gly Arg Arg Gln Gly
1130                1135                1140

Ser His His Glu Gln Ala Arg Asp Ser Ser Arg His Ser Ala Ser
1145                1150                1155

Gln Glu Gly Gln Asp Thr Ile Arg Ala His Pro Gly Ser Arg Arg
1160                1165                1170

Gly Gly Arg Gln Gly Ser His His Glu Gln Ser Val Asp Arg Ser
1175                1180                1185

Gly His Ser Gly Ser His Ser His Thr Thr Ser Gln Gly Arg
1190                1195                1200

Ser Asp Ala Ser His Gly Gln Ser Gly Ser Arg Ser Ala Ser Arg
1205                1210                1215

Gln Thr Arg Lys Asp Lys Gln Ser Gly Asp Gly Ser Arg His Ser
1220                1225                1230

Gly Ser Arg His His Glu Ala Ala Ser Trp Ala Asp Ser Ser Arg
1235                1240                1245

His Ser Gln Val Gly Gln Glu Gln Ser Ser Gly Ser Arg Thr Ser
1250                1255                1260

Arg His Gln Gly Ser Ser Val Ser Gln Asp Ser Asp Ser Glu Arg
1265                1270                1275

His Ser Asp Asp Ser Glu Arg Leu Ser Gly Ser Ala Ser Arg Asn
1280                1285                1290

His His Gly Ser Ser Arg Glu Gln Ser Arg Asp Gly Ser Arg His
1295                1300                1305

Pro Gly Phe His Gln Glu Asp Arg Ala Ser His Gly His Ser Ala
1310                1315                1320

Asp Ser Ser Arg Gln Ser Gly Thr His Thr Glu Ser Ser Ser
1325                1330                1335

His Gly Gln Ala Val Ser Ser His Glu Gln Ala Arg Ser Ser Pro
1340                1345                1350

Gly Glu Arg His Gly Ser Arg His Gln Gln Ser Ala Asp Ser Ser
1355                1360                1365

Arg His Ser Gly Ile Gly His Arg Gln Ala Ser Ser Ala Val Arg
1370                1375                1380

Asp Ser Gly His Arg Gly Ser Gly Ser Gln Val Thr Asn Ser
1385                1390                1395

Glu Gly His Ser Glu Asp Ser Asp Thr Gln Ser Val Ser Ala His
1400                1405                1410

Gly Gln Ala Gly Pro His Gln Gln Ser His Lys Glu Ser Ala Arg
1415                1420                1425

Gly Gln Ser Gly Glu Ser Ser Gly Arg Ser Arg Ser Phe Leu Tyr
1430                1435                1440

Gln Val Ser Ser His Glu Gln Ser Glu Ser Thr His Gly Gln Thr
1445                1450                1455

Ala Pro Ser Thr Gly Gly Arg Gln Gly Ser Arg His Glu Gln Ala
1460                1465                1470

Arg Asn Ser Ser Arg His Ser Ala Ser Gln Asp Gly Gln Asp Thr
1475                1480                1485

Ile Arg Gly His Pro Gly Ser Ser Arg Gly Gly Arg Gln Gly Ser
1490                1495                1500

Tyr His Glu Gln Ser Val Asp Arg Ser Gly His Ser Gly Tyr His
```

-continued

```
              1505                1510                1515

His Ser His Thr Thr Pro Gln Gly Arg Ser Asp Ala Ser His Gly
          1520                1525                1530

Gln Ser Gly Pro Arg Ser Ala Ser Arg Gln Thr Arg Asn Glu Glu
          1535                1540                1545

Gln Ser Gly Asp Gly Ser Arg His Ser Gly Ser Arg His His Glu
          1550                1555                1560

Pro Ser Thr Arg Ala Gly Ser Ser Arg His Ser Gln Val Gly Gln
          1565                1570                1575

Gly Glu Ser Ala Gly Ser Lys Thr Ser Arg Arg Gln Gly Ser Ser
          1580                1585                1590

Val Ser Gln Asp Arg Asp Ser Glu Gly His Ser Glu Asp Ser Glu
          1595                1600                1605

Arg Arg Ser Glu Ser Ala Ser Arg Asn His Tyr Gly Ser Ala Arg
          1610                1615                1620

Glu Gln Ser Arg His Gly Ser Arg Asn Pro Arg Ser His Gln Glu
          1625                1630                1635

Asp Arg Ala Ser His Gly His Ser Ala Glu Ser Ser Arg Gln Ser
          1640                1645                1650

Gly Thr Arg His Ala Glu Thr Ser Ser Gly Gly Gln Ala Ala Ser
          1655                1660                1665

Ser Gln Glu Gln Ala Arg Ser Ser Pro Gly Glu Arg His Gly Ser
          1670                1675                1680

Arg His Gln Gln Ser Ala Asp Ser Ser Thr Asp Ser Gly Thr Gly
          1685                1690                1695

Arg Arg Gln Asp Ser Ser Val Val Gly Asp Ser Gly Asn Arg Gly
          1700                1705                1710

Ser Ser Gly Ser Gln Ala Ser Asp Ser Glu Gly His Ser Glu Glu
          1715                1720                1725

Ser Asp Thr Gln Ser Val Ser Ala His Gly Gln Ala Gly Pro His
          1730                1735                1740

Gln Gln Ser His Gln Glu Ser Thr Arg Gly Gln Ser Gly Glu Arg
          1745                1750                1755

Ser Gly Arg Ser Gly Ser Phe Leu Tyr Gln Val Ser Thr His Glu
          1760                1765                1770

Gln Ser Glu Ser Ala His Gly Arg Thr Gly Pro Ser Thr Gly Gly
          1775                1780                1785

Arg Gln Arg Ser Arg His Glu Gln Ala Arg Asp Ser Ser Arg His
          1790                1795                1800

Ser Ala Ser Gln Glu Gly Gln Asp Thr Ile Arg Gly His Pro Gly
          1805                1810                1815

Ser Ser Arg Gly Gly Arg Gln Gly Ser His Tyr Glu Gln Ser Val
          1820                1825                1830

Asp Ser Ser Gly His Ser Gly Ser His His Ser His Thr Thr Ser
          1835                1840                1845

Gln Glu Arg Ser Asp Val Ser Arg Gly Gln Ser Gly Ser Arg Ser
          1850                1855                1860

Val Ser Arg Gln Thr Arg Asn Glu Lys Gln Ser Gly Asp Gly Ser
          1865                1870                1875

Arg His Ser Gly Ser Arg His His Glu Ala Ser Ser Arg Ala Asp
          1880                1885                1890

Ser Ser Arg His Ser Gln Val Gly Gln Gly Gln Ser Ser Gly Pro
          1895                1900                1905
```

```
Arg Thr Ser Arg Asn Gln Gly Ser Ser Val Ser Gln Asp Ser Asp
    1910            1915                1920

Ser Gln Gly His Ser Glu Asp Ser Glu Arg Trp Ser Gly Ser Ala
    1925            1930                1935

Ser Arg Asn His Leu Gly Ser Ala Trp Glu Gln Ser Arg Asp Gly
    1940            1945                1950

Ser Arg His Pro Gly Ser His His Glu Asp Arg Ala Gly His Gly
    1955            1960                1965

His Ser Ala Asp Ser Ser Arg Gln Ser Gly Thr Arg His Thr Glu
    1970            1975                1980

Ser Ser Ser Arg Gly Gln Ala Ala Ser Ser His Glu Gln Ala Arg
    1985            1990                1995

Ser Ser Ala Gly Glu Arg His Gly Ser His His Gln Leu Gln Ser
    2000            2005                2010

Ala Asp Ser Ser Arg His Ser Gly Ile Gly His Gly Gln Ala Ser
    2015            2020                2025

Ser Ala Val Arg Asp Ser Gly His Arg Gly Tyr Ser Gly Ser Gln
    2030            2035                2040

Ala Ser Asp Ser Glu Gly His Ser Glu Asp Ser Asp Thr Gln Ser
    2045            2050                2055

Val Ser Ala Gln Gly Lys Ala Gly Pro His Gln Gln Ser His Lys
    2060            2065                2070

Glu Ser Ala Arg Gly Gln Ser Gly Glu Ser Ser Gly Arg Ser Gly
    2075            2080                2085

Ser Phe Leu Tyr Gln Val Ser Thr His Glu Gln Ser Glu Ser Thr
    2090            2095                2100

His Gly Gln Ser Ala Pro Ser Thr Gly Gly Arg Gln Gly Ser His
    2105            2110                2115

Tyr Asp Gln Ala Gln Asp Ser Ser Arg His Ser Ala Ser Gln Glu
    2120            2125                2130

Gly Gln Asp Thr Ile Arg Gly His Pro Gly Pro Ser Arg Gly Gly
    2135            2140                2145

Arg Gln Gly Ser His Gln Glu Gln Ser Val Asp Arg Ser Gly His
    2150            2155                2160

Ser Gly Ser His His Ser His Thr Thr Ser Gln Gly Arg Ser Asp
    2165            2170                2175

Ala Ser Arg Gly Gln Ser Gly Ser Arg Ser Ala Ser Arg Lys Thr
    2180            2185                2190

Tyr Asp Lys Glu Gln Ser Gly Asp Gly Ser Arg His Ser Gly Ser
    2195            2200                2205

His His His Glu Ala Ser Ser Trp Ala Asp Ser Ser Arg His Ser
    2210            2215                2220

Leu Val Gly Gln Gly Gln Ser Gly Pro Arg Thr Ser Arg Pro
    2225            2230                2235

Arg Gly Ser Ser Val Ser Gln Asp Ser Asp Ser Glu Gly His Ser
    2240            2245                2250

Glu Asp Ser Glu Arg Arg Ser Gly Ser Ala Ser Arg Asn His His
    2255            2260                2265

Gly Ser Ala Gln Glu Gln Ser Arg Asp Gly Ser Arg His Pro Arg
    2270            2275                2280

Ser His His Glu Asp Arg Ala Gly His Gly His Ser Ala Glu Ser
    2285            2290                2295
```

-continued

```
Ser Arg Gln Ser Gly Thr His His Ala Glu Asn Ser Ser Gly Gly
    2300                2305                2310

Gln Ala Ala Ser Ser His Glu Gln Ala Arg Ser Ser Ala Gly Glu
    2315                2320                2325

Arg His Gly Ser His His Gln Gln Ser Ala Asp Ser Ser Arg His
    2330                2335                2340

Ser Gly Ile Gly His Gly Gln Ala Ser Ser Ala Val Arg Asp Ser
    2345                2350                2355

Gly His Arg Gly Ser Ser Gly Ser Gln Ala Ser Asp Ser Glu Gly
    2360                2365                2370

His Ser Glu Asp Ser Asp Thr Gln Ser Val Ser Ala His Gly Gln
    2375                2380                2385

Ala Gly Pro His Gln Gln Ser His Gln Glu Ser Thr Arg Gly Arg
    2390                2395                2400

Ser Ala Gly Arg Ser Gly Arg Ser Gly Ser Phe Leu Tyr Gln Val
    2405                2410                2415

Ser Thr His Glu Gln Ser Glu Ser Ala His Gly Arg Thr Gly Thr
    2420                2425                2430

Ser Thr Gly Gly Arg Gln Gly Ser His His Lys Gln Ala Arg Asp
    2435                2440                2445

Ser Ser Arg His Ser Thr Ser Gln Glu Gly Gln Asp Thr Ile His
    2450                2455                2460

Gly His Pro Gly Ser Ser Ser Gly Gly Arg Gln Gly Ser His Tyr
    2465                2470                2475

Glu Gln Leu Val Asp Arg Ser Gly His Ser Gly Ser His His Ser
    2480                2485                2490

His Thr Thr Ser Gln Gly Arg Ser Asp Ala Ser His Gly His Ser
    2495                2500                2505

Gly Ser Arg Ser Ala Ser Arg Gln Thr Arg Asn Asp Glu Gln Ser
    2510                2515                2520

Gly Asp Gly Ser Arg His Ser Gly Ser Arg His His Glu Ala Ser
    2525                2530                2535

Ser Arg Ala Asp Ser Ser Gly His Ser Gln Val Gly Gln Gly Gln
    2540                2545                2550

Ser Glu Gly Pro Arg Thr Ser Arg Asn Trp Gly Ser Ser Phe Ser
    2555                2560                2565

Gln Asp Ser Asp Ser Gln Gly His Ser Glu Asp Ser Glu Arg Trp
    2570                2575                2580

Ser Gly Ser Ala Ser Arg Asn His His Gly Ser Ala Gln Glu Gln
    2585                2590                2595

Leu Arg Asp Gly Ser Arg His Pro Arg Ser His Gln Glu Asp Arg
    2600                2605                2610

Ala Gly His Gly His Ser Ala Asp Ser Ser Arg Gln Ser Gly Thr
    2615                2620                2625

Arg His Thr Gln Thr Ser Ser Gly Gly Gln Ala Ala Ser Ser His
    2630                2635                2640

Glu Gln Ala Arg Ser Ser Ala Gly Glu Arg His Gly Ser His His
    2645                2650                2655

Gln Gln Ser Ala Asp Ser Ser Arg His Ser Gly Ile Gly His Gly
    2660                2665                2670

Gln Ala Ser Ser Ala Val Arg Asp Ser Gly His Arg Gly Tyr Ser
    2675                2680                2685

Gly Ser Gln Ala Ser Asp Asn Glu Gly His Ser Glu Asp Ser Asp
```

-continued

```
                2690                2695                2700
Thr Gln Ser Val Ser Ala His Gly Gln Ala Gly Ser His Gln Gln
    2705                2710                2715
Ser His Gln Glu Ser Ala Arg Gly Arg Ser Gly Glu Thr Ser Gly
    2720                2725                2730
His Ser Gly Ser Phe Leu Tyr Gln Val Ser Thr His Glu Gln Ser
    2735                2740                2745
Glu Ser Ser His Gly Trp Thr Gly Pro Ser Thr Arg Gly Arg Gln
    2750                2755                2760
Gly Ser Arg His Glu Gln Ala Gln Asp Ser Ser Arg His Ser Ala
    2765                2770                2775
Ser Gln Asp Gly Gln Asp Thr Ile Arg Gly His Pro Gly Ser Ser
    2780                2785                2790
Arg Gly Gly Arg Gln Gly Tyr His His Glu His Ser Val Asp Ser
    2795                2800                2805
Ser Gly His Ser Gly Ser His His Ser His Thr Thr Ser Gln Gly
    2810                2815                2820
Arg Ser Asp Ala Ser Arg Gly Gln Ser Gly Ser Arg Ser Ala Ser
    2825                2830                2835
Arg Thr Thr Arg Asn Glu Glu Gln Ser Gly Asp Gly Ser Arg His
    2840                2845                2850
Ser Gly Ser Arg His His Glu Ala Ser Thr His Ala Asp Ile Ser
    2855                2860                2865
Arg His Ser Gln Ala Val Gln Gly Gln Ser Glu Gly Ser Arg Arg
    2870                2875                2880
Ser Arg Arg Gln Gly Ser Ser Val Ser Gln Asp Ser Asp Ser Glu
    2885                2890                2895
Gly His Ser Glu Asp Ser Glu Arg Trp Ser Gly Ser Ala Ser Arg
    2900                2905                2910
Asn His His Gly Ser Ala Gln Glu Gln Leu Arg Asp Gly Ser Arg
    2915                2920                2925
His Pro Arg Ser His Gln Glu Asp Arg Ala Gly His Gly His Ser
    2930                2935                2940
Ala Asp Ser Ser Arg Gln Ser Gly Thr Arg His Thr Gln Thr Ser
    2945                2950                2955
Ser Gly Gly Gln Ala Ala Ser Ser His Glu Gln Ala Arg Ser Ser
    2960                2965                2970
Ala Gly Glu Arg His Gly Ser His His Gln Gln Ser Ala Asp Ser
    2975                2980                2985
Ser Arg His Ser Gly Ile Gly His Gly Gln Ala Ser Ser Ala Val
    2990                2995                3000
Arg Asp Ser Gly His Arg Gly Tyr Ser Gly Ser Gln Ala Ser Asp
    3005                3010                3015
Asn Glu Gly His Ser Glu Asp Ser Asp Thr Gln Ser Val Ser Ala
    3020                3025                3030
His Gly Gln Ala Gly Ser His Gln Gln Ser His Gln Glu Ser Ala
    3035                3040                3045
Arg Gly Arg Ser Gly Glu Thr Ser Gly His Ser Gly Ser Phe Leu
    3050                3055                3060
Tyr Gln Val Ser Thr His Glu Gln Ser Glu Ser Ser His Gly Trp
    3065                3070                3075
Thr Gly Pro Ser Thr Arg Gly Arg Gln Gly Ser Arg His Glu Gln
    3080                3085                3090
```

```
Ala Gln Asp Ser Ser Arg His Ser Ala Ser Gln Tyr Gly Gln Asp
    3095                3100                3105

Thr Ile Arg Gly His Pro Gly Ser Ser Arg Gly Gly Arg Gln Gly
    3110                3115                3120

Tyr His His Glu His Ser Val Asp Ser Ser Gly His Ser Gly Ser
    3125                3130                3135

His His Ser His Thr Thr Ser Gln Gly Arg Ser Asp Ala Ser Arg
    3140                3145                3150

Gly Gln Ser Gly Ser Arg Ser Ala Ser Arg Thr Thr Arg Asn Glu
    3155                3160                3165

Glu Gln Ser Gly Asp Ser Ser Arg His Ser Val Ser Arg His His
    3170                3175                3180

Glu Ala Ser Thr His Ala Asp Ile Ser Arg His Ser Gln Ala Val
    3185                3190                3195

Gln Gly Gln Ser Glu Gly Ser Arg Arg Ser Arg Arg Gln Gly Ser
    3200                3205                3210

Ser Val Ser Gln Asp Ser Asp Ser Glu Gly His Ser Glu Asp Ser
    3215                3220                3225

Glu Arg Trp Ser Gly Ser Ala Ser Arg Asn His Arg Gly Ser Val
    3230                3235                3240

Gln Glu Gln Ser Arg His Gly Ser Arg His Pro Arg Ser His His
    3245                3250                3255

Glu Asp Arg Ala Gly His Gly His Ser Ala Asp Arg Ser Arg Gln
    3260                3265                3270

Ser Gly Thr Arg His Ala Glu Thr Ser Ser Gly Gly Gln Ala Ala
    3275                3280                3285

Ser Ser His Glu Gln Ala Arg Ser Ser Pro Gly Glu Arg His Gly
    3290                3295                3300

Ser Arg His Gln Gln Ser Ala Asp Ser Ser Arg His Ser Gly Ile
    3305                3310                3315

Pro Arg Gly Gln Ala Ser Ser Ala Val Arg Asp Ser Arg His Trp
    3320                3325                3330

Gly Ser Ser Gly Ser Gln Ala Ser Asp Ser Glu Gly His Ser Glu
    3335                3340                3345

Glu Ser Asp Thr Gln Ser Val Ser Gly His Gly Gln Ala Gly Pro
    3350                3355                3360

His Gln Gln Ser His Gln Glu Ser Ala Arg Asp Arg Ser Gly Gly
    3365                3370                3375

Arg Ser Gly Arg Ser Gly Ser Phe Leu Tyr Gln Val Ser Thr His
    3380                3385                3390

Glu Gln Ser Glu Ser Ala His Gly Arg Thr Arg Thr Ser Thr Gly
    3395                3400                3405

Arg Arg Gln Gly Ser His His Glu Gln Ala Arg Asp Ser Ser Arg
    3410                3415                3420

His Ser Ala Ser Gln Glu Gly Gln Asp Thr Ile Arg Gly His Pro
    3425                3430                3435

Gly Ser Ser Arg Arg Gly Arg Gln Gly Ser His Tyr Glu Gln Ser
    3440                3445                3450

Val Asp Arg Ser Gly His Ser Gly Ser His His Ser His Thr Thr
    3455                3460                3465

Ser Gln Gly Arg Ser Asp Ala Ser Arg Gly Gln Ser Gly Ser Arg
    3470                3475                3480
```

-continued

```
Ser Ala Ser Arg Gln Thr Arg Asn Asp Glu Gln Ser Gly Asp Gly
    3485                3490                3495

Ser Arg His Ser Trp Ser His His His Glu Ala Ser Thr Gln Ala
    3500                3505                3510

Asp Ser Ser Arg His Ser Gln Ser Gly Gln Gly Gln Ser Ala Gly
    3515                3520                3525

Pro Arg Thr Ser Arg Asn Gln Gly Ser Ser Val Ser Gln Asp Ser
    3530                3535                3540

Asp Ser Gln Gly His Ser Glu Asp Ser Glu Arg Trp Ser Gly Ser
    3545                3550                3555

Ala Ser Arg Asn His Arg Gly Ser Ala Gln Glu Gln Ser Arg Asp
    3560                3565                3570

Gly Ser Arg His Pro Thr Ser His His Glu Asp Arg Ala Gly His
    3575                3580                3585

Gly His Ser Ala Glu Ser Ser Arg Gln Ser Gly Thr His His Ala
    3590                3595                3600

Glu Asn Ser Ser Gly Gly Gln Ala Ala Ser Ser His Glu Gln Ala
    3605                3610                3615

Arg Ser Ser Ala Gly Glu Arg His Gly Ser His His Gln Gln Ser
    3620                3625                3630

Ala Asp Ser Ser Arg His Ser Gly Ile Gly His Gly Gln Ala Ser
    3635                3640                3645

Ser Ala Val Arg Asp Ser Gly His Arg Gly Ser Ser Gly Ser Gln
    3650                3655                3660

Ala Ser Asp Ser Glu Gly His Ser Glu Asp Ser Asp Thr Gln Ser
    3665                3670                3675

Val Ser Ala His Gly Gln Ala Gly Pro His Gln Gln Ser His Gln
    3680                3685                3690

Glu Ser Thr Arg Gly Arg Ser Ala Gly Arg Ser Gly Arg Ser Gly
    3695                3700                3705

Ser Phe Leu Tyr Gln Val Ser Thr His Glu Gln Ser Glu Ser Ala
    3710                3715                3720

His Gly Arg Ala Gly Pro Ser Thr Gly Gly Arg Gln Gly Ser Arg
    3725                3730                3735

His Glu Gln Ala Arg Asp Ser Ser Arg His Ser Ala Ser Gln Glu
    3740                3745                3750

Gly Gln Asp Thr Ile Arg Gly His Pro Gly Ser Arg Arg Gly Gly
    3755                3760                3765

Arg Gln Gly Ser Tyr His Glu Gln Ser Val Asp Arg Ser Gly His
    3770                3775                3780

Ser Gly Ser His His Ser His Thr Thr Ser Gln Gly Arg Ser Asp
    3785                3790                3795

Ala Ser His Gly Gln Ser Gly Ser Arg Ser Ala Ser Arg Glu Thr
    3800                3805                3810

Arg Asn Glu Glu Gln Ser Gly Asp Gly Ser Arg His Ser Gly Ser
    3815                3820                3825

Arg His His Glu Ala Ser Thr Gln Ala Asp Ser Ser Arg His Ser
    3830                3835                3840

Gln Ser Gly Gln Gly Glu Ser Ala Gly Ser Arg Arg Ser Arg Arg
    3845                3850                3855

Gln Gly Ser Ser Val Ser Gln Asp Ser Asp Ser Glu Ala Tyr Pro
    3860                3865                3870

Glu Asp Ser Glu Arg Arg Ser Glu Ser Ala Ser Arg Asn His His
```

```
                3875                3880                3885
Gly Ser Ser Arg Glu Gln Ser Arg Asp Gly Ser Arg His Pro Gly
    3890                3895                3900

Ser Ser His Arg Asp Thr Ala Ser His Val Gln Ser Ser Pro Val
    3905                3910                3915

Gln Ser Asp Ser Ser Thr Ala Lys Glu His Gly His Phe Ser Ser
    3920                3925                3930

Leu Ser Gln Asp Ser Ala Tyr His Ser Gly Ile Gln Ser Arg Gly
    3935                3940                3945

Ser Pro His Ser Ser Ser Tyr His Tyr Gln Ser Glu Gly Thr
    3950                3955                3960

Glu Arg Gln Lys Gly Gln Ser Gly Leu Val Trp Arg His Gly Ser
    3965                3970                3975

Tyr Gly Ser Ala Asp Tyr Asp Tyr Gly Glu Ser Gly Phe Arg His
    3980                3985                3990

Ser Gln His Gly Ser Val Ser Tyr Asn Ser Asn Pro Val Val Phe
    3995                4000                4005

Lys Glu Arg Ser Asp Ile Cys Lys Ala Ser Ala Phe Gly Lys Asp
    4010                4015                4020

His Pro Arg Tyr Tyr Ala Thr Tyr Ile Asn Lys Asp Pro Gly Leu
    4025                4030                4035

Cys Gly His Ser Ser Asp Ile Ser Lys Gln Leu Gly Phe Ser Gln
    4040                4045                4050

Ser Gln Arg Tyr Tyr Tyr Tyr Glu
    4055                4060

<210> SEQ ID NO 2
<211> LENGTH: 4061
<212> TYPE: PRT
<213> ORGANISM: Homo sapiens

<400> SEQUENCE: 2

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
            20                  25                  30

Leu Lys Glu Leu Leu Glu Lys Glu Phe Arg Gln Ile Leu Lys Asn Pro
        35                  40                  45

Asp Asp Pro Asp Met Val Asp Val Phe Met Asp His Leu Asp Ile Asp
    50                  55                  60

His Asn Lys Lys Ile Asp Phe Thr Glu Phe Leu Leu Met Val Phe Lys
65                  70                  75                  80

Leu Ala Gln Ala Tyr Tyr Glu Ser Thr Arg Lys Glu Asn Leu Pro Ile
                85                  90                  95

Ser Gly His Lys His Arg Lys His Ser His His Asp Lys His Glu Asp
            100                 105                 110

Asn Lys Gln Glu Glu Asn Lys Glu Asn Arg Lys Arg Pro Ser Ser Leu
        115                 120                 125

Glu Arg Arg Asn Asn Arg Lys Gly Asn Lys Gly Arg Ser Lys Ser Pro
    130                 135                 140

Arg Glu Thr Gly Gly Lys Arg His Glu Ser Ser Ser Glu Lys Lys Glu
145                 150                 155                 160

Arg Lys Gly Tyr Ser Pro Thr His Arg Glu Glu Glu Tyr Gly Lys Asn
                165                 170                 175
```

```
His His Asn Ser Ser Lys Lys Glu Lys Asn Lys Thr Glu Asn Thr Arg
            180                 185                 190

Leu Gly Asp Asn Arg Lys Arg Leu Ser Glu Arg Leu Glu Glu Lys Glu
        195                 200                 205

Asp Asn Glu Glu Gly Val Tyr Asp Tyr Glu Asn Thr Gly Arg Met Thr
    210                 215                 220

Gln Lys Trp Ile Gln Ser Gly His Ile Ala Thr Tyr Thr Ile Gln
225                 230                 235                 240

Asp Glu Ala Tyr Asp Thr Thr Asp Ser Leu Leu Glu Glu Asn Lys Ile
                245                 250                 255

Tyr Glu Arg Ser Arg Ser Ser Asp Gly Lys Ser Ser Ser Gln Val Asn
            260                 265                 270

Arg Ser Arg His Glu Asn Thr Ser Gln Val Pro Leu Gln Glu Ser Arg
        275                 280                 285

Thr Arg Lys Arg Arg Gly Ser Arg Val Ser Gln Asp Arg Asp Ser Glu
    290                 295                 300

Gly His Ser Glu Asp Ser Glu Arg His Ser Gly Ser Ala Ser Arg Asn
305                 310                 315                 320

His His Gly Ser Ala Trp Glu Gln Ser Arg Asp Gly Ser Arg His Pro
                325                 330                 335

Arg Ser His Asp Glu Asp Arg Ala Ser His Gly His Ser Ala Asp Ser
            340                 345                 350

Ser Arg Gln Ser Gly Thr Arg His Ala Glu Thr Ser Ser Arg Gly Gln
        355                 360                 365

Thr Ala Ser Ser His Glu Gln Ala Arg Ser Ser Pro Gly Glu Arg His
    370                 375                 380

Gly Ser Gly His Gln Gln Ser Ala Asp Ser Ser Arg His Ser Ala Thr
385                 390                 395                 400

Gly Arg Gly Gln Ala Ser Ser Ala Val Ser Asp Arg Gly His Arg Gly
                405                 410                 415

Ser Ser Gly Ser Gln Ala Ser Asp Ser Glu Gly His Ser Glu Asn Ser
            420                 425                 430

Asp Thr Gln Ser Val Ser Gly His Gly Lys Ala Gly Leu Arg Gln Gln
        435                 440                 445

Ser His Gln Glu Ser Thr Arg Gly Arg Ser Gly Glu Arg Ser Gly Arg
    450                 455                 460

Ser Gly Ser Ser Leu Tyr Gln Val Ser Thr His Glu Gln Pro Asp Ser
465                 470                 475                 480

Ala His Gly Arg Thr Gly Thr Ser Thr Gly Gly Arg Gln Gly Ser His
                485                 490                 495

His Glu Gln Ala Arg Asp Ser Ser Arg His Ser Ala Ser Gln Glu Gly
            500                 505                 510

Gln Asp Thr Ile Arg Gly His Pro Gly Ser Ser Arg Gly Gly Arg Gln
        515                 520                 525

Gly Ser His His Glu Gln Ser Val Asn Arg Ser Gly His Ser Gly Ser
    530                 535                 540

His His Ser His Thr Thr Ser Gln Gly Arg Ser Asp Ala Ser His Gly
545                 550                 555                 560

Gln Ser Gly Ser Arg Ser Ala Ser Arg Gln Thr Arg Asn Glu Glu Gln
                565                 570                 575

Ser Gly Asp Gly Thr Arg His Ser Gly Ser Arg His His Glu Ala Ser
            580                 585                 590

Ser Gln Ala Asp Ser Ser Arg His Ser Gln Val Gly Gln Gly Gln Ser
```

```
            595                 600                 605
Ser Gly Pro Arg Thr Ser Arg Asn Gln Gly Ser Ser Val Ser Gln Asp
        610                 615                 620

Ser Asp Ser Gln Gly His Ser Glu Asp Ser Glu Arg Trp Ser Gly Ser
625                 630                 635                 640

Ala Ser Arg Asn His His Gly Ser Ala Gln Glu Gln Ser Arg Asp Gly
                645                 650                 655

Ser Arg His Pro Arg Ser His His Glu Asp Arg Ala Gly His Gly His
            660                 665                 670

Ser Ala Asp Ser Ser Arg Lys Ser Gly Thr Arg His Thr Gln Asn Ser
        675                 680                 685

Ser Ser Gly Gln Ala Ala Ser Ser His Glu Gln Ala Arg Ser Ala
690                 695                 700

Gly Glu Arg His Gly Ser Arg His Gln Leu Gln Ser Ala Asp Ser Ser
705                 710                 715                 720

Arg His Ser Gly Thr Gly His Gly Gln Ala Ser Ser Ala Val Arg Asp
                725                 730                 735

Ser Gly His Arg Gly Ser Ser Gly Ser Gln Ala Thr Asp Ser Glu Gly
            740                 745                 750

His Ser Glu Asp Ser Asp Thr Gln Ser Val Ser Gly His Gly Gln Ala
        755                 760                 765

Gly His His Gln Gln Ser His Gln Glu Ser Ala Arg Asp Arg Ser Gly
    770                 775                 780

Glu Arg Ser Arg Arg Ser Gly Ser Phe Leu Tyr Gln Val Ser Thr His
785                 790                 795                 800

Lys Gln Ser Glu Ser Ser His Gly Trp Thr Gly Pro Ser Thr Gly Val
                805                 810                 815

Arg Gln Gly Ser His His Glu Gln Ala Arg Asp Asn Ser Arg His Ser
            820                 825                 830

Ala Ser Gln Asp Gly Gln Asp Thr Ile Arg Gly His Pro Gly Ser Ser
        835                 840                 845

Arg Arg Gly Arg Gln Gly Ser His His Glu Gln Ser Val Asp Arg Ser
    850                 855                 860

Gly His Ser Gly Ser His His Ser His Thr Thr Ser Gln Gly Arg Ser
865                 870                 875                 880

Asp Ala Ser Arg Gly Gln Ser Gly Ser Arg Ser Ala Ser Arg Thr Thr
                885                 890                 895

Arg Asn Glu Glu Gln Ser Arg Asp Gly Ser Arg His Ser Gly Ser Arg
            900                 905                 910

His His Glu Ala Ser Ser His Ala Asp Ile Ser Arg His Ser Gln Ala
        915                 920                 925

Gly Gln Gly Gln Ser Glu Gly Ser Arg Thr Ser Arg Arg Gln Gly Ser
    930                 935                 940

Ser Val Ser Gln Asp Ser Asp Ser Glu Gly His Ser Glu Asp Ser Glu
945                 950                 955                 960

Arg Trp Ser Gly Ser Ala Ser Arg Asn His Arg Gly Ser Ala Gln Glu
                965                 970                 975

Gln Ser Arg His Gly Ser Arg His Pro Arg Ser His His Glu Asp Arg
            980                 985                 990

Ala Gly His Gly His Ser Ala Asp  Ser Ser Arg Gln Ser  Gly Thr Pro
        995                 1000                 1005

His Ala  Glu Thr Ser Ser Gly  Gly Gln Ala Ala Ser  Ser His Glu
    1010                1015                 1020
```

```
Gln Ala Arg Ser Ser Pro Gly Glu Arg His Gly Ser Arg His Gln
    1025                1030                1035

Gln Ser Ala Asp Ser Ser Arg His Ser Gly Ile Pro Arg Arg Gln
    1040                1045                1050

Ala Ser Ser Ala Val Arg Asp Ser Gly His Trp Gly Ser Ser Gly
    1055                1060                1065

Ser Gln Ala Ser Asp Ser Glu Gly His Ser Glu Ser Asp Thr
    1070                1075                1080

Gln Ser Val Ser Gly His Gly Gln Asp Gly Pro His Gln Gln Ser
    1085                1090                1095

His Gln Glu Ser Ala Arg Asp Trp Ser Gly Gly Arg Ser Gly Arg
    1100                1105                1110

Ser Gly Ser Phe Ile Tyr Gln Val Ser Thr His Glu Gln Ser Glu
    1115                1120                1125

Ser Ala His Gly Arg Thr Arg Thr Ser Thr Gly Arg Arg Gln Gly
    1130                1135                1140

Ser His His Glu Gln Ala Arg Asp Ser Ser Arg His Ser Ala Ser
    1145                1150                1155

Gln Glu Gly Gln Asp Thr Ile Arg Ala His Pro Gly Ser Arg Arg
    1160                1165                1170

Gly Gly Arg Gln Gly Ser His His Glu Gln Ser Val Asp Arg Ser
    1175                1180                1185

Gly His Ser Gly Ser His His Ser His Thr Thr Ser Gln Gly Arg
    1190                1195                1200

Ser Asp Ala Ser His Gly Gln Ser Gly Ser Arg Ser Ala Ser Arg
    1205                1210                1215

Gln Thr Arg Lys Asp Lys Gln Ser Gly Asp Gly Ser Arg His Ser
    1220                1225                1230

Gly Ser Arg His His Glu Ala Ala Ser Trp Ala Asp Ser Ser Arg
    1235                1240                1245

His Ser Gln Val Gly Gln Glu Gln Ser Ser Gly Ser Arg Thr Ser
    1250                1255                1260

Arg His Gln Gly Ser Ser Val Ser Gln Asp Ser Asp Ser Glu Arg
    1265                1270                1275

His Ser Asp Asp Ser Glu Arg Leu Ser Gly Ser Ala Ser Arg Asn
    1280                1285                1290

His His Gly Ser Ser Arg Glu Gln Ser Arg Asp Gly Ser Arg His
    1295                1300                1305

Pro Gly Phe His Gln Glu Asp Arg Ala Ser His Gly His Ser Ala
    1310                1315                1320

Asp Ser Ser Arg Gln Ser Gly Thr His His Thr Glu Ser Ser Ser
    1325                1330                1335

His Gly Gln Ala Val Ser Ser His Glu Gln Ala Arg Ser Ser Pro
    1340                1345                1350

Gly Glu Arg His Gly Ser Arg His Gln Gln Ser Ala Asp Ser Ser
    1355                1360                1365

Arg His Ser Gly Ile Gly Arg Gln Ala Ser Ser Ala Val Arg
    1370                1375                1380

Asp Ser Gly His Arg Gly Ser Ser Gly Ser Gln Val Thr Asn Ser
    1385                1390                1395

Glu Gly His Ser Glu Asp Ser Asp Thr Gln Ser Val Ser Ala His
    1400                1405                1410
```

```
Gly Gln Ala Gly Pro His Gln Gln Ser His Lys Glu Ser Ala Arg
    1415                1420                1425

Gly Gln Ser Gly Glu Ser Ser Gly Arg Ser Arg Ser Phe Leu Tyr
    1430                1435                1440

Gln Val Ser Ser His Glu Gln Ser Glu Ser Thr His Gly Gln Thr
    1445                1450                1455

Ala Pro Ser Thr Gly Gly Arg Gln Gly Ser Arg His Glu Gln Ala
    1460                1465                1470

Arg Asn Ser Ser Arg His Ser Ala Ser Gln Asp Gly Gln Asp Thr
    1475                1480                1485

Ile Arg Gly His Pro Gly Ser Ser Arg Gly Gly Arg Gln Gly Ser
    1490                1495                1500

Tyr His Glu Gln Ser Val Asp Arg Ser Gly His Ser Gly Tyr His
    1505                1510                1515

His Ser His Thr Thr Pro Gln Gly Arg Ser Asp Ala Ser His Gly
    1520                1525                1530

Gln Ser Gly Pro Arg Ser Ala Ser Arg Gln Thr Arg Asn Glu Glu
    1535                1540                1545

Gln Ser Gly Asp Gly Ser Arg His Ser Gly Ser Arg His His Glu
    1550                1555                1560

Pro Ser Thr Arg Ala Gly Ser Ser Arg His Ser Gln Val Gly Gln
    1565                1570                1575

Gly Glu Ser Ala Gly Ser Lys Thr Ser Arg Arg Gln Gly Ser Ser
    1580                1585                1590

Val Ser Gln Asp Arg Asp Ser Glu Gly His Ser Glu Asp Ser Glu
    1595                1600                1605

Arg Arg Ser Glu Ser Ala Ser Arg Asn His Tyr Gly Ser Ala Arg
    1610                1615                1620

Glu Gln Ser Arg His Gly Ser Arg Asn Pro Arg Ser His Gln Glu
    1625                1630                1635

Asp Arg Ala Ser His Gly His Ser Ala Glu Ser Ser Arg Gln Ser
    1640                1645                1650

Gly Thr Arg His Ala Glu Thr Ser Ser Gly Gly Gln Ala Ala Ser
    1655                1660                1665

Ser Gln Glu Gln Ala Arg Ser Ser Pro Gly Glu Arg His Gly Ser
    1670                1675                1680

Arg His Gln Gln Ser Ala Asp Ser Ser Thr Asp Ser Gly Thr Gly
    1685                1690                1695

Arg Arg Gln Asp Ser Ser Val Val Gly Asp Ser Gly Asn Arg Gly
    1700                1705                1710

Ser Ser Gly Ser Gln Ala Ser Asp Ser Glu Gly His Ser Glu Glu
    1715                1720                1725

Ser Asp Thr Gln Ser Val Ser Ala His Gly Gln Ala Gly Pro His
    1730                1735                1740

Gln Gln Ser His Gln Glu Ser Thr Arg Gly Gln Ser Gly Glu Arg
    1745                1750                1755

Ser Gly Arg Ser Gly Ser Phe Leu Tyr Gln Val Ser Thr His Glu
    1760                1765                1770

Gln Ser Glu Ser Ala His Gly Arg Thr Gly Pro Ser Thr Gly Gly
    1775                1780                1785

Arg Gln Arg Ser Arg His Glu Gln Ala Arg Asp Ser Ser Arg His
    1790                1795                1800

Ser Ala Ser Gln Glu Gly Gln Asp Thr Ile Arg Gly His Pro Gly
```

```
                1805                1810                1815

Ser  Ser  Arg  Gly  Arg  Gln  Gly  Ser  His  Tyr  Glu  Gln  Ser  Val
     1820                1825                1830

Asp  Ser  Ser  Gly  His  Ser  Gly  Ser  His  His  Ser  His  Thr  Thr  Ser
     1835                1840                1845

Gln  Glu  Arg  Ser  Asp  Val  Ser  Arg  Gly  Gln  Ser  Gly  Ser  Arg  Ser
     1850                1855                1860

Val  Ser  Arg  Gln  Thr  Arg  Asn  Glu  Lys  Gln  Ser  Gly  Asp  Gly  Ser
     1865                1870                1875

Arg  His  Ser  Gly  Ser  Arg  His  His  Glu  Ala  Ser  Ser  Arg  Ala  Asp
     1880                1885                1890

Ser  Ser  Arg  His  Ser  Gln  Val  Gly  Gln  Gly  Gln  Ser  Ser  Gly  Pro
     1895                1900                1905

Arg  Thr  Ser  Arg  Asn  Gln  Gly  Ser  Ser  Val  Ser  Gln  Asp  Ser  Asp
     1910                1915                1920

Ser  Gln  Gly  His  Ser  Glu  Asp  Ser  Glu  Arg  Trp  Ser  Gly  Ser  Ala
     1925                1930                1935

Ser  Arg  Asn  His  Leu  Gly  Ser  Ala  Trp  Glu  Gln  Ser  Arg  Asp  Gly
     1940                1945                1950

Ser  Arg  His  Pro  Gly  Ser  His  His  Glu  Asp  Arg  Ala  Gly  His  Gly
     1955                1960                1965

His  Ser  Ala  Asp  Ser  Ser  Arg  Gln  Ser  Gly  Thr  Arg  His  Thr  Glu
     1970                1975                1980

Ser  Ser  Ser  Arg  Gly  Gln  Ala  Ala  Ser  Ser  His  Glu  Gln  Ala  Arg
     1985                1990                1995

Ser  Ser  Ala  Gly  Glu  Arg  His  Gly  Ser  His  His  Gln  Leu  Gln  Ser
     2000                2005                2010

Ala  Asp  Ser  Ser  Arg  His  Ser  Gly  Ile  Gly  His  Gly  Gln  Ala  Ser
     2015                2020                2025

Ser  Ala  Val  Arg  Asp  Ser  Gly  His  Arg  Gly  Tyr  Ser  Gly  Ser  Gln
     2030                2035                2040

Ala  Ser  Asp  Ser  Glu  Gly  His  Ser  Glu  Asp  Ser  Asp  Thr  Gln  Ser
     2045                2050                2055

Val  Ser  Ala  Gln  Gly  Lys  Ala  Gly  Pro  His  Gln  Gln  Ser  His  Lys
     2060                2065                2070

Glu  Ser  Ala  Arg  Gly  Gln  Ser  Gly  Glu  Ser  Ser  Gly  Arg  Ser  Gly
     2075                2080                2085

Ser  Phe  Leu  Tyr  Gln  Val  Ser  Thr  His  Glu  Gln  Ser  Glu  Ser  Thr
     2090                2095                2100

His  Gly  Gln  Ser  Ala  Pro  Ser  Thr  Gly  Gly  Arg  Gln  Gly  Ser  His
     2105                2110                2115

Tyr  Asp  Gln  Ala  Gln  Asp  Ser  Ser  Arg  His  Ser  Ala  Ser  Gln  Glu
     2120                2125                2130

Gly  Gln  Asp  Thr  Ile  Arg  Gly  His  Pro  Gly  Pro  Ser  Arg  Gly  Gly
     2135                2140                2145

Arg  Gln  Gly  Ser  His  Gln  Glu  Gln  Ser  Val  Asp  Arg  Ser  Gly  His
     2150                2155                2160

Ser  Gly  Ser  His  His  Ser  His  Thr  Thr  Ser  Gln  Gly  Arg  Ser  Asp
     2165                2170                2175

Ala  Ser  Arg  Gly  Gln  Ser  Gly  Ser  Arg  Ser  Ala  Ser  Arg  Lys  Thr
     2180                2185                2190

Tyr  Asp  Lys  Glu  Gln  Ser  Gly  Asp  Gly  Ser  Arg  His  Ser  Gly  Ser
     2195                2200                2205
```

```
His His His Glu Ala Ser Ser  Trp Ala Asp Ser Ser  Arg His Ser
2210             2215                  2220

Leu Val Gly Gln Gly Gln Ser  Ser Gly Pro Arg Thr  Ser Arg Pro
2225             2230                  2235

Arg Gly Ser Ser Val Ser Gln  Asp Ser Asp Ser Glu  Gly His Ser
2240             2245                  2250

Glu Asp Ser Glu Arg Arg Ser  Gly Ser Ala Ser Arg  Asn His His
2255             2260                  2265

Gly Ser Ala Gln Glu Gln Ser  Arg Asp Gly Ser Arg  His Pro Arg
2270             2275                  2280

Ser His His Glu Asp Arg Ala  Gly His Gly His Ser  Ala Glu Ser
2285             2290                  2295

Ser Arg Gln Ser Gly Thr His  His Ala Glu Asn Ser  Ser Gly Gly
2300             2305                  2310

Gln Ala Ala Ser Ser His Glu  Gln Ala Arg Ser Ser  Ala Gly Glu
2315             2320                  2325

Arg His Gly Ser His His Gln  Gln Ser Ala Asp Ser  Ser Arg His
2330             2335                  2340

Ser Gly Ile Gly His Gly Gln  Ala Ser Ser Ala Val  Arg Asp Ser
2345             2350                  2355

Gly His Arg Gly Ser Ser Gly  Ser Gln Ala Ser Asp  Ser Glu Gly
2360             2365                  2370

His Ser Glu Asp Ser Asp Thr  Gln Ser Val Ser Ala  His Gly Gln
2375             2380                  2385

Ala Gly Pro His Gln Gln Ser  His Gln Glu Ser Thr  Arg Gly Arg
2390             2395                  2400

Ser Ala Gly Arg Ser Gly Arg  Ser Gly Ser Phe Leu  Tyr Gln Val
2405             2410                  2415

Ser Thr His Glu Gln Ser Glu  Ser Ala His Gly Arg  Thr Gly Thr
2420             2425                  2430

Ser Thr Gly Gly Arg Gln Gly  Ser His His Lys Gln  Ala Arg Asp
2435             2440                  2445

Ser Ser Arg His Ser Thr Ser  Gln Glu Gly Gln Asp  Thr Ile His
2450             2455                  2460

Gly His Pro Gly Ser Ser Ser  Gly Gly Arg Gln Gly  Ser His Tyr
2465             2470                  2475

Glu Gln Leu Val Asp Arg Ser  Gly His Ser Gly Ser  His His Ser
2480             2485                  2490

His Thr Thr Ser Gln Gly Arg  Ser Asp Ala Ser His  Gly His Ser
2495             2500                  2505

Gly Ser Arg Ser Ala Ser Arg  Gln Thr Arg Asn Asp  Glu Gln Ser
2510             2515                  2520

Gly Asp Gly Ser Arg His Ser  Gly Ser Arg His His  Glu Ala Ser
2525             2530                  2535

Ser Arg Ala Asp Ser Ser Gly  His Ser Gln Val Gly  Gln Gly Gln
2540             2545                  2550

Ser Glu Gly Pro Arg Thr Ser  Arg Asn Trp Gly Ser  Ser Phe Ser
2555             2560                  2565

Gln Asp Ser Asp Ser Gln Gly  His Ser Glu Asp Ser  Glu Arg Trp
2570             2575                  2580

Ser Gly Ser Ala Ser Arg Asn  His His Gly Ser Ala  Gln Glu Gln
2585             2590                  2595
```

```
Leu Arg Asp Gly Ser Arg His Pro Arg Ser His Gln Glu Asp Arg
2600                 2605                 2610

Ala Gly His Gly His Ser Ala Asp Ser Ser Arg Gln Ser Gly Thr
2615                 2620                 2625

Arg His Thr Gln Thr Ser Ser Gly Gly Gln Ala Ala Ser Ser His
2630                 2635                 2640

Glu Gln Ala Arg Ser Ser Ala Gly Glu Arg His Gly Ser His His
2645                 2650                 2655

Gln Gln Ser Ala Asp Ser Ser Arg His Ser Gly Ile Gly His Gly
2660                 2665                 2670

Gln Ala Ser Ser Ala Val Arg Asp Ser Gly His Arg Gly Tyr Ser
2675                 2680                 2685

Gly Ser Gln Ala Ser Asp Asn Glu Gly His Ser Glu Asp Ser Asp
2690                 2695                 2700

Thr Gln Ser Val Ser Ala His Gly Gln Ala Gly Ser His Gln Gln
2705                 2710                 2715

Ser His Gln Glu Ser Ala Arg Gly Arg Ser Gly Glu Thr Ser Gly
2720                 2725                 2730

His Ser Gly Ser Phe Leu Tyr Gln Val Ser Thr His Glu Gln Ser
2735                 2740                 2745

Glu Ser Ser His Gly Trp Thr Gly Pro Ser Thr Arg Gly Arg Gln
2750                 2755                 2760

Gly Ser Arg His Glu Gln Ala Gln Asp Ser Ser Arg His Ser Ala
2765                 2770                 2775

Ser Gln Asp Gly Gln Asp Thr Ile Arg Gly His Pro Gly Ser Ser
2780                 2785                 2790

Arg Gly Gly Arg Gln Gly Tyr His His Glu His Ser Val Asp Ser
2795                 2800                 2805

Ser Gly His Ser Gly Ser His His Ser His Thr Thr Ser Gln Gly
2810                 2815                 2820

Arg Ser Asp Ala Ser Arg Gly Gln Ser Gly Ser Arg Ser Ala Ser
2825                 2830                 2835

Arg Thr Thr Arg Asn Glu Glu Gln Ser Gly Asp Gly Ser Arg His
2840                 2845                 2850

Ser Gly Ser Arg His His Glu Ala Ser Thr His Ala Asp Ile Ser
2855                 2860                 2865

Arg His Ser Gln Ala Val Gln Gly Gln Ser Glu Gly Ser Arg Arg
2870                 2875                 2880

Ser Arg Arg Gln Gly Ser Ser Val Ser Gln Asp Ser Asp Ser Glu
2885                 2890                 2895

Gly His Ser Glu Asp Ser Glu Arg Trp Ser Gly Ser Ala Ser Arg
2900                 2905                 2910

Asn His His Gly Ser Ala Gln Glu Gln Leu Arg Asp Gly Ser Arg
2915                 2920                 2925

His Pro Arg Ser His Gln Glu Asp Arg Ala Gly His Gly His Ser
2930                 2935                 2940

Ala Asp Ser Ser Arg Gln Ser Gly Thr Arg His Thr Gln Thr Ser
2945                 2950                 2955

Ser Gly Gly Gln Ala Ala Ser Ser His Glu Gln Ala Arg Ser Ser
2960                 2965                 2970

Ala Gly Glu Arg His Gly Ser His His Gln Gln Ser Ala Asp Ser
2975                 2980                 2985

Ser Arg His Ser Gly Ile Gly His Gly Gln Ala Ser Ser Ala Val
```

-continued

```
              2990                2995                3000
Arg Asp Ser Gly His Arg Gly Tyr Ser Gly Ser Gln Ala Ser Asp
    3005                3010                3015
Asn Glu Gly His Ser Glu Asp Ser Asp Thr Gln Ser Val Ser Ala
    3020                3025                3030
His Gly Gln Ala Gly Ser His Gln Gln Ser His Gln Glu Ser Ala
    3035                3040                3045
Arg Gly Arg Ser Gly Glu Thr Ser Gly His Ser Gly Ser Phe Leu
    3050                3055                3060
Tyr Gln Val Ser Thr His Glu Gln Ser Glu Ser His Gly Trp
    3065                3070                3075
Thr Gly Pro Ser Thr Arg Gly Arg Gln Gly Ser Arg His Glu Gln
    3080                3085                3090
Ala Gln Asp Ser Ser Arg His Ser Ala Ser Gln Tyr Gly Gln Asp
    3095                3100                3105
Thr Ile Arg Gly His Pro Gly Ser Ser Arg Gly Gly Arg Gln Gly
    3110                3115                3120
Tyr His His Glu His Ser Val Asp Ser Ser Gly His Ser Gly Ser
    3125                3130                3135
His His Ser His Thr Thr Ser Gln Gly Arg Ser Asp Ala Ser Arg
    3140                3145                3150
Gly Gln Ser Gly Ser Arg Ser Ala Ser Arg Thr Thr Arg Asn Glu
    3155                3160                3165
Glu Gln Ser Gly Asp Ser Ser Arg His Ser Val Ser Arg His His
    3170                3175                3180
Glu Ala Ser Thr His Ala Asp Ile Ser Arg His Ser Gln Ala Val
    3185                3190                3195
Gln Gly Gln Ser Glu Gly Ser Arg Arg Ser Arg Arg Gln Gly Ser
    3200                3205                3210
Ser Val Ser Gln Asp Ser Asp Ser Glu Gly His Ser Glu Asp Ser
    3215                3220                3225
Glu Arg Trp Ser Gly Ser Ala Ser Arg Asn His Arg Gly Ser Val
    3230                3235                3240
Gln Glu Gln Ser Arg His Gly Ser Arg His Pro Arg Ser His His
    3245                3250                3255
Glu Asp Arg Ala Gly His Gly His Ser Ala Asp Arg Ser Arg Gln
    3260                3265                3270
Ser Gly Thr Arg His Ala Glu Thr Ser Ser Gly Gly Gln Ala Ala
    3275                3280                3285
Ser Ser His Glu Gln Ala Arg Ser Ser Pro Gly Glu Arg His Gly
    3290                3295                3300
Ser Arg His Gln Gln Ser Ala Asp Ser Ser Arg His Ser Gly Ile
    3305                3310                3315
Pro Arg Gly Gln Ala Ser Ser Ala Val Arg Asp Ser Arg His Trp
    3320                3325                3330
Gly Ser Ser Gly Ser Gln Ala Ser Asp Ser Glu Gly His Ser Glu
    3335                3340                3345
Glu Ser Asp Thr Gln Ser Val Ser Gly His Gly Gln Ala Gly Pro
    3350                3355                3360
His Gln Gln Ser His Gln Glu Ser Ala Arg Asp Arg Ser Gly Gly
    3365                3370                3375
Arg Ser Gly Arg Ser Gly Ser Phe Leu Tyr Gln Val Ser Thr His
    3380                3385                3390
```

```
Glu Gln Ser Glu Ser Ala His Gly Arg Thr Arg Thr Ser Thr Gly
3395                3400                3405

Arg Arg Gln Gly Ser His His Glu Gln Ala Arg Asp Ser Ser Arg
3410                3415                3420

His Ser Ala Ser Gln Glu Gly Gln Asp Thr Ile Arg Gly His Pro
3425                3430                3435

Gly Ser Ser Arg Arg Gly Arg Gln Gly Ser His Tyr Glu Gln Ser
3440                3445                3450

Val Asp Arg Ser Gly His Ser Gly Ser His Ser His Thr Thr
3455                3460                3465

Ser Gln Gly Arg Ser Asp Ala Ser Arg Gly Gln Ser Gly Ser Arg
3470                3475                3480

Ser Ala Ser Arg Gln Thr Arg Asn Asp Glu Gln Ser Gly Asp Gly
3485                3490                3495

Ser Arg His Ser Trp Ser His His Glu Ala Ser Thr Gln Ala
3500                3505                3510

Asp Ser Ser Arg His Ser Gln Ser Gly Gln Gly Gln Ser Ala Gly
3515                3520                3525

Pro Arg Thr Ser Arg Asn Gln Gly Ser Ser Val Ser Gln Asp Ser
3530                3535                3540

Asp Ser Gln Gly His Ser Glu Asp Ser Glu Arg Trp Ser Gly Ser
3545                3550                3555

Ala Ser Arg Asn His Arg Gly Ser Ala Gln Glu Gln Ser Arg Asp
3560                3565                3570

Gly Ser Arg His Pro Thr Ser His His Glu Asp Arg Ala Gly His
3575                3580                3585

Gly His Ser Ala Glu Ser Ser Arg Gln Ser Gly Thr His His Ala
3590                3595                3600

Glu Asn Ser Ser Gly Gly Gln Ala Ala Ser Ser His Glu Gln Ala
3605                3610                3615

Arg Ser Ser Ala Gly Glu Arg His Gly Ser His His Gln Gln Ser
3620                3625                3630

Ala Asp Ser Ser Arg His Ser Gly Ile Gly His Gly Gln Ala Ser
3635                3640                3645

Ser Ala Val Arg Asp Ser Gly His Arg Gly Ser Ser Gly Ser Gln
3650                3655                3660

Ala Ser Asp Ser Glu Gly His Ser Glu Asp Ser Asp Thr Gln Ser
3665                3670                3675

Val Ser Ala His Gly Gln Ala Gly Pro His Gln Gln Ser His Gln
3680                3685                3690

Glu Ser Thr Arg Gly Arg Ser Ala Gly Arg Ser Gly Arg Ser Gly
3695                3700                3705

Ser Phe Leu Tyr Gln Val Ser Thr His Glu Gln Ser Glu Ser Ala
3710                3715                3720

His Gly Arg Ala Gly Pro Ser Thr Gly Gly Arg Gln Gly Ser Arg
3725                3730                3735

His Glu Gln Ala Arg Asp Ser Ser Arg His Ser Ala Ser Gln Glu
3740                3745                3750

Gly Gln Asp Thr Ile Arg Gly His Pro Gly Ser Arg Arg Gly Gly
3755                3760                3765

Arg Gln Gly Ser Tyr His Glu Gln Ser Val Asp Arg Ser Gly His
3770                3775                3780
```

```
Ser Gly Ser His His Ser His Thr Thr Ser Gln Gly Arg Ser Asp
    3785            3790                3795

Ala Ser His Gly Gln Ser Gly Ser Arg Ser Ala Ser Arg Glu Thr
    3800            3805                3810

Arg Asn Glu Glu Gln Ser Gly Asp Gly Ser Arg His Ser Gly Ser
    3815            3820                3825

Arg His His Glu Ala Ser Thr Gln Ala Asp Ser Ser Arg His Ser
    3830            3835                3840

Gln Ser Gly Gln Gly Glu Ser Ala Gly Ser Arg Arg Ser Arg Arg
    3845            3850                3855

Gln Gly Ser Ser Val Ser Gln Asp Ser Asp Ser Glu Ala Tyr Pro
    3860            3865                3870

Glu Asp Ser Glu Arg Arg Ser Glu Ser Ala Ser Arg Asn His His
    3875            3880                3885

Gly Ser Ser Arg Glu Gln Ser Arg Asp Gly Ser Arg His Pro Gly
    3890            3895                3900

Ser Ser His Arg Asp Thr Ala Ser His Val Gln Ser Ser Pro Val
    3905            3910                3915

Gln Ser Asp Ser Ser Thr Ala Lys Glu His Gly His Phe Ser Ser
    3920            3925                3930

Leu Ser Gln Asp Ser Ala Tyr His Ser Gly Ile Gln Ser Arg Gly
    3935            3940                3945

Ser Pro His Ser Ser Ser Ser Tyr His Tyr Gln Ser Glu Gly Thr
    3950            3955                3960

Glu Arg Gln Lys Gly Gln Ser Gly Leu Val Trp Arg His Gly Ser
    3965            3970                3975

Tyr Gly Ser Ala Asp Tyr Asp Tyr Gly Glu Ser Gly Phe Arg His
    3980            3985                3990

Ser Gln His Gly Ser Val Ser Tyr Asn Ser Asn Pro Val Val Phe
    3995            4000                4005

Lys Glu Arg Ser Asp Ile Cys Lys Ala Ser Ala Phe Gly Lys Asp
    4010            4015                4020

His Pro Arg Tyr Tyr Ala Thr Tyr Ile Asn Lys Asp Pro Gly Leu
    4025            4030                4035

Cys Gly His Ser Ser Asp Ile Ser Lys Gln Leu Gly Phe Ser Gln
    4040            4045                4050

Ser Gln Arg Tyr Tyr Tyr Glu
    4055            4060

<210> SEQ ID NO 3
<211> LENGTH: 4061
<212> TYPE: PRT
<213> ORGANISM: Homo sapiens

<400> SEQUENCE: 3

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
                20                  25                  30

Leu Lys Glu Leu Leu Glu Lys Glu Phe Arg Gln Ile Leu Lys Asn Pro
            35                  40                  45

Asp Asp Pro Asp Met Val Asp Val Phe Met His Leu Asp Ile Asp
        50                  55                  60

His Asn Lys Lys Ile Asp Phe Thr Glu Phe Leu Leu Met Val Phe Lys
65              70                  75                  80
```

-continued

```
Leu Ala Gln Ala Tyr Tyr Glu Ser Thr Arg Lys Glu Asn Leu Pro Ile
                85                  90                  95
Ser Gly His Lys His Arg Lys His Ser His His Asp Lys His Glu Asp
            100                 105                 110
Asn Lys Gln Glu Glu Asn Lys Glu Asn Arg Lys Arg Pro Ser Ser Leu
            115                 120                 125
Glu Arg Arg Asn Asn Arg Lys Gly Asn Lys Gly Arg Ser Lys Ser Pro
130                 135                 140
Arg Glu Thr Gly Gly Lys Arg His Glu Ser Ser Ser Glu Lys Lys Glu
145                 150                 155                 160
Arg Lys Gly Tyr Ser Pro Thr His Arg Glu Glu Glu Tyr Gly Lys Asn
                165                 170                 175
His His Asn Ser Ser Lys Lys Glu Lys Asn Lys Thr Glu Asn Thr Arg
            180                 185                 190
Leu Gly Asp Asn Arg Lys Arg Leu Ser Glu Arg Leu Glu Glu Lys Glu
            195                 200                 205
Asp Asn Glu Glu Gly Val Tyr Asp Tyr Glu Asn Thr Gly Arg Met Thr
210                 215                 220
Gln Lys Trp Ile Gln Ser Gly His Ile Ala Thr Tyr Tyr Thr Ile Gln
225                 230                 235                 240
Asp Glu Ala Tyr Asp Thr Thr Asp Ser Leu Leu Glu Glu Asn Lys Ile
                245                 250                 255
Tyr Glu Arg Ser Arg Ser Ser Asp Gly Lys Ser Ser Ser Gln Val Asn
                260                 265                 270
Arg Ser Arg His Glu Asn Thr Ser Gln Val Pro Leu Gln Glu Ser Arg
            275                 280                 285
Thr Arg Lys Arg Arg Gly Ser Arg Val Ser Gln Asp Arg Asp Ser Glu
290                 295                 300
Gly His Ser Glu Asp Ser Glu Arg His Ser Gly Ser Ala Ser Arg Asn
305                 310                 315                 320
His His Gly Ser Ala Trp Glu Gln Ser Arg Asp Gly Ser Arg His Pro
                325                 330                 335
Arg Ser His Asp Glu Asp Arg Ala Ser His Gly His Ser Ala Asp Ser
            340                 345                 350
Ser Arg Gln Ser Gly Thr Arg His Ala Glu Thr Ser Ser Arg Gly Gln
            355                 360                 365
Thr Ala Ser Ser His Glu Gln Ala Arg Ser Ser Pro Gly Glu Arg His
370                 375                 380
Gly Ser Gly His Gln Gln Ser Ala Asp Ser Ser Arg His Ser Ala Thr
385                 390                 395                 400
Gly Arg Gly Gln Ala Ser Ser Ala Val Ser Asp Arg Gly His Arg Gly
                405                 410                 415
Ser Ser Gly Ser Gln Ala Ser Asp Ser Glu Gly His Ser Glu Asn Ser
            420                 425                 430
Asp Thr Gln Ser Val Ser Gly His Gly Lys Ala Gly Leu Arg Gln Gln
            435                 440                 445
Ser His Gln Glu Ser Thr Arg Gly Arg Ser Gly Glu Arg Ser Gly Arg
450                 455                 460
Ser Gly Ser Ser Leu Tyr Gln Val Ser Thr His Glu Gln Pro Asp Ser
465                 470                 475                 480
Ala His Gly Arg Thr Gly Thr Ser Thr Gly Gly Arg Gln Gly Ser His
                485                 490                 495
```

-continued

His Glu Gln Ala Arg Asp Ser Ser Arg His Ser Ala Ser Gln Gly
             500                 505                 510

Gln Asp Thr Ile Arg Gly His Pro Gly Ser Ser Arg Gly Gly Arg Gln
         515                 520                 525

Gly Ser His His Glu Gln Ser Val Asn Arg Ser Gly His Ser Gly Ser
     530                 535                 540

His His Ser His Thr Thr Ser Gln Gly Arg Ser Asp Ala Ser His Gly
545                 550                 555                 560

Gln Ser Gly Ser Arg Ser Ala Ser Arg Gln Thr Arg Asn Glu Glu Gln
                565                 570                 575

Ser Gly Asp Gly Thr Arg His Ser Gly Ser Arg His His Glu Ala Ser
            580                 585                 590

Ser Gln Ala Asp Ser Ser Arg His Ser Gln Val Gly Gln Gly Gln Ser
        595                 600                 605

Ser Gly Pro Arg Thr Ser Arg Asn Gln Gly Ser Ser Val Ser Gln Asp
    610                 615                 620

Ser Asp Ser Gln Gly His Ser Glu Asp Ser Glu Arg Trp Ser Gly Ser
625                 630                 635                 640

Ala Ser Arg Asn His His Gly Ser Ala Gln Glu Gln Ser Arg Asp Gly
                645                 650                 655

Ser Arg His Pro Arg Ser His His Glu Asp Arg Ala Gly His Gly His
            660                 665                 670

Ser Ala Asp Ser Ser Arg Lys Ser Gly Thr Arg His Thr Gln Asn Ser
        675                 680                 685

Ser Ser Gly Gln Ala Ala Ser Ser His Glu Gln Ala Arg Ser Ser Ala
    690                 695                 700

Gly Glu Arg His Gly Ser Arg His Gln Leu Gln Ser Ala Asp Ser Ser
705                 710                 715                 720

Arg His Ser Gly Thr Gly His Gly Gln Ala Ser Ser Ala Val Arg Asp
                725                 730                 735

Ser Gly His Arg Gly Ser Ser Gly Ser Gln Ala Thr Asp Ser Glu Gly
            740                 745                 750

His Ser Glu Asp Ser Asp Thr Gln Ser Val Ser Gly His Gly Gln Ala
        755                 760                 765

Gly His His Gln Gln Ser His Gln Glu Ser Ala Arg Asp Arg Ser Gly
    770                 775                 780

Glu Arg Ser Arg Arg Ser Gly Ser Phe Leu Tyr Gln Val Ser Thr His
785                 790                 795                 800

Lys Gln Ser Glu Ser Ser His Gly Trp Thr Gly Pro Ser Thr Gly Val
                805                 810                 815

Arg Gln Gly Ser His His Glu Gln Ala Arg Asp Asn Ser Arg His Ser
            820                 825                 830

Ala Ser Gln Asp Gly Gln Asp Thr Ile Arg Gly His Pro Gly Ser Ser
        835                 840                 845

Arg Arg Gly Arg Gln Gly Ser His His Glu Gln Ser Val Asp Arg Ser
    850                 855                 860

Gly His Ser Gly Ser His His Ser His Thr Thr Ser Gln Gly Arg Ser
865                 870                 875                 880

Asp Ala Ser Arg Gly Gln Ser Gly Ser Arg Ser Ala Ser Arg Thr Thr
                885                 890                 895

Arg Asn Glu Glu Gln Ser Arg Asp Gly Ser Arg His Ser Gly Ser Arg
            900                 905                 910

His His Glu Ala Ser Ser His Ala Asp Ile Ser Arg His Ser Gln Ala

```
                915                 920                 925
        Gly Gln Gly Gln Ser Glu Gly Ser Arg Thr Ser Arg Arg Gln Gly Ser
                930                 935                 940

Ser Val Ser Gln Asp Ser Asp Ser Glu Gly His Ser Glu Asp Ser Glu
        945                 950                 955                 960

Arg Trp Ser Gly Ser Ala Ser Arg Asn His Arg Gly Ser Ala Gln Glu
                        965                 970                 975

Gln Ser Arg His Gly Ser Arg His Pro Arg Ser His His Glu Asp Arg
                        980                 985                 990

Ala Gly His Gly His Ser Ala Asp Ser Ser Arg Gln Ser Gly Thr Pro
                    995                1000                1005

His Ala Glu Thr Ser Ser Gly Gly Gln Ala Ala Ser Ser His Glu
                1010                1015                1020

Gln Ala Arg Ser Ser Pro Gly Glu Arg His Gly Ser Arg His Gln
                1025                1030                1035

Gln Ser Ala Asp Ser Ser Arg His Ser Gly Ile Pro Arg Arg Gln
                1040                1045                1050

Ala Ser Ser Ala Val Arg Asp Ser Gly His Trp Gly Ser Ser Gly
                1055                1060                1065

Ser Gln Ala Ser Asp Ser Glu Gly His Ser Glu Glu Ser Asp Thr
                1070                1075                1080

Gln Ser Val Ser Gly His Gly Gln Asp Gly Pro His Gln Gln Ser
                1085                1090                1095

His Gln Glu Ser Ala Arg Asp Trp Ser Gly Gly Arg Ser Gly Arg
                1100                1105                1110

Ser Gly Ser Phe Ile Tyr Gln Val Ser Thr His Glu Gln Ser Glu
                1115                1120                1125

Ser Ala His Gly Arg Thr Arg Thr Ser Thr Gly Arg Arg Gln Gly
                1130                1135                1140

Ser His His Glu Gln Ala Arg Asp Ser Ser Arg His Ser Ala Ser
                1145                1150                1155

Gln Glu Gly Gln Asp Thr Ile Arg Ala His Pro Gly Ser Arg Arg
                1160                1165                1170

Gly Gly Arg Gln Gly Ser His His Glu Gln Ser Val Asp Arg Ser
                1175                1180                1185

Gly His Ser Gly Ser His His Ser His Thr Thr Ser Gln Gly Arg
                1190                1195                1200

Ser Asp Ala Ser His Gly Gln Ser Gly Ser Arg Ser Ala Ser Arg
                1205                1210                1215

Gln Thr Arg Lys Asp Lys Gln Ser Gly Asp Gly Ser Arg His Ser
                1220                1225                1230

Gly Ser Arg His His Glu Ala Ala Ser Trp Ala Asp Ser Ser Arg
                1235                1240                1245

His Ser Gln Val Gly Gln Glu Gln Ser Ser Gly Ser Arg Thr Ser
                1250                1255                1260

Arg His Gln Gly Ser Ser Val Ser Gln Asp Ser Asp Ser Glu Arg
                1265                1270                1275

His Ser Asp Asp Ser Glu Arg Leu Ser Gly Ser Ala Ser Arg Asn
                1280                1285                1290

His His Gly Ser Ser Arg Glu Gln Ser Arg Asp Gly Ser Arg His
                1295                1300                1305

Pro Gly Phe His Gln Glu Asp Arg Ala Ser His Gly His Ser Ala
                1310                1315                1320
```

-continued

```
Asp Ser Ser Arg Gln Ser Gly Thr His His Thr Glu Ser Ser Ser
    1325            1330            1335

His Gly Gln Ala Val Ser Ser His Glu Gln Ala Arg Ser Ser Pro
    1340            1345            1350

Gly Glu Arg His Gly Ser Arg His Gln Gln Ser Ala Asp Ser Ser
    1355            1360            1365

Arg His Ser Gly Ile Gly His Arg Gln Ala Ser Ser Ala Val Arg
    1370            1375            1380

Asp Ser Gly His Arg Gly Ser Ser Gly Ser Gln Val Thr Asn Ser
    1385            1390            1395

Glu Gly His Ser Glu Asp Ser Asp Thr Gln Ser Val Ser Ala His
    1400            1405            1410

Gly Gln Ala Gly Pro His Gln Gln Ser His Lys Glu Ser Ala Arg
    1415            1420            1425

Gly Gln Ser Gly Glu Ser Ser Gly Arg Ser Arg Ser Phe Leu Tyr
    1430            1435            1440

Gln Val Ser Ser His Glu Gln Ser Glu Ser Thr His Gly Gln Thr
    1445            1450            1455

Ala Pro Ser Thr Gly Gly Arg Gln Gly Ser Arg His Glu Gln Ala
    1460            1465            1470

Arg Asn Ser Ser Arg His Ser Ala Ser Gln Asp Gly Gln Asp Thr
    1475            1480            1485

Ile Arg Gly His Pro Gly Ser Ser Arg Gly Gly Arg Gln Gly Ser
    1490            1495            1500

Tyr His Glu Gln Ser Val Asp Arg Ser Gly His Ser Gly Tyr His
    1505            1510            1515

His Ser His Thr Thr Pro Gln Gly Arg Ser Asp Ala Ser His Gly
    1520            1525            1530

Gln Ser Gly Pro Arg Ser Ala Ser Arg Gln Thr Arg Asn Glu Glu
    1535            1540            1545

Gln Ser Gly Asp Gly Ser Arg His Ser Gly Ser Arg His His Glu
    1550            1555            1560

Pro Ser Thr Arg Ala Gly Ser Ser Arg His Ser Gln Val Gly Gln
    1565            1570            1575

Gly Glu Ser Ala Gly Ser Lys Thr Ser Arg Arg Gln Gly Ser Ser
    1580            1585            1590

Val Ser Gln Asp Arg Asp Ser Glu Gly His Ser Glu Asp Ser Glu
    1595            1600            1605

Arg Arg Ser Glu Ser Ala Ser Arg Asn His Tyr Gly Ser Ala Arg
    1610            1615            1620

Glu Gln Ser Arg His Gly Ser Arg Asn Pro Arg Ser His Gln Glu
    1625            1630            1635

Asp Arg Ala Ser His Gly His Ser Ala Glu Ser Ser Arg Gln Ser
    1640            1645            1650

Gly Thr Arg His Ala Glu Thr Ser Ser Gly Gly Gln Ala Ala Ser
    1655            1660            1665

Ser Gln Glu Gln Ala Arg Ser Ser Pro Gly Glu Arg His Gly Ser
    1670            1675            1680

Arg His Gln Gln Ser Ala Asp Ser Ser Thr Asp Ser Gly Thr Gly
    1685            1690            1695

Arg Arg Gln Asp Ser Ser Val Val Gly Asp Ser Gly Asn Arg Gly
    1700            1705            1710
```

```
Ser Ser Gly Ser Gln Ala Ser  Asp Ser Glu Gly His  Ser Glu Glu
    1715                1720                1725

Ser Asp Thr Gln Ser Val Ser  Ala His Gly Gln Ala  Gly Pro His
    1730                1735                1740

Gln Gln Ser His Gln Glu Ser  Thr Arg Gly Gln Ser  Gly Glu Arg
    1745                1750                1755

Ser Gly Arg Ser Gly Ser Phe  Leu Tyr Gln Val Ser  Thr His Glu
    1760                1765                1770

Gln Ser Glu Ser Ala His Gly  Arg Thr Gly Pro Ser  Thr Gly Gly
    1775                1780                1785

Arg Gln Arg Ser Arg His Glu  Gln Ala Arg Asp Ser  Ser Arg His
    1790                1795                1800

Ser Ala Ser Gln Glu Gly Gln  Asp Thr Ile Arg Gly  His Pro Gly
    1805                1810                1815

Ser Ser Arg Gly Gly Arg Gln  Gly Ser His Tyr Glu  Gln Ser Val
    1820                1825                1830

Asp Ser Ser Gly His Ser Gly  Ser His His Ser His  Thr Thr Ser
    1835                1840                1845

Gln Glu Arg Ser Asp Val Ser  Arg Gly Gln Ser Gly  Ser Arg Ser
    1850                1855                1860

Val Ser Arg Gln Thr Arg Asn  Glu Lys Gln Ser Gly  Asp Gly Ser
    1865                1870                1875

Arg His Ser Gly Ser Arg His  His Glu Ala Ser Ser  Arg Ala Asp
    1880                1885                1890

Ser Ser Arg His Ser Gln Val  Gly Gln Gly Gln Ser  Ser Gly Pro
    1895                1900                1905

Arg Thr Ser Arg Asn Gln Gly  Ser Ser Val Ser Gln  Asp Ser Asp
    1910                1915                1920

Ser Gln Gly His Ser Glu Asp  Ser Glu Arg Trp Ser  Gly Ser Ala
    1925                1930                1935

Ser Arg Asn His Leu Gly Ser  Ala Trp Glu Gln Ser  Arg Asp Gly
    1940                1945                1950

Ser Arg His Pro Gly Ser His  His Glu Asp Arg Ala  Gly His Gly
    1955                1960                1965

His Ser Ala Asp Ser Ser Arg  Gln Ser Gly Thr Arg  His Thr Glu
    1970                1975                1980

Ser Ser Ser Arg Gly Gln Ala  Ala Ser Ser His Glu  Gln Ala Arg
    1985                1990                1995

Ser Ser Ala Gly Glu Arg His  Gly Ser His His Gln  Leu Gln Ser
    2000                2005                2010

Ala Asp Ser Ser Arg His Ser  Gly Ile Gly His Gly  Gln Ala Ser
    2015                2020                2025

Ser Ala Val Arg Asp Ser Gly  His Arg Gly Tyr Ser  Gly Ser Gln
    2030                2035                2040

Ala Ser Asp Ser Glu Gly His  Ser Glu Asp Ser Asp  Thr Gln Ser
    2045                2050                2055

Val Ser Ala Gln Gly Lys Ala  Gly Pro His Gln Gln  Ser His Lys
    2060                2065                2070

Glu Ser Ala Arg Gly Gln Ser  Gly Glu Ser Ser Gly  Arg Ser Gly
    2075                2080                2085

Ser Phe Leu Tyr Gln Val Ser  Thr His Glu Gln Ser  Glu Ser Thr
    2090                2095                2100

His Gly Gln Ser Ala Pro Ser  Thr Gly Gly Arg Gln  Gly Ser His
```

-continued

| | 2105 | | | | 2110 | | | | 2115 | | |
|---|---|---|---|---|---|---|---|---|---|---|---|

Tyr Asp Gln Ala Gln Asp Ser Ser Arg His Ser Ala Ser Gln Glu
    2120                        2125                          2130

Gly Gln Asp Thr Ile Arg Gly His Pro Gly Pro Ser Arg Gly Gly
    2135                        2140                          2145

Arg Gln Gly Ser His Gln Glu Gln Ser Val Asp Arg Ser Gly His
    2150                        2155                          2160

Ser Gly Ser His His Ser His Thr Thr Ser Gln Gly Arg Ser Asp
    2165                        2170                          2175

Ala Ser Arg Gly Gln Ser Gly Ser Arg Ser Ala Ser Arg Lys Thr
    2180                        2185                          2190

Tyr Asp Lys Glu Gln Ser Gly Asp Gly Ser Arg His Ser Gly Ser
    2195                        2200                          2205

His His His Glu Ala Ser Ser Trp Ala Asp Ser Ser Arg His Ser
    2210                        2215                          2220

Leu Val Gly Gln Gly Gln Ser Ser Gly Pro Arg Thr Ser Arg Pro
    2225                        2230                          2235

Arg Gly Ser Ser Val Ser Gln Asp Ser Asp Ser Glu Gly His Ser
    2240                        2245                          2250

Glu Asp Ser Glu Arg Arg Ser Gly Ser Ala Ser Arg Asn His His
    2255                        2260                          2265

Gly Ser Ala Gln Glu Gln Ser Arg Asp Gly Ser Arg His Pro Arg
    2270                        2275                          2280

Ser His His Glu Asp Arg Ala Gly His Gly His Ser Ala Glu Ser
    2285                        2290                          2295

Ser Arg Gln Ser Gly Thr His His Ala Glu Asn Ser Ser Gly Gly
    2300                        2305                          2310

Gln Ala Ala Ser Ser His Glu Gln Ala Arg Ser Ser Ala Gly Glu
    2315                        2320                          2325

Arg His Gly Ser His His Gln Gln Ser Ala Asp Ser Ser Arg His
    2330                        2335                          2340

Ser Gly Ile Gly His Gly Gln Ala Ser Ser Ala Val Arg Asp Ser
    2345                        2350                          2355

Gly His Arg Gly Ser Ser Gly Ser Gln Ala Ser Asp Ser Glu Gly
    2360                        2365                          2370

His Ser Glu Asp Ser Asp Thr Gln Ser Val Ser Ala His Gly Gln
    2375                        2380                          2385

Ala Gly Pro His Gln Gln Ser His Gln Glu Ser Thr Arg Gly Arg
    2390                        2395                          2400

Ser Ala Gly Arg Ser Gly Arg Ser Gly Ser Phe Leu Tyr Gln Val
    2405                        2410                          2415

Ser Thr His Glu Gln Ser Glu Ser Ala His Gly Arg Thr Gly Thr
    2420                        2425                          2430

Ser Thr Gly Gly Arg Gln Gly Ser His His Lys Gln Ala Arg Asp
    2435                        2440                          2445

Ser Ser Arg His Ser Thr Ser Gln Glu Gly Gln Asp Thr Ile His
    2450                        2455                          2460

Gly His Pro Gly Ser Ser Ser Gly Gly Arg Gln Gly Ser His Tyr
    2465                        2470                          2475

Glu Gln Leu Val Asp Arg Ser Gly His Ser Gly Ser His His Ser
    2480                        2485                          2490

His Thr Thr Ser Gln Gly Arg Ser Asp Ala Ser His Gly His Ser
    2495                        2500                          2505

```
Gly Ser Arg Ser Ala Ser Arg Gln Thr Arg Asn Asp Glu Gln Ser
    2510                2515                2520

Gly Asp Gly Ser Arg His Ser Gly Ser Arg His His Glu Ala Ser
    2525                2530                2535

Ser Arg Ala Asp Ser Ser Gly His Ser Gln Val Gly Gln Gly Gln
    2540                2545                2550

Ser Glu Gly Pro Arg Thr Ser Arg Asn Trp Gly Ser Ser Phe Ser
    2555                2560                2565

Gln Asp Ser Asp Ser Gln Gly His Ser Glu Asp Ser Glu Arg Trp
    2570                2575                2580

Ser Gly Ser Ala Ser Arg Asn His His Gly Ser Ala Gln Glu Gln
    2585                2590                2595

Leu Arg Asp Gly Ser Arg His Pro Arg Ser His Gln Glu Asp Arg
    2600                2605                2610

Ala Gly His Gly His Ser Ala Asp Ser Ser Arg Gln Ser Gly Thr
    2615                2620                2625

Arg His Thr Gln Thr Ser Ser Gly Gly Gln Ala Ala Ser Ser His
    2630                2635                2640

Glu Gln Ala Arg Ser Ser Ala Gly Glu Arg His Gly Ser His His
    2645                2650                2655

Gln Gln Ser Ala Asp Ser Ser Arg His Ser Gly Ile Gly His Gly
    2660                2665                2670

Gln Ala Ser Ser Ala Val Arg Asp Ser Gly His Arg Gly Tyr Ser
    2675                2680                2685

Gly Ser Gln Ala Ser Asp Asn Glu Gly His Ser Glu Asp Ser Asp
    2690                2695                2700

Thr Gln Ser Val Ser Ala His Gly Gln Ala Gly Ser His Gln Gln
    2705                2710                2715

Ser His Gln Glu Ser Ala Arg Gly Arg Ser Gly Glu Thr Ser Gly
    2720                2725                2730

His Ser Gly Ser Phe Leu Tyr Gln Val Ser Thr His Glu Gln Ser
    2735                2740                2745

Glu Ser Ser His Gly Trp Thr Gly Pro Ser Thr Arg Gly Arg Gln
    2750                2755                2760

Gly Ser Arg His Glu Gln Ala Gln Asp Ser Ser Arg His Ser Ala
    2765                2770                2775

Ser Gln Asp Gly Gln Asp Thr Ile Arg Gly His Pro Gly Ser Ser
    2780                2785                2790

Arg Gly Gly Arg Gln Gly Tyr His His Glu His Ser Val Asp Ser
    2795                2800                2805

Ser Gly His Ser Gly Ser His His Ser His Thr Thr Ser Gln Gly
    2810                2815                2820

Arg Ser Asp Ala Ser Arg Gly Gln Ser Gly Ser Arg Ser Ala Ser
    2825                2830                2835

Arg Thr Thr Arg Asn Glu Glu Gln Ser Gly Asp Gly Ser Arg His
    2840                2845                2850

Ser Gly Ser Arg His His Glu Ala Ser Thr His Ala Asp Ile Ser
    2855                2860                2865

Arg His Ser Gln Ala Val Gln Gly Gln Ser Glu Gly Ser Arg Arg
    2870                2875                2880

Ser Arg Arg Gln Gly Ser Ser Val Ser Gln Asp Ser Asp Ser Glu
    2885                2890                2895
```

```
Gly His Ser Glu Asp Ser Glu Arg Trp Ser Gly Ser Ala Ser Arg
    2900                2905                2910

Asn His His Gly Ser Ala Gln Glu Gln Leu Arg Asp Gly Ser Arg
    2915                2920                2925

His Pro Arg Ser His Gln Glu Asp Arg Ala Gly His Gly His Ser
    2930                2935                2940

Ala Asp Ser Ser Arg Gln Ser Gly Thr Arg His Thr Gln Thr Ser
    2945                2950                2955

Ser Gly Gly Gln Ala Ala Ser Ser His Glu Gln Ala Arg Ser Ser
    2960                2965                2970

Ala Gly Glu Arg His Gly Ser His His Gln Gln Ser Ala Asp Ser
    2975                2980                2985

Ser Arg His Ser Gly Ile Gly His Gly Gln Ala Ser Ser Ala Val
    2990                2995                3000

Arg Asp Ser Gly His Arg Gly Tyr Ser Gly Ser Gln Ala Ser Asp
    3005                3010                3015

Asn Glu Gly His Ser Glu Asp Ser Asp Thr Gln Ser Val Ser Ala
    3020                3025                3030

His Gly Gln Ala Gly Ser His Gln Gln Ser His Gln Glu Ser Ala
    3035                3040                3045

Arg Gly Arg Ser Gly Glu Thr Ser Gly His Ser Gly Ser Phe Leu
    3050                3055                3060

Tyr Gln Val Ser Thr His Glu Gln Ser Glu Ser Ser His Gly Trp
    3065                3070                3075

Thr Gly Pro Ser Thr Arg Gly Arg Gln Gly Ser Arg His Glu Gln
    3080                3085                3090

Ala Gln Asp Ser Ser Arg His Ser Ala Ser Gln Tyr Gly Gln Asp
    3095                3100                3105

Thr Ile Arg Gly His Pro Gly Ser Ser Arg Gly Arg Gln Gly
    3110                3115                3120

Tyr His His Glu His Ser Val Asp Ser Ser Gly His Ser Gly Ser
    3125                3130                3135

His His Ser His Thr Thr Ser Gln Gly Arg Ser Asp Ala Ser Arg
    3140                3145                3150

Gly Gln Ser Gly Ser Arg Ser Ala Ser Arg Thr Thr Arg Asn Glu
    3155                3160                3165

Glu Gln Ser Gly Asp Ser Ser Arg His Ser Val Ser Arg His His
    3170                3175                3180

Glu Ala Ser Thr His Ala Asp Ile Ser Arg His Ser Gln Ala Val
    3185                3190                3195

Gln Gly Gln Ser Glu Gly Ser Arg Arg Ser Arg Arg Gln Gly Ser
    3200                3205                3210

Ser Val Ser Gln Asp Ser Asp Ser Glu Gly His Ser Glu Asp Ser
    3215                3220                3225

Glu Arg Trp Ser Gly Ser Ala Ser Arg Asn His Arg Gly Ser Val
    3230                3235                3240

Gln Glu Gln Ser Arg His Gly Ser Arg His Pro Arg Ser His His
    3245                3250                3255

Glu Asp Arg Ala Gly His Gly His Ser Ala Asp Arg Ser Arg Gln
    3260                3265                3270

Ser Gly Thr Arg His Ala Glu Thr Ser Ser Gly Gly Gln Ala Ala
    3275                3280                3285

Ser Ser His Glu Gln Ala Arg Ser Ser Pro Gly Glu Arg His Gly
```

```
            3290                3295                3300
Ser Arg His Gln Gln Ser Ala Asp Ser Ser Arg His Ser Gly Ile
            3305                3310                3315
Pro Arg Gly Gln Ala Ser Ser Ala Val Arg Asp Ser Arg His Trp
            3320                3325                3330
Gly Ser Ser Gly Ser Gln Ala Ser Asp Ser Glu Gly His Ser Glu
            3335                3340                3345
Glu Ser Asp Thr Gln Ser Val Ser Gly His Gly Gln Ala Gly Pro
            3350                3355                3360
His Gln Gln Ser His Gln Glu Ser Ala Arg Asp Arg Ser Gly Gly
            3365                3370                3375
Arg Ser Gly Arg Ser Gly Ser Phe Leu Tyr Gln Val Ser Thr His
            3380                3385                3390
Glu Gln Ser Glu Ser Ala His Gly Arg Thr Arg Thr Ser Thr Gly
            3395                3400                3405
Arg Arg Gln Gly Ser His His Glu Gln Ala Arg Asp Ser Ser Arg
            3410                3415                3420
His Ser Ala Ser Gln Glu Gly Gln Asp Thr Ile Arg Gly His Pro
            3425                3430                3435
Gly Ser Ser Arg Arg Gly Arg Gln Gly Ser His Tyr Glu Gln Ser
            3440                3445                3450
Val Asp Arg Ser Gly His Ser Gly Ser His His Ser His Thr Thr
            3455                3460                3465
Ser Gln Gly Arg Ser Asp Ala Ser Arg Gly Gln Ser Gly Ser Arg
            3470                3475                3480
Ser Ala Ser Arg Gln Thr Arg Asn Asp Glu Gln Ser Gly Asp Gly
            3485                3490                3495
Ser Arg His Ser Trp Ser His His His Glu Ala Ser Thr Gln Ala
            3500                3505                3510
Asp Ser Ser Arg His Ser Gln Ser Gly Gln Gly Gln Ser Ala Gly
            3515                3520                3525
Pro Arg Thr Ser Arg Asn Gln Gly Ser Ser Val Ser Gln Asp Ser
            3530                3535                3540
Asp Ser Gln Gly His Ser Glu Asp Ser Glu Arg Trp Ser Gly Ser
            3545                3550                3555
Ala Ser Arg Asn His Arg Gly Ser Ala Gln Glu Gln Ser Arg Asp
            3560                3565                3570
Gly Ser Arg His Pro Thr Ser His His Glu Asp Arg Ala Gly His
            3575                3580                3585
Gly His Ser Ala Glu Ser Ser Arg Gln Ser Gly Thr His His Ala
            3590                3595                3600
Glu Asn Ser Ser Gly Gly Gln Ala Ala Ser Ser His Glu Gln Ala
            3605                3610                3615
Arg Ser Ser Ala Gly Glu Arg His Gly Ser His His Gln Gln Ser
            3620                3625                3630
Ala Asp Ser Ser Arg His Ser Gly Ile Gly His Gly Gln Ala Ser
            3635                3640                3645
Ser Ala Val Arg Asp Ser Gly His Arg Gly Ser Ser Gly Ser Gln
            3650                3655                3660
Ala Ser Asp Ser Glu Gly His Ser Glu Asp Ser Asp Thr Gln Ser
            3665                3670                3675
Val Ser Ala His Gly Gln Ala Gly Pro His Gln Gln Ser His Gln
            3680                3685                3690
```

```
Glu Ser Thr Arg Gly Arg Ser Ala Gly Arg Ser Gly Arg Ser Gly
    3695                3700                3705

Ser Phe Leu Tyr Gln Val Ser Thr His Glu Gln Ser Glu Ser Ala
    3710                3715                3720

His Gly Arg Ala Gly Pro Ser Thr Gly Gly Arg Gln Gly Ser Arg
    3725                3730                3735

His Glu Gln Ala Arg Asp Ser Ser Arg His Ser Ala Ser Gln Glu
    3740                3745                3750

Gly Gln Asp Thr Ile Arg Gly His Pro Gly Ser Arg Arg Gly Gly
    3755                3760                3765

Arg Gln Gly Ser Tyr His Glu Gln Ser Val Asp Arg Ser Gly His
    3770                3775                3780

Ser Gly Ser His His Ser His Thr Thr Ser Gln Gly Arg Ser Asp
    3785                3790                3795

Ala Ser His Gly Gln Ser Gly Ser Arg Ser Ala Ser Arg Glu Thr
    3800                3805                3810

Arg Asn Glu Glu Gln Ser Gly Asp Gly Ser Arg His Ser Gly Ser
    3815                3820                3825

Arg His His Glu Ala Ser Thr Gln Ala Asp Ser Ser Arg His Ser
    3830                3835                3840

Gln Ser Gly Gln Gly Glu Ser Ala Gly Ser Arg Arg Ser Arg Arg
    3845                3850                3855

Gln Gly Ser Ser Val Ser Gln Asp Ser Asp Ser Glu Ala Tyr Pro
    3860                3865                3870

Glu Asp Ser Glu Arg Arg Ser Glu Ser Ala Ser Arg Asn His His
    3875                3880                3885

Gly Ser Ser Arg Glu Gln Ser Arg Asp Gly Ser Arg His Pro Gly
    3890                3895                3900

Ser Ser His Arg Asp Thr Ala Ser His Val Gln Ser Ser Pro Val
    3905                3910                3915

Gln Ser Asp Ser Ser Thr Ala Lys Glu His Gly His Phe Ser Ser
    3920                3925                3930

Leu Ser Gln Asp Ser Ala Tyr His Ser Gly Ile Gln Ser Arg Gly
    3935                3940                3945

Ser Pro His Ser Ser Ser Tyr His Tyr Gln Ser Glu Gly Thr
    3950                3955                3960

Glu Arg Gln Lys Gly Gln Ser Gly Leu Val Trp Arg His Gly Ser
    3965                3970                3975

Tyr Gly Ser Ala Asp Tyr Asp Tyr Gly Glu Ser Gly Phe Arg His
    3980                3985                3990

Ser Gln His Gly Ser Val Ser Tyr Asn Ser Asn Pro Val Val Phe
    3995                4000                4005

Lys Glu Arg Ser Asp Ile Cys Lys Ala Ser Ala Phe Gly Lys Asp
    4010                4015                4020

His Pro Arg Tyr Tyr Ala Thr Tyr Ile Asn Lys Asp Pro Gly Leu
    4025                4030                4035

Cys Gly His Ser Ser Asp Ile Ser Lys Gln Leu Gly Phe Ser Gln
    4040                4045                4050

Ser Gln Arg Tyr Tyr Tyr Tyr Glu
    4055                4060

<210> SEQ ID NO 4
<211> LENGTH: 4061
```

<212> TYPE: PRT
<213> ORGANISM: Homo sapiens

<400> SEQUENCE: 4

Met Ser Thr Leu Leu Glu Asn Ile Phe Ala Ile Ile Asn Leu Phe Lys
1               5                   10                  15
Gln Tyr Ser Lys Lys Asp Lys Asn Thr Asp Thr Leu Ser Lys Lys Glu
            20                  25                  30
Leu Lys Glu Leu Leu Glu Lys Glu Phe Arg Gln Ile Leu Lys Asn Pro
        35                  40                  45
Asp Asp Pro Asp Met Val Asp Val Phe Met Asp His Leu Asp Ile Asp
    50                  55                  60
His Asn Lys Lys Ile Asp Phe Thr Glu Phe Leu Leu Met Val Phe Lys
65                  70                  75                  80
Leu Ala Gln Ala Tyr Tyr Glu Ser Thr Arg Lys Glu Asn Leu Pro Ile
                85                  90                  95
Ser Gly His Lys His Arg Lys His Ser His His Asp Lys His Glu Asp
            100                 105                 110
Asn Lys Gln Glu Glu Asn Lys Glu Asn Arg Lys Arg Pro Ser Ser Leu
        115                 120                 125
Glu Arg Arg Asn Asn Arg Lys Gly Asn Lys Gly Arg Ser Lys Ser Pro
    130                 135                 140
Arg Glu Thr Gly Gly Lys Arg His Glu Ser Ser Glu Lys Lys Glu
145                 150                 155                 160
Arg Lys Gly Tyr Ser Pro Thr His Arg Glu Glu Tyr Gly Lys Asn
                165                 170                 175
His His Asn Ser Ser Lys Lys Glu Lys Asn Lys Thr Glu Asn Thr Arg
            180                 185                 190
Leu Gly Asp Asn Arg Lys Arg Leu Ser Glu Arg Leu Glu Glu Lys Glu
        195                 200                 205
Asp Asn Glu Glu Gly Val Tyr Asp Tyr Glu Asn Thr Gly Arg Met Thr
    210                 215                 220
Gln Lys Trp Ile Gln Ser Gly His Ile Ala Thr Tyr Tyr Thr Ile Gln
225                 230                 235                 240
Asp Glu Ala Tyr Asp Thr Thr Asp Ser Leu Leu Glu Glu Asn Lys Ile
                245                 250                 255
Tyr Glu Arg Ser Arg Ser Ser Asp Gly Lys Ser Ser Ser Gln Val Asn
            260                 265                 270
Arg Ser Arg His Glu Asn Thr Ser Gln Val Pro Leu Gln Glu Ser Arg
        275                 280                 285
Thr Arg Lys Arg Arg Gly Ser Arg Val Ser Gln Asp Arg Asp Ser Glu
    290                 295                 300
Gly His Ser Glu Asp Ser Glu Arg His Ser Gly Ser Ala Ser Arg Asn
305                 310                 315                 320
His His Gly Ser Ala Trp Glu Gln Ser Arg Asp Gly Ser Arg His Pro
                325                 330                 335
Arg Ser His Asp Glu Asp Arg Ala Ser His Gly His Ser Ala Asp Ser
            340                 345                 350
Ser Arg Gln Ser Gly Thr Arg His Ala Glu Thr Ser Ser Arg Gly Gln
        355                 360                 365
Thr Ala Ser Ser His Glu Gln Ala Arg Ser Ser Pro Gly Glu Arg His
    370                 375                 380
Gly Ser Gly His Gln Gln Ser Ala Asp Ser Ser Arg His Ser Ala Thr
385                 390                 395                 400

```
Gly Arg Gly Gln Ala Ser Ser Ala Val Ser Asp Arg Gly His Arg Gly
            405                 410                 415

Ser Ser Gly Ser Gln Ala Ser Asp Ser Glu Gly His Ser Glu Asn Ser
            420                 425                 430

Asp Thr Gln Ser Val Ser Gly His Gly Lys Ala Gly Leu Arg Gln Gln
            435                 440                 445

Ser His Gln Glu Ser Thr Arg Gly Arg Ser Gly Glu Arg Ser Gly Arg
        450                 455                 460

Ser Gly Ser Ser Leu Tyr Gln Val Ser Thr His Glu Gln Pro Asp Ser
465                 470                 475                 480

Ala His Gly Arg Thr Gly Thr Ser Thr Gly Gly Arg Gln Gly Ser His
                485                 490                 495

His Glu Gln Ala Arg Asp Ser Ser Arg His Ser Ala Ser Gln Glu Gly
            500                 505                 510

Gln Asp Thr Ile Arg Gly His Pro Gly Ser Ser Arg Gly Gly Arg Gln
            515                 520                 525

Gly Ser His His Glu Gln Ser Val Asn Arg Ser Gly His Ser Gly Ser
        530                 535                 540

His His Ser His Thr Thr Ser Gln Gly Arg Ser Asp Ala Ser His Gly
545                 550                 555                 560

Gln Ser Gly Ser Arg Ser Ala Ser Arg Gln Thr Arg Asn Glu Glu Gln
                565                 570                 575

Ser Gly Asp Gly Thr Arg His Ser Gly Ser Arg His His Glu Ala Ser
            580                 585                 590

Ser Gln Ala Asp Ser Ser Arg His Ser Gln Val Gly Gln Gly Gln Ser
            595                 600                 605

Ser Gly Pro Arg Thr Ser Arg Asn Gln Gly Ser Ser Val Ser Gln Asp
            610                 615                 620

Ser Asp Ser Gln Gly His Ser Glu Asp Ser Glu Arg Trp Ser Gly Ser
625                 630                 635                 640

Ala Ser Arg Asn His His Gly Ser Ala Gln Glu Gln Ser Arg Asp Gly
                645                 650                 655

Ser Arg His Pro Arg Ser His His Glu Asp Arg Ala Gly His Gly His
            660                 665                 670

Ser Ala Asp Ser Ser Arg Lys Ser Gly Thr Arg His Thr Gln Asn Ser
            675                 680                 685

Ser Ser Gly Gln Ala Ala Ser Ser His Glu Gln Ala Arg Ser Ser Ala
        690                 695                 700

Gly Glu Arg His Gly Ser Arg His Gln Leu Gln Ser Ala Asp Ser Ser
705                 710                 715                 720

Arg His Ser Gly Thr Gly His Gly Gln Ala Ser Ser Ala Val Arg Asp
                725                 730                 735

Ser Gly His Arg Gly Ser Ser Gly Ser Gln Ala Thr Asp Ser Glu Gly
            740                 745                 750

His Ser Glu Asp Ser Asp Thr Gln Ser Val Ser Gly His Gly Gln Ala
            755                 760                 765

Gly His His Gln Gln Ser His Gln Glu Ser Ala Arg Asp Arg Ser Gly
        770                 775                 780

Glu Arg Ser Arg Arg Ser Gly Ser Phe Leu Tyr Gln Val Ser Thr His
785                 790                 795                 800

Lys Gln Ser Glu Ser Ser His Gly Trp Thr Gly Pro Ser Thr Gly Val
                805                 810                 815
```

-continued

```
Arg Gln Gly Ser His His Glu Gln Ala Arg Asp Asn Ser Arg His Ser
            820                 825                 830

Ala Ser Gln Asp Gly Gln Asp Thr Ile Arg Gly His Pro Gly Ser Ser
            835                 840                 845

Arg Arg Gly Arg Gln Gly Ser His His Glu Gln Ser Val Asp Arg Ser
            850                 855                 860

Gly His Ser Gly Ser His His Ser His Thr Thr Ser Gln Gly Arg Ser
865                 870                 875                 880

Asp Ala Ser Arg Gly Gln Ser Gly Ser Arg Ser Ala Ser Arg Thr Thr
                885                 890                 895

Arg Asn Glu Glu Gln Ser Arg Asp Gly Ser Arg His Ser Gly Ser Arg
            900                 905                 910

His His Glu Ala Ser Ser His Ala Asp Ile Ser Arg His Ser Gln Ala
            915                 920                 925

Gly Gln Gly Gln Ser Glu Gly Ser Arg Thr Ser Arg Arg Gln Gly Ser
            930                 935                 940

Ser Val Ser Gln Asp Ser Asp Ser Glu Gly His Ser Glu Asp Ser Glu
945                 950                 955                 960

Arg Trp Ser Gly Ser Ala Ser Arg Asn His Arg Gly Ser Ala Gln Glu
            965                 970                 975

Gln Ser Arg His Gly Ser Arg His Pro Arg Ser His His Glu Asp Arg
            980                 985                 990

Ala Gly His Gly His Ser Ala Asp Ser Ser Arg Gln Ser Gly Thr Pro
            995                 1000                1005

His Ala Glu Thr Ser Ser Gly Gly Gln Ala Ala Ser Ser His Glu
            1010                1015                1020

Gln Ala Arg Ser Ser Pro Gly Glu Arg His Gly Ser Arg His Gln
            1025                1030                1035

Gln Ser Ala Asp Ser Ser Arg His Ser Gly Ile Pro Arg Arg Gln
            1040                1045                1050

Ala Ser Ser Ala Val Arg Asp Ser Gly His Trp Gly Ser Ser Gly
            1055                1060                1065

Ser Gln Ala Ser Asp Ser Glu Gly His Ser Glu Glu Ser Asp Thr
            1070                1075                1080

Gln Ser Val Ser Gly His Gly Gln Asp Gly Pro His Gln Gln Ser
            1085                1090                1095

His Gln Glu Ser Ala Arg Asp Trp Ser Gly Gly Arg Ser Gly Arg
            1100                1105                1110

Ser Gly Ser Phe Ile Tyr Gln Val Ser Thr His Glu Gln Ser Glu
            1115                1120                1125

Ser Ala His Gly Arg Thr Arg Thr Ser Thr Gly Arg Arg Gln Gly
            1130                1135                1140

Ser His His Glu Gln Ala Arg Asp Ser Ser Arg His Ser Ala Ser
            1145                1150                1155

Gln Glu Gly Gln Asp Thr Ile Arg Ala His Pro Gly Ser Arg Arg
            1160                1165                1170

Gly Gly Arg Gln Gly Ser His Glu Gln Ser Val Asp Arg Ser
            1175                1180                1185

Gly His Ser Gly Ser His His Ser His Thr Thr Ser Gln Gly Arg
            1190                1195                1200

Ser Asp Ala Ser His Gly Gln Ser Gly Ser Arg Ser Ala Ser Arg
            1205                1210                1215

Gln Thr Arg Lys Asp Lys Gln Ser Gly Asp Gly Ser Arg His Ser
```

-continued

```
            1220                1225                1230
Gly Ser Arg His His Glu Ala Ala Ser Trp Ala Asp Ser Ser Arg
            1235                1240                1245
His Ser Gln Val Gly Gln Glu Gln Ser Ser Gly Ser Arg Thr Ser
            1250                1255                1260
Arg His Gln Gly Ser Ser Val Ser Gln Asp Ser Asp Ser Glu Arg
            1265                1270                1275
His Ser Asp Asp Ser Glu Arg Leu Ser Gly Ser Ala Ser Arg Asn
            1280                1285                1290
His His Gly Ser Ser Arg Glu Gln Ser Arg Asp Gly Ser Arg His
            1295                1300                1305
Pro Gly Phe His Gln Glu Asp Arg Ala Ser His Gly His Ser Ala
            1310                1315                1320
Asp Ser Ser Arg Gln Ser Gly Thr His Thr Glu Ser Ser Ser
            1325                1330                1335
His Gly Gln Ala Val Ser Ser His Glu Gln Ala Arg Ser Ser Pro
            1340                1345                1350
Gly Glu Arg His Gly Ser Arg His Gln Gln Ser Ala Asp Ser Ser
            1355                1360                1365
Arg His Ser Gly Ile Gly His Arg Gln Ala Ser Ser Ala Val Arg
            1370                1375                1380
Asp Ser Gly His Arg Gly Ser Ser Gly Ser Gln Val Thr Asn Ser
            1385                1390                1395
Glu Gly His Ser Glu Asp Ser Asp Thr Gln Ser Val Ser Ala His
            1400                1405                1410
Gly Gln Ala Gly Pro His Gln Gln Ser His Lys Glu Ser Ala Arg
            1415                1420                1425
Gly Gln Ser Gly Glu Ser Ser Gly Arg Ser Arg Ser Phe Leu Tyr
            1430                1435                1440
Gln Val Ser Ser His Glu Gln Ser Glu Ser Thr His Gly Gln Thr
            1445                1450                1455
Ala Pro Ser Thr Gly Gly Arg Gln Gly Ser Arg His Glu Gln Ala
            1460                1465                1470
Arg Asn Ser Ser Arg His Ser Ala Ser Gln Asp Gly Gln Asp Thr
            1475                1480                1485
Ile Arg Gly His Pro Gly Ser Ser Arg Gly Gly Arg Gln Gly Ser
            1490                1495                1500
Tyr His Glu Gln Ser Val Asp Arg Ser Gly His Ser Gly Tyr His
            1505                1510                1515
His Ser His Thr Thr Pro Gln Gly Arg Ser Asp Ala Ser His Gly
            1520                1525                1530
Gln Ser Gly Pro Arg Ser Ala Ser Arg Gln Thr Arg Asn Glu Glu
            1535                1540                1545
Gln Ser Gly Asp Gly Ser Arg His Ser Gly Ser Arg His His Glu
            1550                1555                1560
Pro Ser Thr Arg Ala Gly Ser Ser Arg His Ser Gln Val Gly Gln
            1565                1570                1575
Gly Glu Ser Ala Gly Ser Lys Thr Ser Arg Arg Gln Gly Ser Ser
            1580                1585                1590
Val Ser Gln Asp Arg Asp Ser Glu Gly His Ser Glu Asp Ser Glu
            1595                1600                1605
Arg Arg Ser Glu Ser Ala Ser Arg Asn His Tyr Gly Ser Ala Arg
            1610                1615                1620
```

Glu Gln Ser Arg His Gly Ser Arg Asn Pro Arg Ser His Gln Glu
1625                1630                1635

Asp Arg Ala Ser His Gly His Ser Ala Glu Ser Ser Arg Gln Ser
1640                1645                1650

Gly Thr Arg His Ala Glu Thr Ser Ser Gly Gly Gln Ala Ala Ser
1655                1660                1665

Ser Gln Glu Gln Ala Arg Ser Ser Pro Gly Glu Arg His Gly Ser
1670                1675                1680

Arg His Gln Gln Ser Ala Asp Ser Ser Thr Asp Ser Gly Thr Gly
1685                1690                1695

Arg Arg Gln Asp Ser Ser Val Val Gly Asp Ser Gly Asn Arg Gly
1700                1705                1710

Ser Ser Gly Ser Gln Ala Ser Asp Ser Glu Gly His Ser Glu Glu
1715                1720                1725

Ser Asp Thr Gln Ser Val Ser Ala His Gly Gln Ala Gly Pro His
1730                1735                1740

Gln Gln Ser His Gln Glu Ser Thr Arg Gly Gln Ser Gly Glu Arg
1745                1750                1755

Ser Gly Arg Ser Gly Ser Phe Leu Tyr Gln Val Ser Thr His Glu
1760                1765                1770

Gln Ser Glu Ser Ala His Gly Arg Thr Gly Pro Ser Thr Gly Gly
1775                1780                1785

Arg Gln Arg Ser Arg His Glu Gln Ala Arg Asp Ser Ser Arg His
1790                1795                1800

Ser Ala Ser Gln Glu Gly Gln Asp Thr Ile Arg Gly His Pro Gly
1805                1810                1815

Ser Ser Arg Gly Gly Arg Gln Gly Ser His Tyr Glu Gln Ser Val
1820                1825                1830

Asp Ser Ser Gly His Ser Gly Ser His His Ser His Thr Thr Ser
1835                1840                1845

Gln Glu Arg Ser Asp Val Ser Arg Gly Gln Ser Gly Ser Arg Ser
1850                1855                1860

Val Ser Arg Gln Thr Arg Asn Glu Lys Gln Ser Gly Asp Gly Ser
1865                1870                1875

Arg His Ser Gly Ser Arg His His Glu Ala Ser Arg Ala Asp
1880                1885                1890

Ser Ser Arg His Ser Gln Val Gly Gln Gly Gln Ser Ser Gly Pro
1895                1900                1905

Arg Thr Ser Arg Asn Gln Gly Ser Ser Val Ser Gln Asp Ser Asp
1910                1915                1920

Ser Gln Gly His Ser Glu Asp Ser Glu Arg Trp Ser Gly Ser Ala
1925                1930                1935

Ser Arg Asn His Leu Gly Ser Ala Trp Glu Gln Ser Arg Asp Gly
1940                1945                1950

Ser Arg His Pro Gly Ser His His Glu Asp Arg Ala Gly His Gly
1955                1960                1965

His Ser Ala Asp Ser Ser Arg Gln Ser Gly Thr Arg His Thr Glu
1970                1975                1980

Ser Ser Ser Arg Gly Gln Ala Ala Ser Ser His Glu Gln Ala Arg
1985                1990                1995

Ser Ser Ala Gly Glu Arg His Gly Ser His Gln Leu Gln Ser
2000                2005                2010

```
Ala Asp Ser Ser Arg His Ser Gly Ile Gly His Gly Gln Ala Ser
    2015                2020                2025

Ser Ala Val Arg Asp Ser Gly His Arg Gly Tyr Ser Gly Ser Gln
    2030                2035                2040

Ala Ser Asp Ser Glu Gly His Ser Glu Asp Ser Asp Thr Gln Ser
    2045                2050                2055

Val Ser Ala Gln Gly Lys Ala Gly Pro His Gln Gln Ser His Lys
    2060                2065                2070

Glu Ser Ala Arg Gly Gln Gly Glu Ser Gly Arg Ser Gly
    2075                2080                2085

Ser Phe Leu Tyr Gln Val Ser Thr His Glu Gln Ser Glu Ser Thr
    2090                2095                2100

His Gly Gln Ser Ala Pro Ser Thr Gly Arg Gln Gly Ser His
    2105                2110                2115

Tyr Asp Gln Ala Gln Asp Ser Ser Arg His Ser Ala Ser Gln Glu
    2120                2125                2130

Gly Gln Asp Thr Ile Arg Gly His Pro Gly Pro Ser Arg Gly Gly
    2135                2140                2145

Arg Gln Gly Ser His Gln Glu Gln Ser Val Asp Arg Ser Gly His
    2150                2155                2160

Ser Gly Ser His His Ser His Thr Thr Ser Gln Gly Arg Ser Asp
    2165                2170                2175

Ala Ser Arg Gly Gln Ser Gly Ser Arg Ser Ala Ser Arg Lys Thr
    2180                2185                2190

Tyr Asp Lys Glu Gln Ser Gly Asp Gly Ser Arg His Ser Gly Ser
    2195                2200                2205

His His His Glu Ala Ser Ser Trp Ala Asp Ser Ser Arg His Ser
    2210                2215                2220

Leu Val Gly Gln Gly Gln Ser Ser Gly Pro Arg Thr Ser Arg Pro
    2225                2230                2235

Arg Gly Ser Ser Val Ser Gln Asp Ser Asp Ser Glu Gly His Ser
    2240                2245                2250

Glu Asp Ser Glu Arg Arg Ser Gly Ser Ala Ser Arg Asn His His
    2255                2260                2265

Gly Ser Ala Gln Glu Gln Ser Arg Asp Gly Ser Arg His Pro Arg
    2270                2275                2280

Ser His His Glu Asp Arg Ala Gly His Gly His Ser Ala Glu Ser
    2285                2290                2295

Ser Arg Gln Ser Gly Thr His His Ala Glu Asn Ser Ser Gly Gly
    2300                2305                2310

Gln Ala Ala Ser Ser His Glu Gln Ala Arg Ser Ala Gly Glu
    2315                2320                2325

Arg His Gly Ser His His Gln Gln Ser Ala Asp Ser Ser Arg His
    2330                2335                2340

Ser Gly Ile Gly His Gly Gln Ala Ser Ser Ala Val Arg Asp Ser
    2345                2350                2355

Gly His Arg Gly Ser Gly Ser Gln Ala Ser Asp Ser Glu Gly
    2360                2365                2370

His Ser Glu Asp Ser Asp Thr Gln Ser Val Ser Ala His Gly Gln
    2375                2380                2385

Ala Gly Pro His Gln Gln Ser His Gln Glu Ser Thr Arg Gly Arg
    2390                2395                2400

Ser Ala Gly Arg Ser Gly Arg Ser Gly Ser Phe Leu Tyr Gln Val
```

-continued

```
                2405                2410                2415
Ser Thr His Glu Gln Ser Glu Ala His Gly Arg Thr Gly Thr
        2420                2425                2430
Ser Thr Gly Gly Arg Gln Gly Ser His His Lys Gln Ala Arg Asp
        2435                2440                2445
Ser Ser Arg His Ser Thr Ser Gln Glu Gly Gln Asp Thr Ile His
        2450                2455                2460
Gly His Pro Gly Ser Ser Ser Gly Gly Arg Gln Gly Ser His Tyr
        2465                2470                2475
Glu Gln Leu Val Asp Arg Ser Gly His Ser Gly Ser His His Ser
        2480                2485                2490
His Thr Thr Ser Gln Gly Arg Ser Asp Ala Ser His Gly His Ser
        2495                2500                2505
Gly Ser Arg Ser Ala Ser Arg Gln Thr Arg Asn Asp Glu Gln Ser
        2510                2515                2520
Gly Asp Gly Ser Arg His Ser Gly Ser Arg His His Glu Ala Ser
        2525                2530                2535
Ser Arg Ala Asp Ser Ser Gly His Ser Gln Val Gly Gln Gly Gln
        2540                2545                2550
Ser Glu Gly Pro Arg Thr Ser Arg Asn Trp Gly Ser Ser Phe Ser
        2555                2560                2565
Gln Asp Ser Asp Ser Gln Gly His Ser Glu Asp Ser Glu Arg Trp
        2570                2575                2580
Ser Gly Ser Ala Ser Arg Asn His His Gly Ser Ala Gln Glu Gln
        2585                2590                2595
Leu Arg Asp Gly Ser Arg His Pro Arg Ser His Gln Glu Asp Arg
        2600                2605                2610
Ala Gly His Gly His Ser Ala Asp Ser Ser Arg Gln Ser Gly Thr
        2615                2620                2625
Arg His Thr Gln Thr Ser Ser Gly Gly Gln Ala Ala Ser Ser His
        2630                2635                2640
Glu Gln Ala Arg Ser Ser Ala Gly Glu Arg His Gly Ser His His
        2645                2650                2655
Gln Gln Ser Ala Asp Ser Ser Arg His Ser Gly Ile Gly His Gly
        2660                2665                2670
Gln Ala Ser Ser Ala Val Arg Asp Ser Gly His Arg Gly Tyr Ser
        2675                2680                2685
Gly Ser Gln Ala Ser Asp Asn Glu Gly His Ser Glu Asp Ser Asp
        2690                2695                2700
Thr Gln Ser Val Ser Ala His Gly Gln Ala Gly Ser His Gln Gln
        2705                2710                2715
Ser His Gln Glu Ser Ala Arg Gly Arg Ser Gly Glu Thr Ser Gly
        2720                2725                2730
His Ser Gly Ser Phe Leu Tyr Gln Val Ser Thr His Glu Gln Ser
        2735                2740                2745
Glu Ser Ser His Gly Trp Thr Gly Pro Ser Thr Arg Gly Arg Gln
        2750                2755                2760
Gly Ser Arg His Glu Gln Ala Gln Asp Ser Ser Arg His Ser Ala
        2765                2770                2775
Ser Gln Asp Gly Gln Asp Thr Ile Arg Gly His Pro Gly Ser Ser
        2780                2785                2790
Arg Gly Gly Arg Gln Gly Tyr His His Glu His Ser Val Asp Ser
        2795                2800                2805
```

-continued

```
Ser Gly His Ser Gly Ser His His Ser His Thr Thr Ser Gln Gly
2810                2815                2820

Arg Ser Asp Ala Ser Arg Gly Gln Ser Gly Ser Arg Ser Ala Ser
2825                2830                2835

Arg Thr Thr Arg Asn Glu Glu Gln Ser Gly Asp Gly Ser Arg His
2840                2845                2850

Ser Gly Ser Arg His His Glu Ala Ser Thr His Ala Asp Ile Ser
2855                2860                2865

Arg His Ser Gln Ala Val Gln Gly Gln Ser Glu Gly Ser Arg Arg
2870                2875                2880

Ser Arg Arg Gln Gly Ser Ser Val Ser Gln Asp Ser Asp Ser Glu
2885                2890                2895

Gly His Ser Glu Asp Ser Glu Arg Trp Ser Gly Ser Ala Ser Arg
2900                2905                2910

Asn His His Gly Ser Ala Gln Glu Gln Leu Arg Asp Gly Ser Arg
2915                2920                2925

His Pro Arg Ser His Gln Glu Asp Arg Ala Gly His Gly His Ser
2930                2935                2940

Ala Asp Ser Ser Arg Gln Ser Gly Thr Arg His Thr Gln Thr Ser
2945                2950                2955

Ser Gly Gly Gln Ala Ala Ser Ser His Glu Gln Ala Arg Ser Ser
2960                2965                2970

Ala Gly Glu Arg His Gly Ser His His Gln Gln Ser Ala Asp Ser
2975                2980                2985

Ser Arg His Ser Gly Ile Gly His Gly Gln Ala Ser Ser Ala Val
2990                2995                3000

Arg Asp Ser Gly His Arg Gly Tyr Ser Gly Ser Gln Ala Ser Asp
3005                3010                3015

Asn Glu Gly His Ser Glu Asp Ser Asp Thr Gln Ser Val Ser Ala
3020                3025                3030

His Gly Gln Ala Gly Ser His Gln Gln Ser His Gln Glu Ser Ala
3035                3040                3045

Arg Gly Arg Ser Gly Glu Thr Ser Gly His Ser Gly Ser Phe Leu
3050                3055                3060

Tyr Gln Val Ser Thr His Glu Gln Ser Glu Ser His Gly Trp
3065                3070                3075

Thr Gly Pro Ser Thr Arg Gly Arg Gln Gly Ser Arg His Glu Gln
3080                3085                3090

Ala Gln Asp Ser Ser Arg His Ser Ala Ser Gln Tyr Gly Gln Asp
3095                3100                3105

Thr Ile Arg Gly His Pro Gly Ser Ser Arg Gly Gly Arg Gln Gly
3110                3115                3120

Tyr His His Glu His Ser Val Asp Ser Ser Gly His Ser Gly Ser
3125                3130                3135

His His Ser His Thr Thr Ser Gln Gly Arg Ser Asp Ala Ser Arg
3140                3145                3150

Gly Gln Ser Gly Ser Arg Ser Ala Ser Arg Thr Thr Arg Asn Glu
3155                3160                3165

Glu Gln Ser Gly Asp Ser Ser Arg His Ser Val Ser Arg His His
3170                3175                3180

Glu Ala Ser Thr His Ala Asp Ile Ser Arg His Ser Gln Ala Val
3185                3190                3195
```

-continued

```
Gln Gly Gln Ser Glu Gly Ser Arg Arg Ser Arg Arg Gln Gly Ser
3200                3205                3210

Ser Val Ser Gln Asp Ser Asp Ser Glu Gly His Ser Glu Asp Ser
3215                3220                3225

Glu Arg Trp Ser Gly Ser Ala Ser Arg Asn His Arg Gly Ser Val
3230                3235                3240

Gln Glu Gln Ser Arg His Gly Ser Arg His Pro Arg Ser His His
3245                3250                3255

Glu Asp Arg Ala Gly His Gly His Ser Ala Asp Arg Ser Arg Gln
3260                3265                3270

Ser Gly Thr Arg His Ala Glu Thr Ser Ser Gly Gly Gln Ala Ala
3275                3280                3285

Ser Ser His Glu Gln Ala Arg Ser Ser Pro Gly Glu Arg His Gly
3290                3295                3300

Ser Arg His Gln Gln Ser Ala Asp Ser Ser Arg His Ser Gly Ile
3305                3310                3315

Pro Arg Gly Gln Ala Ser Ser Ala Val Arg Asp Ser Arg His Trp
3320                3325                3330

Gly Ser Ser Gly Ser Gln Ala Ser Asp Ser Glu Gly His Ser Glu
3335                3340                3345

Glu Ser Asp Thr Gln Ser Val Ser Gly His Gly Gln Ala Gly Pro
3350                3355                3360

His Gln Gln Ser His Gln Glu Ser Ala Arg Asp Arg Ser Gly Gly
3365                3370                3375

Arg Ser Gly Arg Ser Gly Ser Phe Leu Tyr Gln Val Ser Thr His
3380                3385                3390

Glu Gln Ser Glu Ser Ala His Gly Arg Thr Arg Thr Ser Thr Gly
3395                3400                3405

Arg Arg Gln Gly Ser His His Glu Gln Ala Arg Asp Ser Ser Arg
3410                3415                3420

His Ser Ala Ser Gln Glu Gly Gln Asp Thr Ile Arg Gly His Pro
3425                3430                3435

Gly Ser Ser Arg Arg Gly Arg Gln Gly Ser His Tyr Glu Gln Ser
3440                3445                3450

Val Asp Arg Ser Gly His Ser Gly Ser His His Ser His Thr Thr
3455                3460                3465

Ser Gln Gly Arg Ser Asp Ala Ser Arg Gly Gln Ser Gly Ser Arg
3470                3475                3480

Ser Ala Ser Arg Gln Thr Arg Asn Asp Glu Gln Ser Gly Asp Gly
3485                3490                3495

Ser Arg His Ser Trp Ser His His His Glu Ala Ser Thr Gln Ala
3500                3505                3510

Asp Ser Ser Arg His Ser Gln Ser Gly Gln Gly Gln Ser Ala Gly
3515                3520                3525

Pro Arg Thr Ser Arg Asn Gln Gly Ser Ser Val Ser Gln Asp Ser
3530                3535                3540

Asp Ser Gln Gly His Ser Glu Asp Ser Glu Arg Trp Ser Gly Ser
3545                3550                3555

Ala Ser Arg Asn His Arg Gly Ser Ala Gln Glu Gln Ser Arg Asp
3560                3565                3570

Gly Ser Arg His Pro Thr Ser His His Glu Asp Arg Ala Gly His
3575                3580                3585

Gly His Ser Ala Glu Ser Ser Arg Gln Ser Gly Thr His His Ala
```

-continued

```
            3590                3595                3600
Glu Asn Ser Ser Gly Gly Gln Ala Ala Ser Ser His Glu Gln Ala
        3605                3610                3615
Arg Ser Ser Ala Gly Glu Arg His Gly Ser His His Gln Gln Ser
        3620                3625                3630
Ala Asp Ser Ser Arg His Ser Gly Ile Gly His Gly Gln Ala Ser
        3635                3640                3645
Ser Ala Val Arg Asp Ser Gly His Arg Gly Ser Ser Gly Ser Gln
        3650                3655                3660
Ala Ser Asp Ser Glu Gly His Ser Glu Asp Ser Asp Thr Gln Ser
        3665                3670                3675
Val Ser Ala His Gly Gln Ala Gly Pro His Gln Gln Ser His Gln
        3680                3685                3690
Glu Ser Thr Arg Gly Arg Ser Ala Gly Arg Ser Gly Arg Ser Gly
        3695                3700                3705
Ser Phe Leu Tyr Gln Val Ser Thr His Glu Gln Ser Glu Ser Ala
        3710                3715                3720
His Gly Arg Ala Gly Pro Ser Thr Gly Gly Arg Gln Gly Ser Arg
        3725                3730                3735
His Glu Gln Ala Arg Asp Ser Ser Arg His Ser Ala Ser Gln Glu
        3740                3745                3750
Gly Gln Asp Thr Ile Arg Gly His Pro Gly Ser Arg Arg Gly Gly
        3755                3760                3765
Arg Gln Gly Ser Tyr His Glu Gln Ser Val Asp Arg Ser Gly His
        3770                3775                3780
Ser Gly Ser His His Ser His Thr Thr Ser Gln Gly Arg Ser Asp
        3785                3790                3795
Ala Ser His Gly Gln Ser Gly Ser Arg Ser Ala Ser Arg Glu Thr
        3800                3805                3810
Arg Asn Glu Glu Gln Ser Gly Asp Gly Ser Arg His Ser Gly Ser
        3815                3820                3825
Arg His His Glu Ala Ser Thr Gln Ala Asp Ser Ser Arg His Ser
        3830                3835                3840
Gln Ser Gly Gln Gly Glu Ser Ala Gly Ser Arg Arg Ser Arg Arg
        3845                3850                3855
Gln Gly Ser Ser Val Ser Gln Asp Ser Asp Ser Glu Ala Tyr Pro
        3860                3865                3870
Glu Asp Ser Glu Arg Arg Ser Glu Ser Ala Ser Arg Asn His His
        3875                3880                3885
Gly Ser Ser Arg Glu Gln Ser Arg Asp Gly Ser Arg His Pro Gly
        3890                3895                3900
Ser Ser His Arg Asp Thr Ala Ser His Val Gln Ser Ser Pro Val
        3905                3910                3915
Gln Ser Asp Ser Ser Thr Ala Lys Glu His Gly His Phe Ser Ser
        3920                3925                3930
Leu Ser Gln Asp Ser Ala Tyr His Ser Gly Ile Gln Ser Arg Gly
        3935                3940                3945
Ser Pro His Ser Ser Ser Ser Tyr His Tyr Gln Ser Glu Gly Thr
        3950                3955                3960
Glu Arg Gln Lys Gly Gln Ser Gly Leu Val Trp Arg His Gly Ser
        3965                3970                3975
Tyr Gly Ser Ala Asp Tyr Asp Tyr Gly Glu Ser Gly Phe Arg His
        3980                3985                3990
```

```
Ser Gln His Gly Ser Val Ser Tyr Asn Ser Asn Pro Val Val Phe
    3995                4000                4005

Lys Glu Arg Ser Asp Ile Cys Lys Ala Ser Ala Phe Gly Lys Asp
    4010                4015                4020

His Pro Arg Tyr Tyr Ala Thr Tyr Ile Asn Lys Asp Pro Gly Leu
    4025                4030                4035

Cys Gly His Ser Ser Asp Ile Ser Lys Gln Leu Gly Phe Ser Gln
    4040                4045                4050

Ser Gln Arg Tyr Tyr Tyr Tyr Glu
    4055                4060

<210> SEQ ID NO 5
<211> LENGTH: 4061
<212> TYPE: PRT
<213> ORGANISM: Homo sapiens

<400> SEQUENCE: 5

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
            20                  25                  30

Leu Lys Glu Leu Leu Glu Lys Glu Phe Arg Gln Ile Leu Lys Asn Pro
        35                  40                  45

Asp Asp Pro Asp Met Val Asp Val Phe Met Asp His Leu Asp Ile Asp
    50                  55                  60

His Asn Lys Lys Ile Asp Phe Thr Glu Phe Leu Leu Met Val Phe Lys
65                  70                  75                  80

Leu Ala Gln Ala Tyr Tyr Glu Ser Thr Arg Lys Glu Asn Leu Pro Ile
                85                  90                  95

Ser Gly His Lys His Arg Lys His Ser His His Asp Lys His Glu Asp
            100                 105                 110

Asn Lys Gln Glu Glu Asn Lys Glu Asn Arg Lys Arg Pro Ser Ser Leu
        115                 120                 125

Glu Arg Arg Asn Asn Arg Lys Gly Asn Lys Gly Arg Ser Lys Ser Pro
    130                 135                 140

Arg Glu Thr Gly Gly Lys Arg His Glu Ser Ser Ser Glu Lys Lys Glu
145                 150                 155                 160

Arg Lys Gly Tyr Ser Pro Thr His Arg Glu Glu Tyr Gly Lys Asn
                165                 170                 175

His His Asn Ser Ser Lys Lys Glu Lys Asn Lys Thr Glu Asn Thr Arg
            180                 185                 190

Leu Gly Asp Asn Arg Lys Arg Leu Ser Glu Arg Leu Glu Glu Lys Glu
        195                 200                 205

Asp Asn Glu Glu Gly Val Tyr Asp Tyr Glu Asn Thr Gly Arg Met Thr
    210                 215                 220

Gln Lys Trp Ile Gln Ser Gly His Ile Ala Thr Tyr Tyr Thr Ile Gln
225                 230                 235                 240

Asp Glu Ala Tyr Asp Thr Thr Asp Ser Leu Leu Glu Glu Asn Lys Ile
                245                 250                 255

Tyr Glu Arg Ser Arg Ser Ser Asp Gly Lys Ser Ser Gln Val Asn
            260                 265                 270

Arg Ser Arg His Glu Asn Thr Ser Gln Val Pro Leu Gln Glu Ser Arg
        275                 280                 285

Thr Arg Lys Arg Arg Gly Ser Arg Val Ser Gln Asp Arg Asp Ser Glu
```

```
            290                 295                 300
Gly His Ser Glu Asp Ser Glu Arg His Ser Gly Ser Ala Ser Arg Asn
305                 310                 315                 320

His His Gly Ser Ala Trp Glu Gln Ser Arg Asp Gly Ser Arg His Pro
                325                 330                 335

Arg Ser His Asp Glu Asp Arg Ala Ser His Gly His Ser Ala Asp Ser
                340                 345                 350

Ser Arg Gln Ser Gly Thr Arg His Ala Glu Thr Ser Ser Arg Gly Gln
                355                 360                 365

Thr Ala Ser Ser His Glu Gln Ala Arg Ser Ser Pro Gly Glu Arg His
            370                 375                 380

Gly Ser Gly His Gln Gln Ser Ala Asp Ser Ser Arg His Ser Ala Thr
385                 390                 395                 400

Gly Arg Gly Gln Ala Ser Ser Ala Val Ser Asp Arg Gly His Arg Gly
                405                 410                 415

Ser Ser Gly Ser Gln Ala Ser Asp Ser Glu Gly His Ser Glu Asn Ser
                420                 425                 430

Asp Thr Gln Ser Val Ser Gly His Gly Lys Ala Gly Leu Arg Gln Gln
            435                 440                 445

Ser His Gln Glu Ser Thr Arg Gly Arg Ser Gly Glu Arg Ser Gly Arg
            450                 455                 460

Ser Gly Ser Ser Leu Tyr Gln Val Ser Thr His Glu Gln Pro Asp Ser
465                 470                 475                 480

Ala His Gly Arg Thr Gly Thr Ser Thr Gly Gly Arg Gln Gly Ser His
                485                 490                 495

His Glu Gln Ala Arg Asp Ser Ser Arg His Ser Ala Ser Gln Glu Gly
                500                 505                 510

Gln Asp Thr Ile Arg Gly His Pro Gly Ser Ser Arg Gly Gly Arg Gln
            515                 520                 525

Gly Ser His His Glu Gln Ser Val Asn Arg Ser Gly His Ser Gly Ser
            530                 535                 540

His His Ser His Thr Thr Ser Gln Gly Arg Ser Asp Ala Ser His Gly
545                 550                 555                 560

Gln Ser Gly Ser Arg Ser Ala Ser Arg Gln Thr Arg Asn Glu Glu Gln
                565                 570                 575

Ser Gly Asp Gly Thr Arg His Ser Gly Ser Arg His His Glu Ala Ser
                580                 585                 590

Ser Gln Ala Asp Ser Ser Arg His Ser Gln Val Gly Gln Gly Gln Ser
            595                 600                 605

Ser Gly Pro Arg Thr Ser Arg Asn Gln Gly Ser Ser Val Ser Gln Asp
            610                 615                 620

Ser Asp Ser Gln Gly His Ser Glu Asp Ser Glu Arg Trp Ser Gly Ser
625                 630                 635                 640

Ala Ser Arg Asn His His Gly Ser Ala Gln Glu Gln Ser Arg Asp Gly
                645                 650                 655

Ser Arg His Pro Arg Ser His His Glu Asp Arg Ala Gly His Gly His
                660                 665                 670

Ser Ala Asp Ser Ser Arg Lys Ser Gly Thr Arg His Thr Gln Asn Ser
            675                 680                 685

Ser Ser Gly Gln Ala Ala Ser Ser His Glu Gln Ala Arg Ser Ser Ala
            690                 695                 700

Gly Glu Arg His Gly Ser Arg His Gln Leu Gln Ser Ala Asp Ser Ser
705                 710                 715                 720
```

```
Arg His Ser Gly Thr Gly His Gly Gln Ala Ser Ser Ala Val Arg Asp
            725                 730                 735

Ser Gly His Arg Gly Ser Ser Gly Ser Gln Ala Thr Asp Ser Glu Gly
            740                 745                 750

His Ser Glu Asp Ser Asp Thr Gln Ser Val Ser Gly His Gly Gln Ala
            755                 760                 765

Gly His His Gln Gln Ser His Gln Glu Ser Ala Arg Asp Arg Ser Gly
            770                 775                 780

Glu Arg Ser Arg Arg Ser Gly Ser Phe Leu Tyr Gln Val Ser Thr His
785                 790                 795                 800

Lys Gln Ser Glu Ser Ser His Gly Trp Thr Gly Pro Ser Thr Gly Val
            805                 810                 815

Arg Gln Gly Ser His His Glu Gln Ala Arg Asp Asn Ser Arg His Ser
            820                 825                 830

Ala Ser Gln Asp Gly Gln Asp Thr Ile Arg Gly His Pro Gly Ser Ser
            835                 840                 845

Arg Arg Gly Arg Gln Gly Ser His His Glu Gln Ser Val Asp Arg Ser
850                 855                 860

Gly His Ser Gly Ser His His Ser His Thr Thr Ser Gln Gly Arg Ser
865                 870                 875                 880

Asp Ala Ser Arg Gly Gln Ser Gly Ser Arg Ser Ala Ser Arg Thr Thr
            885                 890                 895

Arg Asn Glu Glu Gln Ser Arg Asp Gly Ser Arg His Ser Gly Ser Arg
            900                 905                 910

His His Glu Ala Ser Ser His Ala Asp Ile Ser Arg His Ser Gln Ala
            915                 920                 925

Gly Gln Gly Gln Ser Glu Gly Ser Arg Thr Ser Arg Arg Gln Gly Ser
            930                 935                 940

Ser Val Ser Gln Asp Ser Asp Ser Glu Gly His Ser Glu Asp Ser Glu
945                 950                 955                 960

Arg Trp Ser Gly Ser Ala Ser Arg Asn His Arg Gly Ser Ala Gln Glu
            965                 970                 975

Gln Ser Arg His Gly Ser Arg His Pro Arg Ser His Glu Asp Arg
            980                 985                 990

Ala Gly His Gly His Ser Ala Asp Ser Ser Arg Gln Ser Gly Thr Pro
            995                 1000                1005

His Ala Glu Thr Ser Ser Gly Gly Gln Ala Ala Ser Ser His Glu
            1010                1015                1020

Gln Ala Arg Ser Ser Pro Gly Glu Arg His Gly Ser Arg His Gln
            1025                1030                1035

Gln Ser Ala Asp Ser Ser Arg His Ser Gly Ile Pro Arg Arg Gln
            1040                1045                1050

Ala Ser Ser Ala Val Arg Asp Ser Gly His Trp Gly Ser Ser Gly
            1055                1060                1065

Ser Gln Ala Ser Asp Ser Glu Gly His Ser Glu Glu Ser Asp Thr
            1070                1075                1080

Gln Ser Val Ser Gly His Gly Gln Asp Gly Pro His Gln Gln Ser
            1085                1090                1095

His Gln Glu Ser Ala Arg Asp Trp Ser Gly Gly Arg Ser Gly Arg
            1100                1105                1110

Ser Gly Ser Phe Ile Tyr Gln Val Ser Thr His Glu Gln Ser Glu
            1115                1120                1125
```

-continued

```
Ser Ala His Gly Arg Thr Arg Thr Ser Thr Gly Arg Arg Gln Gly
    1130                1135                1140

Ser His His Glu Gln Ala Arg Asp Ser Ser Arg His Ser Ala Ser
    1145                1150                1155

Gln Glu Gly Gln Asp Thr Ile Arg Ala His Pro Gly Ser Arg Arg
    1160                1165                1170

Gly Gly Arg Gln Gly Ser His His Glu Gln Ser Val Asp Arg Ser
    1175                1180                1185

Gly His Ser Gly Ser His His Ser His Thr Thr Ser Gln Gly Arg
    1190                1195                1200

Ser Asp Ala Ser His Gly Gln Ser Gly Ser Arg Ser Ala Ser Arg
    1205                1210                1215

Gln Thr Arg Lys Asp Lys Gln Ser Gly Asp Gly Ser Arg His Ser
    1220                1225                1230

Gly Ser Arg His His Glu Ala Ala Ser Trp Ala Asp Ser Ser Arg
    1235                1240                1245

His Ser Gln Val Gly Gln Glu Gln Ser Ser Gly Ser Arg Thr Ser
    1250                1255                1260

Arg His Gln Gly Ser Ser Val Ser Gln Asp Ser Asp Ser Glu Arg
    1265                1270                1275

His Ser Asp Asp Ser Glu Arg Leu Ser Gly Ser Ala Ser Arg Asn
    1280                1285                1290

His His Gly Ser Ser Arg Glu Gln Ser Arg Asp Gly Ser Arg His
    1295                1300                1305

Pro Gly Phe His Gln Glu Asp Arg Ala Ser His Gly His Ser Ala
    1310                1315                1320

Asp Ser Ser Arg Gln Ser Gly Thr His His Thr Glu Ser Ser Ser
    1325                1330                1335

His Gly Gln Ala Val Ser Ser His Glu Gln Ala Arg Ser Ser Pro
    1340                1345                1350

Gly Glu Arg His Gly Ser Arg His Gln Gln Ser Ala Asp Ser Ser
    1355                1360                1365

Arg His Ser Gly Ile Gly His Arg Gln Ala Ser Ser Ala Val Arg
    1370                1375                1380

Asp Ser Gly His Arg Gly Ser Ser Gly Ser Gln Val Thr Asn Ser
    1385                1390                1395

Glu Gly His Ser Glu Asp Ser Asp Thr Gln Ser Val Ser Ala His
    1400                1405                1410

Gly Gln Ala Gly Pro His Gln Ser His Lys Glu Ser Ala Arg
    1415                1420                1425

Gly Gln Ser Gly Glu Ser Ser Gly Arg Ser Arg Ser Phe Leu Tyr
    1430                1435                1440

Gln Val Ser Ser His Glu Gln Ser Glu Ser Thr His Gly Gln Thr
    1445                1450                1455

Ala Pro Ser Thr Gly Gly Arg Gln Gly Ser Arg His Glu Gln Ala
    1460                1465                1470

Arg Asn Ser Ser Arg His Ser Ala Ser Gln Asp Gly Gln Asp Thr
    1475                1480                1485

Ile Arg Gly His Pro Gly Ser Ser Arg Gly Gly Arg Gln Gly Ser
    1490                1495                1500

Tyr His Glu Gln Ser Val Asp Arg Ser Gly His Ser Gly Tyr His
    1505                1510                1515

His Ser His Thr Thr Pro Gln Gly Arg Ser Asp Ala Ser His Gly
```

```
            1520                1525                1530

Gln Ser Gly Pro Arg Ser Ala Ser Arg Gln Thr Arg Asn Glu Glu
    1535                1540                1545

Gln Ser Gly Asp Gly Ser Arg His Ser Gly Ser Arg His His Glu
    1550                1555                1560

Pro Ser Thr Arg Ala Gly Ser Ser Arg His Ser Gln Val Gly Gln
    1565                1570                1575

Gly Glu Ser Ala Gly Ser Lys Thr Ser Arg Arg Gln Gly Ser Ser
    1580                1585                1590

Val Ser Gln Asp Arg Asp Ser Glu Gly His Ser Glu Asp Ser Glu
    1595                1600                1605

Arg Arg Ser Glu Ser Ala Ser Arg Asn His Tyr Gly Ser Ala Arg
    1610                1615                1620

Glu Gln Ser Arg His Gly Ser Arg Asn Pro Arg Ser His Gln Glu
    1625                1630                1635

Asp Arg Ala Ser His Gly His Ser Ala Glu Ser Ser Arg Gln Ser
    1640                1645                1650

Gly Thr Arg His Ala Glu Thr Ser Ser Gly Gly Gln Ala Ala Ser
    1655                1660                1665

Ser Gln Glu Gln Ala Arg Ser Ser Pro Gly Glu Arg His Gly Ser
    1670                1675                1680

Arg His Gln Gln Ser Ala Asp Ser Ser Thr Asp Ser Gly Thr Gly
    1685                1690                1695

Arg Arg Gln Asp Ser Ser Val Val Gly Asp Ser Gly Asn Arg Gly
    1700                1705                1710

Ser Ser Gly Ser Gln Ala Ser Asp Ser Glu Gly His Ser Glu Glu
    1715                1720                1725

Ser Asp Thr Gln Ser Val Ser Ala His Gly Gln Ala Gly Pro His
    1730                1735                1740

Gln Gln Ser His Gln Glu Ser Thr Arg Gly Gln Ser Gly Glu Arg
    1745                1750                1755

Ser Gly Arg Ser Gly Ser Phe Leu Tyr Gln Val Ser Thr His Glu
    1760                1765                1770

Gln Ser Glu Ser Ala His Gly Arg Thr Gly Pro Ser Thr Gly Gly
    1775                1780                1785

Arg Gln Arg Ser Arg His Glu Gln Ala Arg Asp Ser Ser Arg His
    1790                1795                1800

Ser Ala Ser Gln Glu Gly Gln Asp Thr Ile Arg Gly His Pro Gly
    1805                1810                1815

Ser Ser Arg Gly Gly Arg Gln Gly Ser His Tyr Glu Gln Ser Val
    1820                1825                1830

Asp Ser Ser Gly His Ser Gly Ser His His Ser His Thr Thr Ser
    1835                1840                1845

Gln Glu Arg Ser Asp Val Ser Arg Gly Gln Ser Gly Ser Arg Ser
    1850                1855                1860

Val Ser Arg Gln Thr Arg Asn Glu Lys Gln Ser Gly Asp Gly Ser
    1865                1870                1875

Arg His Ser Gly Ser Arg His His Glu Ala Ser Ser Arg Ala Asp
    1880                1885                1890

Ser Ser Arg His Ser Gln Val Gly Gln Gly Gln Ser Ser Gly Pro
    1895                1900                1905

Arg Thr Ser Arg Asn Gln Gly Ser Ser Val Ser Gln Asp Ser Asp
    1910                1915                1920
```

-continued

Ser Gln Gly His Ser Glu Asp Ser Glu Arg Trp Ser Gly Ser Ala
1925                1930                1935

Ser Arg Asn His Leu Gly Ser Ala Trp Glu Gln Ser Arg Asp Gly
1940                1945                1950

Ser Arg His Pro Gly Ser His His Glu Asp Arg Ala Gly His Gly
1955                1960                1965

His Ser Ala Asp Ser Ser Arg Gln Ser Gly Thr Arg His Thr Glu
1970                1975                1980

Ser Ser Ser Arg Gly Gln Ala Ala Ser Ser His Glu Gln Ala Arg
1985                1990                1995

Ser Ser Ala Gly Glu Arg His Gly Ser His His Gln Leu Gln Ser
2000                2005                2010

Ala Asp Ser Ser Arg His Ser Gly Ile Gly His Gly Gln Ala Ser
2015                2020                2025

Ser Ala Val Arg Asp Ser Gly His Arg Gly Tyr Ser Gly Ser Gln
2030                2035                2040

Ala Ser Asp Ser Glu Gly His Ser Glu Asp Ser Asp Thr Gln Ser
2045                2050                2055

Val Ser Ala Gln Gly Lys Ala Gly Pro His Gln Gln Ser His Lys
2060                2065                2070

Glu Ser Ala Arg Gly Gln Ser Gly Glu Ser Ser Gly Arg Ser Gly
2075                2080                2085

Ser Phe Leu Tyr Gln Val Ser Thr His Glu Gln Ser Glu Ser Thr
2090                2095                2100

His Gly Gln Ser Ala Pro Ser Thr Gly Gly Arg Gln Gly Ser His
2105                2110                2115

Tyr Asp Gln Ala Gln Asp Ser Ser Arg His Ser Ala Ser Gln Glu
2120                2125                2130

Gly Gln Asp Thr Ile Arg Gly His Pro Gly Pro Ser Arg Gly Gly
2135                2140                2145

Arg Gln Gly Ser His Gln Glu Gln Ser Val Asp Arg Ser Gly His
2150                2155                2160

Ser Gly Ser His His Ser His Thr Thr Ser Gln Gly Arg Ser Asp
2165                2170                2175

Ala Ser Arg Gly Gln Ser Gly Ser Arg Ser Ala Ser Arg Lys Thr
2180                2185                2190

Tyr Asp Lys Glu Gln Ser Gly Asp Gly Ser Arg His Ser Gly Ser
2195                2200                2205

His His His Glu Ala Ser Ser Trp Ala Asp Ser Ser Arg His Ser
2210                2215                2220

Leu Val Gly Gln Gly Gln Ser Ser Gly Pro Arg Thr Ser Arg Pro
2225                2230                2235

Arg Gly Ser Ser Val Ser Gln Asp Ser Asp Ser Glu Gly His Ser
2240                2245                2250

Glu Asp Ser Glu Arg Arg Ser Gly Ser Ala Ser Arg Asn His His
2255                2260                2265

Gly Ser Ala Gln Glu Gln Ser Arg Asp Gly Ser Arg His Pro Arg
2270                2275                2280

Ser His His Glu Asp Arg Ala Gly His Gly His Ser Ala Glu Ser
2285                2290                2295

Ser Arg Gln Ser Gly Thr His His Ala Glu Asn Ser Ser Gly Gly
2300                2305                2310

```
Gln Ala  Ala Ser Ser His Glu  Gln Ala Arg Ser  Ala Gly Glu
    2315                 2320             2325

Arg His  Gly Ser His His Gln  Gln Ser Ala Asp  Ser Arg His
    2330                 2335             2340

Ser Gly  Ile Gly His Gly Gln  Ala Ser Ser Ala Val  Arg Asp Ser
    2345                 2350                 2355

Gly His  Arg Gly Ser Ser Gly  Ser Gln Ala Ser Asp  Ser Glu Gly
    2360                 2365                 2370

His Ser  Glu Asp Ser Asp Thr  Gln Ser Val Ser Ala  His Gly Gln
    2375                 2380                 2385

Ala Gly  Pro His Gln Gln Ser  His Gln Glu Ser Thr  Arg Gly Arg
    2390                 2395                 2400

Ser Ala  Gly Arg Ser Gly Arg  Ser Gly Ser Phe Leu  Tyr Gln Val
    2405                 2410                 2415

Ser Thr  His Glu Gln Ser Glu  Ser Ala His Gly Arg  Thr Gly Thr
    2420                 2425                 2430

Ser Thr  Gly Gly Arg Gln Gly  Ser His His Lys Gln  Ala Arg Asp
    2435                 2440                 2445

Ser Ser  Arg His Ser Thr Ser  Gln Glu Gly Gln Asp  Thr Ile His
    2450                 2455                 2460

Gly His  Pro Gly Ser Ser Ser  Gly Gly Arg Gln Gly  Ser His Tyr
    2465                 2470                 2475

Glu Gln  Leu Val Asp Arg Ser  Gly His Ser Gly Ser  His His Ser
    2480                 2485                 2490

His Thr  Thr Ser Gln Gly Arg  Ser Asp Ala Ser His  Gly His Ser
    2495                 2500                 2505

Gly Ser  Arg Ser Ala Ser Arg  Gln Thr Arg Asn Asp  Glu Gln Ser
    2510                 2515                 2520

Gly Asp  Gly Ser Arg His Ser  Gly Ser Arg His His  Glu Ala Ser
    2525                 2530                 2535

Ser Arg  Ala Asp Ser Ser Gly  His Ser Gln Val Gly  Gln Gly Gln
    2540                 2545                 2550

Ser Glu  Gly Pro Arg Thr Ser  Arg Asn Trp Gly Ser  Ser Phe Ser
    2555                 2560                 2565

Gln Asp  Ser Asp Ser Gln Gly  His Ser Glu Asp Ser  Glu Arg Trp
    2570                 2575                 2580

Ser Gly  Ser Ala Ser Arg Asn  His His Gly Ser Ala  Gln Glu Gln
    2585                 2590                 2595

Leu Arg  Asp Gly Ser Arg His  Pro Arg Ser His Gln  Glu Asp Arg
    2600                 2605                 2610

Ala Gly  His Gly His Ser Ala  Asp Ser Ser Arg Gln  Ser Gly Thr
    2615                 2620                 2625

Arg His  Thr Gln Thr Ser Ser  Gly Gly Gln Ala Ala  Ser Ser His
    2630                 2635                 2640

Glu Gln  Ala Arg Ser Ser Ala  Gly Glu Arg His Gly  Ser His His
    2645                 2650                 2655

Gln Gln  Ser Ala Asp Ser Ser  Arg His Ser Gly Ile  Gly His Gly
    2660                 2665                 2670

Gln Ala  Ser Ser Ala Val Arg  Asp Ser Gly His Arg  Gly Tyr Ser
    2675                 2680                 2685

Gly Ser  Gln Ala Ser Asp Asn  Glu Gly His Ser Glu  Asp Ser Asp
    2690                 2695                 2700

Thr Gln  Ser Val Ser Ala His  Gly Gln Ala Gly Ser  His Gln Gln
```

```
                    2705                2710                2715
Ser His Gln Glu Ser Ala Arg Gly Arg Ser Gly Glu Thr Ser Gly
    2720                2725                2730
His Ser Gly Ser Phe Leu Tyr Gln Val Ser Thr His Glu Gln Ser
    2735                2740                2745
Glu Ser Ser His Gly Trp Thr Gly Pro Ser Thr Arg Gly Arg Gln
    2750                2755                2760
Gly Ser Arg His Glu Gln Ala Gln Asp Ser Ser Arg His Ser Ala
    2765                2770                2775
Ser Gln Asp Gly Gln Asp Thr Ile Arg Gly His Pro Gly Ser Ser
    2780                2785                2790
Arg Gly Gly Arg Gln Gly Tyr His His Glu His Ser Val Asp Ser
    2795                2800                2805
Ser Gly His Ser Gly Ser His His Ser His Thr Thr Ser Gln Gly
    2810                2815                2820
Arg Ser Asp Ala Ser Arg Gly Gln Ser Gly Ser Arg Ser Ala Ser
    2825                2830                2835
Arg Thr Thr Arg Asn Glu Glu Gln Ser Gly Asp Gly Ser Arg His
    2840                2845                2850
Ser Gly Ser Arg His His Glu Ala Ser Thr His Ala Asp Ile Ser
    2855                2860                2865
Arg His Ser Gln Ala Val Gln Gly Gln Ser Glu Gly Ser Arg Arg
    2870                2875                2880
Ser Arg Arg Gln Gly Ser Ser Val Ser Gln Asp Ser Asp Ser Glu
    2885                2890                2895
Gly His Ser Glu Asp Ser Glu Arg Trp Ser Gly Ser Ala Ser Arg
    2900                2905                2910
Asn His His Gly Ser Ala Gln Glu Gln Leu Arg Asp Gly Ser Arg
    2915                2920                2925
His Pro Arg Ser His Gln Glu Asp Arg Ala Gly His Gly His Ser
    2930                2935                2940
Ala Asp Ser Ser Arg Gln Ser Gly Thr Arg His Thr Gln Thr Ser
    2945                2950                2955
Ser Gly Gly Gln Ala Ala Ser Ser His Glu Gln Ala Arg Ser Ser
    2960                2965                2970
Ala Gly Glu Arg His Gly Ser His His Gln Gln Ser Ala Asp Ser
    2975                2980                2985
Ser Arg His Ser Gly Ile Gly His Gly Gln Ala Ser Ser Ala Val
    2990                2995                3000
Arg Asp Ser Gly His Arg Gly Tyr Ser Gly Ser Gln Ala Ser Asp
    3005                3010                3015
Asn Glu Gly His Ser Glu Asp Ser Asp Thr Gln Ser Val Ser Ala
    3020                3025                3030
His Gly Gln Ala Gly Ser His Gln Gln Ser His Gln Glu Ser Ala
    3035                3040                3045
Arg Gly Arg Ser Gly Glu Thr Ser Gly His Ser Gly Ser Phe Leu
    3050                3055                3060
Tyr Gln Val Ser Thr His Glu Gln Ser Glu Ser Ser His Gly Trp
    3065                3070                3075
Thr Gly Pro Ser Thr Arg Gly Arg Gln Gly Ser Arg His Glu Gln
    3080                3085                3090
Ala Gln Asp Ser Ser Arg His Ser Ala Ser Gln Tyr Gly Gln Asp
    3095                3100                3105
```

-continued

```
Thr Ile Arg Gly His Pro Gly Ser Ser Arg Gly Gly Arg Gln Gly
3110            3115                3120

Tyr His His Glu His Ser Val Asp Ser Ser Gly His Ser Gly Ser
3125            3130                3135

His His Ser His Thr Thr Ser Gln Gly Arg Ser Asp Ala Ser Arg
3140            3145                3150

Gly Gln Ser Gly Ser Arg Ser Ala Ser Arg Thr Thr Arg Asn Glu
3155            3160                3165

Glu Gln Ser Gly Asp Ser Ser Arg His Ser Val Ser Arg His His
3170            3175                3180

Glu Ala Ser Thr His Ala Asp Ile Ser Arg His Ser Gln Ala Val
3185            3190                3195

Gln Gly Gln Ser Glu Gly Ser Arg Arg Ser Arg Arg Gln Gly Ser
3200            3205                3210

Ser Val Ser Gln Asp Ser Asp Ser Glu Gly His Ser Glu Asp Ser
3215            3220                3225

Glu Arg Trp Ser Gly Ser Ala Ser Arg Asn His Arg Gly Ser Val
3230            3235                3240

Gln Glu Gln Ser Arg His Gly Ser Arg His Pro Arg Ser His His
3245            3250                3255

Glu Asp Arg Ala Gly His Gly His Ser Ala Asp Arg Ser Arg Gln
3260            3265                3270

Ser Gly Thr Arg His Ala Glu Thr Ser Ser Gly Gly Gln Ala Ala
3275            3280                3285

Ser Ser His Glu Gln Ala Arg Ser Ser Pro Gly Glu Arg His Gly
3290            3295                3300

Ser Arg His Gln Gln Ser Ala Asp Ser Ser Arg His Ser Gly Ile
3305            3310                3315

Pro Arg Gly Gln Ala Ser Ser Ala Val Arg Asp Ser Arg His Trp
3320            3325                3330

Gly Ser Ser Gly Ser Gln Ala Ser Asp Ser Glu Gly His Ser Glu
3335            3340                3345

Glu Ser Asp Thr Gln Ser Val Ser Gly His Gly Gln Ala Gly Pro
3350            3355                3360

His Gln Gln Ser His Gln Glu Ser Ala Arg Asp Arg Ser Gly Gly
3365            3370                3375

Arg Ser Gly Arg Ser Gly Ser Phe Leu Tyr Gln Val Ser Thr His
3380            3385                3390

Glu Gln Ser Glu Ser Ala His Gly Arg Thr Arg Thr Ser Thr Gly
3395            3400                3405

Arg Arg Gln Gly Ser His His Glu Gln Ala Arg Asp Ser Ser Arg
3410            3415                3420

His Ser Ala Ser Gln Glu Gly Gln Asp Thr Ile Arg Gly His Pro
3425            3430                3435

Gly Ser Ser Arg Arg Gly Arg Gln Gly Ser His Tyr Glu Gln Ser
3440            3445                3450

Val Asp Arg Ser Gly His Ser Gly Ser His His Ser His Thr Thr
3455            3460                3465

Ser Gln Gly Arg Ser Asp Ala Ser Arg Gly Gln Ser Gly Ser Arg
3470            3475                3480

Ser Ala Ser Arg Gln Thr Arg Asn Asp Glu Gln Ser Gly Asp Gly
3485            3490                3495
```

```
Ser Arg His Ser Trp Ser His His Glu Ala Ser Thr Gln Ala
    3500            3505            3510

Asp Ser Ser Arg His Ser Gln Ser Gly Gln Gly Gln Ser Ala Gly
    3515            3520            3525

Pro Arg Thr Ser Arg Asn Gln Gly Ser Ser Val Ser Gln Asp Ser
    3530            3535            3540

Asp Ser Gln Gly His Ser Glu Asp Ser Glu Arg Trp Ser Gly Ser
    3545            3550            3555

Ala Ser Arg Asn His Arg Gly Ser Ala Gln Glu Gln Ser Arg Asp
    3560            3565            3570

Gly Ser Arg His Pro Thr Ser His His Glu Asp Arg Ala Gly His
    3575            3580            3585

Gly His Ser Ala Glu Ser Ser Arg Gln Ser Gly Thr His His Ala
    3590            3595            3600

Glu Asn Ser Ser Gly Gly Gln Ala Ala Ser Ser His Glu Gln Ala
    3605            3610            3615

Arg Ser Ser Ala Gly Glu Arg His Gly Ser His His Gln Gln Ser
    3620            3625            3630

Ala Asp Ser Ser Arg His Ser Gly Ile Gly His Gly Gln Ala Ser
    3635            3640            3645

Ser Ala Val Arg Asp Ser Gly His Arg Gly Ser Ser Gly Ser Gln
    3650            3655            3660

Ala Ser Asp Ser Glu Gly His Ser Glu Asp Ser Asp Thr Gln Ser
    3665            3670            3675

Val Ser Ala His Gly Gln Ala Gly Pro His Gln Gln Ser His Gln
    3680            3685            3690

Glu Ser Thr Arg Gly Arg Ser Ala Gly Arg Ser Gly Arg Ser Gly
    3695            3700            3705

Ser Phe Leu Tyr Gln Val Ser Thr His Glu Gln Ser Glu Ser Ala
    3710            3715            3720

His Gly Arg Ala Gly Pro Ser Thr Gly Gly Arg Gln Gly Ser Arg
    3725            3730            3735

His Glu Gln Ala Arg Asp Ser Ser Arg His Ser Ala Ser Gln Glu
    3740            3745            3750

Gly Gln Asp Thr Ile Arg Gly His Pro Gly Ser Arg Arg Gly Gly
    3755            3760            3765

Arg Gln Gly Ser Tyr His Glu Gln Ser Val Asp Arg Ser Gly His
    3770            3775            3780

Ser Gly Ser His His Ser His Thr Thr Ser Gln Gly Arg Ser Asp
    3785            3790            3795

Ala Ser His Gly Gln Ser Gly Ser Arg Ser Ala Ser Arg Glu Thr
    3800            3805            3810

Arg Asn Glu Glu Gln Ser Gly Asp Gly Ser Arg His Ser Gly Ser
    3815            3820            3825

Arg His His Glu Ala Ser Thr Gln Ala Asp Ser Ser Arg His Ser
    3830            3835            3840

Gln Ser Gly Gln Gly Glu Ser Ala Gly Ser Arg Arg Ser Arg Arg
    3845            3850            3855

Gln Gly Ser Ser Val Ser Gln Asp Ser Asp Ser Glu Ala Tyr Pro
    3860            3865            3870

Glu Asp Ser Glu Arg Arg Ser Glu Ser Ala Ser Arg Asn His His
    3875            3880            3885

Gly Ser Ser Arg Glu Gln Ser Arg Asp Gly Ser Arg His Pro Gly
```

```
                    3890                    3895                    3900
Ser Ser His Arg Asp Thr Ala Ser His Val Gln Ser Ser Pro Val
    3905                    3910                    3915
Gln Ser Asp Ser Ser Thr Ala Lys Glu His Gly His Phe Ser Ser
    3920                    3925                    3930
Leu Ser Gln Asp Ser Ala Tyr His Ser Gly Ile Gln Ser Arg Gly
    3935                    3940                    3945
Ser Pro His Ser Ser Ser Tyr His Tyr Gln Ser Glu Gly Thr
    3950                    3955                    3960
Glu Arg Gln Lys Gly Gln Ser Gly Leu Val Trp Arg His Gly Ser
    3965                    3970                    3975
Tyr Gly Ser Ala Asp Tyr Asp Tyr Gly Glu Ser Gly Phe Arg His
    3980                    3985                    3990
Ser Gln His Gly Ser Val Ser Tyr Asn Ser Asn Pro Val Val Phe
    3995                    4000                    4005
Lys Glu Arg Ser Asp Ile Cys Lys Ala Ser Ala Phe Gly Lys Asp
    4010                    4015                    4020
His Pro Arg Tyr Tyr Ala Thr Tyr Ile Asn Lys Asp Pro Gly Leu
    4025                    4030                    4035
Cys Gly His Ser Ser Asp Ile Ser Lys Gln Leu Gly Phe Ser Gln
    4040                    4045                    4050
Ser Gln Arg Tyr Tyr Tyr Tyr Glu
    4055                    4060

<210> SEQ ID NO 6
<211> LENGTH: 554
<212> TYPE: PRT
<213> ORGANISM: Mus musculus

<400> SEQUENCE: 6

Met Ser Ala Leu Leu Glu Ser Ile Thr Ser Met Ile Glu Ile Phe Gln
 1               5                  10                  15
Gln Tyr Ser Thr Ser Asp Lys Glu Glu Glu Thr Leu Ser Lys Glu Glu
                20                  25                  30
Leu Lys Glu Leu Leu Glu Gly Gln Leu Gln Ala Val Leu Lys Asn Pro
            35                  40                  45
Asp Asp Gln Asp Ile Ala Glu Val Phe Met Gln Met Leu Asp Val Asp
        50                  55                  60
His Asp Asp Lys Leu Asp Phe Ala Glu Tyr Leu Leu Val Leu Lys
 65                  70                  75                  80
Leu Ala Lys Ala Tyr Tyr Glu Ala Ser Lys Asn Glu Ser Phe Gln Thr
                85                  90                  95
His Gly Ser Asn Gly Arg Ser Lys Thr Asp Tyr Lys Gly Leu Glu Glu
               100                 105                 110
Glu Gly Glu Glu Gly Asn Glu Gln Asn Leu Arg Arg Arg His Gly Gly
           115                 120                 125
Thr Asp Gly Lys Arg Lys Ser Asp Arg Thr Arg Ser Pro Asn Gly Lys
       130                 135                 140
Arg Gly Lys Arg Gln Glu Ser Arg Cys Arg Ser Glu Gly Lys Asp Lys
145                 150                 155                 160
His Arg Arg Glu Pro Glu Lys His Arg His Gln Asp Ser Lys Arg
               165                 170                 175
Lys Gln Arg His Gly Ser Gly Ser Thr Glu Arg Lys Asp Asn Arg Asn
           180                 185                 190
```

```
Lys Lys Asn Arg Gln Ser Lys Glu Arg Asn Tyr Asp Glu Ile Tyr Asp
            195                 200                 205

Asn Gly Lys Tyr Asn Glu Asp Trp Glu Ala Ser Tyr Asn Asn Cys Tyr
        210                 215                 220

Tyr Lys Thr Gln Asn Thr Thr Leu Asp Gln Arg Glu Gly Asn Arg Arg
225                 230                 235                 240

Pro Arg Ala Asp Ser Gln Lys Glu Pro Gln Ser Phe His Gly Gln Ala
                245                 250                 255

Asp Asn Ser Asp Ser Glu Gly Gly Arg Gln Gln Ser His Ser Lys Pro
            260                 265                 270

Ser Pro Val Arg Ala Asp Gln Arg Arg Ser Arg Ala Gly Gln Ala Gly
        275                 280                 285

Ser Ser Lys Val Ser Ala Arg Ser Gly Ser Gly Gly Arg Gly Gln Ser
    290                 295                 300

Pro Asp Gly Ser Gly Arg Ser Ser Asn Arg Arg Asp Arg Pro Arg Gln
305                 310                 315                 320

Pro Ser Pro Ser Gln Ser Ser Asp Ser Gln Val His Ser Gly Val Gln
                325                 330                 335

Val Glu Gly Arg Arg Gly Gln Ser Ser Ser Ala Asn Arg Arg Ala Gly
            340                 345                 350

Ser Ser Ser Gly Ser Gly Val Gln Gly Ala Ser Ala Gly Gly Leu Ala
        355                 360                 365

Ala Asp Ala Ser Arg Arg Thr Gly Ala Leu Gln Gly Gln Ala Ser Ala
    370                 375                 380

Gln Gly Arg Ala Gly Ser Gln Gly Gln Ala Gln Gly Arg Val Gly Ser
385                 390                 395                 400

Ser Ala Asp Arg Gln Gly Arg Arg Gly Val Ser Glu Ser Gln Ala Ser
                405                 410                 415

Asp Ser Glu Gly Gln Ser Asp Phe Ser Glu Gly Gln Ala Val Gly Ala
            420                 425                 430

His Arg Gln Ser Gly Ala Gly Gln Arg His Glu Gln Arg Ser Ser Arg
        435                 440                 445

Gly Gln Tyr Gly Ser Gly Phe Tyr Pro Val Tyr Tyr Tyr Tyr Glu Gln
    450                 455                 460

Glu His Ser Glu Glu Ser Asp Ser Gln His Gly His Gln His Glu
465                 470                 475                 480

Gln Gln Arg Gly His Gln His Gln His Glu His Glu Gln Pro
                485                 490                 495

Glu Ser Gly His Arg Gln Gln Ser Ser Arg Gly His Gln Gly
            500                 505                 510

Ala His Gln Glu Gln Gly Arg Asp Ser Ala Arg Ser Arg Gly Ser Asn
        515                 520                 525

Gln Gly His Ser Ser Ser Arg His Gln Ala Asp Ser Pro Arg Val Ser
    530                 535                 540

Val Arg Ser Gly Ser Gly Gly Arg Gly Gln
545                 550
```

<210> SEQ ID NO 7
<211> LENGTH: 336
<212> TYPE: PRT
<213> ORGANISM: Mus musculus

<400> SEQUENCE: 7

```
Pro Asp Gly Ser Gly Arg Ser Ser Asn Arg Arg Asp Arg Pro Arg Gln
1               5                   10                  15
```

```
Leu Ser Pro Ser Gln Ser Ser Asp Ser Gln Val His Ser Gly Val Gln
            20                  25                  30

Val Glu Gly Arg Arg Gly His Ser Ser Ala Asn Arg Arg Ala Gly
        35                  40                  45

Ser Ser Ser Gly Ser Gly Val Gln Gly Ala Ser Ala Gly Gly Leu Ala
    50                  55                  60

Ala Asp Ala Ser Arg Arg Ser Gly Ala Arg Gln Gly Gln Ala Ser Ala
65                  70                  75                  80

Gln Gly Arg Ala Gly Ser Gln Gly Gln Ala Gln Gly Arg Val Ser Ser
                85                  90                  95

Ser Ala Asp Arg Gln Gly Arg Arg Gly Val Ser Glu Ser Arg Ala Ser
                100                 105                 110

Asp Ser Glu Gly His Ser Asp Phe Ser Glu Gly Gln Ala Val Gly Ala
            115                 120                 125

His Arg Gln Ser Gly Ala Gly Gln Arg His Glu Gln Arg Ser Ser Arg
            130                 135                 140

Gly Gln His Gly Ser Gly Tyr Tyr Tyr Glu Gln His Ser Glu Glu
145                 150                 155                 160

Glu Ser Asp Ser Gln His Gln His Gly His Gln His Glu Gln Gln Arg
                165                 170                 175

Gly His Gln His Gln His Gln His Gln His Glu His Glu Gln Pro Glu
            180                 185                 190

Ser Gly His Arg Gln Gln Gln Ser Ser Gly Arg Gly His Gln Gly Ala
            195                 200                 205

His Gln Glu Gln Gly Arg Asp Ser Ala Arg Pro Arg Gly Ser Asn Gln
            210                 215                 220

Gly His Ser Ser Ser Arg His Gln Ala Asp Ser Pro Arg Val Ser Ala
225                 230                 235                 240

Arg Ser Gly Ser Gly Gly Arg Gly Gln Ser Pro Asp Ala Ser Gly Arg
                245                 250                 255

Ser Ser Asn Arg Arg Asp Arg Pro Arg Gln Pro Ser Pro Ser Gln Ser
                260                 265                 270

Ser Asp Ser Gln Val His Ser Gly Val Gln Val Glu Ala Gln Arg Gly
            275                 280                 285

Gln Ser Ser Ser Ala Asn Arg Arg Ala Gly Ser Ser Ser Gly Ser Gly
            290                 295                 300

Val Gln Gly Ala Ala Ala Ser Gly Gln Gly Gly Tyr Glu Ser Ile Phe
305                 310                 315                 320

Thr Ala Lys His Leu Asp Phe Asn Gln Ser His Ser Tyr Tyr Tyr Tyr
                325                 330                 335

<210> SEQ ID NO 8
<211> LENGTH: 250
<212> TYPE: PRT
<213> ORGANISM: Mus musculus

<400> SEQUENCE: 8

Gly Gly Leu Ala Ala Asp Ala Ser Arg Arg Ser Gly Ala Leu Gln Gly
1               5                   10                  15

Gln Ala Ser Ala Gln Gly Arg Ala Gly Ser Gln Gly Gln Ala Gln Gly
                20                  25                  30

Arg Val Gly Ser Ser Ala Asp Arg Gln Gly Arg Arg Gly Val Ser Glu
            35                  40                  45

Ser Gln Ala Ser Asp Ser Glu Gly His Ser Asp Phe Ser Glu Gly Gln
```

```
Ala Val Gly Ala His Arg Gln Ser Gly Ala Gly Gln Arg His Glu Gln
 65                  70                  75                  80

Arg Ser Ser Arg Gly Gln His Gly Ser Gly Tyr Tyr Tyr Glu Gln Glu
                 85                  90                  95

His Ser Glu Glu Glu Ser Asp Ser Gln His Gln His Gly His Gln His
            100                 105                 110

Glu Gln Gln Arg Gly His Gln His Gln His Gln His Gln His Glu His
            115                 120                 125

Glu Gln Pro Glu Ser Gly His Arg Gln Gln Ser Ser Gly Arg Gly
        130                 135                 140

His Gln Gly Ala His Gln Glu Gln Gly Arg Asp Ser Ala Arg Ser Arg
145                 150                 155                 160

Gly Ser Asn Gln Gly His Ser Ser Arg His Gln Ala Asp Ser Pro
                165                 170                 175

Arg Val Ser Ala Arg Ser Gly Ser Gly Arg Gly Gln Ser Pro Asp
                180                 185                 190

Ala Ser Gly Arg Ser Ser Asn Arg Arg Asp Arg Pro Arg Gln Pro Ser
                195                 200                 205

Pro Ser Gln Ser Ser Asp Ser Gln Val His Ser Gly Val Gln Val Glu
        210                 215                 220

Gly Arg Gly Gln Ser Ser Ser Ala Asn Arg Arg Ala Gly Ser Ser
225                 230                 235                 240

Ser Ser Ser Gly Val Gln Gly Ala Ser Ala
                245                 250

<210> SEQ ID NO 9
<211> LENGTH: 255
<212> TYPE: PRT
<213> ORGANISM: Mus musculus

<400> SEQUENCE: 9

Gly Gly Leu Ala Ala Asp Ala Ser Arg Arg Ser Gly Ala Arg Gln Gly
  1               5                  10                  15

Gln Ala Ser Ala Gln Gly Arg Ala Gly Ser Gln Gly Gln Ala Gln Gly
             20                  25                  30

Arg Val Gly Ser Ser Ala Asp Arg Gln Gly Arg Arg Gly Val Ser Glu
         35                  40                  45

Ser Gln Ala Ser Asp Ser Glu Gly His Ser Asp Phe Ser Glu Gly Gln
     50                  55                  60

Ala Val Gly Ala His Arg Gln Ser Gly Ala Gly Gln Arg His Glu Gln
 65                  70                  75                  80

Arg Ser Ser Arg Gly Gln His Gly Ser Gly Phe Tyr Pro Val Tyr Tyr
                 85                  90                  95

Tyr Tyr Glu Gln Glu His Ser Glu Glu Glu Ser Asp Ser Gln His Gln
            100                 105                 110

His Gly His Gln His Glu Gln Gln Arg Gly His Gln His Gln His Gln
            115                 120                 125

His Gln His Glu His Glu Gln Pro Glu Ser Gly His Arg Gln Gln
        130                 135                 140

Ser Ser Gly Arg Gly His Gln Gly Ala His Gln Glu Gln Gly Arg Asp
145                 150                 155                 160

Ser Ala Arg Ser Arg Gly Ser Asn Gln Gly His Ser Ser Arg His
                165                 170                 175
```

Gln Ala Asp Ser Pro Arg Val Ser Ala Arg Ser Gly Ser Gly Arg
            180                 185                 190

Gly Gln Ser Pro Asp Ala Ser Gly Arg Ser Ser Asn Arg Arg Asp Arg
        195                 200                 205

Pro Arg Gln Pro Ser Pro Ser Gln Ser Ser Asp Ser Gln Val His Ser
    210                 215                 220

Gly Val Gln Val Glu Gly Arg Arg Gly Gln Ser Ser Ala Asn Arg
225                 230                 235                 240

Arg Ala Gly Ser Ser Ser Gly Ser Gly Val Gln Gly Ala Ser Ala
                245                 250                 255

<210> SEQ ID NO 10
<211> LENGTH: 4838
<212> TYPE: PRT
<213> ORGANISM: Mus musculus

<400> SEQUENCE: 10

Met Ser Ala Leu Leu Glu Ser Ile Thr Ser Met Ile Glu Ile Phe Gln
1               5                   10                  15

Gln Tyr Ser Thr Ser Asp Lys Glu Glu Thr Leu Ser Lys Glu Glu
            20                  25                  30

Leu Lys Glu Leu Leu Glu Gly Gln Leu Gln Ala Val Leu Lys Ile Ile
        35                  40                  45

Gln Leu Leu Asp Asp Tyr Pro Lys Cys Phe Ile Val Gly Ala Asp Asn
    50                  55                  60

Val Gly Ser Lys Gln Met Gln Gln Ile Arg Met Ser Leu Arg Gly Lys
65                  70                  75                  80

Ala Val Val Leu Met Gly Lys Lys Thr Met Met Arg Lys Ala Ile Arg
                85                  90                  95

Gly His Leu Glu Asn Asn Pro Ala Leu Glu Lys Leu Leu Pro His Ile
            100                 105                 110

Arg Gly Asn Val Gly Phe Val Phe Thr Lys Glu Asp Leu Thr Glu Ile
        115                 120                 125

Arg Ala Met Leu Leu Ala Asn Lys Val Pro Ala Ala Ala Arg Val Gly
    130                 135                 140

Ala Ile Ala Pro Cys Glu Val Thr Met Pro Ala Gln Asn Thr Gly Leu
145                 150                 155                 160

Gly Pro Glu Lys Ile Ser Phe Phe Gln Ala Leu Gly Ile Thr Thr Arg
                165                 170                 175

Ile Ser Arg Gly Thr Ile Glu Ile Leu Ser Asp Val Gln Leu Ile Lys
            180                 185                 190

Thr Gly Asp Lys Val Gly Val Ser Glu Ala Thr Leu Leu Asn Met Leu
        195                 200                 205

Asn Ile Ser Pro Ser Ser Phe Gly Leu Ile Ile Gln Gln Val Phe Asp
    210                 215                 220

Asn Gly Ser Ile Tyr Asn Pro Glu Val Leu Asp Ile Thr Glu Gln Ala
225                 230                 235                 240

Leu His Ser Arg Phe Leu Glu Gly Val His Asn Val Ala Ser Val Cys
                245                 250                 255

Leu Gln Ile Gly Tyr Leu Thr Val Asp Ser Val Leu His Ser Phe Ile
            260                 265                 270

Asn Gly Tyr Lys Arg Val Leu Ala Leu Ser Val Glu Thr Glu Tyr Thr
        275                 280                 285

Phe Pro Leu Ala Glu Lys Val Lys Ala Phe Leu Ala Asn Pro Ser Ala
    290                 295                 300

```
Phe Ala Thr Ala Ala Ile Thr Ala Ala Pro Ala Ala Ala Thr Ala Pro
305                 310                 315                 320

Ala Lys Pro Glu Asn Pro Asp Asp Gln Asp Ile Ala Glu Val Phe Met
            325                 330                 335

Gln Met Leu Asp Val Asp His Asp Asp Lys Leu Asp Phe Ala Glu Tyr
                340                 345                 350

Leu Leu Leu Val Leu Lys Leu Ala Lys Ala Tyr Tyr Glu Ala Ser Lys
            355                 360                 365

Asn Glu Ser Phe Gln Thr His Gly Ser Asn Gly Arg Ser Lys Thr Asp
370                 375                 380

Tyr Lys Gly Leu Glu Glu Glu Gly Glu Glu Asn Lys Gln Asn Leu
385                 390                 395                 400

Arg Arg Arg His Gly Gly Thr Asp Gly Lys Arg Lys Ser Asp Arg Thr
                405                 410                 415

Arg Ser Pro Asn Gly Lys Arg Gly Lys Arg Gln Glu Ser Arg Cys Arg
                420                 425                 430

Ser Glu Gly Lys Asp Lys His Arg Arg Glu Pro Glu Lys His Arg His
            435                 440                 445

Gln Gln Asp Ser Lys Arg Lys Gln Arg His Gly Ser Gly Ser Thr Glu
450                 455                 460

Arg Lys Asp Asn Arg Asn Lys Lys Asn Arg Gln Ser Lys Glu Arg Asn
465                 470                 475                 480

Tyr Asp Glu Ile Tyr Asp Asn Gly Lys Tyr Asn Glu Asp Trp Glu Ala
                485                 490                 495

Ser Tyr Asn Asn Cys Tyr Tyr Lys Thr Gln Asn Thr Thr Leu Asp Gln
            500                 505                 510

Arg Glu Gly Asn Arg Arg Pro Arg Ala Asp Ser Gln Lys Glu Pro Gln
            515                 520                 525

Ser Ser His Gly Gln Ala Asp Asn Ser Asp Ser Glu Gly Gly Arg Gln
530                 535                 540

Gln Ser His Ser Lys Pro Ser Pro Val Arg Ala Asp Gln Arg Arg Ser
545                 550                 555                 560

Arg Ala Gly Gln Ala Gly Ser Ser Lys Val Ser Ala Arg Ser Gly Ser
                565                 570                 575

Gly Gly Arg Gly Gln Ser Pro Asp Gly Ser Gly Arg Ser Ser Asn Arg
                580                 585                 590

Arg Asp Arg Pro Arg Gln Pro Ser Pro Ser Gln Ser Ser Asp Ser Gln
                595                 600                 605

Val His Ser Gly Val Gln Val Glu Gly Arg Gly Gln Ser Ser Ser
            610                 615                 620

Ala Asn Arg Arg Ala Gly Ser Ser Ser Gly Ser Gly Val Gln Gly Ala
625                 630                 635                 640

Ser Ala Gly Gly Leu Ala Ala Asp Ala Ser Arg Arg Ser Gly Ala Arg
                645                 650                 655

Gln Gly Gln Ala Ser Ala Gly Arg Ala Gly Ser Gln Gly Gln Ala
            660                 665                 670

Gln Gly Arg Val Gly Ser Ser Ala Asp Arg Gln Gly Arg Arg Gly Val
            675                 680                 685

Ser Glu Ser Gln Ala Ser Asp Ser Glu Gly His Ser Asp Phe Ser Glu
            690                 695                 700

Gly Gln Ala Val Gly Ala His Arg Gln Ser Gly Ala Gly Gln Arg His
705                 710                 715                 720
```

-continued

Glu Gln Arg Ser Ser Arg Gly Gln His Gly Ser Gly Phe Tyr Pro Val
                725                 730                 735

Tyr Tyr Tyr Tyr Glu Gln Glu His Ser Glu Glu Glu Ser Asp Ser Gln
            740                 745                 750

His Gln His Gly His Gln His Glu Gln Gln Arg Gly His Gln His Gln
        755                 760                 765

His Gln His Gln His Glu His Glu Gln Pro Glu Ser Gly His Arg Gln
    770                 775                 780

Gln Gln Phe Ser Gly Arg Gly His Gly Ala His Gln Glu Gln Gly
785                 790                 795                 800

Arg Asp Ser Ala Arg Ser Arg Gly Ser Asn Gln Gly His Ser Ser
                805                 810                 815

Arg His Gln Ala Asp Ser Pro Arg Val Ser Ala Arg Ser Gly Ser Gly
            820                 825                 830

Gly Arg Gly Gln Ser Pro Asp Ala Ser Gly Arg Ser Ser Asn Arg Arg
        835                 840                 845

Asp Arg Pro Arg Gln Pro Ser Pro Ser Gln Ser Ser Asp Ser Gln Val
    850                 855                 860

Ile Leu Glu Ser Arg Ser Lys Ala Gly Ala Gly Ser Pro His Leu Pro
865                 870                 875                 880

Thr Gly Gly Pro Asp Pro Ala Pro Ala Gln Gly Ser Arg Gly Pro Leu
                885                 890                 895

Gln Val Asp Trp Gln Leu Thr Pro Pro Gly Ala Leu Gly Arg Val Lys
            900                 905                 910

Ala Arg His Leu Pro Arg Val Ala Gln Gly His Lys Ala Lys His Arg
        915                 920                 925

Ala Ala Ser Ala Arg Gln Leu Thr Gly Lys Gly Val Glu Gly Ser Ala
    930                 935                 940

Arg Val Arg Pro Ala Thr Ala Arg Ala Thr Leu Thr Ser Gln Lys Ala
945                 950                 955                 960

Arg Gln Gln Gln Gln Ser Ser Gly Arg Gly Asn Gln Gly Ala His Gln
                965                 970                 975

Glu Gln Gly Arg Asp Ser Ala Arg Ser Arg Gly Ser Asn Gln Gly His
            980                 985                 990

Ser Ser Ser Arg His Gln Ala Asp Ser Pro Arg Val Ser Ala Arg Ser
        995                 1000                1005

Gly Ser Gly Gly Arg Gly Gln Ser Pro Asp Ala Ser Gly Arg Ser
            1010                1015                1020

Ser Asn Arg Arg Asp Arg Pro Arg Gln Pro Ser Pro Ser Gln Ser
            1025                1030                1035

Ser Asp Ser His Val His Ser Gly Val Gln Val Glu Gly Arg Arg
            1040                1045                1050

Gly Gln Ser Ser Ser Ala Asn Arg Arg Ala Gly Ser Ser Ser Gly
            1055                1060                1065

Ser Gly Val Gln Gly Ala Ser Ala Gly Gly Leu Ala Ala Asp Ala
            1070                1075                1080

Ser Arg Arg Ser Gly Ala Arg Gln Gly Gln Ala Ser Ala Gln Gly
            1085                1090                1095

Arg Ala Gly Ser Gln Gly Gln Ala Gln Gly Arg Val Gly Ser Ser
            1100                1105                1110

Ala Asp Arg Gln Gly Arg Arg Gly Val Ser Glu Ser Gln Ala Ser
            1115                1120                1125

Asp Ser Glu Gly His Ser Asp Phe Ser Glu Gly Gln Ala Val Gly

-continued

```
               1130                1135                1140

Ala  His  Arg  Gln  Ser  Gly  Ala  Gly  Gln  Arg  His  Glu  Gln  Arg  Ser
          1145                1150                1155

Ser  Arg  Gly  Gln  His  Gly  Ser  Arg  Tyr  Tyr  Tyr  Glu  Gln  Glu  His
     1160                1165                1170

Ser  Glu  Glu  Glu  Ser  Asp  Ser  Gln  His  Gln  His  Gly  His  Gln  His
     1175                1180                1185

Glu  Gln  Gln  Arg  Gly  His  Gln  His  Gln  His  Glu  His  Glu  Gln  Pro
     1190                1195                1200

Glu  Ser  Gly  His  Arg  Gln  Gln  Ser  Ser  Gly  Arg  Gly  His  Gln
     1205                1210                1215

Gly  Ala  His  Gln  Glu  Gln  Gly  Arg  Asp  Ser  Ala  Arg  Ser  Arg  Gly
     1220                1225                1230

Ser  Asn  Gln  Gly  His  Ser  Ser  Arg  His  Gln  Ala  Asp  Ser  Pro
     1235                1240                1245

Arg  Val  Ser  Ala  Arg  Ser  Gly  Ser  Gly  Gly  Arg  Gly  Gln  Ser  Pro
     1250                1255                1260

Asp  Ala  Ser  Gly  Arg  Ser  Ser  Asn  Arg  Arg  Asp  Arg  Pro  Arg  Gln
     1265                1270                1275

Pro  Ser  Pro  Ser  Gln  Ser  Ser  Asp  Ser  Gln  Val  His  Ser  Gly  Val
     1280                1285                1290

Gln  Val  Glu  Gly  Arg  Arg  Gly  Gln  Ser  Ser  Ala  Asn  Arg  Arg
     1295                1300                1305

Ala  Gly  Ser  Ser  Ser  Gly  Ser  Gly  Val  Gln  Gly  Ala  Ser  Ala  Gly
     1310                1315                1320

Gly  Leu  Ala  Ala  Asp  Ala  Ser  Arg  Arg  Ser  Gly  Ala  Arg  Gln  Gly
     1325                1330                1335

Gln  Ala  Ser  Ala  Gln  Gly  Arg  Ala  Gly  Ser  Gln  Gly  Gln  Ala  Gln
     1340                1345                1350

Gly  Arg  Ile  Gly  Ser  Ser  Ala  Asp  Arg  Gln  Gly  Arg  Arg  Gly  Val
     1355                1360                1365

Ser  Glu  Ser  Gln  Ala  Ser  Asp  Ser  Glu  Gly  His  Ser  Asp  Phe  Ser
     1370                1375                1380

Glu  Gly  Gln  Ala  Val  Gly  Ala  His  Arg  Gln  Ser  Glu  Ala  Gly  Gln
     1385                1390                1395

Arg  His  Glu  Gln  Arg  Ser  Ser  Arg  Gly  Gln  His  Gly  Ser  Gly  Tyr
     1400                1405                1410

Tyr  Tyr  Glu  Gln  Glu  His  Ser  Glu  Glu  Glu  Ser  Asp  Ser  Gln  His
     1415                1420                1425

Gln  His  Gly  His  Gln  His  Glu  Gln  Gln  Arg  Gly  Thr  Gln  His  Gln
     1430                1435                1440

His  Glu  His  Gln  Gln  Pro  Glu  Ser  Gly  His  Arg  Gln  Gln  Gln  Ser
     1445                1450                1455

Ser  Gly  Arg  Gly  His  Gln  Gly  Thr  His  Gln  Glu  Gln  Gly  Arg  Asp
     1460                1465                1470

Ser  Ala  Arg  Ser  Arg  Gly  Ser  Asn  Gln  Gly  His  Ser  Ser  Ser  Arg
     1475                1480                1485

His  Gln  Ala  Asp  Ser  Pro  Arg  Val  Ser  Ala  Arg  Ser  Gly  Ser  Gly
     1490                1495                1500

Gly  Arg  Gly  Gln  Ser  Pro  Asp  Ala  Ser  Gly  Arg  Ser  Ser  Asn  Arg
     1505                1510                1515

Arg  Asp  Arg  Pro  Arg  Gln  Pro  Ser  Pro  Ser  Gln  Ser  Ser  Asp  Ser
     1520                1525                1530
```

```
Gln Val His Ser Gly Val Gln Val Glu Gly Arg Arg Arg Gln Ser
    1535            1540                1545

Ser Ser Ala Asn Arg Arg Ala Gly Ser Ser Gly Ser Gly Val
    1550            1555                1560

Gln Gly Ala Ser Ala Gly Gly Leu Ala Ala Asp Ala Ser Arg Arg
    1565            1570                1575

Ser Gly Ala Arg Gln Gly Gln Ala Ser Ala Gln Gly Arg Ala Gly
    1580            1585                1590

Ser Gln Gly Gln Ala Gln Gly Arg Val Gly Ser Ala Asp Arg
    1595            1600                1605

Gln Gly Arg Arg Gly Val Ser Glu Ser Gln Ala Ser Asp Ser Glu
    1610            1615                1620

Gly His Ser Asp Phe Ser Glu Gly Gln Ala Val Gly Ala His Arg
    1625            1630                1635

Gln Ser Gly Ala Gly Gln Arg His Glu Gln Arg Ser Ser Arg Gly
    1640            1645                1650

Gln His Gly Ser Gly Phe Tyr Pro Val Tyr Tyr Tyr Glu Gln
    1655            1660                1665

Glu His Ser Glu Glu Ser Asp Ser Gln His Gln His Gly His
    1670            1675                1680

Gln His Glu Gln Gln Arg Gly His Gln His Gln His Gln His Glu
    1685            1690                1695

His Glu Gln Pro Glu Ser Gly His Arg Gln Gln Ser Ser Gly
    1700            1705                1710

Arg Gly His Gln Gly Ala His Gln Glu Gln Gly Arg Asp Ser Ala
    1715            1720                1725

Arg Ser Arg Gly Ser Asn Gln Gly His Ser Ser Arg His Gln
    1730            1735                1740

Ala Asp Ser Pro Arg Val Ser Ala Arg Ser Gly Ser Gly Gly Arg
    1745            1750                1755

Gly Gln Ser Pro Asp Ala Ser Gly Arg Ser Ser Asn Arg Arg Asp
    1760            1765                1770

Arg Pro Arg Gln Pro Ser Pro Ser Gln Ser Ser Asp Ser Gln Val
    1775            1780                1785

His Ser Gly Val Gln Val Glu Gly Arg Arg Gly Gln Ser Ser Ser
    1790            1795                1800

Ala Asn Arg Arg Ala Gly Ser Ser Ser Gly Ser Gly Val Gln Gly
    1805            1810                1815

Ala Ser Ala Gly Gly Leu Ala Ala Asp Ala Ser Arg Arg Ser Gly
    1820            1825                1830

Ala Leu Gln Gly Gln Ala Ser Ala Gln Gly Arg Ala Gly Ser Gln
    1835            1840                1845

Gly Gln Ala Gln Gly Arg Val Gly Ser Ser Ala Asp Arg Gln Gly
    1850            1855                1860

Arg Arg Gly Val Ser Glu Ser Gln Ala Ser Asp Ser Glu Gly His
    1865            1870                1875

Ser Asp Phe Ser Glu Gly Gln Ala Val Gly Ala His Arg Gln Ser
    1880            1885                1890

Gly Ala Gly Gln Arg His Glu Gln Arg Ser Ser Arg Gly Gln His
    1895            1900                1905

Gly Ser Gly Tyr Tyr Tyr Glu Gln Glu His Ser Glu Glu Glu Ser
    1910            1915                1920
```

Asp Ser Gln His Gln His Gly His Gln His Glu Gln Gln Arg Gly
1925                    1930                1935

His Gln His Gln His Gln His Gln His Glu His Glu Gln Pro Glu
1940                    1945                1950

Ser Gly His Arg Gln Gln Ser Ser Gly Arg Gly Asn Gln Gly
1955                    1960                1965

Ala His Gln Glu Gln Gly Arg Asp Ser Ala Arg Ser Arg Gly Ser
1970                    1975                1980

Asn Gln Gly His Ser Ser Arg His Gln Ala Asp Ser Pro Arg
1985                    1990                1995

Val Ser Ala Arg Ser Gly Ser Gly Gly Arg Gly Gln Ser Pro Asp
2000                    2005                2010

Ala Ser Gly Arg Ser Ser Asn Arg Arg Asp Arg Pro Arg Gln Pro
2015                    2020                2025

Ser Pro Ser Gln Ser Ser Asp Ser His Val His Ser Gly Val Gln
2030                    2035                2040

Val Glu Gly Arg Arg Gly Gln Ser Ser Ser Ala Asn Arg Arg Ala
2045                    2050                2055

Gly Ser Ser Ser Ser Gly Val Gln Gly Ala Ser Ala Gly Gly
2060                    2065                2070

Leu Ala Ala Asp Ala Ser Arg Arg Ser Gly Ala Arg Gln Gly Gln
2075                    2080                2085

Ala Ser Ala Gln Gly Arg Ala Gly Ser Gln Gly Gln Ala Gln Gly
2090                    2095                2100

Arg Val Gly Ser Ser Ala Asp Arg Gln Gly Arg Arg Gly Val Ser
2105                    2110                2115

Glu Ser Gln Ala Ser Asp Ser Glu Gly His Ser Asp Phe Ser Glu
2120                    2125                2130

Gly Gln Ala Val Gly Ala His Arg Gln Ser Gly Ala Gly Gln Arg
2135                    2140                2145

His Glu Gln Arg Ser Ser Arg Gly Gln His Gly Ser Gly Phe Tyr
2150                    2155                2160

Pro Val Tyr Tyr Tyr Tyr Glu Gln Glu His Ser Glu Glu Glu Ser
2165                    2170                2175

Asp Ser Gln His Gln His Gly His Gln His Glu Gln Gln Arg Gly
2180                    2185                2190

His Gln His Gln His Gln His Gln His Glu His Glu Gln Pro Glu
2195                    2200                2205

Ser Gly His Arg Gln Gln Gln Phe Ser Gly Arg Gly His Gln Gly
2210                    2215                2220

Ala His Gln Glu Gln Gly Arg Asp Ser Ala Arg Ser Arg Gly Ser
2225                    2230                2235

Asn Gln Gly His Ser Ser Arg His Gln Ala Asp Ser Pro Arg
2240                    2245                2250

Val Ser Ala Arg Ser Gly Ser Gly Gly Arg Gly Gln Ser Pro Asp
2255                    2260                2265

Ala Ser Val Arg Ser Ser Asn Arg Arg Asp Arg Pro Arg Gln Pro
2270                    2275                2280

Ser Pro Ser Gln Ser Ser Asp Ser His Val His Ser Gly Val Gln
2285                    2290                2295

Val Glu Gly Arg Arg Gly Gln Ser Ser Ser Ala Asn Arg Arg Ala
2300                    2305                2310

Gly Ser Ser Ser Gly Ser Gly Val Gln Gly Ala Ser Ala Gly Gly

-continued

```
            2315                2320                2325

Leu Ala Ala Asp Ala Ser Arg Arg Ser Gly Ala Arg Gln Gly Gln
            2330                2335                2340

Ala Ser Ala Gln Gly Arg Ala Gly Ser Gln Gly Gln Ala Gln Gly
            2345                2350                2355

Arg Val Gly Ser Ser Ala Asp Arg Gln Gly Arg Gly Val Ser
            2360                2365                2370

Glu Ser Gln Ala Ser Asp Ser Glu Gly His Ser Asp Phe Ser Glu
            2375                2380                2385

Gly Gln Ala Val Gly Ala His Arg Gln Ser Gly Ala Gly Gln Arg
            2390                2395                2400

His Glu Gln Arg Ser Ser Arg Gly Gln His Gly Ser Gly Phe Tyr
            2405                2410                2415

Pro Val Tyr Tyr Tyr Tyr Glu Gln Glu His Ser Glu Glu Glu Ser
            2420                2425                2430

Asp Ser Gln His Gln His Gly His Gln His Glu Gln Gln Arg Gly
            2435                2440                2445

His Gln His Gln His Lys His Glu His Glu Gln Pro Glu Ser Gly
            2450                2455                2460

His Arg Gln Gln Gln Phe Ser Gly Arg Gly His Gln Gly Ala His
            2465                2470                2475

Gln Glu Gln Gly Arg Asp Ser Ala Arg Ser Arg Gly Ser Asn Gln
            2480                2485                2490

Gly His Ser Ser Ser Arg His Gln Ala Asp Ser Pro Arg Val Ser
            2495                2500                2505

Ala Arg Ser Gly Ser Gly Gly Arg Gly Gln Ser Pro Asp Ala Ser
            2510                2515                2520

Gly Arg Ser Ser Asn Arg Arg Asp Arg Pro Arg Gln Pro Ser Pro
            2525                2530                2535

Ser Gln Ser Ser Asp Ser Gln Val His Ser Gly Val Gln Val Glu
            2540                2545                2550

Gly Arg Arg Gly Gln Ser Ser Ser Ala Asn Arg Arg Ala Gly Ser
            2555                2560                2565

Ser Ser Ser Ser Gly Val Gln Gly Ala Ser Ala Gly Gly Leu Ala
            2570                2575                2580

Ala Asp Ala Ser Arg Arg Ser Gly Ala Arg Gln Gly Gln Ala Ser
            2585                2590                2595

Ala Gln Gly Arg Ala Gly Ser Gln Gly Gln Ala Gln Gly Arg Val
            2600                2605                2610

Gly Ser Ser Ala Asp Arg Gln Gly Arg Arg Gly Val Ser Glu Ser
            2615                2620                2625

Gln Ala Ser Asp Ser Glu Gly His Ser Asp Phe Ser Glu Gly Gln
            2630                2635                2640

Ala Val Gly Ala His Arg Gln Ser Gly Ala Gly Gln Arg His Glu
            2645                2650                2655

Gln Arg Ser Ser Arg Gly Gln His Gly Ser Gly Phe Tyr Pro Val
            2660                2665                2670

Tyr Tyr Tyr Tyr Glu Gln Glu His Ser Glu Glu Glu Ser Asp Ser
            2675                2680                2685

Gln His Gln His Gly His Gln His Glu Gln Gln Arg Gly His Gln
            2690                2695                2700

His Gln His Gln His Gln His Glu His Glu Gln Pro Glu Ser Gly
            2705                2710                2715
```

```
His Arg Gln Gln Gln Phe Ser Gly Arg Gly His Gln Gly Ala His
2720                2725                2730
Gln Glu Gln Gly Arg Asp Ser Ala Arg Ser Arg Gly Ser Asn Gln
2735                2740                2745
Gly His Ser Ser Ser Arg His Gln Ala Asp Ser Pro Arg Val Ser
2750                2755                2760
Ala Arg Ser Gly Ser Gly Gly Arg Gly Gln Ser Pro Asp Ala Ser
2765                2770                2775
Gly Arg Ser Ser Asn Arg Arg Asp Arg Pro Arg Gln Pro Ser Pro
2780                2785                2790
Ser Gln Ser Ser Asp Ser Gln Val His Ser Gly Val Gln Val Glu
2795                2800                2805
Gly Arg Arg Gly Gln Ser Ser Ser Ala Asn Arg Arg Ala Gly Ser
2810                2815                2820
Ser Ser Gly Ser Gly Val Gln Gly Ala Ser Ala Gly Gly Leu Ala
2825                2830                2835
Ala Asp Ala Ser Arg Arg Ser Gly Ala Arg Gln Gly Gln Ala Ser
2840                2845                2850
Ala Gln Gly Arg Ala Gly Ser Gln Gly Gln Ala Gln Gly Arg Val
2855                2860                2865
Gly Ser Ser Ala Asp Arg Gln Gly Arg Arg Gly Val Ser Glu Ser
2870                2875                2880
Gln Ala Ser Asp Ser Glu Gly His Ser Asp Phe Ser Glu Gly Gln
2885                2890                2895
Ala Val Gly Ala His Arg Gln Ser Gly Ala Gly Gln Arg His Glu
2900                2905                2910
Gln Arg Ser Ser Arg Gly Gln His Gly Ser Gly Tyr Tyr Tyr Glu
2915                2920                2925
Gln Glu His Ser Glu Glu Gln Gln Gln Phe Ser Gly Arg Gly
2930                2935                2940
His Gln Gly Ala His Gln Glu Gln Gly Arg Asp Ser Ala Arg Ser
2945                2950                2955
Arg Gly Ser Asn Gln Gly His Ser Ser Ser Arg His Gln Ala Asp
2960                2965                2970
Ser Pro Arg Val Ser Ala Arg Ser Gly Ser Gly Gly Arg Gly Gln
2975                2980                2985
Ser Pro Asp Ala Ser Gly Arg Ser Ser Asn Arg Arg Asp Arg Pro
2990                2995                3000
Arg Gln Pro Ser Pro Ser Gln Ser Ser Asp Ser Gln Val His Ser
3005                3010                3015
Gly Val Gln Val Glu Gly Arg Arg Gly Gln Ser Ser Ser Ala Asn
3020                3025                3030
Arg Arg Ala Gly Ser Ser Gly Ser Gly Val Gln Gly Ala Ser
3035                3040                3045
Ala Gly Gly Leu Ala Ala Asp Ala Ser Arg Arg Ser Gly Ala Arg
3050                3055                3060
Gln Gly Gln Ala Ser Ala Gln Gly Arg Ala Gly Ser Gln Gly Gln
3065                3070                3075
Ala Gln Gly Arg Val Gly Ser Ser Ala Asp Arg Gln Gly Arg Arg
3080                3085                3090
Gly Val Ser Glu Ser Gln Ala Ser Asp Ser Glu Gly His Ser Asp
3095                3100                3105
```

-continued

```
Phe Ser Glu Gly Gln Ala Val Gly Ala His Arg Gln Ser Gly Ala
    3110            3115               3120
Gly Gln Arg His Glu Gln Arg Ser Ser Arg Gly Gln His Gly Ser
    3125            3130               3135
Gly Phe Tyr Pro Val Tyr Tyr Tyr Glu Gln Glu His Ser Glu
    3140            3145               3150
Glu Glu Ser Asp Ser Gln His Gln His Gly His Gln His Glu Gln
    3155            3160               3165
Gln Arg Gly His Gln His Gln His Gln His Glu His Glu Gln Pro
    3170            3175               3180
Glu Ser Gly His Arg Gln Gln Ser Ser Gly Arg Gly His Gln
    3185            3190               3195
Gly Ala His Gln Glu Gln Gly Arg Asp Ser Ala Arg Ser Arg Gly
    3200            3205               3210
Ser Asn Gln Gly His Ser Ser Arg His Gln Ala Asp Ser Pro
    3215            3220               3225
Arg Val Ser Ala Arg Ser Gly Ser Gly Gly Arg Gly Gln Ser Pro
    3230            3235               3240
Asp Ala Ser Gly Arg Ser Ser Asn Arg Arg Asp Arg Pro Arg Gln
    3245            3250               3255
Pro Ser Pro Ser Gln Ser Ser Asp Ser Gln Val His Ser Gly Val
    3260            3265               3270
Gln Val Glu Gly Arg Arg Gly Gln Ser Ser Ala Asn Arg Arg
    3275            3280               3285
Ala Gly Ser Ser Ser Gly Ser Gly Val Gln Gly Thr Ser Ala Gly
    3290            3295               3300
Gly Leu Ala Ala Asp Ala Ser Arg Arg Ser Gly Ala Arg Gln Gly
    3305            3310               3315
Gln Ala Ser Ala Gln Gly Arg Ala Gly Ser Gln Gly Gln Ala Gln
    3320            3325               3330
Gly Arg Val Gly Ser Ser Ala Asp Arg Gln Gly Arg Arg Gly Val
    3335            3340               3345
Ser Glu Ser Gln Ala Ser Asp Ser Glu Gly His Ser Asp Phe Ser
    3350            3355               3360
Glu Gly Gln Ala Val Gly Ala His Arg Gln Ser Gly Ala Gly Gln
    3365            3370               3375
Arg His Glu Gln Arg Ser Ser Arg Gly Gln His Gly Ser Gly Tyr
    3380            3385               3390
Tyr Tyr Glu Gln Glu His Ser Glu Glu Glu Ser Asp Ser Gln His
    3395            3400               3405
Gln His Gly His Gln His Glu Gln Gln Arg Gly His Gln His Gln
    3410            3415               3420
His Gln His Gln His Glu His Glu Gln Pro Glu Ser Gly His Arg
    3425            3430               3435
Gln Gln Gln Ser Ser Gly Arg Gly Asn Gln Gly Ala His Gln Lys
    3440            3445               3450
Gln Gly Arg Asp Ser Ala Arg Ser Arg Gly Ser Asn Gln Gly His
    3455            3460               3465
Ser Ser Ser Arg His Gln Ala Asp Ser Pro Arg Val Ser Ala Arg
    3470            3475               3480
Ser Gly Ser Gly Gly Arg Gly Gln Ser Pro Asp Ala Ser Gly Arg
    3485            3490               3495
Ser Ser Asn Arg Arg Asp Arg Pro Arg Gln Pro Ser Pro Ser Gln
```

```
                3500                3505                3510

Ser  Ser  Asp  Ser  His  Val  His  Ser  Gly  Val  Gln  Val  Glu  Gly  Arg
     3515                3520                3525

Arg  Gly  Gln  Ser  Ser  Ser  Ala  Asn  Arg  Arg  Ala  Gly  Ser  Ser  Ser
     3530                3535                3540

Gly  Ser  Gly  Val  Gln  Gly  Ala  Ser  Ala  Gly  Gly  Leu  Ala  Ala  Asp
     3545                3550                3555

Ala  Ser  Arg  Arg  Ser  Gly  Ala  Arg  Gln  Gly  Gln  Ala  Ser  Ala  Gln
     3560                3565                3570

Gly  Arg  Ala  Gly  Ser  Gln  Gly  Gln  Ala  Gln  Gly  Arg  Val  Gly  Ser
     3575                3580                3585

Ser  Ala  Asp  Arg  Gln  Gly  Arg  Arg  Gly  Val  Ser  Glu  Ser  Gln  Ala
     3590                3595                3600

Ser  Asp  Ser  Glu  Gly  His  Ser  Asp  Phe  Ser  Glu  Gly  Gln  Ala  Val
     3605                3610                3615

Gly  Ala  His  Arg  Gln  Ser  Gly  Ala  Gly  Gln  Arg  His  Glu  Gln  Arg
     3620                3625                3630

Ser  Ser  Arg  Gly  Gln  His  Gly  Ser  Gly  Phe  Tyr  Pro  Val  Tyr  Tyr
     3635                3640                3645

Tyr  Tyr  Glu  Gln  Glu  His  Ser  Glu  Glu  Glu  Ser  Asp  Ser  Gln  His
     3650                3655                3660

Gln  His  Gly  His  Gln  His  Glu  Gln  Gln  Arg  Gly  His  Gln  His  Gln
     3665                3670                3675

His  Gln  His  Gln  His  Glu  His  Glu  Gln  Pro  Glu  Ser  Gly  His  Arg
     3680                3685                3690

Gln  Gln  Gln  Ser  Ser  Gly  Arg  Gly  His  Gln  Gly  Ala  His  Gln  Glu
     3695                3700                3705

Gln  Gly  Arg  Asp  Ser  Ala  Arg  Ser  Arg  Gly  Ser  Asn  Gln  Gly  His
     3710                3715                3720

Ser  Ser  Ser  Arg  His  Gln  Ala  Asp  Ser  Pro  Arg  Val  Ser  Ala  Arg
     3725                3730                3735

Ser  Gly  Ser  Gly  Gly  Arg  Gly  Gln  Ser  Pro  Asp  Ala  Ser  Gly  Arg
     3740                3745                3750

Ser  Ser  Asn  Arg  Arg  Asp  Arg  Pro  Arg  Gln  Pro  Ser  Pro  Ser  Gln
     3755                3760                3765

Ser  Ser  Asp  Ser  Gln  Val  His  Ser  Gly  Val  Gln  Val  Glu  Gly  Arg
     3770                3775                3780

Arg  Gly  Gln  Ser  Ser  Ser  Ala  Asn  Arg  Arg  Ala  Gly  Ser  Ser  Ser
     3785                3790                3795

Gly  Ser  Gly  Val  Gln  Gly  Ala  Ser  Ala  Gly  Gly  Leu  Ala  Ala  Asp
     3800                3805                3810

Ala  Ser  Arg  Arg  Ser  Gly  Ala  Arg  Gln  Gly  Gln  Ala  Ser  Ala  Gln
     3815                3820                3825

Gly  Arg  Ala  Gly  Ser  Gln  Gly  Gln  Ala  Gln  Gly  Arg  Val  Gly  Ser
     3830                3835                3840

Ser  Ala  Asp  Arg  Gln  Gly  Arg  Arg  Gly  Val  Ser  Gly  Ser  Gln  Ala
     3845                3850                3855

Ser  Asp  Ser  Glu  Gly  His  Ser  Asp  Phe  Ser  Glu  Gly  Gln  Ala  Val
     3860                3865                3870

Gly  Ala  His  Arg  Gln  Ser  Gly  Ala  Gly  Gln  Arg  His  Glu  Gln  Arg
     3875                3880                3885

Ser  Ser  Arg  Gly  Gln  His  Gly  Ser  Gly  Tyr  Tyr  Tyr  Glu  Gln  Glu
     3890                3895                3900
```

```
His Ser Glu Glu Ser Asp Ser Gln His Gln His Gly His Gln
    3905            3910                3915

His Glu Gln Gln Arg Gly His Gln His Gln His Gln His Gln His
    3920            3925                3930

Glu His Glu Gln Pro Glu Ser Gly His Arg Gln Gln Phe Ser
    3935            3940                3945

Gly Arg Gly His Gln Gly Ala His Gln Glu Gln Gly Arg Asp Ser
    3950            3955                3960

Ala Arg Ser Arg Gly Ser Asn Gln Gly His Ser Ser Arg His
    3965            3970                3975

Gln Ala Asp Ser Pro Arg Val Ser Ala Arg Ser Gly Ser Gly Gly
    3980            3985                3990

Arg Gly Gln Ser Pro Asp Ala Ser Gly Arg Ser Asn Arg Arg
    3995            4000                4005

Asp Arg Pro Arg Gln Pro Ser Pro Ser Gln Ser Ser Asp Ser Gln
    4010            4015                4020

Val His Ser Gly Val Gln Val Glu Gly Arg Arg Gly Gln Ser Ser
    4025            4030                4035

Ser Ala Asn Arg Arg Ala Gly Ser Ser Ser Gly Ser Gly Val Gln
    4040            4045                4050

Gly Ala Ser Ala Gly Gly Leu Ala Ala Asp Ala Ser Arg Arg Ser
    4055            4060                4065

Gly Ala Leu Gln Gly Gln Ala Ser Ala Gln Gly Arg Ala Gly Ser
    4070            4075                4080

Gln Gly Gln Ala Gln Gly Arg Val Gly Ser Ser Ala Asp Arg Gln
    4085            4090                4095

Gly Arg Arg Gly Val Ser Glu Ser Gln Ala Ser Asp Ser Glu Gly
    4100            4105                4110

His Ser Asp Phe Ser Glu Gly Gln Ala Val Gly Ala His Arg Gln
    4115            4120                4125

Ser Gly Ala Gly Gln Arg His Glu Gln Arg Ser Arg Gly Gln
    4130            4135                4140

His Gly Ser Gly Tyr Tyr Tyr Glu Gln Glu His Ser Glu Glu Glu
    4145            4150                4155

Ser Asp Ser Gln His Gln His Gly His Gln His Glu Gln Gln Arg
    4160            4165                4170

Gly His Gln His Gln His Gln His Gln His Glu His Glu Gln Pro
    4175            4180                4185

Glu Ser Gly His Arg Gln Gln Ser Ser Gly Arg Gly His Gln
    4190            4195                4200

Gly Ala His Gln Glu Gln Gly Arg Asp Ser Ala Arg Ser Arg Gly
    4205            4210                4215

Ser Asn Gln Gly His Ser Ser Arg His Gln Ala Asp Ser Pro
    4220            4225                4230

Arg Val Ser Ala Arg Ser Gly Ser Gly Gly Arg Gly Gln Ser Pro
    4235            4240                4245

Asp Ala Ser Gly Arg Ser Ser Asn Arg Arg Asp Arg Pro Arg Gln
    4250            4255                4260

Pro Ser Pro Ser Gln Ser Ser Asp Ser Gln Val His Ser Gly Val
    4265            4270                4275

Gln Val Glu Gly Arg Arg Gly Gln Ser Ser Ser Ala Asn Arg Arg
    4280            4285                4290
```

```
Ala Gly Ser Ser Ser Ser Ser Gly Val Gln Gly Ala  Ser Ala Gly
4295                4300                     4305

Gly Leu Ala Ala Asp Ala Ser Arg Arg Ser Gly Ala  Arg Gln Gly
4310                4315                     4320

Gln Ala Ser Ala Gln Gly Arg Ala Gly Ser Gln Gly  Gln Ala Gln
4325                4330                     4335

Gly Arg Val Gly Ser Ser Ala Asp Arg Gln Gly Arg  Arg Gly Val
4340                4345                     4350

Ser Glu Ser Gln Ala Ser Asp Ser Glu Gly His Ser  Asp Phe Ser
4355                4360                     4365

Glu Gly Gln Ala Val Gly Ala His Arg Gln Ser Gly  Ala Gly Gln
4370                4375                     4380

Arg His Glu Gln Arg Ser Ser Arg Gly Gln His Gly  Ser Gly Phe
4385                4390                     4395

Tyr Pro Val Tyr Tyr Tyr Tyr Glu Gln Glu His Ser  Glu Glu Glu
4400                4405                     4410

Ser Asp Ser Gln His Gln His Gly His Gln His Glu  Gln Gln Arg
4415                4420                     4425

Gly His Gln His Gln His Gln His Gln His Glu His  Glu Gln Pro
4430                4435                     4440

Glu Ser Gly His Arg Gln Gln Gln Phe Ser Gly Arg  Gly His Gln
4445                4450                     4455

Gly Ala His Gln Glu Gln Gly Arg Asp Ser Ala Arg  Ser Arg Gly
4460                4465                     4470

Ser Asn Gln Gly His Ser Ser Ser Arg His Gln Ala  Asp Ser Pro
4475                4480                     4485

Arg Val Ser Ala Arg Ser Gly Ser Gly Gly Arg Gly  Gln Ser Pro
4490                4495                     4500

Asp Ala Ser Gly Arg Ser Ser Asn Arg Arg Asp Arg  Pro Arg Gln
4505                4510                     4515

Pro Ser Pro Ser Gln Ser Ser Asp Ser Gln Val His  Ser Gly Val
4520                4525                     4530

Gln Val Glu Gly Arg Arg Gly Gln Ser Ser Ser Ala  Asn Arg Arg
4535                4540                     4545

Ala Gly Ser Ser Ser Gly Ser Gly Val Gln Gly Ala  Ser Ala Gly
4550                4555                     4560

Gly Leu Ala Ala Asp Ala Ser Arg Arg Ser Gly Ala  Arg Gln Gly
4565                4570                     4575

Gln Ala Ser Ala Gln Gly Arg Ala Gly Ser Gln Gly  Gln Ala Gln
4580                4585                     4590

Gly Arg Val Gly Ser Ser Ala Asp Arg Gln Gly Arg  Arg Gly Val
4595                4600                     4605

Ser Glu Ser Gln Ala Ser Asp Ser Glu Gly His Ser  Asp Phe Ser
4610                4615                     4620

Glu Gly Gln Ala Val Gly Ala His Arg Gln Ser Gly  Ala Gly Gln
4625                4630                     4635

Arg His Glu Gln Arg Ser Ser Arg Gly Gln His Gly  Ser Gly Tyr
4640                4645                     4650

Tyr Tyr Glu Gln Glu His Ser Glu Glu Glu Ser Asp  Ser Gln His
4655                4660                     4665

Gln Gln Gly His Gln His Glu Gln Gln Arg Gly His  Gln His Gln
4670                4675                     4680

His Gln His Gln His Glu His Glu Gln Pro Glu Ser  Gly His Arg
```

```
                    4685              4690              4695
Gln Gln Gln Ser Ser Gly Arg Gly His Gln Gly Ala His Gln Glu
    4700              4705              4710
Gln Gly Arg Asp Ser Ala Arg Ser Arg Gly Ser Asn Gln Gly His
    4715              4720              4725
Ser Ser Ser Arg His Gln Ala Asp Ser Pro Arg Val Ser Ala Arg
    4730              4735              4740
Ser Gly Ser Gly Gly Arg Gly Gln Ser Pro Asp Gly Ser Gly Arg
    4745              4750              4755
Ser Ser Asn Arg Arg Asp Arg Pro Arg Gln Pro Ser Ala Ser Gln
    4760              4765              4770
Ser Ser Asp Ser Gln Val His Ser Gly Val Gln Val Glu Ala Gln
    4775              4780              4785
Arg Gly Gln Ser Ser Ser Ala Asn Arg Arg Ala Gly Ser Ser Ser
    4790              4795              4800
Gly Ser Gly Val Gln Ser Ala Ala Ala Ser Gly Gln Gly Gly Tyr
    4805              4810              4815
Glu Ser Ile Phe Thr Ala Lys His Leu Asp Phe Asn Gln Ser His
    4820              4825              4830
Ser Tyr Tyr Tyr Tyr
    4835

<210> SEQ ID NO 11
<211> LENGTH: 336
<212> TYPE: PRT
<213> ORGANISM: Mus musculus

<400> SEQUENCE: 11

Pro Asp Gly Ser Gly Arg Ser Ser Asn Arg Arg Asp Arg Pro Arg Gln
1               5                   10                  15
Leu Ser Pro Ser Gln Ser Ser Asp Ser Gln Val His Ser Gly Val Gln
                20                  25                  30
Val Glu Gly Arg Arg Gly His Ser Ser Ala Asn Arg Arg Ala Gly
            35                  40                  45
Ser Ser Ser Gly Ser Gly Val Gln Gly Ala Ser Ala Gly Gly Leu Ala
        50                  55                  60
Ala Asp Ala Ser Arg Arg Ser Gly Ala Arg Gln Gly Gln Ala Ser Ala
65                  70                  75                  80
Gln Gly Arg Ala Gly Ser Gln Gly Gln Ala Gln Gly Arg Val Ser Ser
                85                  90                  95
Ser Ala Asp Arg Gln Gly Arg Arg Gly Val Ser Glu Ser Arg Ala Ser
                100                 105                 110
Asp Ser Glu Gly His Ser Asp Phe Ser Glu Gly Gln Ala Val Gly Ala
            115                 120                 125
His Arg Gln Ser Gly Ala Gly Gln Arg His Glu Gln Arg Ser Ser Arg
        130                 135                 140
Gly Gln His Gly Ser Gly Tyr Tyr Tyr Glu Gln Glu His Ser Glu Glu
145                 150                 155                 160
Glu Ser Asp Ser Gln His Gln His Gly His Gln His Glu Gln Gln Arg
                165                 170                 175
Gly His Gln His Gln His Gln His Gln His Glu His Glu Gln Pro Glu
            180                 185                 190
Ser Gly His Arg Gln Gln Gln Ser Ser Gly Arg Gly His Gln Gly Ala
        195                 200                 205
```

```
His Gln Glu Gln Gly Arg Asp Ser Ala Arg Pro Gly Ser Asn Gln
    210                 215                 220

Gly His Ser Ser Arg His Gln Ala Asp Ser Pro Arg Val Ser Ala
225                 230                 235                 240

Arg Ser Gly Ser Gly Arg Gly Gln Ser Pro Asp Ala Ser Gly Arg
                245                 250                 255

Ser Ser Asn Arg Arg Asp Arg Pro Gln Pro Ser Pro Ser Gln Ser
            260                 265                 270

Ser Asp Ser Gln Val His Ser Gly Val Gln Val Glu Ala Gln Arg Gly
        275                 280                 285

Gln Ser Ser Ser Ala Asn Arg Arg Ala Gly Ser Ser Gly Ser Gly
    290                 295                 300

Val Gln Gly Ala Ala Ser Gly Gln Gly Gly Tyr Glu Ser Ile Phe
305                 310                 315                 320

Thr Ala Lys His Leu Asp Phe Asn Gln Ser His Ser Tyr Tyr Tyr
                325                 330                 335

<210> SEQ ID NO 12
<211> LENGTH: 357
<212> TYPE: PRT
<213> ORGANISM: Mus musculus

<400> SEQUENCE: 12

Met Ser Ala Leu Leu Glu Ser Ile Thr Ser Met Ile Glu Ile Phe Gln
1               5                   10                  15

Gln Tyr Ser Thr Ser Asp Lys Glu Glu Glu Thr Leu Ser Lys Glu Glu
                20                  25                  30

Leu Lys Glu Leu Leu Glu Gly Gln Leu Gln Ala Val Leu Lys Asn Pro
            35                  40                  45

Asp Asp Gln Asp Ile Ala Glu Val Phe Met Gln Met Leu Asp Val Asp
        50                  55                  60

His Asp Asp Lys Leu Asp Phe Ala Glu Tyr Leu Leu Leu Val Leu Lys
65                  70                  75                  80

Leu Ala Lys Ala Tyr Tyr Glu Ala Ser Lys Asn Glu Ser Phe Gln Thr
                85                  90                  95

His Gly Ser Asn Gly Arg Ser Lys Thr Asp Tyr Lys Gly Leu Glu Glu
            100                 105                 110

Glu Gly Glu Gly Asn Lys Gln Asn Leu Arg Arg Arg His Gly Gly
        115                 120                 125

Thr Asp Gly Lys Arg Lys Ser Asp Arg Thr Arg Ser Pro Asn Gly Lys
130                 135                 140

Arg Gly Lys Arg Gln Glu Ser Arg Cys Arg Ser Gly Lys Asp Lys
145                 150                 155                 160

His Arg Arg Glu Pro Glu Lys His Arg His Gln Gln Asp Ser Lys Arg
                165                 170                 175

Lys Gln Arg His Gly Ser Gly Ser Thr Glu Arg Lys Asp Asn Arg Asn
            180                 185                 190

Lys Lys Asn Arg Gln Ser Lys Glu Arg Asn Tyr Asp Glu Ile Tyr Asp
        195                 200                 205

Asn Gly Lys Tyr Asn Glu Asp Trp Glu Ala Ser Tyr Asn Asn Cys Tyr
    210                 215                 220

Tyr Lys Thr Gln Asn Thr Thr Leu Asp Gln Arg Glu Gly Asn Arg Arg
225                 230                 235                 240

Pro Arg Ala Asp Ser Gln Lys Glu Pro Gln Ser Ser His Gly Gln Ala
                245                 250                 255
```

```
Asp Asn Ser Asp Ser Glu Gly Gly Arg Gln Gln Ser His Ser Lys Pro
            260                 265                 270

Ser Pro Val Arg Ala Asp Gln Arg Ser Arg Ala Gly Gln Ala Gly
        275                 280                 285

Ser Ser Lys Val Ser Ala Arg Ser Gly Ser Gly Gly Arg Gly Gln Ser
    290                 295                 300

Pro Asp Gly Ser Gly Arg Ser Ser Asn Arg Arg Asp Arg Pro Arg Gln
305                 310                 315                 320

Pro Ser Pro Ser Gln Ser Ser Asp Ser Gln Val His Ser Gly Val Gln
                325                 330                 335

Val Glu Gly Arg Arg Gly Gln Ser Ser Ala Asn Arg Arg Ala Gly
            340                 345                 350

Ser Ser Ser Gly Ser
            355

<210> SEQ ID NO 13
<211> LENGTH: 687
<212> TYPE: PRT
<213> ORGANISM: Rattus norvegicus

<400> SEQUENCE: 13

Met Asn Arg Asn Glu Asn Met Asn Thr Asn Ser Gln Ser Pro Ala Thr
1               5                   10                  15

Gly Ser Arg Gly Pro Val Gly Glu Arg Thr Gly Gln Leu Ala Met Asn
            20                  25                  30

Arg Lys Ala Thr Ala Pro Gly Lys Gly Ala Leu Thr Arg Thr Ala
        35                  40                  45

Pro Leu Ala Pro Arg Arg Ser His Ala Glu Gly Leu Glu Pro Val
    50                  55                  60

Pro Val Arg Val Arg Gly Pro Arg Gly Arg Leu Pro Gly Thr Ala Leu
65              70                  75                  80

Ser Thr Pro Ser Pro Glu Gly Ala Arg Pro Ser Ala Val Asp Ala Gln
            85                  90                  95

Asp Thr Pro Leu Gly Glu Pro Thr Lys Thr Ala Thr Ser Arg Gln Gln
            100                 105                 110

Thr Ala Leu Pro Ala Pro Gly Pro Gly Glu Ala Arg Pro Ala Pro Thr
        115                 120                 125

Val Arg Ala Arg Pro Pro Val Val Arg Pro Ala Ala Glu Ala Leu Gln
    130                 135                 140

Pro Pro Gly Thr His Leu Ala Pro Asn Ser Leu Gln Thr Leu Leu Ala
145                 150                 155                 160

Gly Pro Asp Pro Ala Val Asp Ser Ser Pro Pro Asn Asp Met Leu Thr
            165                 170                 175

Gln Pro Arg Ala Ala Gln Glu Pro Ala Pro Glu Glu Glu Ser Pro
            180                 185                 190

Gln Leu Ala Ser Ser Pro Thr Glu Pro Gly Thr Ser Asn Pro Gly
        195                 200                 205

Gly Val Glu Pro Gly Arg Pro Ala Pro Ala Ser Pro Val Thr Ala Lys
    210                 215                 220

Ala Ile Leu Glu Pro Met Pro Gly Ser Gly Lys Gly Arg Pro Gln Pro
225                 230                 235                 240

Leu Thr Gly Gly Gln Ala Pro Ala Gln Gly Ala Ser Gly Pro Leu Leu
            245                 250                 255

Val Ala Lys Gln Leu Thr Pro Pro Val Ala Gln Gly Pro Val Lys Ala
```

-continued

```
                260                 265                 270
Arg His Gln Ala Arg Val Val Gln Gly Pro Glu Ala Gly Lys Leu Arg
            275                 280                 285
Ala Ser Leu Val Met Gly Ser Arg Gln Thr Ala Thr Gly Thr Leu Gly
        290                 295                 300
Pro Gly Lys His Lys Pro Thr Gln Pro Gln Ala Leu Thr Ala Gly Gly
305                 310                 315                 320
Leu Ala Gly Pro Ala Arg Val Arg Pro Ala Thr Ala Arg Ala Thr Pro
                325                 330                 335
Thr Thr Gln Lys His Thr His Arg Gly Ala His Gly Gly Ile Gln Thr
            340                 345                 350
Ser Gln Arg His Glu Gln Arg Pro Ser Arg Gly Gln Gln Gly Ser Gly
        355                 360                 365
His Pro Gln Val Tyr Tyr Tyr Gly Val Glu Thr Glu Asp Glu Ser
        370                 375                 380
Asp Ala Gln Gln Gly His His Gln Gln Gln Gln Gln Arg Gln Gln
385                 390                 395                 400
Gln Arg Gln Arg His Gln His Glu Gln Glu Arg Glu His Glu His Gln
                405                 410                 415
Gln Pro Glu Ser Ser His Arg Gln Gln Gly Ser Ser Gly Arg Thr His
            420                 425                 430
Arg Ala Ala Arg His Glu Gln Glu Ser Asp Ser Thr Arg Gln Arg Gly
        435                 440                 445
Ser His Gln Ala His Ser Ser Ala Arg Thr Gln Glu Glu Ile Ala Arg
        450                 455                 460
Gly Arg Ser Gly Ala Ser Ala Ser Glu Gly Pro Gly Pro Gln Arg Glu
465                 470                 475                 480
Ala Ala Arg Asp Ser Ser Glu His Ala Gln Ser Arg Arg Ser Glu Thr
                485                 490                 495
Ile Ser Arg Gly Arg Ser Gly His Ser Thr Gly Arg Ala His Glu Asp
            500                 505                 510
Arg His Glu Gln Ala Thr Asp Arg Ser Ala Arg Ser Gly Ser Arg Gly
        515                 520                 525
Gly Gln Ala Gly Ser His Ser Glu Ser Glu Ala Ser Gly Gly Gln Ala
        530                 535                 540
Gly Arg Arg Gly Thr Ala Ala Thr Arg His Thr Ser Arg Pro Glu Gln
545                 550                 555                 560
Ser Pro Asp Thr Ala Gly Arg Thr Gly Ser Ser Arg Gly Gln Gln Ser
                565                 570                 575
Ala Gln Arg His Ala Asp Ser Thr Pro Gly Ser Thr Arg Thr Gly Ser
            580                 585                 590
Arg Gly Arg Gly Glu Ser Pro Ala Gly Gln Gln Ser Pro Asp Arg Ala
        595                 600                 605
Arg His Ile Glu Ser Arg Arg Gly Arg Thr Arg Glu Ala Ser Ala Ser
        610                 615                 620
Gln Ser Ser Asp Ser Glu Gly His Ser Gly Ala His Ala Gly Ile Gly
625                 630                 635                 640
Gln Gly Gln Thr Ser Thr Thr His Arg Arg Ala Gly Ser Ser Ser Gly
                645                 650                 655
Ser Gln Gln Ala Ser Val Glu Gly Ser Asp Gly Tyr Asp Ser Ile Val
            660                 665                 670
Lys Ser Lys Tyr Leu Ser Phe Ser Gln Ser His Cys Tyr Tyr Tyr
        675                 680                 685
```

<210> SEQ ID NO 14
<211> LENGTH: 3088
<212> TYPE: PRT
<213> ORGANISM: Pan troglodytes

<400> SEQUENCE: 14

```
Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
            20                  25                  30

Leu Lys Glu Leu Leu Glu Lys Glu Phe Arg Gln Ile Leu Lys Asn Pro
        35                  40                  45

Asp Asp Pro Asp Met Val Asp Val Phe Met Asp His Leu Asp Ile Asp
    50                  55                  60

His Asn Lys Lys Ile Asp Phe Thr Glu Phe Leu Leu Met Val Phe Lys
65                  70                  75                  80

Leu Ala Gln Ala Tyr Tyr Glu Ser Thr Arg Lys Glu Asn Leu Pro Ile
                85                  90                  95

Ser Gly His Lys His Arg Lys His Ser His His Asp Lys His Glu Asp
            100                 105                 110

Asn Lys Gln Glu Glu Asn Lys Glu Asn Arg Lys Arg Pro Ser Ser Leu
        115                 120                 125

Glu Arg Arg Asn Asn Arg Lys Gly Asn Lys Gly Arg Ser Lys Ser Pro
    130                 135                 140

Arg Glu Thr Gly Gly Lys Arg His Glu Ser Ser Ser Glu Lys Lys Glu
145                 150                 155                 160

Arg Lys Gly Tyr Ser Pro Thr His Arg Glu Glu Tyr Gly Lys Asn
                165                 170                 175

His His Asn Ser Ser Lys Lys Gln Lys Asn Lys Thr Glu Asn Thr Arg
            180                 185                 190

Leu Glu Asp Asn Arg Lys Arg Leu Ser Glu Arg Leu Glu Glu Lys Glu
        195                 200                 205

Asp Asn Glu Glu Gly Gly Tyr Asp Tyr Glu Asn Thr Gly Arg Met Thr
    210                 215                 220

Gln Lys Trp Ile Gln Ser Gly His Ile Ala Thr Tyr Tyr Thr Ile Gln
225                 230                 235                 240

Asp Glu Ala Tyr Asp Thr Thr Asp Asn Leu Leu Glu Glu Asn Lys Ile
                245                 250                 255

Tyr Glu Arg Ser Arg Ser Ser Asp Asp Lys Ser Ser Ser Gln Val Asn
            260                 265                 270

Arg Ser Arg His Glu Asn Thr Ser Gln Val Pro Leu Gln Glu Ser Arg
        275                 280                 285

Thr Arg Lys Arg Arg Gly Ser Arg Val Ser Gln Asp Arg Asp Ser Glu
    290                 295                 300

Gly His Ser Glu Asp Ser Glu Arg His Ser Gly Ser Ala Ser Arg Asn
305                 310                 315                 320

His Pro Gly Ser Ala Arg Gln Gln Ser Arg Asp Gly Ser Arg His Pro
                325                 330                 335

Arg Ser His Asp Glu Asp Arg Ala His Gly His Ser Ala Asp Ser
            340                 345                 350

Ser Arg Gln Ser Gly Thr Arg His Ala Glu Thr Ser Ser Arg Gly Gln
        355                 360                 365

Thr Ala Ser Ser His Glu Gln Ala Arg Ser Ser Pro Gly Glu Arg His
```

```
            370                 375                 380
Gly Ser Arg His Gln Gln Ser Ala Asp Ser Ser Arg His Ser Ala Thr
385                 390                 395                 400

Gly Arg Gly Gln Ala Ser Ser Ala Val Ser Asp Arg Gly Pro Arg Gly
                405                 410                 415

Ser Ser Gly Ser Gln Ala Ser Asp Ser Glu Gly His Ser Glu Asn Ser
                420                 425                 430

Asp Thr Gln Ser Val Ser Gly His Gly Lys Ala Gly Pro Arg Gln Gln
                435                 440                 445

Ser His Gln Glu Ser Ala Arg Gly Arg Ser Gly Glu Arg Ser Gly His
                450                 455                 460

Ser Gly Ser Phe Leu Tyr Gln Val Ser Thr His Glu Gln Ser Asp Ser
465                 470                 475                 480

Ala His Gly Arg Thr Gly Thr Ser Thr Gly Gly Arg Gln Gly Ser His
                485                 490                 495

His Glu Gln Ala Arg Asp Ser Ser Arg His Ser Ala Ser Gln Glu Gly
                500                 505                 510

Gln Asp Thr Ile Arg Gly His Pro Gly Ser Ser Arg Gly Gly Arg Gln
                515                 520                 525

Gly Ser His His Glu Gln Leu Val Asn Arg Ser Gly His Ser Gly Ser
530                 535                 540

His His Ser His Thr Thr Ser Gln Gly Arg Ser Asp Ala Ser His Gly
545                 550                 555                 560

Gln Ser Gly Ser Arg Ser Ala Ser Arg Gln Thr Arg Asn Glu Glu Gln
                565                 570                 575

Ser Gly Asp Gly Ser Arg His Ser Gly Ser Arg His His Glu Ala Ser
                580                 585                 590

Ser Gln Ala Asp Ser Ser Arg His Ser Gln Val Gly Gln Gly Gln Ser
                595                 600                 605

Ser Gly Pro Arg Thr Ser Ser His Gln Gly Ser Ser Val Ser Gln Asp
                610                 615                 620

Ser Asp Ser Glu Gly His Ser Glu Asp Ser Glu Arg Trp Ser Gly Ser
625                 630                 635                 640

Ala Ser Arg Asn His His Gly Ser Ala Arg Glu Gln Ser Arg Asp Gly
                645                 650                 655

Ser Arg His Pro Arg Ser His Glu Asp Arg Ala Gly His Gly His
                660                 665                 670

Ser Ala Asp Ser Ser Arg Gln Ser Gly Thr Arg His Thr Glu Ser Ser
                675                 680                 685

Ser Arg Gly Gln Ala Val Ser Ser His Glu Gln Ala Arg Ser Ser Pro
                690                 695                 700

Gly Glu Arg His Gly Ser Arg His Gln Gln Ala Asp Ser Ser Arg
705                 710                 715                 720

His Ser Gly Ile Gly His Gly Gln Ala Ser Ser Ala Val Arg Asp Ser
                725                 730                 735

Gly His Arg Gly Ser Ser Gly Ser Gln Ala Ile Asp Ser Glu Gly His
                740                 745                 750

Ser Glu Asp Ser Asp Thr Gln Ser Val Ser Ser His Gly Gln Ala Gly
                755                 760                 765

Pro His Gln Gln Ser His Lys Glu Ser Ala Arg Gly Gln Ser Gly Glu
                770                 775                 780

Ser Ser Gly Arg Ser Gly Ser Phe Leu Tyr Gln Val Ser Ser His Glu
785                 790                 795                 800
```

-continued

```
Gln Ser Glu Ser Thr Tyr Gly Gln Thr Ala Pro Ser Thr Gly Gly Arg
                805                 810                 815
Gln Gly Ser Arg His Glu Gln Ala Arg Asn Ser Ser Arg His Ser Ala
            820                 825                 830
Ser Gln Asp Gly Gln Asp Thr Ile Arg Gly His Pro Gly Ser Ser Arg
        835                 840                 845
Gly Gly Arg Gln Gly Ser Tyr His Glu Gln Ser Val Asp Arg Ser Gly
    850                 855                 860
His Ser Gly Tyr His His Ser His Thr Thr Pro Gln Gly Arg Ser Asp
865                 870                 875                 880
Ala Ser His Gly Gln Ser Gly Pro Arg Ser Ala Ser Arg Gln Thr Arg
                885                 890                 895
Asn Glu Glu Gln Ser Gly Asp Gly Ser Arg His Ser Gly Ser Arg His
            900                 905                 910
His Glu Pro Ser Thr Arg Ala Ser Ser Arg His Ser Gln Val Gly
        915                 920                 925
Gln Gly Glu Ser Ala Val Ser Lys Thr Ser Arg Arg Gln Gly Ser Ser
    930                 935                 940
Val Ser Gln Asp Arg Asp Ser Glu Gly His Ser Glu Asp Ser Glu Arg
945                 950                 955                 960
Gln Ser Glu Ser Ala Ser Arg Asn His Tyr Gly Ser Ala Arg Glu Gln
                965                 970                 975
Ser Arg His Gly Ser Arg Asn Pro Arg Ser His Gln Glu Asp Arg Ala
            980                 985                 990
Ser His Gly His Ser Ala Glu Ser  Ser Arg Gln Ser Gly  Thr His His
        995                 1000                1005
Ala Glu  Thr Ser Ser His Gly  Gln Ala Ala Ser  Gln Glu Gln
        1010                1015                1020
Ala Arg  Ser Ser Arg Gly Glu  Arg His Gly Ser Arg  His Gln Gln
        1025                1030                1035
Ser Ala  Asp Ser Ser Thr Asp  Ser Gly Thr Gly Gly  Arg Gln Ala
        1040                1045                1050
Ser Ser  Val Val Gly Asp Ser  Gly Asn Arg Gly Ser  Ser Gly Ser
        1055                1060                1065
Gln Ala  Ser Asp Ser Glu Gly  His Ser Glu Asp Ser  Asp Thr Gln
        1070                1075                1080
Ser Val  Ser Ala His Gly Gln  Ala Gly Pro Arg Gln  Gln Ser His
        1085                1090                1095
Gln Glu  Ser Thr Arg Gly Gln  Ser Gly Glu Arg Ser  Gly Arg Ser
        1100                1105                1110
Gly Ser  Phe Leu Tyr Gln Val  Ser Thr His Glu Gln  Ser Glu Ser
        1115                1120                1125
Ala His  Gly Arg Thr Gly Pro  Ser Thr Gly Gly Arg  Gln Arg Ser
        1130                1135                1140
Arg His  Glu Gln Ala Arg Asp  Ser Ser Arg His Ser  Ala Ser Gln
        1145                1150                1155
Glu Ser  Gln Asp Ile Ile His  Ala His Pro Gly Ser  Ser Arg Gly
        1160                1165                1170
Gly Arg  Gln Gly Ser His Tyr  Glu Gln Ser Val Asp  Arg Ser Gly
        1175                1180                1185
His Ser  Gly Ser His His Ser  His Thr Thr Ser Gln  Glu Arg Ser
        1190                1195                1200
```

-continued

Asn Ala Ser His Gly Gln Ser Gly Ser Arg Ser Ala Ser Arg Gln
1205                    1210                    1215

Thr Arg Asn Glu Glu Gln Ser Gly Asp Gly Ser Arg His Ser Gly
1220                    1225                    1230

Ser Arg His His Glu Ala Ser Ser Arg Ala Asp Ser Ser Arg His
1235                    1240                    1245

Ser Gln Val Gly Gln Gly Gln Ser Ser Gly Pro Arg Thr Ser Arg
1250                    1255                    1260

Asn Gln Gly Ser Ser Val Ser Gln Asp Ser Asp Ser Gln Gly His
1265                    1270                    1275

Ser Glu Asp Ser Glu Arg Trp Ser Gly Ser Ala Ser Arg Asn His
1280                    1285                    1290

His Gly Ser Ala Trp Glu Gln Ser Arg Asp Gly Ser Arg His Pro
1295                    1300                    1305

Gly Ser His Gln Glu Asp Arg Ala Gly His Gly His Ser Ala Asp
1310                    1315                    1320

Ser Ser Arg Gln Ser Gly Thr His His Thr Glu Ser Ser Ser Arg
1325                    1330                    1335

Gly Gln Ala Ala Ser Ser His Glu His Ala Arg Ser Ser Ala Gly
1340                    1345                    1350

Glu Arg His Gly Ser His His Gln Gln Ser Ala Asp Ser Ser Arg
1355                    1360                    1365

His Ser Gly Ile Gly His Gly Gln Ala Ser Ser Ala Val Arg Asp
1370                    1375                    1380

Ser Gly His Arg Gly Ser Ser Gly Ser Gln Ala Ser Asp Ser Glu
1385                    1390                    1395

Gly His Ser Glu Asp Ser Asp Thr Gln Ser Leu Ser Ala His Gly
1400                    1405                    1410

Gln Ala Gly Pro His Gln Gln Ser His Gln Glu Ser Thr Arg Gly
1415                    1420                    1425

Arg Ser Ala Glu Arg Ser Gly Arg Ser Gly Ser Phe Leu Tyr Gln
1430                    1435                    1440

Val Ser Thr His Glu Gln Ser Glu Ser Ala His Gly Arg Thr Gly
1445                    1450                    1455

Thr Ser Thr Gly Gly Arg Lys Arg Ser Leu His Glu Gln Ala Arg
1460                    1465                    1470

Asp Ser Ser Arg His Ser Val Ser Gln Glu Gly Gln Asp Thr Ile
1475                    1480                    1485

His Gly His Ala Gly Ser Ser Ser Gly Gly Arg Gln Gly Ser His
1490                    1495                    1500

Tyr Glu Gln Leu Val Asp Arg Ser Gly His Ser Gly Ser His His
1505                    1510                    1515

Ser His Thr Thr Ser Gln Gly Arg Ser Asp Ala Tyr His Gly Gln
1520                    1525                    1530

Ser Gly Ser Arg Ser Ala Ser Arg Gln Thr His Asn Asp Glu Gln
1535                    1540                    1545

Ser Gly Asp Gly Phe Arg His Ser Gly Ser His His His Glu Ala
1550                    1555                    1560

Ser Ser Arg Ala Asp Ser Ser Arg His Ser Gln Val Gly Gln Gly
1565                    1570                    1575

Gln Ser Glu Gly Pro Arg Thr Ser Arg His Arg Glu Ser Ser Val
1580                    1585                    1590

Ser Gln Asp Ser Asp Ser Glu Gly His Ser Glu Asp Ser Glu Arg

```
                1595                1600                1605

Trp Ser Gly Ser Ala Ser Arg Asn His His Gly Ser Ala Arg Glu
    1610                1615                1620

Gln Ser Arg Asp Gly Ser Arg His Pro Arg Ser His His Glu Asp
    1625                1630                1635

Arg Ala Gly His Gly His Ser Ala Asp Ser Ser Arg Gln Ser Gly
    1640                1645                1650

Thr Arg His Thr Gln Thr Ser Ser Gly Gly Gln Ala Ala Ser Ser
    1655                1660                1665

His Glu Gln Gly Arg Ser Ser Ala Gly Glu Arg His Gly Ser Arg
    1670                1675                1680

His Gln Gln Ser Ala Asp Ser Ser Arg His Ser Gly Ile Gly His
    1685                1690                1695

Gly Gln Ala Ser Ser Ala Val Arg Asp Ser Gly His Arg Gly Tyr
    1700                1705                1710

Ser Gly Ser Gln Ala Ser Asp Ser Glu Gly His Ser Glu Asp Ser
    1715                1720                1725

Asp Thr Gln Ser Val Ser Ala His Gly Gln Ala Gly Ser His Gln
    1730                1735                1740

Gln Ser His Gln Glu Ser Ala Arg Gly Arg Ser Gly Glu Arg Ser
    1745                1750                1755

Gly Arg Ser Gly Ser Phe Leu Tyr Gln Val Ser Thr His Glu Gln
    1760                1765                1770

Ser Glu Ser Ser His Gly Trp Thr Gly Pro Ser Thr Arg Gly Arg
    1775                1780                1785

Gln Gly Ser Arg His Glu Gln Ala Gln Asp Ser Arg His Ser
    1790                1795                1800

Ala Ser Gln Glu Gly Gln Asp Thr Ile Arg Gly His Pro Gly Pro
    1805                1810                1815

Ser Arg Gly Gly Arg Gln Gly Tyr His His Glu Gln Ser Val Asp
    1820                1825                1830

Ser Ser Gly His Ser Gly Ser His His Ser His Ile Thr Ser Gln
    1835                1840                1845

Gly Ser Ser His Ala Ser His Gly Gln Ser Gly Ser Arg Ser Ala
    1850                1855                1860

Ser Arg Thr Thr Arg Asn Asp Glu Gln Ser Val Asp Gly Ser Arg
    1865                1870                1875

His Ser Gly Ser Arg His His Glu Ala Ser Thr His Ala Asp Ile
    1880                1885                1890

Ser Arg His Ser Gln Ala Gly Gln Gly Gln Ser Glu Gly Ser Arg
    1895                1900                1905

Thr Ser Arg Arg Gln Gly Ser Ser Val Ser Gln Asp Ser Asp Ser
    1910                1915                1920

Glu Gly His Ser Glu Asp Ser Glu Arg Trp Ser Gly Ser Ala Ser
    1925                1930                1935

Arg Asn His Arg Gly Ser Ala Gln Glu Gln Ser Arg Asp Gly Ser
    1940                1945                1950

Arg His Pro Arg Ser His His Glu Asp Arg Ala Gly His Gly His
    1955                1960                1965

Ser Ala Asp Ser Ser Arg Gln Ser Gly Thr His Ala Glu Thr
    1970                1975                1980

Ser Ser Gly Gly Gln Ala Ala Ser Ser Arg Glu Gln Ala Arg Ser
    1985                1990                1995
```

```
Ser Pro Gly Glu Arg His Gly Ser Arg His Gln Gln Ser Ala Asp
    2000            2005                2010

Ser Ser Arg His Ser Gly Ile Arg Arg Gly Gln Ala Ser Ser Ala
    2015            2020                2025

Val Arg Asp Ser Gly His Trp Gly Ser Ser Gly Ser Gln Ala Ser
    2030            2035                2040

Asp Ser Glu Gly His Ser Glu Glu Ser Asp Thr Gln Ser Val Ser
    2045            2050                2055

Gly His Gly Gln Asp Gly Pro His Gln Ser His Gln Glu Ser
    2060            2065                2070

Ala Arg Asp Arg Ser Gly Gly Arg Ser Gly Arg Ser Gly Ser Phe
    2075            2080                2085

Leu Tyr Gln Val Ser Thr His Glu Gln Ser Glu Ser Thr His Gly
    2090            2095                2100

Gln Thr Gly Thr Ser Thr Gly Gly Arg Gln Gly Ser His His Glu
    2105            2110                2115

Gln Ala Arg Asp Ser Ser Arg His Ser Ala Ser Gln Glu Gly Gln
    2120            2125                2130

Asp Thr Ile His Ala His Pro Gly Ser Ser Arg Gly Gly Arg Gln
    2135            2140                2145

Gly Ser His His Glu Gln Ser Val Asp Thr Ser Gly His Ser Gly
    2150            2155                2160

Ser His His Ser His Thr Thr Ser Gln Gly Arg Ser Asp Ala Ser
    2165            2170                2175

His Gly Gln Ser Gly Ser Arg Ser Ala Ser Arg Gln Thr Arg Asn
    2180            2185                2190

Asp Glu Gln Ser Gly Asp Gly Ser Arg His Ser Gly Ser His His
    2195            2200                2205

His Glu Ala Phe Thr Gln Ala Asp Ser Ser Arg His Ser Gln Ser
    2210            2215                2220

Gly Gln Gly Glu Ser Ala Gly Ser Arg Arg Ser Arg Arg Gln Gly
    2225            2230                2235

Ser Ser Val Ser Gln Asp Ser Asp Ser Gln Gly His Ser Glu Asp
    2240            2245                2250

Ser Glu Arg Trp Ser Gly Ser Ala Ser Arg Asn Gln His Gly Ser
    2255            2260                2265

Ala Arg Glu Gln Ser Arg Asp Gly Ser Arg His Pro Gly Ser His
    2270            2275                2280

Gln Glu Asp Arg Ala Gly His Gly His Ser Ala Asp Ser Ser Arg
    2285            2290                2295

Gln Ser Gly Thr Arg His Thr Glu Ser Ser Ser Arg Gly Gln Ala
    2300            2305                2310

Ala Ser Ser His Glu Gln Ala Arg Ser Ser Ala Gly Glu Arg His
    2315            2320                2325

Gly Ser Arg His Gln Leu Gln Ser Ala Asp Ser Ser Arg His Ser
    2330            2335                2340

Gly Ile Gly His Gly Gln Ala Ser Ser Ala Val Arg Asp Ser Gly
    2345            2350                2355

His Arg Gly Ser Ser Gly Ser Gln Ala Ile Asp Ser Glu Gly His
    2360            2365                2370

Ser Glu Asp Ser Asp Thr Gln Ser Val Ser Ala Gln Gly Gln Ala
    2375            2380                2385
```

```
Gly Pro His Gln Arg Ser His Lys Glu Ser Ala Arg Gly Gln Ser
            2390                2395                2400
Gly Glu Ser Ser Gly Arg Ser Gly Ser Phe Leu Tyr Gln Val Ser
            2405                2410                2415
Thr His Glu Gln Pro Glu Ser Thr His Gly Gln Ser Ala Pro Ser
            2420                2425                2430
Thr Gly Gly Arg Gln Gly Ser His His Asp Gln Ala Gln Asp Ser
            2435                2440                2445
Ser Arg His Ser Ala Ser Gln Glu Gly Gln Asp Thr Ile Arg Gly
            2450                2455                2460
His Pro Gly Pro Ser Arg Gly Gly Arg Gln Gly Ser His His Lys
            2465                2470                2475
Gln Ser Val Asp Arg Ser Gly His Ser Gly Ser His His Ser His
            2480                2485                2490
Thr Thr Ser Gln Gly Arg Ser Asp Ala Ser Arg Gly Gln Ser Gly
            2495                2500                2505
Ser Arg Ser Ala Ser Arg Gln Thr His Asp Lys Glu Gln Ser Gly
            2510                2515                2520
Asp Gly Ser Arg His Ser Gly Ser Arg His His Glu Ala Ser Ser
            2525                2530                2535
Trp Ala Asp Ser Ser Arg His Ser Gln Ala Gly Gln Gly Gln Ser
            2540                2545                2550
Glu Gly Ser Arg Thr Ser Arg Arg Gln Gly Ser Ser Phe Ser Gln
            2555                2560                2565
Asp Ser Asp Ser Glu Gly His Ser Glu Asp Ser Glu Arg Arg Ser
            2570                2575                2580
Gly Ser Ala Ser Arg Asn His Arg Gly Ser Ala Gln Glu Gln Ser
            2585                2590                2595
Arg Asp Gly Ser Arg His Pro Arg Ser His His Glu Asp Arg Ala
            2600                2605                2610
Gly His Gly His Ser Ala Asp Ser Ser Arg Gln Ser Gly Thr His
            2615                2620                2625
His Ala Gln Asn Ser Ser Gly Gly Gln Ala Ala Ser Phe His Glu
            2630                2635                2640
Gln Ala Arg Ser Ser Ala Gly Glu Arg His Gly Ser His His Gln
            2645                2650                2655
Gln Ser Ala Asp Ser Ser Arg His Ser Gly Ile Gly His Gly Gln
            2660                2665                2670
Ala Ser Ser Ala Val Arg Asp Ser Gly His Arg Gly Ser Ser Gly
            2675                2680                2685
Ser Gln Ala Ser Asp Ser Glu Gly His Ser Glu Asp Ser Asp Thr
            2690                2695                2700
Gln Ser Val Ser Ala His Gly Gln Ala Gly Pro His Gln Gln Ser
            2705                2710                2715
His Gln Glu Ser Thr Arg Gly Arg Ser Ala Glu Arg Ser Gly Arg
            2720                2725                2730
Ser Gly Ser Phe Leu Tyr Gln Val Ser Thr His Glu Gln Ser Glu
            2735                2740                2745
Ser Ala His Gly Arg Thr Gly Pro Ser Thr Gly Gly Arg Gln Gly
            2750                2755                2760
Ser Arg His Glu Gln Ala Arg Asp Ser Ser Arg His Ser Ala Ser
            2765                2770                2775
Gln Glu Gly Gln Asp Thr Ile His Gly His Pro Gly Ser Arg Arg
```

```
                    2780              2785              2790

Gly Gly Arg Gln Gly Ser Tyr His Glu Gln Ser Val Asp Arg Ser
        2795              2800              2805

Gly His Ser Gly Ser His His Ser His Thr Thr Ser Gln Gly Arg
        2810              2815              2820

Ser Asp Ala Ser His Gly Gln Ser Gly Ser Arg Ser Ala Ser Arg
        2825              2830              2835

Gln Thr Arg Asn Glu Gln Gln Ser Gly Asp Gly Ser Arg His Ser
        2840              2845              2850

Gly Ser Ser His His Glu Ala Ser Thr Gln Ala Asp Ser Ser Arg
        2855              2860              2865

His Ser Gln Ser Gly Gln Gly Glu Ser Ala Gly Ser Arg Arg Ser
        2870              2875              2880

Arg Arg Gln Gly Ser Ser Val Ser Gln Asp Ser Asp Ser Glu Ala
        2885              2890              2895

Tyr Pro Glu Asp Ser Glu Arg Arg Ser Glu Ser Ala Ser Arg Asn
        2900              2905              2910

Arg His Gly Ser Ser Arg Glu Gln Ser Arg Asp Gly Ser Arg His
        2915              2920              2925

Pro Gly Ser Ser His Arg Asp Thr Thr Arg His Val Gln Ser Ser
        2930              2935              2940

Pro Val Gln Ser Asp Ser Ser Thr Ala Lys Glu His Gly His Phe
        2945              2950              2955

Ser Ser Leu Ser Gln Asp Ser Ala Tyr Arg Ser Gly Ile Gln Ser
        2960              2965              2970

Arg Gly Ser Pro His Ser Ser Ser Ser Tyr His Tyr Gln Ser Glu
        2975              2980              2985

Gly Thr Glu Arg Gln Lys Gly Gln Ser Gly Leu Val Trp Arg His
        2990              2995              3000

Gly Ser Tyr Gly Ser Ala Asp Tyr Asp Tyr Gly Glu Ser Gly Phe
        3005              3010              3015

Arg His Ser Gln His Gly Ser Val Ser Tyr Asn Ser Asn Pro Val
        3020              3025              3030

Val Phe Lys Glu Arg Ser Asp Ile Cys Lys Ala Ser Ala Phe Gly
        3035              3040              3045

Lys Asp His Pro Arg Tyr Tyr Ala Thr Tyr Ile Asn Lys Asp Pro
        3050              3055              3060

Gly Leu Cys Gly His Ser Ser Asp Ile Ser Lys Gln Leu Gly Phe
        3065              3070              3075

Ser Gln Ser Gln Arg Tyr Tyr Tyr Tyr Glu
        3080              3085

<210> SEQ ID NO 15
<211> LENGTH: 2764
<212> TYPE: PRT
<213> ORGANISM: Pan troglodytes

<400> SEQUENCE: 15

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
            20                  25                  30

Leu Lys Glu Leu Leu Glu Lys Glu Phe Arg Gln Ile Leu Lys Asn Pro
        35                  40                  45
```

```
Asp Asp Pro Asp Met Val Asp Val Phe Met Asp His Leu Asp Ile Asp
 50              55                  60
His Asn Lys Lys Ile Asp Phe Thr Glu Phe Leu Leu Met Val Phe Lys
 65                  70                  75                  80
Leu Ala Gln Ala Tyr Tyr Glu Ser Thr Arg Lys Glu Asn Leu Pro Ile
                 85                  90                  95
Ser Gly His Lys His Arg Lys His Ser His His Asp Lys His Glu Asp
            100                 105                 110
Asn Lys Gln Glu Glu Asn Lys Glu Asn Arg Lys Arg Pro Ser Ser Leu
            115                 120                 125
Glu Arg Arg Asn Asn Arg Lys Gly Asn Lys Gly Arg Ser Lys Ser Pro
130                 135                 140
Arg Glu Thr Gly Gly Lys Arg His Glu Ser Ser Glu Lys Lys Glu
145                 150                 155                 160
Arg Lys Gly Tyr Ser Pro Thr His Arg Glu Glu Tyr Gly Lys Asn
                165                 170                 175
His His Asn Ser Ser Lys Lys Gln Lys Asn Lys Thr Glu Asn Thr Arg
            180                 185                 190
Leu Glu Asp Asn Arg Lys Arg Leu Ser Glu Arg Leu Glu Glu Lys Glu
            195                 200                 205
Asp Asn Glu Glu Gly Gly Tyr Asp Tyr Glu Asn Thr Gly Arg Met Thr
210                 215                 220
Gln Lys Trp Ile Gln Ser Gly His Ile Ala Thr Tyr Tyr Thr Ile Gln
225                 230                 235                 240
Asp Glu Ala Tyr Asp Thr Thr Asp Asn Leu Leu Glu Glu Asn Lys Ile
                245                 250                 255
Tyr Glu Arg Ser Arg Ser Ser Asp Asp Lys Ser Ser Ser Gln Val Asn
            260                 265                 270
Arg Ser Arg His Glu Asn Thr Ser Gln Val Pro Leu Gln Glu Ser Arg
            275                 280                 285
Thr Arg Lys Arg Arg Gly Ser Arg Val Ser Gln Asp Arg Asp Ser Glu
            290                 295                 300
Gly His Ser Glu Asp Ser Glu Arg His Ser Gly Ser Ala Ser Arg Asn
305                 310                 315                 320
His Pro Gly Ser Ala Arg Gln Gln Ser Arg Asp Gly Ser Arg His Pro
                325                 330                 335
Arg Ser His Asp Glu Asp Arg Ala Ser His Gly His Ser Ala Asp Ser
            340                 345                 350
Ser Arg Gln Ser Gly Thr Arg His Ala Glu Thr Ser Ser Arg Gly Gln
            355                 360                 365
Thr Ala Ser Ser His Glu Gln Ala Arg Ser Ser Pro Gly Glu Arg His
370                 375                 380
Gly Ser Arg His Gln Gln Ser Ala Asp Ser Ser Arg His Ser Ala Thr
385                 390                 395                 400
Gly Arg Gly Gln Ala Ser Ser Ala Val Ser Asp Arg Gly Pro Arg Gly
                405                 410                 415
Ser Ser Gly Ser Gln Ala Ser Asp Ser Glu Gly His Ser Glu Asn Ser
            420                 425                 430
Asp Thr Gln Ser Val Ser Gly His Gly Lys Ala Gly Pro Arg Gln Gln
            435                 440                 445
Ser His Gln Glu Ser Ala Arg Gly Arg Ser Gly Glu Arg Ser Gly His
            450                 455                 460
Ser Gly Ser Phe Leu Tyr Gln Val Ser Thr His Glu Gln Ser Asp Ser
```

```
                465                 470                 475                 480
            Ala His Gly Arg Thr Gly Thr Ser Thr Gly Gly Arg Gln Gly Ser His
                            485                 490                 495
            His Glu Gln Ala Arg Asp Ser Ser Arg His Ser Ala Ser Gln Glu Gly
                            500                 505                 510
            Gln Asp Thr Ile Arg Gly His Pro Gly Ser Ser Arg Gly Gly Arg Gln
                            515                 520                 525
            Gly Ser His His Glu Gln Leu Val Asn Arg Ser Gly His Ser Gly Ser
                            530                 535                 540
            His His Ser His Thr Thr Ser Gln Gly Arg Ser Asp Ala Ser His Gly
            545                 550                 555                 560
            Gln Ser Gly Ser Arg Ser Ala Ser Arg Gln Thr Arg Asn Glu Glu Gln
                                565                 570                 575
            Ser Gly Asp Gly Ser Arg His Ser Gly Ser Arg His His Glu Ala Ser
                            580                 585                 590
            Ser Gln Ala Asp Ser Ser Arg His Ser Gln Val Gly Gln Gly Gln Ser
                            595                 600                 605
            Ser Gly Pro Arg Thr Ser Ser His Gln Gly Ser Ser Val Ser Gln Asp
                            610                 615                 620
            Ser Asp Ser Glu Gly His Ser Glu Asp Ser Glu Arg Trp Ser Gly Ser
            625                 630                 635                 640
            Ala Ser Arg Asn His His Gly Ser Ala Arg Glu Gln Ser Arg Asp Gly
                                645                 650                 655
            Ser Arg His Pro Arg Ser His His Glu Asp Arg Ala Gly His Gly His
                            660                 665                 670
            Ser Ala Asp Ser Ser Arg Gln Ser Gly Thr Arg His Thr Glu Ser Ser
                            675                 680                 685
            Ser Arg Gly Gln Ala Val Ser Ser His Glu Gln Ala Arg Ser Ser Pro
                            690                 695                 700
            Gly Glu Arg His Gly Ser Arg His Gln Gln Ser Ala Asp Ser Ser Arg
            705                 710                 715                 720
            His Ser Gly Ile Gly His Gly Gln Ala Ser Ser Ala Val Arg Asp Ser
                            725                 730                 735
            Gly His Arg Gly Ser Ser Gly Ser Gln Ala Ile Asp Ser Glu Gly His
                            740                 745                 750
            Ser Glu Asp Ser Asp Thr Gln Ser Val Ser Ser His Gly Gln Ala Gly
                            755                 760                 765
            Pro His Gln Gln Ser His Lys Glu Ser Ala Arg Gly Gln Ser Gly Glu
                            770                 775                 780
            Ser Ser Gly Arg Ser Gly Ser Phe Leu Tyr Gln Val Ser Ser His Glu
            785                 790                 795                 800
            Gln Ser Glu Ser Thr Tyr Gly Gln Thr Ala Pro Ser Thr Gly Gly Arg
                            805                 810                 815
            Gln Gly Ser Arg His Glu Gln Ala Arg Asn Ser Ser Arg His Ser Ala
                            820                 825                 830
            Ser Gln Asp Gly Gln Asp Thr Ile Arg Gly His Pro Gly Ser Ser Arg
                            835                 840                 845
            Gly Gly Arg Gln Gly Ser Tyr His Glu Gln Ser Val Asp Arg Ser Gly
                            850                 855                 860
            His Ser Gly Tyr His His Ser His Thr Thr Pro Gln Gly Arg Ser Asn
            865                 870                 875                 880
            Ala Ser His Gly Gln Ser Gly Ser Arg Ser Ala Ser Arg Gln Thr Arg
                                885                 890                 895
```

-continued

```
Asn Glu Glu Gln Ser Gly Asp Gly Ser Arg His Ser Gly Ser Arg His
            900                 905                 910

His Glu Ala Ser Ser Arg Ala Asp Ser Ser Arg His Ser Gln Val Gly
            915                 920                 925

Gln Gly Gln Ser Ser Gly Pro Arg Thr Ser Arg Asn Gln Gly Ser Ser
            930                 935                 940

Val Ser Gln Asp Ser Asp Ser Gln Gly His Ser Glu Asp Ser Glu Arg
945                 950                 955                 960

Trp Ser Gly Ser Ala Ser Arg Asn His His Gly Ser Ala Trp Glu Gln
                965                 970                 975

Ser Arg Asp Gly Ser Arg His Pro Gly Ser His Gln Glu Asp Arg Ala
            980                 985                 990

Gly His Gly His Ser Ala Asp Ser Ser Arg Gln Ser Gly Thr His His
            995                1000                1005

Thr Glu Ser Ser Ser Arg Gly Gln Ala Ala Ser Ser His Glu His
       1010                1015                1020

Ala Arg Ser Ser Ala Gly Glu Arg His Gly Ser His Gln Gln
       1025                1030                1035

Ser Ala Asp Ser Ser Arg His Ser Gly Ile Gly His Gly Gln Ala
       1040                1045                1050

Ser Ser Ala Val Arg Asp Ser Gly His Arg Gly Ser Gly Ser
       1055                1060                1065

Gln Ala Ser Asp Ser Glu Gly His Ser Glu Asp Ser Asp Thr Gln
       1070                1075                1080

Ser Leu Ser Ala His Gly Gln Ala Gly Pro His Gln Gln Ser His
       1085                1090                1095

Gln Glu Ser Thr Arg Gly Arg Ser Ala Glu Arg Ser Gly Arg Ser
       1100                1105                1110

Gly Ser Phe Leu Tyr Gln Val Ser Thr His Glu Gln Ser Glu Ser
       1115                1120                1125

Ala His Gly Arg Thr Gly Thr Ser Thr Gly Gly Arg Lys Arg Ser
       1130                1135                1140

Leu His Glu Gln Ala Arg Asp Ser Ser Arg His Ser Val Ser Gln
       1145                1150                1155

Glu Gly Gln Asp Thr Ile His Gly His Ala Gly Ser Ser Ser Gly
       1160                1165                1170

Gly Arg Gln Gly Ser His Tyr Glu Gln Leu Val Asp Arg Ser Gly
       1175                1180                1185

His Ser Gly Ser His His Ser His Thr Thr Ser Gln Gly Arg Ser
       1190                1195                1200

Asp Ala Tyr His Gly Gln Ser Gly Ser Arg Ser Ala Ser Arg Gln
       1205                1210                1215

Thr His Asn Asp Glu Gln Ser Gly Asp Gly Phe Arg His Ser Gly
       1220                1225                1230

Ser His His His Glu Ala Ser Ser Arg Ala Asp Ser Ser Arg His
       1235                1240                1245

Ser Gln Val Gly Gln Gly Gln Ser Glu Gly Pro Arg Thr Ser Arg
       1250                1255                1260

His Arg Glu Ser Ser Val Ser Gln Asp Ser Asp Ser Glu Gly His
       1265                1270                1275

Ser Glu Asp Ser Glu Arg Trp Ser Gly Ser Ala Ser Arg Asn His
       1280                1285                1290
```

```
His Gly Ser Ala Arg Glu Gln Ser Arg Asp Gly Ser Arg His Pro
1295                1300                1305

Arg Ser His His Glu Asp Arg Ala Gly His Gly His Ser Ala Asp
1310                1315                1320

Ser Ser Arg Gln Ser Gly Thr Arg His Thr Gln Thr Ser Ser Gly
1325                1330                1335

Gly Gln Ala Ala Ser Ser His Glu Gln Gly Arg Ser Ser Ala Gly
1340                1345                1350

Glu Arg His Gly Ser Arg His Gln Gln Ser Ala Asp Ser Ser Arg
1355                1360                1365

His Ser Gly Ile Gly His Gly Gln Ala Ser Ser Ala Val Arg Asp
1370                1375                1380

Ser Gly His Arg Gly Tyr Ser Gly Ser Gln Ala Ser Asp Ser Glu
1385                1390                1395

Gly His Ser Glu Asp Ser Asp Thr Gln Ser Val Ser Ala His Gly
1400                1405                1410

Gln Ala Gly Ser His Gln Gln Ser His Gln Glu Ser Ala Arg Gly
1415                1420                1425

Arg Ser Gly Glu Arg Ser Gly Arg Ser Gly Ser Phe Leu Tyr Gln
1430                1435                1440

Val Ser Thr His Glu Gln Ser Glu Ser Ser His Gly Trp Thr Gly
1445                1450                1455

Pro Ser Thr Arg Gly Arg Gln Gly Ser Arg His Glu Gln Ala Gln
1460                1465                1470

Asp Ser Ser Arg His Ser Ala Ser Gln Glu Gly Gln Asp Thr Ile
1475                1480                1485

Arg Gly His Pro Gly Pro Ser Arg Gly Gly Arg Gln Gly Tyr His
1490                1495                1500

His Glu Gln Ser Val Asp Ser Ser Gly His Ser Gly Ser His His
1505                1510                1515

Ser His Ile Thr Ser Gln Gly Ser Ser His Ala Ser His Gly Gln
1520                1525                1530

Ser Gly Ser Arg Ser Ala Ser Arg Thr Thr Arg Asn Asp Glu Gln
1535                1540                1545

Ser Val Asp Gly Ser Arg His Ser Gly Ser Arg His His Glu Ala
1550                1555                1560

Ser Thr His Ala Asp Ile Ser Arg His Ser Gln Ala Gly Gln Gly
1565                1570                1575

Gln Ser Glu Gly Ser Arg Thr Ser Arg Arg Gln Gly Ser Ser Val
1580                1585                1590

Ser Gln Asp Ser Asp Ser Glu Gly His Ser Glu Asp Ser Glu Arg
1595                1600                1605

Trp Ser Gly Ser Ala Ser Arg Asn His Arg Gly Ser Ala Gln Glu
1610                1615                1620

Gln Ser Arg Asp Gly Ser Arg His Pro Arg Ser His His Glu Asp
1625                1630                1635

Arg Ala Gly His Gly His Ser Ala Asp Ser Ser Arg Gln Ser Gly
1640                1645                1650

Thr His His Ala Glu Thr Ser Ser Gly Gly Gln Ala Ala Ser Ser
1655                1660                1665

Arg Glu Gln Ala Arg Ser Ser Pro Gly Glu Arg His Gly Ser Arg
1670                1675                1680

His Gln Gln Ser Ala Asp Ser Ser Arg His Ser Gly Ile Arg Arg
```

```
            1685                1690                1695

Gly Gln Ala Ser Ser Ala Val Arg Asp Ser Gly His Trp Gly Ser
            1700                1705                1710

Ser Gly Ser Gln Ala Ser Asp Ser Glu Gly His Ser Glu Glu Ser
            1715                1720                1725

Asp Thr Gln Ser Val Ser Gly His Gly Gln Asp Gly Pro His Gln
            1730                1735                1740

Gln Ser His Gln Glu Ser Ala Arg Asp Arg Ser Gly Gly Arg Ser
            1745                1750                1755

Gly Arg Ser Gly Ser Phe Leu Tyr Gln Val Ser Thr His Glu Gln
            1760                1765                1770

Ser Glu Ser Thr His Gly Gln Thr Gly Thr Ser Thr Gly Gly Arg
            1775                1780                1785

Gln Gly Ser His His Glu Gln Ala Arg Asp Ser Ser Arg His Ser
            1790                1795                1800

Ala Ser Gln Glu Gly Gln Asp Thr Ile His Ala His Pro Gly Ser
            1805                1810                1815

Ser Arg Gly Gly Arg Gln Gly Ser His His Glu Gln Ser Val Asp
            1820                1825                1830

Thr Ser Gly His Ser Gly Ser His His Ser His Thr Thr Ser Gln
            1835                1840                1845

Gly Arg Ser Asp Ala Ser His Gly Gln Ser Gly Ser Arg Ser Ala
            1850                1855                1860

Ser Arg Gln Thr Arg Asn Asp Glu Gln Ser Gly Asp Gly Ser Arg
            1865                1870                1875

His Ser Gly Ser His His His Glu Ala Phe Thr Gln Ala Asp Ser
            1880                1885                1890

Ser Arg His Ser Gln Ser Gly Gln Gly Glu Ser Ala Gly Ser Arg
            1895                1900                1905

Arg Ser Arg Arg Gln Gly Ser Ser Val Ser Gln Asp Ser Asp Ser
            1910                1915                1920

Gln Gly His Ser Glu Asp Ser Glu Arg Trp Ser Gly Ser Ala Ser
            1925                1930                1935

Arg Asn Gln His Gly Ser Ala Arg Glu Gln Ser Arg Asp Gly Ser
            1940                1945                1950

Arg His Pro Gly Ser His Gln Glu Asp Arg Ala Gly His Gly His
            1955                1960                1965

Ser Ala Asp Ser Ser Arg Gln Ser Gly Thr Arg His Thr Glu Ser
            1970                1975                1980

Ser Ser Arg Gly Gln Ala Ala Ser Ser His Glu Gln Ala Arg Ser
            1985                1990                1995

Ser Ala Gly Glu Arg His Gly Ser Arg His Gln Leu Gln Ser Ala
            2000                2005                2010

Asp Ser Ser Arg His Ser Gly Ile Gly His Gly Gln Ala Ser Ser
            2015                2020                2025

Ala Val Arg Asp Ser Gly His Arg Gly Ser Ser Gly Ser Gln Ala
            2030                2035                2040

Ile Asp Ser Glu Gly His Ser Glu Asp Ser Asp Thr Gln Ser Val
            2045                2050                2055

Ser Ala Gln Gly Gln Ala Gly Pro His Gln Arg Ser His Lys Glu
            2060                2065                2070

Ser Ala Arg Gly Gln Ser Gly Glu Ser Ser Gly Arg Ser Gly Ser
            2075                2080                2085
```

-continued

Phe Leu Tyr Gln Val Ser Thr His Glu Gln Pro Glu Ser Thr His
2090            2095            2100

Gly Gln Ser Ala Pro Ser Thr Gly Gly Arg Gln Gly Ser His His
2105            2110            2115

Asp Gln Ala Gln Asp Ser Ser Arg His Ser Ala Ser Gln Glu Gly
2120            2125            2130

Gln Asp Thr Ile Arg Gly His Pro Gly Pro Ser Arg Gly Gly Arg
2135            2140            2145

Gln Gly Ser His His Lys Gln Ser Val Asp Arg Ser Gly His Ser
2150            2155            2160

Gly Ser His His Ser His Thr Thr Ser Gln Gly Arg Ser Asp Ala
2165            2170            2175

Ser Arg Gly Gln Ser Gly Ser Arg Ser Ala Ser Arg Gln Thr His
2180            2185            2190

Asp Lys Glu Gln Ser Gly Asp Gly Ser Arg His Ser Gly Ser Arg
2195            2200            2205

His His Glu Ala Ser Ser Trp Ala Asp Ser Ser Arg His Ser Gln
2210            2215            2220

Ala Gly Gln Gly Gln Ser Glu Gly Ser Arg Thr Ser Arg Arg Gln
2225            2230            2235

Gly Ser Ser Phe Ser Gln Asp Ser Asp Ser Glu Gly His Ser Glu
2240            2245            2250

Asp Ser Glu Arg Arg Ser Gly Ser Ala Ser Arg Asn His Arg Gly
2255            2260            2265

Ser Ala Gln Glu Gln Ser Arg Asp Gly Ser Arg His Pro Arg Ser
2270            2275            2280

His His Glu Asp Arg Ala Gly His Gly His Ser Ala Asp Ser Ser
2285            2290            2295

Arg Gln Ser Gly Thr His His Ala Gln Asn Ser Ser Gly Gly Gln
2300            2305            2310

Ala Ala Ser Phe His Glu Gln Ala Arg Ser Ser Ala Gly Glu Arg
2315            2320            2325

His Gly Ser His His Gln Gln Ser Ala Asp Ser Ser Arg His Ser
2330            2335            2340

Gly Ile Gly His Gly Gln Ala Ser Ser Ala Val Arg Asp Ser Gly
2345            2350            2355

His Arg Gly Ser Ser Gly Ser Gln Ala Ser Asp Ser Glu Gly His
2360            2365            2370

Ser Glu Asp Ser Asp Thr Gln Ser Val Ser Ala His Gly Gln Ala
2375            2380            2385

Gly Pro His Gln Gln Ser His Gln Glu Ser Thr Arg Gly Arg Ser
2390            2395            2400

Ala Glu Arg Ser Gly Arg Ser Gly Ser Phe Leu Tyr Gln Val Ser
2405            2410            2415

Thr His Glu Gln Ser Glu Ser Ala His Gly Arg Thr Gly Pro Ser
2420            2425            2430

Thr Gly Gly Arg Gln Gly Ser Arg His Glu Gln Ala Arg Asp Ser
2435            2440            2445

Ser Arg His Ser Ala Ser Gln Glu Gly Gln Asp Thr Ile His Gly
2450            2455            2460

His Pro Gly Ser Arg Arg Gly Gly Arg Gln Gly Ser Tyr His Glu
2465            2470            2475

-continued

Gln Ser Val Asp Arg Ser Gly His Ser Gly His Ser His
    2480              2485              2490

Thr Thr Ser Gln Gly Arg Ser Asp Ala Ser His Gly Gln Ser Gly
    2495              2500              2505

Ser Arg Ser Ala Ser Arg Gln Thr Arg Asn Glu Gln Gln Ser Gly
    2510              2515              2520

Asp Gly Ser Arg His Ser Gly Ser Ser His His Glu Ala Ser Thr
    2525              2530              2535

Gln Ala Asp Ser Ser Arg His Ser Gln Ser Gly Gln Gly Glu Ser
    2540              2545              2550

Ala Gly Ser Arg Arg Ser Arg Arg Gln Gly Ser Ser Val Ser Gln
    2555              2560              2565

Asp Ser Asp Ser Glu Ala Tyr Pro Glu Asp Ser Glu Arg Arg Ser
    2570              2575              2580

Glu Ser Ala Ser Arg Asn Arg His Gly Ser Ser Arg Glu Gln Ser
    2585              2590              2595

Arg Asp Gly Ser Arg His Pro Gly Ser Ser His Arg Asp Thr Thr
    2600              2605              2610

Arg His Val Gln Ser Ser Pro Val Gln Ser Asp Ser Ser Thr Ala
    2615              2620              2625

Lys Glu His Gly His Phe Ser Ser Leu Ser Gln Asp Ser Ala Tyr
    2630              2635              2640

Arg Ser Gly Ile Gln Ser Arg Gly Ser Pro His Ser Ser Ser Ser
    2645              2650              2655

Tyr His Tyr Gln Ser Glu Gly Thr Glu Arg Gln Lys Gly Gln Ser
    2660              2665              2670

Gly Leu Val Trp Arg His Gly Ser Tyr Gly Ser Ala Asp Tyr Asp
    2675              2680              2685

Tyr Gly Glu Ser Gly Phe Arg His Ser Gln His Gly Ser Val Ser
    2690              2695              2700

Tyr Asn Ser Asn Pro Val Val Phe Lys Glu Arg Ser Asp Ile Cys
    2705              2710              2715

Lys Ala Ser Ala Phe Gly Lys Asp His Pro Arg Tyr Tyr Ala Thr
    2720              2725              2730

Tyr Ile Asn Lys Asp Pro Gly Leu Cys Gly His Ser Ser Asp Ile
    2735              2740              2745

Ser Lys Gln Leu Gly Phe Ser Gln Ser Gln Arg Tyr Tyr Tyr Tyr
    2750              2755              2760

Glu

<210> SEQ ID NO 16
<211> LENGTH: 1183
<212> TYPE: PRT
<213> ORGANISM: Macaca mulatta

<400> SEQUENCE: 16

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
            20                  25                  30

Leu Lys Glu Leu Leu Glu Lys Glu Phe Arg Pro Ile Leu Lys Asn Pro
        35                  40                  45

Asp Asp Pro Asp Thr Val Glu Val Phe Met Asp His Leu Asp Ile Asp
    50                  55                  60

```
His Asn Lys Lys Ile Asp Phe Thr Glu Phe Leu Met Val Phe Lys
 65                  70                  75                  80

Leu Ala Gln Ala Tyr Tyr Glu Ser Thr Arg Lys Gln Asn Leu Pro Ile
                 85                  90                  95

Ala Gly His Lys His Arg Lys His Ser His His Asp Lys His Glu Asp
            100                 105                 110

Asn Lys Glu Glu Glu Asn Lys Glu Lys Arg Lys Arg Pro Leu Ser Leu
        115                 120                 125

Glu Arg Arg Asn Asn Arg Lys Gly Asn Thr Gly Arg Ser Lys Ser Pro
130                 135                 140

Arg Glu Arg Gly Gly Lys Arg His Glu Ser Ser Phe Glu Lys Lys Glu
145                 150                 155                 160

Arg Lys Gly Tyr Ser Pro Thr Tyr Glu Glu Glu Tyr Gly Gln Asn
                165                 170                 175

His His Lys Ser Ser Lys Lys Glu Lys Asn Lys Thr Glu Ile Thr Arg
            180                 185                 190

Leu Glu His Glu Gly Lys Arg Ile Ser Glu Arg Pro Glu Lys Lys Glu
            195                 200                 205

Glu Lys Glu Asp Gly Gln Phe Asp Tyr Glu Asn Ala Gly Arg Met Asp
210                 215                 220

Glu Lys Trp Thr Glu Ser Gly His Ile Ala Ile Tyr His Ala Ile Gln
225                 230                 235                 240

Asp Glu Val Asp Asp Thr Thr Glu Asn Ile Leu Glu Glu Asn Arg Arg
                245                 250                 255

Tyr Glu Thr Ser Arg Ser Pro His Asp Lys Ser Ser Leu Arg Val Asn
                260                 265                 270

Arg Ser Pro Asn Ala Asn Thr Ser Gln Ile Pro Leu Val Glu Pro Arg
            275                 280                 285

Arg Arg Thr Arg Gln Arg Ser Ser Val Ser Gln Asp Ser Asp Ser Glu
            290                 295                 300

Gly His Ser Glu Asp Ser Glu Arg Gln Ser Glu Ser Ala Ser Arg Asn
305                 310                 315                 320

His His Gly Ser Val Arg Glu Gln Ser Arg His Gly Ser Arg His Pro
                325                 330                 335

Gly Ser His His Glu Asp Arg Ala Gly His Gly His Ser Ala Asp Ser
                340                 345                 350

Ser Thr Gln Ser Gly Thr Arg His Thr Glu Thr Ser Ser Arg Gly Gln
            355                 360                 365

Ala Val Ser Ser His Glu Gln Ala Arg Ser Ser Pro Gly Glu Arg His
370                 375                 380

Gly Ser Arg His Gln Gln Ser Ala Glu Ser Ser Arg His Ser Gly Ile
385                 390                 395                 400

Gly Arg Gly Gln Ala Ser Ser Ala Val Ser Asp Arg Gly His Gln Gly
                405                 410                 415

Pro Ser Gly Ser His Phe Ser Asp Ser Glu Gly His Ser Glu His Ser
            420                 425                 430

Asp Thr Gln Ser Val Ser Gly His Gly Gln Ala Gly Pro His Pro His
            435                 440                 445

Ser His Gln Glu Ser Ala Arg Gly Arg Ser Arg Glu Ser Gly Arg
            450                 455                 460

Ser Gly Ser Phe Leu Tyr Gln Val Ser Thr His Glu Gln Ser Glu Ser
465                 470                 475                 480

Thr His Gly Arg Thr Gly Pro Ser Ser Ala Gly Arg Gln Gly Ser Arg
```

```
                    485                 490                 495

Asn Glu Gln Ala Arg Asp Ser Ser Arg His Ser Ala Ser His Glu Val
                500                 505                 510

Gln Asp Thr Val His Gly His His Gly Ser Ser Arg Gly Arg Arg Gln
            515                 520                 525

Gly Ser His His Glu Gln Leu Val Asp Ser Ser Gly His Ser Gly Ser
        530                 535                 540

His His Ser His Thr Thr Ser Gln Gly Arg Ser Asp Ala Ser Arg Gly
545                 550                 555                 560

Glu Ser Gly Ala Arg Ser Ala Ser Arg Gln Thr Arg His Glu Glu Gln
                565                 570                 575

Ser Gly Asp Gly Ser Arg His Ser Gly Ser Arg His His Glu Ser Ser
            580                 585                 590

Asn Arg Ala Asp Ser Ser Arg His Ala Gln Ser Ser Gln Gly Gln Ser
        595                 600                 605

Ala Gly Phe Arg Thr Ser Thr Arg Arg Gly Ser Ser Val Ser Gln Asp
    610                 615                 620

Ser Asp Ser Glu Gly His Ser Glu Asp Ser Glu Arg Gln Ser Glu Ser
625                 630                 635                 640

Ala Ser Arg Asn His His Gly Ser Val Arg Glu Gln Ser Arg His Gly
                645                 650                 655

Ser Gly His Ser Gly Ser His His Gln Asp Lys Val Gly His Arg Tyr
            660                 665                 670

Ser Gly Asp Ser Ser Arg Gln Ser Gly Thr His His Val Glu Thr Ser
        675                 680                 685

Ser His Gly Gln Ala Ala Ser Ser His Glu Gln Thr Arg Ser Ser Pro
    690                 695                 700

Gly Glu Arg His Gly Ser His His Gln Gln Ala Asp Ser Ser Arg
705                 710                 715                 720

His Ser Gly Thr Gly Arg Gly Gln Ala Ser Ser Ala Val Ser Asp Arg
                725                 730                 735

Gly His Gln Gly Pro Ser Gly Ser His Phe Ser Asp Ser Glu Gly His
            740                 745                 750

Ser Glu His Ser Asp Thr Gln Ser Val Ser Gly Gln Gly Gln Ala Gly
        755                 760                 765

Arg His Pro His Ser His Gln Glu Ser Ala Arg Gly Arg Ser Gly Glu
    770                 775                 780

Arg Ser Gly Arg Ser Gly Ser Phe Val Tyr Gln Val Ser Thr His Glu
785                 790                 795                 800

Gln Ser Glu Ser Thr His Gly Arg Thr Gly Pro Ser Thr Gly Gly Arg
                805                 810                 815

Gln Gly Ser Arg Asn Glu Gln Ala Arg Asp Ser Ser Arg His Ser Val
            820                 825                 830

Ser His Glu Gly Gln Asp Thr Ile His Gly His His Gly Ser Ser Arg
        835                 840                 845

Gly Gly Arg Gln Gly Ser His His Glu Gln Ser Val Asp Ser Ser Gly
    850                 855                 860

His Ser Gly Ser His His Ser His Thr Thr Ser Gln Gly Arg Ser Asp
865                 870                 875                 880

Ala Ser Arg Gly Glu Ser Gly Ala Arg Ser Ala Ser Arg Gln Thr Arg
                885                 890                 895

His Glu Glu Gln Ser Gly Asp Gly Ser Arg His Ser Gly Ser Arg His
            900                 905                 910
```

-continued

```
His Glu Ala Ser Asn Arg Ala Asp Ser Ser Arg His Ala Gln Ser Gly
            915                 920                 925

Gln Gly Gln Ser Ala Gly Phe Arg Thr Ser Thr Arg Arg Gly Ser Ser
    930                 935                 940

Val Ser Gln Asp Ser Asp Ser Glu Gly His Ser Glu Asp Ser Glu Arg
945                 950                 955                 960

Gln Ser Glu Ser Ala Ser Arg Asn His His Gly Ser Val Arg Glu Gln
            965                 970                 975

Ser Arg His Gly Ser Arg His Pro Gly Ser His His Glu Asp Arg Ala
        980                 985                 990

Gly His Gly His Ser Ala Asp Ser Ser Arg Gln Ser Gly Thr Arg His
        995                 1000                1005

Thr Glu Thr Ser Ser Arg Gly Gln Ala Val Ser Ser His Glu Gln
        1010                1015                1020

Ala Arg Ser Ser Pro Gly Glu Arg His Gly Ser Arg His Gln Gln
        1025                1030                1035

Ser Ala Glu Ser Ser Arg His Ser Gly Ile Gly Arg Gly Gln Ala
        1040                1045                1050

Ser Ser Ala Val Ser Asp Arg Gly His Gln Gly Pro Ser Gly Ser
        1055                1060                1065

His Phe Ser Asp Ser Glu Gly His Ser Glu His Ser Asp Thr Gln
        1070                1075                1080

Ser Val Ser Gly His Gly Gln Ala Gly Pro His Pro His Ser His
        1085                1090                1095

Gln Glu Ser Ala Arg Gly Arg Ser Gly Glu Arg Ser Gly Arg Ser
        1100                1105                1110

Gly Ser Phe Leu Tyr Gln Val Ser Thr His Glu Gln Ser Glu Ser
        1115                1120                1125

Thr His Gly Arg Thr Gly Pro Ser Ser Ala Gly Arg Gln Gly Ser
        1130                1135                1140

Arg Asn Glu Gln Ala Arg Asp Ser Ser Arg His Ser Ala Ser His
        1145                1150                1155

Glu Val Gln Asp Thr Val His Gly His His Gly Ser Ser Arg Gly
        1160                1165                1170

Gly Arg Gln Gly Ser His His Glu Gln Ser
        1175                1180

<210> SEQ ID NO 17
<211> LENGTH: 2949
<212> TYPE: PRT
<213> ORGANISM: Macaca mulatta
<220> FEATURE:
<221> NAME/KEY: misc_feature
<222> LOCATION: (2160)..(2164)
<223> OTHER INFORMATION: Any naturally occuring amino acid

<400> SEQUENCE: 17

Met Thr Asp Leu Leu Arg Ser Val Val Thr Val Ile Asp Val Phe Tyr
1               5                   10                  15

Lys Tyr Thr Lys Gln Asp Gly Glu Cys Gly Thr Leu Ser Lys Asp Glu
            20                  25                  30

Leu Lys Glu Leu Leu Glu Lys Glu Phe His Pro Val Leu Lys Asn Pro
        35                  40                  45

Asp Asp Pro Asp Thr Val Asp Val Ile Met His Met Leu Asp Arg Asp
    50                  55                  60
```

-continued

```
His Asp Arg Arg Leu Asp Phe Thr Glu Phe Leu Leu Met Ile Phe Lys
 65                  70                  75                  80

Leu Thr Met Ala Cys Asn Lys Val Leu Ser Lys Glu Tyr Cys Lys Ala
                 85                  90                  95

Ser Gly Ser Lys Lys His Arg Arg Gly His Arg His Gln Glu Glu Glu
            100                 105                 110

Ser Glu Thr Glu Glu Asp Glu Glu Asp Thr Pro Glu His Lys Ser Gly
        115                 120                 125

Tyr Arg His Ser Ser Trp Ser Glu Gly Glu His Gly Tyr Ser Ser
    130                 135                 140

Gly His Ser Arg Gly Thr Val Lys Arg His Gly Ser Asn Ser Arg
145                 150                 155                 160

Arg Leu Gly Arg Gln Gly His Leu Ser Ser Gly Asn Gln Glu Arg
            165                 170                 175

Ser Gln Lys Arg Tyr His Arg Ser Ser Ser Gly His Ser Trp Ser Ser
            180                 185                 190

Gly Lys Glu Arg His Gly Phe Ser Ser Gly Leu Arg Glu Arg Ile
            195                 200                 205

Asn Lys Ser His Val Ser Pro Ser Arg Glu Phe Gly Glu Glu Tyr Glu
    210                 215                 220

Ser Gly Ser Gly Ser Lys Ser Trp Glu Arg Lys Gly His Gly Gly Leu
225                 230                 235                 240

Ser Cys Gly Leu Glu Ile Ser Gly His Glu Ser Asn Ser Thr Gln Ser
                245                 250                 255

Arg Ser Ser Gly Gln Lys Leu Gly Ser Ser Arg Ser Cys Ser Gly Asp
            260                 265                 270

Ser Arg Arg Arg Ser His Ala Cys Gly Tyr Ser Asn Ser Ser Gly Cys
            275                 280                 285

Gly Arg Pro Gln Asn Ala Ser Asn Ser Cys Gln His Arg Phe Gly Gly
            290                 295                 300

Gln Val Asn Gln Ser Ser Tyr Ile Gln Ser Gly Cys Gln Ser Gly Ile
305                 310                 315                 320

Asn Gly Glu Gln Gly His Asp Cys Val Ser Gly Gly Gln Pro Ser Gly
                325                 330                 335

Cys Gly Gln Pro Glu Ser Asn Ser Cys Ser Gln Ser Tyr Ser Gln Arg
            340                 345                 350

Gly Tyr Gly Ala Arg Glu Asn Gly Gln Pro Gln Asn Cys Gly Gly Gln
            355                 360                 365

Gln Arg Thr Gly Ser Ser Gln Ser Ser Phe Cys Gly Gln Tyr Glu Ser
            370                 375                 380

Gly Gly Ser Gln Ser Cys Ser Asn Gly Gln His Glu His Gly Ser Cys
385                 390                 395                 400

Gly Arg Phe Ser Asn Ser Ser Ser Asn Glu Phe Ser Lys Cys Gly
            405                 410                 415

Lys His Arg Ser Gly Ser Gly Gln Phe Thr Ser Cys Glu Gln His Gly
            420                 425                 430

Thr Gly Leu Ser Gln Ser Ser Gly Phe Glu Gln Gln Val Ala Gly Ser
            435                 440                 445

Ser Gln Thr Cys Ser Gln Tyr Gly Ser Arg Ser Ser Gln Ser Ser Gly
            450                 455                 460

Tyr Asp Glu His Gly Ser Ser Ser Gly Lys Thr Ser Gly Phe Gly Gln
465                 470                 475                 480

His Arg Ser Gly Ser Gly His Ser Ser Gly Phe Gly Gln His Gly Ser
```

```
                485                 490                 495
Gly Ser Gly Gln Ser Phe Gly Phe Gly Gln His Gly Ser Gly Ser Gly
            500                 505                 510
Gln Ser Ser Gly Phe Gly Gln His Glu Ser Arg Ser Cys Gln Ser Ser
            515                 520                 525
Tyr Gly Gln His Gly Ser Gly Ser Gln Ser Ser Gly Tyr Gly Gln
            530                 535                 540
His Ala Ser Arg Gln Thr Ser Gly Phe Gly Gln His Gly Leu Gly Ser
545                 550                 555                 560
Gly Gln Ser Thr Gly Phe Gly Gln Tyr Gly Ser Gly Ser Gly Gln Ser
                565                 570                 575
Ser Gly Phe Gly Gln His Gly Ser Gly Ser Gly Gln Ser Ser Gly Phe
            580                 585                 590
Gly Gln His Glu Ser Arg Ser Gly Gln Ser Ser Tyr Gly Gln His Ser
            595                 600                 605
Ser Ser Ser Ser Gln Ser Ser Gly Tyr Gly Gln His Gly Ser Arg Gln
            610                 615                 620
Thr Ser Gly Phe Gly Gln His Gly Ser Gly Ser Gly Gln Ser Thr Gly
625                 630                 635                 640
Phe Gly Gln Tyr Gly Ser Ser Leu Gly Gln Ser Ser Gly Phe Gly Gln
                645                 650                 655
His Gly Ser Gly Ser Gly Gln Ser Ser Gly Phe Gly Gln His Glu Ser
            660                 665                 670
Thr Ser Gly Gln Ser Ser Tyr Gly Gln His Gly Phe Gly Ser Ser Gln
            675                 680                 685
Ser Ser Gly Cys Gly Gln His Gly Leu Ser Ser Gly Gln Thr Ser Gly
            690                 695                 700
Phe Gly Gln His Glu Leu Ser Ser Gly Gln Ser Ser Phe Gly Gln
705                 710                 715                 720
His Gly Ser Gly Ser Gly Gln Ser Ser Gly Phe Arg Gln His Glu Ser
                725                 730                 735
Gly Ser Gly Gln Ser Ser Gly Phe Gly Gln His Glu Ser Arg Ser His
            740                 745                 750
Gln Ser Ser Tyr Gly Pro His Gly Ser Gly Ser Gly Gln Ser Ser Gly
            755                 760                 765
Tyr Gly Gln His Gly Ser Ser Ser Gly Gln Thr Ser Gly Phe Gly Gln
            770                 775                 780
Gln Gly Ser Ser Ser Ser Gln Tyr Ser Gly Phe Gly Gln His Gly Ser
785                 790                 795                 800
Gly Leu Gly Gln Ser Ser Gly Phe Gly Gln His Gly Thr Gly Ser Gly
                805                 810                 815
Gln Phe Ser Gly Phe Gly Gln His Glu Ser Arg Ser His Gln Ser Ser
            820                 825                 830
Tyr Gly Gln His Gly Ser Gly Ser Ser Gln Ser Ser Gly Tyr Gly Gln
            835                 840                 845
His Gly Ser Ser Ser Gly His Thr Thr Gly Phe Gly Gln His Arg Ser
            850                 855                 860
Ser Ser Gly Gln Tyr Ser Gly Phe Gly Gln His Gly Ser Gly Leu Gly
865                 870                 875                 880
Gln Ser Ser Gly Phe Gly Gln His Gly Thr Gly Ser Gly Gln Ser Ser
                885                 890                 895
Phe Gly Gln His Glu Ser Arg Ser His Gln Ser Ser Tyr Gly Gln His
            900                 905                 910
```

-continued

```
Gly Ser Gly Ser Ser Gln Ser Ser Tyr Gly Gln His Gly Ser Ser
        915                 920                 925

Ser Gly Gln Thr Ser Gly Phe Gly Gln His Arg Ser Gly Ser Gly Gln
930                 935                 940

Ser Ser Gly Phe Gly Gln Tyr Gly Leu Gly Ser Gly Ser Gly Phe Gly
945                 950                 955                 960

Gln His Gly Ser Gly Thr Gly Gln Ser Ser Gly Phe Ala Arg His Glu
                965                 970                 975

Tyr Arg Ser Gly Gln Ser Ser Tyr Gly Gln His Gly Thr Gly Ser Ser
                980                 985                 990

Gln Ser Ser Gly Cys Gly Gln Arg Glu Ser Gly Ser Gly Pro Thr Thr
                995                1000                1005

Gly Phe Gly Gln His Val Ser Gly Ser Asp Asn Phe Ser Ser Ser
        1010                1015                1020

Gly Gln His Ile Ser Gly Ser Asp Gln Ser Thr Gly Phe Gly Gln
        1025                1030                1035

Tyr Gly Ser Gly Ser Gly Gln Ser Thr Gly Leu Gly Gln Val Glu
        1040                1045                1050

Ser Gln Gln Val Ala Ser Gly Ser Thr Val His Gly Arg Gln Glu
        1055                1060                1065

Thr Thr His Gly Gln Thr Ile Asn Thr Ala Arg His Ser Gln Ser
        1070                1075                1080

Gly Gln Gly Gln Ser Thr Gln Thr Gly Ser Arg Val Ser Arg Arg
        1085                1090                1095

Arg Arg Ser Ser Gln Ser Glu Asn Ile Asp Ser Glu Val His Ser
        1100                1105                1110

Arg Val Ser His Arg His Ser Glu His Ile Asp Thr Gln Val Gly
        1115                1120                1125

Ser His Tyr Pro Glu Ser Gly Ser Thr Val His Arg Arg Gln Gly
        1130                1135                1140

Thr Thr His Gly Gln Arg Gly Asp Thr Thr Arg His Ser His Ser
        1145                1150                1155

Gly His Gly Gln Ser Thr Gln Thr Gly Ser Arg Thr Thr Gly Arg
        1160                1165                1170

Gln Arg Phe Ser His Ser Asp Ala Thr Asp Ser Glu Val His Ser
        1175                1180                1185

Gly Val Ser His Arg Pro His Ser Gln Glu His Thr His Gly Gln
        1190                1195                1200

Asp Gly Ser Gln Leu Gly Glu Ser Gln Ser Thr Val His Glu Arg
        1205                1210                1215

His Glu Thr Thr Tyr Gly Gln Thr Gly Asp Ala Thr Gly His Gly
        1220                1225                1230

Tyr Ser Gly His Gly Gln Ser Thr Gln Ile Gly Ser Arg Thr Ser
        1235                1240                1245

Gly Arg Arg Gly Ser Gly His Ser Glu Ser Ser Asp Thr Glu Val
        1250                1255                1260

His Ser Gly Gly Ser His Arg Pro His Ser Gln Glu Gln Thr His
        1265                1270                1275

Gly Gln Ala Arg Ser Gln His Gly Glu Ser Arg Ser Thr Val His
        1280                1285                1290

Glu Arg His Gly Thr Thr His Gly Gln Thr Gly Asp Thr Thr Arg
        1295                1300                1305
```

```
Tyr Ala His Tyr His Asn Gly Gln Ser Ala Gln Arg Gly Ser Arg
    1310            1315                1320
Thr Thr Gly Arg Gly Ser His Ser Glu Tyr Ser Asp Ser Glu
    1325            1330                1335
Leu Tyr Ser Gly Gly Ser His Thr Tyr Ser Gly His Thr His Gly
    1340            1345                1350
Gln Ala Gly Ser Gln His Gly Glu Ser Asp Ser Ile Val His Glu
    1355            1360                1365
Arg Tyr Gly Thr Thr His Gly Gln Thr Gly Asp Thr Thr Arg His
    1370            1375                1380
Ala His Tyr Ser His Gly Gln Ser Lys Gln Arg Gly Ser Arg Thr
    1385            1390                1395
Thr Gly Arg Arg Gly Ser Gly His Ser Glu Tyr Ser Asp Ser Glu
    1400            1405                1410
Gly His Ser Gly Gly Ser His Thr His Ser Gly His Thr His Gly
    1415            1420                1425
His Thr His Gly Gln Ala Gly Ser Gln His Gly Glu Ser Gly Ser
    1430            1435                1440
Ser Gly His Gly Gly Gln Gly Thr Thr His Gly Gln Thr Gly Asp
    1445            1450                1455
Thr Thr Arg His Ala His Tyr Gly His Gly Gln Ser Thr Gln Arg
    1460            1465                1470
Gly Ser Arg Thr Ala Gly Arg Arg Gly Ser Gly His Ser Glu Tyr
    1475            1480                1485
Ser Asp Ser Glu Gly His Ser Gly Val Ser His Thr His Ser Gly
    1490            1495                1500
His Thr His Gly Gln Ala Gly Ser Gln His Gly Glu Ser Glu Ser
    1505            1510                1515
Thr Val His Glu Arg Gln Gln Thr Thr His Gly Gln Thr Gly Asp
    1520            1525                1530
Thr Thr Arg His Ala His Tyr Gly His Gly Gln Ser Thr Gln Thr
    1535            1540                1545
Gly Ser Arg Thr Thr Gly Arg Arg Gly Ser Gly His Ser Glu Tyr
    1550            1555                1560
Ser Asp Ser Glu Gly His Ser Gly Val Ser His Thr His Ser Gly
    1565            1570                1575
His Thr His Gly Gln Ala Arg Ser Gln His Gly Glu Ser Gly Ser
    1580            1585                1590
Ala Ile His Gly Arg Gln Gly Thr Ile His Gly Gln Thr Gly Asp
    1595            1600                1605
Thr Thr Arg His Gly Gln Ser Gly His Gly Gln Ser Thr Gln Thr
    1610            1615                1620
Gly Ser Arg Thr Thr Gly Arg Arg Gly Ser Gly His Ser Glu Tyr
    1625            1630                1635
Ser Asp Ser Glu Gly His Ser Gly Gly Ser His Thr His Ser Gly
    1640            1645                1650
His Thr His Gly Gln Ala Gly Ser Gln His Gly Glu Ser Gly Ser
    1655            1660                1665
Thr Val His Gly Arg Gln Gly Thr Ile His Gly Gln Thr Gly Asp
    1670            1675                1680
Thr Thr Arg His Gly Gln Ser Gly His Gly Gln Ser Ile Glu Thr
    1685            1690                1695
Gly Ser Arg Thr Thr Gly Arg Arg Gly Ser Gly His Ser Glu Tyr
```

```
                 1700                1705                1710

Ser Asp Ser Glu Gly His Ser Gly Val Ser His Thr His Ser Gly
    1715                1720                1725

His Thr His Gly Gln Ala Gly Ser Gln His Gly Glu Ser Glu Ser
    1730                1735                1740

Thr Val His Glu Arg Gln Gln Thr Thr His Gly Gln Thr Gly Asp
    1745                1750                1755

Ile Thr Glu His Gly His Ser Ser His Gly Gln Thr Thr Gln Thr
    1760                1765                1770

Gly Ser Arg Thr Thr Gly Arg Arg Gly Ser Gly His Ser Glu Tyr
    1775                1780                1785

Ser Asp Ser Glu Trp His Ser Gly Ser His Thr His Ser Gly His
    1790                1795                1800

Thr His Gly Gln Ala Gly Phe Gln His Gly Glu Ser Gly Ser Ala
    1805                1810                1815

Val His Gly Arg Gln Gly Thr Ile His Gly Gln Thr Gly Asp Thr
    1820                1825                1830

Thr Arg His Gly Gln Ser Gly His Gly Glu Ser Ile Gln Thr Gly
    1835                1840                1845

Ser Arg Thr Ile Gly Arg Arg Gly Ser Gly His Ser Glu Tyr Ser
    1850                1855                1860

Asp Ser Glu Gly His Ser Gly Ile Ser His Thr His Ser Gly His
    1865                1870                1875

Thr His Gly Gln Ala Gly Ser Gln His Gly Glu Ser Gly Ser Ser
    1880                1885                1890

Gly His Gly Arg Gln Gly Thr Ala His Gly Gln Thr Gly Asp Thr
    1895                1900                1905

Thr Arg His Ala His Tyr Asp His Gly Gln Ser Thr Gln Arg Gly
    1910                1915                1920

Ser Arg Thr Ala Gly Arg Arg Gly Ser Gly His Ser Glu Tyr Ser
    1925                1930                1935

Asp Ser Glu Gly His Ser Gly Val Ser His Thr His Ser Gly His
    1940                1945                1950

Thr His Gly Gln Ala Gly Ser Gln His Gly Glu Ser Gly Ala Ala
    1955                1960                1965

Val His Gly Arg Gln Gly Ile Ile His Gly Gln Thr Gly Asp Thr
    1970                1975                1980

Thr Arg His Gly Gln Ser Gly Gln Gly Gln Ser Thr Gln Arg Gly
    1985                1990                1995

Ser Arg Thr Thr Gly Arg Arg Gly Ser Gly His Ser Glu Tyr Ser
    2000                2005                2010

Asp Ser Val Gly His Ser Gly Val Ser His Thr His Ser Gly His
    2015                2020                2025

Thr His Gly Leu Ala Gly Ser Gln His Gly Glu Ser Gly Ser Ser
    2030                2035                2040

Gly His Gly Arg Gln Gly Thr Leu His Gly Gln Thr Gly Asp Thr
    2045                2050                2055

Thr Arg His Ala His Tyr Gly His Gly Gln Ser Thr Gln Arg Gly
    2060                2065                2070

Ser Arg Thr Ala Gly Arg Arg Gly Ser Gly His Ser Glu Tyr Ser
    2075                2080                2085

Asp Ser Glu Trp His Ser Gly Gly Ser His Thr His Ser Gly His
    2090                2095                2100
```

```
Thr His Gly Gln Ala Gly Ser  Gln His Gly Glu Ser  Gly Ser Ala
2105              2110                2115

Val His Gly Arg Gln Gly Thr  Ile His Gly Gln Thr  Gly Asp Thr
2120              2125                2130

Thr Arg His Gly Gln Ser Gly  His Gly Gln Ser Thr  Gln Ile Gly
2135              2140                2145

Ser Arg Thr Thr Gly Arg Arg  Gly Ser Gly His Xaa  Xaa Xaa Xaa
2150              2155                2160

Xaa Arg His Thr Glu Thr Ser  Ser Arg Gly Gln Ala  Val Ser Ser
2165              2170                2175

His Glu Gln Ala Arg Ser Ser  Pro Gly Glu Arg His  Gly Ser Arg
2180              2185                2190

His Gln Gln Ser Ala Glu Ser  Ser Arg His Ser Gly  Ile Gly Arg
2195              2200                2205

Gly Gln Ala Ser Ser Ala Val  Ser Glu Arg Gly His  Gln Gly Pro
2210              2215                2220

Ser Gly Ser Leu Phe Ser Asp  Ser Glu Gly His Ser  Glu His Ser
2225              2230                2235

Asp Thr Gln Ser Val Ser Gly  His Gly Gln Ala Gly  Pro His Pro
2240              2245                2250

His Ser His Gln Glu Ser Ala  Arg Gly Arg Ser Gly  Glu Arg Ser
2255              2260                2265

Gly Arg Ser Gly Ser Phe Leu  Tyr Gln Val Ser Thr  His Glu Gln
2270              2275                2280

Ser Glu Ser Thr His Gly Trp  Thr Gly Pro Ser Ser  Ala Gly Arg
2285              2290                2295

Gln Gly Ser Arg Asn Glu Gln  Ala Arg Asp Ser Ser  Arg His Ser
2300              2305                2310

Val Ser His Glu Val Gln Asp  Thr Val His Gly His  Ser Gly Ser
2315              2320                2325

Ser Arg Gly Arg Arg Gln Gly  Ser His His Glu Gln  Leu Val Asp
2330              2335                2340

Ser Ser Gly His Ser Gly Ser  His His Ser His Thr  Thr Ser Gln
2345              2350                2355

Gly Arg Ser Asp Ala Ser Arg  Gly Glu Ser Gly Ala  Arg Ser Ala
2360              2365                2370

Ser Arg Gln Thr Arg His Glu  Glu Gln Ser Gly Asp  Gly Ser Arg
2375              2380                2385

His Ser Gly Ser Arg His His  Glu Ala Ser Asn Arg  Ala Asp Ser
2390              2395                2400

Ser Arg His Ala Gln Ser Gly  Gln Gly Gln Ser Ala  Gly Phe Arg
2405              2410                2415

Thr Ser Thr Arg Arg Gly Ser  Ser Val Ser Gln Asp  Ser Asp Ser
2420              2425                2430

Glu Gly His Ser Glu Asp Ser  Glu Arg Gln Ser Glu  Ser Ala Ser
2435              2440                2445

Arg Asn His His Gly Ser Val  Arg Glu Gln Ser Arg  His Gly Ser
2450              2455                2460

Arg Tyr Pro Gly Ser His His  Glu Asp Gly Ala Gly  His Gly His
2465              2470                2475

Thr Ala Asp Ser Pro Arg Gln  Ser Gly Thr His His  Val Glu Thr
2480              2485                2490
```

```
Ser Ser His Gly Gln Ala Ala Ser Ser His Glu Gln Thr Arg Ser
    2495                2500                2505

Ser Pro Gly Glu Arg His Gly Ser Arg His Gln Gln Ser Ala Glu
    2510                2515                2520

Ser Ser Arg His Ser Gly Ile Gly Arg Gly Gln Ala Ser Ser Ala
    2525                2530                2535

Val Ser Glu Arg Gly His Gln Gly Pro Ser Gly Ser Gln Phe Ser
    2540                2545                2550

Asp Ser Glu Gly His Ser Glu His Ser Asp Thr Gln Ser Val Ser
    2555                2560                2565

Gly His Gly Gln Ala Gly Pro His Pro His Ser His Gln Glu Ser
    2570                2575                2580

Ala Arg Gly Arg Ser Gly Glu Arg Ser Gly Arg Ser Gly Ser Phe
    2585                2590                2595

Val Tyr Gln Val Ser Thr His Glu Gln Ser Glu Ser Thr His Gly
    2600                2605                2610

Gln Thr Gly Pro Ser Thr Gly Gly Arg Gln Gly Ser Arg Asn Glu
    2615                2620                2625

Gln Ala Arg Asp Ser Ser Arg His Ser Val Ser His Glu Gly Gln
    2630                2635                2640

Asp Thr Ile His Gly His Ser Glu Ser Ser Ile Gly Gly Arg Gln
    2645                2650                2655

Gly Ser His His Glu Gln Ser Val Asp Ser Ser Gly His Ser Gly
    2660                2665                2670

Ser His His Ser His Thr Thr Ser Gln Gly Arg Ser Asp Ala Ser
    2675                2680                2685

Arg Gly Gln Ser Gly Ser Arg Ser Ala Ser Arg Gln Thr Arg His
    2690                2695                2700

Glu Glu Gln Ser Gly Asp Gly Tyr Arg His Ser Gly Ser Arg Leu
    2705                2710                2715

His Glu Ala Ser Thr Gln Ala Asp Ser Phe Arg His Ser His Ser
    2720                2725                2730

Gly Gln Gly Gln Ser Ala Gly Ser Arg Arg Ser Thr Leu Arg Gly
    2735                2740                2745

Ser Ser Val Asn Gln Asp Ser Ala Ser Glu Gly His Ser Glu Asp
    2750                2755                2760

Ser Glu Arg Gln Ser Glu Ser Ala Ser Arg Asn Pro His Gly Ala
    2765                2770                2775

Val Arg Glu Gln Ser Arg Asp Val Ser Arg His Pro Arg Ser Tyr
    2780                2785                2790

His His Asp Thr Gly Asn His Val Gln Ser Ser Ser Val Tyr Ser
    2795                2800                2805

Asp Thr Thr Thr Ser Lys Glu His Gly His Phe Gly Ser Leu Ser
    2810                2815                2820

Gln Asp Ser Ala Tyr His Ser Gly Ile Gln Ser Arg Gly Ser Pro
    2825                2830                2835

His Ser Ser Ser Ser Tyr Asn Tyr His Ser Glu Gly Thr Glu Arg
    2840                2845                2850

Glu Arg Gly Gln Ser Gly Leu Val Trp Arg His Gly Ser Tyr Gly
    2855                2860                2865

Ser Ala Asp Tyr Asp Tyr Gly Glu Ser Arg Phe Arg His Ser Gln
    2870                2875                2880

His Gly Ser Val Ser Tyr Asn Ser Asn Pro Val Val Phe Lys Glu
```

```
            2885                2890                2895

Arg Ser  Asp Ile Arg Lys Ala  Ser Ala Phe Gly Glu  Asp His Pro
     2900                 2905                2910

Arg Tyr  Tyr Ala Arg Tyr Val  Asn Arg Gln Pro Gly  Leu Tyr Arg
     2915                 2920                2925

His Ser  Ser Asp Ile Ser Lys  Gln Leu Gly Phe Ser  Gln Ser Gln
     2930                 2935                2940

Arg Tyr  Tyr Tyr Tyr Glu
     2945
```

<210> SEQ ID NO 18
<211> LENGTH: 25
<212> TYPE: PRT
<213> ORGANISM: Staphylococcus epidermidis

<400> SEQUENCE: 18

```
Met Lys Lys Leu Ala Phe Ala Ile Thr Ala Ala Ser Gly Ala Ala Ala
1               5                   10                  15

Val Leu Ser His His Asp Ala Glu Ala
            20                  25
```

<210> SEQ ID NO 19
<211> LENGTH: 30
<212> TYPE: PRT
<213> ORGANISM: Staphylococcus epidermidis

<400> SEQUENCE: 19

```
Trp Leu Asp Asn Arg Ala Phe Ser Lys Lys Phe Val Pro Val Val Met
1               5                   10                  15

Ala Thr Ser Val Ala Leu Phe Phe Leu Asn Leu Ala Phe Ala
            20                  25                  30
```

<210> SEQ ID NO 20
<211> LENGTH: 29
<212> TYPE: PRT
<213> ORGANISM: Staphylococcus epidermidis

<400> SEQUENCE: 20

```
Met Ala Lys Lys Phe Asn Tyr Lys Leu Pro Ser Met Val Ala Leu Thr
1               5                   10                  15

Leu Phe Gly Thr Ala Phe Thr Ala His Gln Ala Asn Ala
            20                  25
```

<210> SEQ ID NO 21
<211> LENGTH: 27
<212> TYPE: PRT
<213> ORGANISM: Staphylococcus epidermidis

<400> SEQUENCE: 21

```
Met Lys Lys Arg Phe Leu Ser Ile Cys Thr Met Thr Ile Ala Ala Leu
1               5                   10                  15

Ala Thr Thr Thr Met Val Asn Thr Ser Tyr Ala
            20                  25
```

<210> SEQ ID NO 22
<211> LENGTH: 30
<212> TYPE: PRT
<213> ORGANISM: Staphylococcus epidermidis

<400> SEQUENCE: 22

```
Asn Leu Lys Lys Gln Ser Lys Leu Ile Leu Ile Phe Ile Cys Ile Phe
```

```
                1               5                   10                  15
Thr Phe Phe Ile Met Ile Ile Gln Ser Gln Phe Leu Met Gly
                20                  25                  30

<210> SEQ ID NO 23
<211> LENGTH: 26
<212> TYPE: PRT
<213> ORGANISM: Staphylococcus epidermidis

<400> SEQUENCE: 23

Met Lys Ile Phe Lys Leu Thr Ser Leu Thr Leu Ala Ala Leu Thr Leu
1               5                   10                  15

Ala Phe Pro Phe Ser His Val Ala Gln Ala
                20                  25

<210> SEQ ID NO 24
<211> LENGTH: 28
<212> TYPE: PRT
<213> ORGANISM: Staphylococcus epidermidis

<400> SEQUENCE: 24

Met Lys Lys Thr Val Ile Ala Ser Thr Leu Ala Val Ser Leu Gly Ile
1               5                   10                  15

Ala Gly Tyr Gly Leu Ser Gly His Glu Ala His Ala
                20                  25

<210> SEQ ID NO 25
<211> LENGTH: 27
<212> TYPE: PRT
<213> ORGANISM: Staphylococcus epidermidis

<400> SEQUENCE: 25

Met Lys Lys Asn Lys Phe Leu Val Tyr Leu Leu Ser Thr Ala Leu Ile
1               5                   10                  15

Thr Pro Thr Phe Ala Thr Gln Thr Ala Phe Ala
                20                  25

<210> SEQ ID NO 26
<211> LENGTH: 35
<212> TYPE: PRT
<213> ORGANISM: Staphylococcus epidermidis

<400> SEQUENCE: 26

Met Lys Thr Arg Gln Asn Lys Tyr Ser Ile Arg Lys Phe Ser Val Gly
1               5                   10                  15

Ala Ser Ser Ile Leu Ile Ala Ala Leu Leu Phe Met Gly Gly Gly Ser
                20                  25                  30

Ala Gln Ala
        35

<210> SEQ ID NO 27
<211> LENGTH: 37
<212> TYPE: PRT
<213> ORGANISM: Staphylococcus epidermidis

<400> SEQUENCE: 27

Met Lys Asn Asn Asn Glu Thr Arg Arg Phe Ser Ile Arg Lys Tyr Thr
1               5                   10                  15

Val Gly Val Val Ser Ile Ile Thr Gly Ile Thr Ile Phe Val Ser Gly
                20                  25                  30

Gln His Ala Gln Ala
```

<210> SEQ ID NO 28
<211> LENGTH: 30
<212> TYPE: PRT
<213> ORGANISM: Staphylococcus epidermidis

<400> SEQUENCE: 28

Met Lys Lys Lys Leu Ser Tyr Met Ile Thr Ile Met Leu Ala Phe Thr
1               5                   10                  15

Leu Ser Leu Ala Leu Gly Leu Phe Phe Asn Ser Ala His Ala
            20                  25                  30

<210> SEQ ID NO 29
<211> LENGTH: 13
<212> TYPE: PRT
<213> ORGANISM: Human immunodeficiency virus

<400> SEQUENCE: 29

Gly Arg Lys Lys Arg Arg Gln Arg Arg Pro Pro Gln
1               5                   10

<210> SEQ ID NO 30
<211> LENGTH: 27
<212> TYPE: PRT
<213> ORGANISM: Artificial sequence
<220> FEATURE:
<223> OTHER INFORMATION: Synthetic

<400> SEQUENCE: 30

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 31
<211> LENGTH: 18
<212> TYPE: PRT
<213> ORGANISM: Artificial sequence
<220> FEATURE:
<223> OTHER INFORMATION: Synthetic

<400> SEQUENCE: 31

Lys Leu Ala Leu Lys Leu Ala Leu Lys Ala Leu Lys Ala Ala Leu Lys
1               5                   10                  15

Leu Ala

<210> SEQ ID NO 32
<211> LENGTH: 30
<212> TYPE: PRT
<213> ORGANISM: Artificial sequence
<220> FEATURE:
<223> OTHER INFORMATION: Synthetic

<400> SEQUENCE: 32

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 33
<211> LENGTH: 21
<212> TYPE: PRT
<213> ORGANISM: Artificial sequence

```
<220> FEATURE:
<223> OTHER INFORMATION: Synthetic

<400> SEQUENCE: 33

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 34
<211> LENGTH: 9
<212> TYPE: PRT
<213> ORGANISM: Artificial sequence
<220> FEATURE:
<223> OTHER INFORMATION: Synthetic

<400> SEQUENCE: 34

Arg Arg Arg Arg Arg Arg Arg Arg Arg
1               5

<210> SEQ ID NO 35
<211> LENGTH: 24
<212> TYPE: PRT
<213> ORGANISM: Artificial sequence
<220> FEATURE:
<223> OTHER INFORMATION: Synthetic

<400> SEQUENCE: 35

Leu Gly Thr Tyr Thr Gln Asp Phe Asn Lys Phe His Thr Phe Pro Gln
1               5                   10                  15

Thr Ala Ile Gly Val Gly Ala Pro
            20
```

THERAPEUTIC TREATMENT OF SKIN DISEASE WITH RECOMBINANT COMMENSAL SKIN MICROORGANISMS

CROSS-REFERENCE TO RELATED APPLICATIONS

The present application is the National Stage of International Application No. PCT/US15/032972, filed on May 28, 2015, which claims benefit to U.S. Provisional Application Nos. 62/005,558 and 62/005,652, both filed on May 30, 2014. The entire contents of the above applications are incorporated by reference as if recited in full herein.

INCORPORATION BY REFERENCE OF SEQUENCE LISTING

This application contains references to amino acids and/or nucleic acid sequences that have been filed as sequence listing text file "0550663_Corrected-SEQ-listing.txt", file size of 333 KB, created on Sep. 20, 2017. The aforementioned sequence listing is hereby incorporated by reference in its entirety pursuant to 37 C.F.R. § 1.52(e)(5).

FIELD OF THE INVENTION

The present invention relates generally to the fields of synthetic biology, microbiology, protein chemistry, skin care, extracellular protein transport, intracellular transport, and the treatment and prevention of skin disease. More specifically, it concerns methods and compositions employing engineered strains of commensal skin bacteria that produce recombinant polypeptides for the therapeutic treatment and prevention of skin diseases, in particular employing an engineered strain of *Staphylococcus epidermidis* that produces recombinant filaggrin.

BACKGROUND OF THE INVENTION

The advent of compounds that are generated using recombinant DNA technology has facilitated development of a vast array of therapeutic agents having the potential to treat a great variety of disease states in animals, in particular in humans. These agents are primarily protein in nature.

The epidermis, the squamous stratified epithelium of the skin, consists of multiple sublayers and is one of the most important barriers of the body against the outside world. The stratum corneum is the outermost layer of the epidermis and develops as a result of the final anucleated step in keratinocyte differentiation from the cells in nucleated epidermal layers. Although the stratum corneum is recognized as the most important physical barrier, the nucleated epidermal layers are also significant in barrier function (Proksch. Brandner et al. 2008). Together, the skin barrier protects against extensive water loss in one direction (inside-outside barrier) and against the invasion of harmful substances from the environment (outside-inside barrier) (Proksch, Brandner et al. 2008). The maintenance of the barrier is also important for balanced proliferation in the basal layer and preservation of the calcium ion gradient and thus proper epidermal differentiation (Lee, Jeong et al. 2006).

Recent work suggests that skin commensal microorganisms are essential to maintaining healthy skin and maintaining the skin barrier. Commensal microorganisms are ones that are beneficial to their subject. e.g., human, hosts. Studies also suggest that certain skin diseases (such as acne vulgaris and atopic dermatitis) can be associated with disruptions to the normal microflora (Lin, Wang et al. 2007). Therefore, the idea that the skin microflora can be modulated using specific skin commensals to promote health or inhibit disease has received some attention (Muizzuddin, Maher et al. 2012). Many skin commensal bacteria are not considered pathogenic, therefore, these bacteria can potentially be used topically if they have therapeutic value (Nakatsuji and Gallo 2014). So far the limited amount of research in this area suggests that conventional probiotic bacteria can be of significant value when used on the skin. For example, topical application of a *Bifidobacterium longum* lysate has been shown to induce clinical improvement of "reactive skin" (Gueniche, Bastien et al. 2010). This is skin that is more sensitive to physical changes such as atmospheric temperature, and to chemical changes such as seen with topically applied products (Gueniche, Bastien et al. 2010). Application of the *B. longum* lysate to the skin of volunteers was shown to decrease sensitivity and decrease transepidermal water loss (TEWL) after tape stripping. Additionally, application of the lysate to ex vivo skin was shown to decrease signs of inflammation such as vasodilation, edema and TNF-α release (Gueniche, Bastien et al. 2010, Nakatsuji and Gallo 2014, Volz, Skabytska et al. 2014). Topical application of *Lactobacillus plantarum* has also been demonstrated to improve tissue repair in a burned mouse model and prevent infection in chronic leg ulcers and burns in humans (Peral. Martinez et al. 2009, Peral, Rachid et al. 2010, Brachkova, Marques et al. 2011).

A number of current limitations exist in the treatment of skin, however. Many treatments, such as topical corticosteroids or expensive biologics, do not treat the underlying issues of deficient intrinsic protein in the epidermis or imbalances in the microbial diversity in the skin. While recombinant proteins represent a promising group of therapeutic agents in the treatment of skin disease, several problems accompany their use in the context. Traditional methods employ the use of purification of recombinant proteins that are extracted from bacterial systems, purified, concentrated, and incorporated into a delivery system. The purification of recombinant proteins is often a very costly method of obtaining protein. Moreover, a number of issues accompany this, including proteolytic degradation, inefficient delivery, and the need for repeated application overtime to achieve therapeutic effect.

Our method, in contrast, addresses these issues by allowing bacteria to colonize the skin and continually secrete therapeutic polypeptides of benefit to the skin. This approach reduces need for multiple topical applications by creating a sustainable delivery system for therapeutic proteins.

Most of the microorganisms until now used for the production of recombinant proteins cannot be in safely administered to humans and animals, not being usual components of the physiological flora or being devoid of any pathogenic risk. This is particularly true for *Escherichia coli*, which is considered pathogenic in many cases. However, here, we describe methods of production of recombinant proteins using microorganisms that can be safety administered to humans and animals, particularly *Staphylococcus epidermidis*.

Other species, already used for the production of recombinant proteins, can also be used provided they meet the requisites of non-pathogenicity and ability to colonize human or animal mucosae. For example, *Bacillus subtilis* has been widely used as a cloning vector for producing a large number of eukaryotic proteins in view of its recognized advantageous properties (Simonen and Palva 1993). The present invention allows therefore, by suitably selecting and adapting the microorganism, the polypeptide to be expressed and the expression vectors, previously used for the production in laboratory or industrial environment, to address specific skin diseases (see FIG. 1). The present invention concerns therefore the therapeutic use of said engineered microorganisms and compositions containing the same, thereby satisfying a long felt need in the area of therapeutic delivery of drugs to treat skin conditions in humans.

Atopic dermatitis (AD), which is also known as eczema, is a chronic inflammatory skin disease that usually involves a defect in the stratum corneum of the skin, which is the protective layer comprising the outermost part of the skin. This defect is caused by a confluence of genetic, environmental, and immunological factors and is associated with an overgrowth of Staphylococcus aureus. The genetic basis of AD appears to involve a defect in the filaggrin gene (FLG), seen in approximately 50% of AD patients (McAleer 2013). The prevalence of atopic dermatitis is increasing, and affects 0.1-1% of the population worldwide, with higher rates in developed countries. AD is more common in children, affecting as many as 20% of children (McAleer 2013). Of these children, 25% never recover and continue to suffer from atopic dermatitis into adulthood. In many cases, AD can lead to more severe allergic conditions, including asthma, through a process known as the "atopic march."

The pathogenesis of AD is not completely understood, but defects in filaggrin expression are attributed to most cases of atopic dermatitis, and the pathogenesis is related to an immune response. It has been shown that AD can be caused by a combination of dry skin, skin that is prone to itching more than the average person, infections caused by bacteria, viruses, fungi, etc., and emotional and environmental factors. Filaggrin is encoded by the FLG gene on the 1q21 epidermal differentiation complex. Filaggrin is a protein produced by differentiating keratinocytes, and functions to aggregate keratin filaments into a cytoskeleton that, in combination with other components, comprises the cornified cell envelope (Brown & McLean 2012). Filaggrin loss of function mutations (R501X and 2282del4) cause ichthyosis vulgaris, the most common inherited disorder of keratinization. The same mutations also are associated with other skin and allergic conditions including AD, irritant contact dermatitis, asthma, and food allergy. Several studies have shown that increasing filaggrin on the skin helps to mitigate the AD phenotype (e.g. Stout et al. 2014, Otsuka et al. 2014).

Currently, the major therapies for AD include topical corticosteroids and antibiotics, both of which have limited efficacy in more severe cases of AD. Major drawbacks of antibiotics include issues of antibiotic resistance and dysregulation of the microbiome ecology. The microbiome is the aggregate of microorganisms present in a particular environment. The microbiome mentioned herein, is the totality of the microorganisms present on the largest human organ, the skin. Topical corticosteroids provide respite from symptoms for mild AD patients, but do not address the needs of those with chronic or severe disease. While some targeted therapies for AD treatment are under development, the competitive landscape in this market is characterized by a largely unmet need for an effective, targeted therapy for AD. One biologic therapy, Dupilumab, is an anti-IL4/13-receptor monoclonal antibody that is under Phase II clinical trial for AD, being developed by Regeneron Pharmaceuticals and Sanofi. This drug has shown promising efficacy, and is expected to reach markets in the next five years. Other similar biologic therapeutics for immunomodulation of AD are under development. However, these drugs are expected to cost tens of thousands of dollars for consumers due to high production and R&D costs, and insurance companies may not necessarily cover these costs. While these drugs attenuate the immune response, they do not have direct effects on re-establishing the skin barrier and normalizing the microbial ecology to prevent S. aureus infections. Thus, new compositions and methods for the effective treatment and prevention of abnormal skin conditions such as AD, while minimizing unwanted side effects are required.

BRIEF DESCRIPTION OF THE FIGURES

FIG. 8 depicts *S. epidermidis* ATCC12228 transformed with pCM11 containing the GFP (green fluorescent protein) insert, which was in turn applied on the dorsal skin of mice for three days. Sections of the skin were then taken postmortem for light microscopy (FIGS. 8A & 8B). FIG. 8A shows fluorescence of GFP indicating not only that *S. epidermidis* colonizes the skin after three days, but also that expression of GFP is maintained at that time. FIG. 8A shows fluorescence from GFP while FIG. 8B shows a section of skin stained with both DAPI (4',6-diamidino-2-phenylindole) and an anti-GFP monoclonal antibody. FIG. 8C demonstrates a section of the skin visualized using two-photon microscopy, demonstrating the extent of *S. epidermidis* colonization and GFP expression, as indicated by the fluorescence.

SUMMARY OF THE INVENTION

Figure 1:
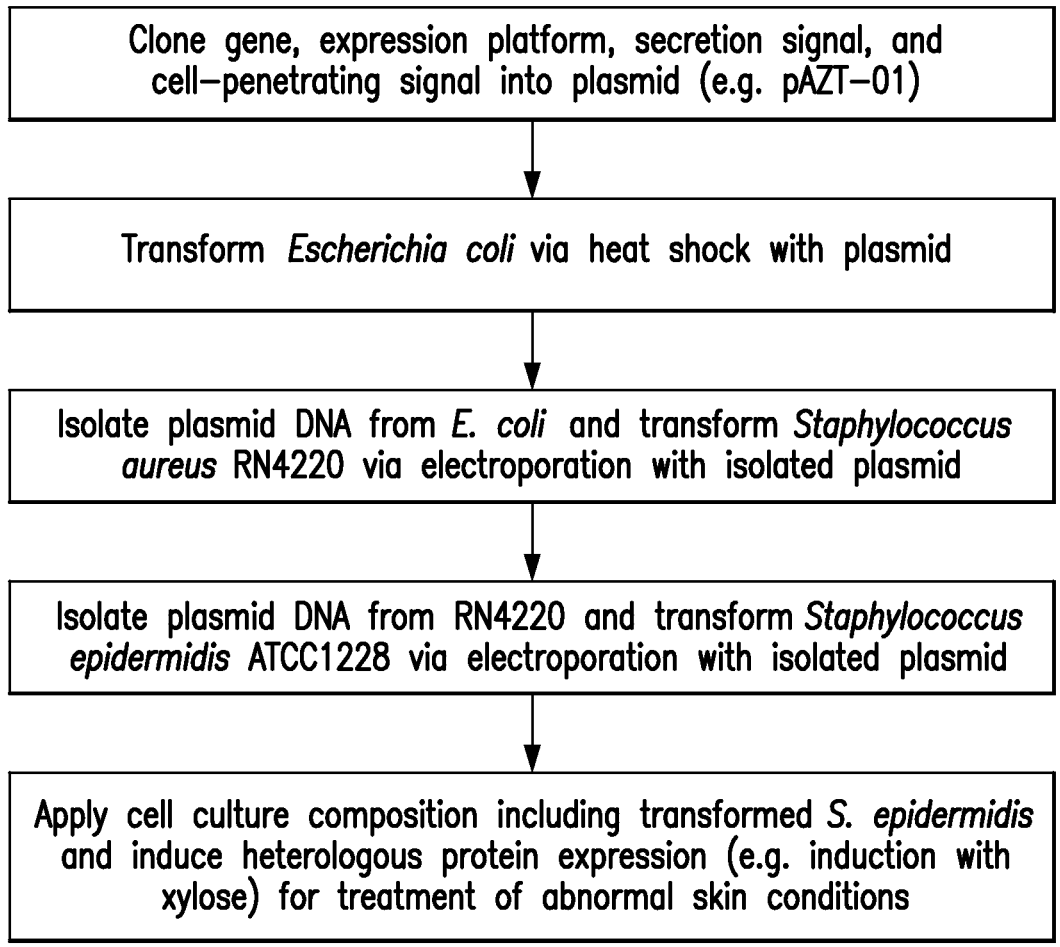
FIG. 1 depicts a flowchart of the present invention, demonstrating the creation of an engineered bacterial strain that produces a recombinant polypeptide for therapeutic treatment or prevention of an abnormal skin condition.

The invention refers to pharmaceutical compositions containing, as the active principle, engineered microorganisms expressing non-vaccinogenic, pharmacologically active recombinant therapeutic polypeptides (i.e. proteins, peptides, or amino acids) in order to treat skin conditions. Such non-vaccinogenic polypeptides, in contrast to those employed in vaccines, are those that generally do not incite an immune response and yet are therapeutically effective.

The present invention relates to a method of treating or preventing abnormal skin conditions in a patient (human or animal subject) in need thereof, the method comprising administering to said patient a cell culture composition comprising a bacterial strain selected from *Bifidobacterium, Brevibacterium, Propionibacterium, Lactococcus, Streptococcus, Staphylococcus* (e.g., *S. epidermidis*), *Lactobacillus* (e.g., *L. acidophilus*), *Enterococcus, Pediococcus, Leuconostoc*, or *Oenococcus*, and mixtures thereof, wherein the composition comprises at least one engineered bacterial strain that produces a therapeutically effective amount of a recombinant polypeptide for therapeutic treatment or prevention of the abnormal skin condition.

In one aspect the present invention relates to a method wherein said composition comprises bacterial strain containing human target DNA recombined with bacterial DNA to make an engineered bacterial strain.

In another aspect the present invention relates to a method wherein the composition comprises an engineered strain of *Staphylococcus epidermidis*.

In another aspect the present invention relates to a method wherein the cell culture composition is a living cell culture composition.

In another aspect the present invention relates to a method wherein the skin condition is selected from psoriasis, acne, atopic dermatitis, allergic contact dermatitis, epidermolytic hyperkeratosis, seborrheic dermatitis, eczema, dry skin, allergy, rashes, UV-irritated skin, detergent irritated skin (including irritation caused by enzymes and molecules used in washing detergents and sodium lauryl sulfate), thinning skin (e.g. skin from the elderly and children), bullous pemphigoid, pemphigus vulgaris, impetigo, vitiligio, baldness, and hirsutism.

In another aspect the present invention relates to a method wherein said skin condition is eczema.

In another aspect the present invention relates to a method wherein said eczema is a mild eczema.

In another aspect the present invention relates to a method wherein said eczema is a moderate eczema.

In another aspect the present invention relates to a method wherein said eczema is a severe eczema.

In another aspect the present invention relates to a method wherein said skin condition is hand eczema.

In another aspect the present invention relates to a method of treating or preventing abnormal skin conditions in a patient (human or animal subject) in need thereof, the method comprising administering to said patient a cell culture composition comprising a bacterial strain selected from *Bifidobacterium, Brevibacterium, Propionibacterium, Lactococcus, Streptococcus, Staphylococcus* (e.g., *S. epidermidis*), *Lactobacillus* (e.g., *L. acidophilus*), *Enterococcus, Pediococcus, Leuconostoc*, or *Oenococcus*, and mixtures thereof wherein the cell culture composition comprises at least one engineered bacterial strain that produces a therapeutically effective amount of a recombinant polypeptide comprising (a) a filaggrin amino acid sequence, (b) a secretion signal, and (c) a cell penetrating peptide for therapeutic treatment or prevention of the abnormal skin condition.

In another aspect the present invention relates to a method wherein the cell culture composition comprises *Staphylococcus epidermidis*.

In another aspect the present invention relates to a method wherein the cell culture composition is a living culture composition.

In another aspect the present invention relates to a method wherein the filaggrin amino acid sequence comprises a sequence selected from SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, or SEQ ID NO 17, and combinations thereof.

In another aspect the present invention relates to a method wherein the filaggrin amino acid sequence comprises SEQ ID NO 1.

In another aspect the present invention relates to a method wherein the filaggrin amino acid sequence has at least about 75% homology to SEQ ID NO 1.

In another aspect the present invention relates to a method wherein the filaggrin amino acid sequence has at least about 80% homology to SEQ ID NO 1.

In another aspect the present invention relates to a method wherein the filaggrin amino acid sequence has at least about 85% homology to SEQ ID NO 1.

In another aspect the present invention relates to a method wherein the filaggrin amino acid sequence has at least about 90% homology to SEQ ID NO 1.

In another aspect the present invention relates to a method wherein the filaggrin amino acid sequence has at least about 95% homology to SEQ ID NO 1.

In another aspect the present invention relates to a method wherein the filaggrin amino acid sequence has at least about 75% homology, or 80% homology, or 85% homology, or 90% homology, or 95% homology to a sequence selected from SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, or SEQ ID NO 17.

In another aspect the present invention relates to a method wherein the skin condition is selected from psoriasis, acne, atopic dermatitis, allergic contact dermatitis, epidermolytic hyperkeratosis, seborrheic dermatitis, eczema, dry skin, allergy, rashes, UV-irritated skin, detergent irritated skin (including irritation caused by enzymes and molecules used in washing detergents and sodium lauryl sulfate), thinning skin (e.g. skin from the elderly and children), bullous pemphigoid, pemphigus vulgaris, impetigo, vitiligio, baldness, and hirsutism.

In another aspect the present invention relates to a method wherein the skin condition is eczema.

In another aspect the present invention relates to a pharmaceutical composition for treating or preventing abnormal skin conditions in a patient (human or animal subject) in need thereof, comprising (a) a cell culture composition comprising a bacterial strain selected from *Bifidobacterium, Brevibacterium, Propionibacterium, Lactococcus, Streptococcus, Staphylococcus* (e.g., *S. epidermidis*). *Lactobacillus* (e.g., *L. acidophilus*), *Enterococcus, Pediococcus, Leuconostoc*, or *Oenococcus*, and mixtures thereof, wherein the cell culture composition comprises at least one engineered bacterial strain that produces a therapeutically effective amount of a recombinant polypeptide for therapeutic treatment or prevention of abnormal skin conditions and (b) a pharmaceutically acceptable carrier.

In another aspect the present invention relates to a pharmaceutical composition wherein said composition comprises a bacterial strain containing human target DNA recombined with bacterial DNA.

In another aspect the present invention relates to a pharmaceutical composition wherein said composition comprises an engineered strain of *Staphylococcus epidermidis*.

In another aspect the present invention relates to a pharmaceutical composition wherein said composition comprises a living cell culture composition.

In another aspect the present invention relates to a pharmaceutical composition wherein said composition comprises 0% water to no more than about 90% water.

In another aspect the present invention relates to a pharmaceutically acceptable carrier that is selected from an aqueous solution, an emulsion, a cream, a lotion, a gel, or an ointment.

In another aspect the present invention relates to a pharmaceutical composition for treating or preventing abnormal skin conditions in a patient (human or animal subject) in need thereof, comprising (I) a cell culture composition comprising a bacterial strain selected from *Bifidobacterium, Brevibacterium, Propionibacterium, Lactococcus, Streptococcus, Staphylococcus* (e.g., *S. epidermidis*), *Lactobacillus* (e.g., *L. acidophilus*), *Enterococcus, Pediococcus, Leuconostoc*, or *Oenococcus*, and mixtures thereof, wherein the cell culture composition comprises at least one engineered bacterial strain that produces a therapeutically effective amount of a recombinant polypeptide comprising (a) a filaggrin amino acid sequence, (b) a secretion signal, and (c) a cell penetrating peptide and (II) a pharmaceutically acceptable carrier for therapeutic treatment or prevention of the abnormal skin condition.

In another aspect the present invention relates to a pharmaceutical composition wherein the cell culture composition comprises a bacterial strain containing human target DNA recombined with bacterial DNA.

In another aspect the present invention relates to a pharmaceutical composition wherein the cell culture composition comprises *Staphylococcus epidermidis*.

In another aspect the present invention relates to a pharmaceutical composition wherein the cell culture composition is a living cell culture composition.

In another aspect the present invention relates to a pharmaceutical composition wherein the filaggrin amino acid sequence comprises a sequence selected from SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, or SEQ ID NO 17, and combinations thereof.

In another aspect the present invention relates to a pharmaceutical composition wherein the filaggrin amino acid sequence comprises SEQ ID NO: 1.

In another aspect the present invention relates to a pharmaceutical composition wherein the filaggrin amino acid sequence has at least about 75% homology to SEQ ID NO 1.

In another aspect the present invention relates to a pharmaceutical composition wherein the filaggrin amino acid sequence has at least about 80% homology to SEQ ID NO 1.

In another aspect the present invention relates to a pharmaceutical composition wherein the filaggrin amino acid sequence has at least about 85% homology to SEQ ID NO 1.

In another aspect the present invention relates to a pharmaceutical composition wherein the filaggrin amino acid sequence has at least about 90% homology to SEQ ID NO 1.

In another aspect the present invention relates to a pharmaceutical composition wherein the filaggrin amino acid sequence has at least about 95% homology to SEQ ID NO 1.

In another aspect the present invention relates to a pharmaceutical composition wherein the filaggrin amino acid sequence has at least about 75% homology, or 80% homology, or 85% homology, or 90% homology, or 95% homology to a sequence selected from SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, or SEQ ID NO 17.

In another aspect the present invention relates to a pharmaceutical composition wherein the composition comprises 0% water to no more than about 90% water.

In another aspect the present invention relates to a pharmaceutical composition wherein the pharmaceutically acceptable carrier is an aqueous solution, an emulsion, a cream, a lotion, a gel, or an ointment.

In another aspect the present invention relates to use of a cell culture composition for the manufacture of a medicament for treating or preventing abnormal skin conditions in a patient (human or animal subject) in need thereof, said cell culture composition comprising a bacterial strain selected from *Bifidobacterium, Brevibacterium, Propionibacterium, Lactococcus, Streptococcus, Staphylococcus* (e.g., *S. epidermidis*), *Lactobacillus* (e.g., *L. acidophilus*), *Enterococcus, Pediococcus, Leuconostoc*, or *Oenococcus*, and mixtures thereof wherein the cell culture composition comprises at least one engineered bacterial strain that produces a therapeutically effective amount of a recombinant polypeptide for treating or preventing the abnormal skin condition.

In another aspect the present invention relates to use of a cell culture composition for the manufacture of a medicament for treating or preventing abnormal skin conditions in a patient (human or animal subject) in need thereof, said cell culture composition comprising a bacterial strain selected from *Bifidobacterium, Brevibacterium, Propionibacterium, Lactococcus, Streptococcus, Staphylococcus* (e.g., *S. epider-*

*midis*), *Lactobacillus* (e.g., *L. acidophilus*), *Enterococcus*, *Pediococcus*, *Leuconostoc*, or *Oenococcus*, and mixtures thereof wherein the cell culture composition comprises at least one engineered bacterial strain that produces a therapeutically effective amount of a recombinant polypeptide comprising (a) a filaggrin amino acid sequence, (b) a secretion signal, and (c) a cell penetrating peptide for therapeutic treatment or prevention of the abnormal skin condition.

Definitions

As used herein, the following terms have the following meanings unless expressly stated to the contrary:

As used herein, the term "abnormal skin condition" refers to a skin state or condition that is generally undesirable or deleterious compared to the normal or baseline condition of human skin. Examples of abnormal skin conditions include: psoriasis, acne, atopic dermatitis, allergic contact dermatitis, epidermolytic hyperkeratosis, seborrheic dermatitis, eczema, dry skin, allergy, rashes, UV-irritated skin, detergent irritated skin (including irritation caused by enzymes and molecules used in washing detergents and sodium lauryl sulfate), thinning skin (e.g. skin from the elderly and children), bullous pemphigoid, pemphigus vulgaris, impetigo, vitiligio, baldness, and hirsutism.

As used herein, the terms "patient" or "subject", refers to a human or animal (in the case of an animal, more typically a mammal such as domesticated mammals, or animals such as poultry animals and fish and other seafood or freshwater food creatures), that would be subjected to the treatments and compositions of the present invention. Such patient or subject would be considered to be in need of the pharmaceutical compositions of the present invention or of the methods of treating, preventing, or reducing the risk of an abnormal skin condition.

As used herein, the term "therapeutically effective amount" refers to an amount of a pharmaceutical active compound, or a combination of compounds, or an amount of pharmaceutical active compound delivered by an engineered bacterial strain or strains, for example a skin treatment agent or agents, when administered alone or in combination, to treat, prevent, or reduce the risk of a disease state or condition, for example an abnormal skin condition. The term also refers to an amount of a pharmaceutical composition containing an active compound or combination of compounds or an engineered bacterial strain or strains that delivers a pharmaceutical active compound. For example, an effective amount refers to an amount of the compound or an amount of the compound delivered by an engineered bacterial strain or strains present in a formulation given to a recipient patient or subject sufficient to elicit biological activity, for example, activity for treating or preventing an abnormal skin condition.

As used herein, the phrase "pharmaceutically acceptable" refers to those active compounds, materials, engineered bacterial strain or strains, compositions, carriers, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

As used herein, the term "treating" refers to providing a therapeutic intervention to cure or ameliorate an abnormal skin condition.

As used herein, the term "preventing", refers to completely or almost completely stopping an abnormal skin condition from occurring, for example when the patient or subject is predisposed to an abnormal skin condition or at risk of contracting an abnormal skin condition. Preventing can also include inhibiting, i.e. arresting the development, of an abnormal skin condition.

As used herein, the term "reducing the risk of", refers to lowering the likelihood or probability of an abnormal skin condition from occurring, for example when the patient or subject is predisposed to an abnormal skin condition or at risk of contracting an abnormal skin condition.

As used herein, the term "engineered bacterial strain," refers to a strain of bacteria that has been "genetically modified" or "engineered" by the introduction of DNA prepared outside the organism into the bacterial strain. For example, the introduction of plasmid DNA containing new genes into bacteria will allow the bacteria to express those genes. Alternatively, the DNA containing new genes can be introduced to the bacteria and then integrated into the bacteria's genome, where the bacteria will express those genes.

As used herein, the terms "carriers", "carrier system" or "vehicles" refer to compatible substances that are suitable for delivering, containing, or "carrying" a pharmaceutical active ingredient or other materials for administration in a topically applied composition to a patient or subject. Carriers useful herein should be pharmaceutically acceptable. Carriers and vehicles useful herein include any such materials known in the art, which are non-toxic and do not interact with other components of the formulation in which it is contained in a deleterious manner. The term "aqueous" refers to a formulation that contains water or that becomes water-containing following application to the skin or mucosal tissue. Further examples of "carriers" include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such carriers.

As used herein, the terms "polypeptide" or "protein" refer to biological molecules, or macromolecules composed of amino-acid residues bonding together in a chain. The definition of polypeptides used herein is intended to encompass proteins (generally higher molecular weight) composed of one or more long chains of amino acid residues and small peptides (generally lower molecular weight) of a few amino acids. In other embodiments, a single amino acid, although not technically a polypeptide, is also considered within the scope of the invention.

DETAILED DESCRIPTION OF THE INVENTION

The present invention provides skin-colonizing bacteria that are genetically altered to express recombinant therapeutic polypeptides for the treatment or prevention of skin disease (FIG. 1). Using genetically engineered protein-producing bacteria has several advantages over the prior art method of treating skin disease. Therapeutic proteins are able to treat the underlying cause of defects leading to the skin condition. Further, bacteria are able to self-replicate while retaining the inserted gene to continuously produce the therapeutic protein.

The present invention provides skin-colonizing bacteria, such as for example, *Staphylococcus epidermidis*, that are genetically altered to express human filaggrin. Using genetically engineered filaggrin-producing bacteria has several advantages over using filaggrin supplementation. First, bacteria are able to self-replicate while retaining the inserted filaggrin gene. Second, *S. epidermidis* is normally present on the skin and has been shown to inhibit growth of *Staphylococcus aureus*, a bacterial species of the same genre that dominates the skin flora in AD flares.

1. Bacterial Strains
Cell Culture Compositions

A wide range of bacteria are suitable for use in the present invention. Examples include, but are not limited to, non-pathogenic and commensal bacteria. Bacteria suitable for use in the present invention include, but are not limited to, *Bifidobacterium*, *Brevibacterium*, *Propionibacterium*, *Lactococcus*, *Streptococcus*, *Staphylococcus* (e.g., *S. epidermidis*), *Lactobacillus* (e.g., *L. acidophilus*), *Pediococcus*, *Leuconostoc*, or *Oenococcus*.

Certain embodiments involve the use of bacterium *Staphylococcus epidermidis*. The strain of *S. epidermidis* to be used is incapable of producing biofilms. An example of this is *S. epidermidis* strain ATCC12228.

However, other related or similar species found on the skin can also be used.

2. Filaggrin and Filaggrin Gene

A useful gene selected in an embodiment for this invention is a mammalian gene encoding filaggrin (FLG). Filaggrin is a protein produced by differentiating keratinocytes and functions to aggregate keratin filaments into a cytoskeleton that, in combination with other components, comprises the cornified cell envelope. FLG is a large gene located on chromosome 1q21 and produces profilaggrin, an insoluble polyprotein that is proteolyzed to release functional filaggrin monomers (Armengot-Carbo et al. 2014). The gene for this invention can be from any mammal. Non-limiting examples include mouse, rat, rabbit, goat, sheep, horse, cow, dog, primate, or human gene sequence. In preferred embodiments, the gene sequence is a human gene sequence. Non-limiting examples of filaggrin proteins are set forth in Table 1 and the sequences are further described in the corresponding Sequence IDs.

TABLE 1

Examples of filaggrin protein sequences

| Sequence | GenBank Accession No. | SEQ ID NO. |
|---|---|---|
| Filaggrin, *Homo sapiens* | NM_002016 | 1 |
| Filaggrin, *Homo sapiens* | NP_002007 | 2 |
| Filaggrin, *Homo sapiens* | AAA52454 | 3 |
| Filaggrin, *Homo sapiens* | CAI19595 | 4 |
| Filaggrin, *Homo sapiens* | P20930 | 5 |
| Filaggrin, *Mus musculus* | AAM23016 | 6 |
| Filaggrin, *Mus musculus* | AAA75559 | 7 |
| Filaggrin, *Mus musculus* | AAA37626 | 8 |
| Filaggrin, *Mus musculus* | AAA37625 | 9 |
| Filaggrin, *Mus musculus* | XP_485270 | 10 |
| Filaggrin, *Mus musculus* | P11088 | 11 |
| Filaggrin, *Mus musculus* | EDL00668.1 | 12 |
| Filaggrin, *Rattus norvegicus* | EDL87862 | 13 |
| Filaggrin, *Pan troglodytes* | XP_001134714 | 14 |
| Filaggrin, *Pan troglodytes* | XP_513808 | 15 |
| Filaggrin, *Macaca mulatta* | XP_001101725.1 | 16 |
| Filaggrin, *Macaca mulatta* | XP_001109011.1 | 17 |

3. Secretion Signals

Secretion signals or export signals are peptides on a protein that indicate the protein is destined for the secretory pathway and therefore secreted from the cell. Any secretion signal that facilitates exit of a protein such as a filaggrin molecule out of the bacterial cell is contemplated as a secretion signal. Non-limiting examples of secretion signals are set forth in Table 2.

TABLE 2

Examples of secretion signals

| Sequence | SEQ ID NO. |
|---|---|
| MKKLAFAITAASGAAAVLSHHDAEA | 18 |
| WLDNRAFSKKFVPVVMATSVALFFLNLAFA | 19 |
| MAKKFNYKLPSMVALTLFGTAFTAHQANA | 20 |
| MKKRFLSICTMTIAALATTTMVNTSYA | 21 |
| NLKKQSKLILIFICIFTFFIMIIQSQFLMG | 22 |
| MKIFKLTSLTLAALTLAFPFSHVAQA | 23 |
| MKKTVIASTLAVSLGIAGYGLSGHEAHA | 24 |
| MKKNKFLVYLLSTALITPTFATQTAFA | 25 |
| MKTRQNKYSIRKFSVGASSILIAALLFMGGGSAQA | 26 |
| MKNNNETRRFSIRKYTVGVVSIITGITIFVSGQHAQA | 27 |
| MKKKLSYMITIMLAFTLSLALGLFFNSAHA | 28 |

4. Cell Penetrating Peptides

A cell penetrating peptide can be used to mediate delivery of cargo in vivo without using any receptors and without causing any significant membrane damage. Cell penetrating peptides that facilitate skin entry into the skin keratinocytes are contemplated as a cell penetrating peptides of the present invention. Non-limiting examples are set forth in Table 3.

TABLE 3

Examples of cell penetrating peptides

| Sequence | SEQ ID NO. |
|---|---|
| GRKKRRQRRRPPQ | 29 |
| GWTLNSAGYLLGKINLKALAALAKKIL | 30 |
| KLALKLALKALKAALKLA | 31 |
| WEAKLAKALAKALAKHLAKALAKALKACEA | 32 |
| KETWWETWWTEWSQPKKKRKV | 33 |
| RRRRRRRRR | 34 |
| LGTYTQDFNKFHTFPQTAIGVGAP | 35 |

References for Seq. IDs 29-35 of Table 3: Seq ID 29. Jeong J G et al. (2011). Seq ID 30. Ostenson C G et al. (1997). Seq ID 31. Oehike J et al. (1998). Seq ID 32. Wyman T B, et al. (1997). Seq IDs 33.-35. J. Ma et al. (2014).

5. Genetic Construct

Figure 2:
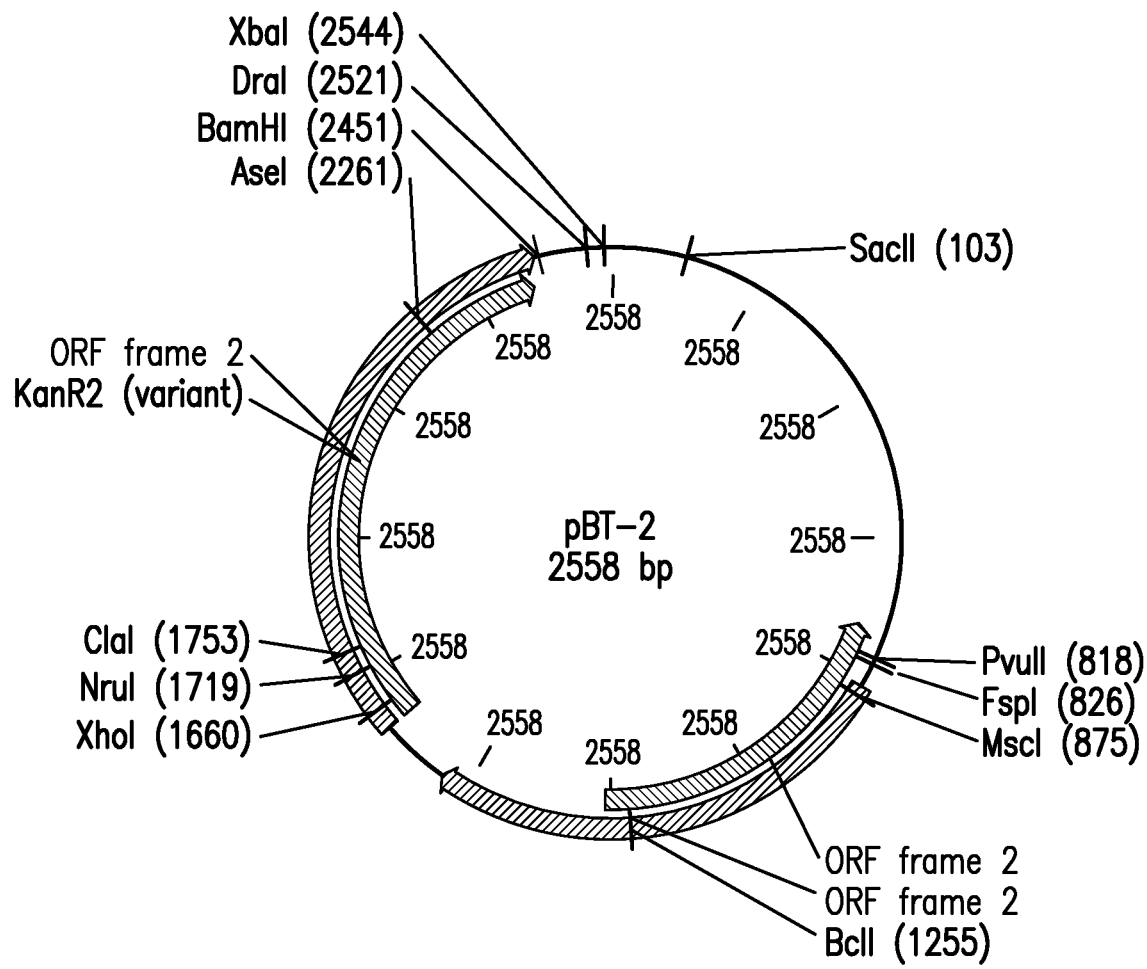
FIG. 2 depicts a vector design of the plasmid and shuttle vector pBT-2. Vector pBT-2 is exemplary of alternative shuttle vectors that can be used for cloning in E. coli and expression in Staphylococcus.
Figure 3:
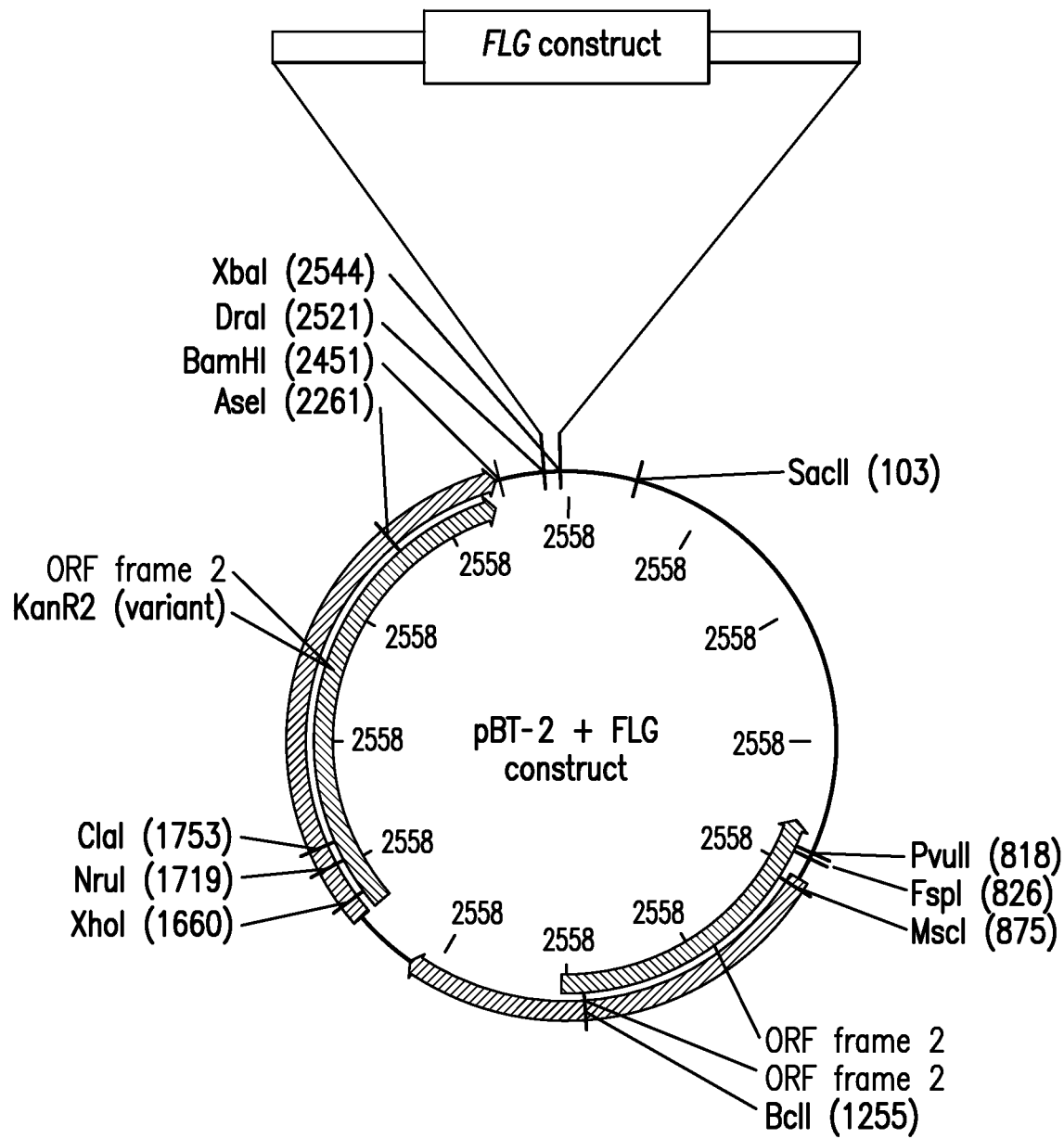
FIG. 3 depicts a vector design of a modified version of the shuttle vector pBT-2 including the FLG (filaggrin) gene insert, described in FIG. 4. This construct is exemplary of alternative constructs for filaggrin expression in S. epidermidis and has previously been described as pAZT-01.
Figure 4:
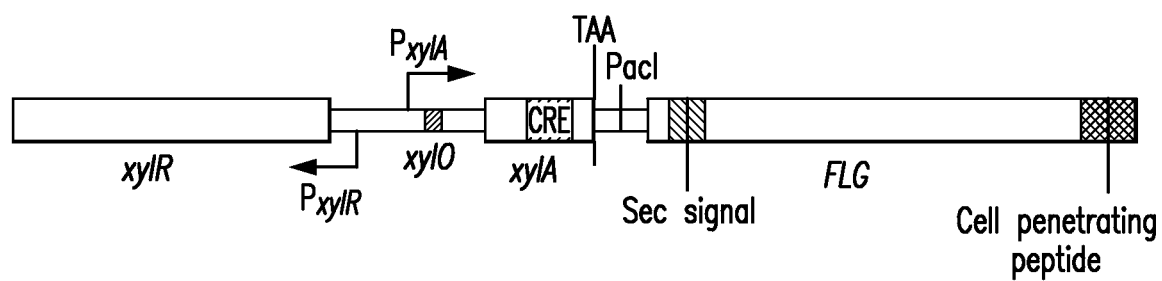
FIG. 4 is a detailed map of the FLG gene insert that was cloned into the plasmid pBT-2, shown previously in FIG. 2, and can be cloned into various vectors for expression in Staphylococcus. This insert includes xylose repressor (xylR), xylose operator (xylO), xylose isomerase gene (xylA) including the cis-acting catabolite-responsive element (CRE), the Sec (secretion pathway) export signal, gene encoding filaggrin (FLG), and the cell penetrating peptide.

The invention utilizes standard molecular biology techniques. e.g., those described in (Sambrook et al. 2001). An example of the genetic construct used for this invention is based on a plasmid vector pBT-2 (FIG. 2), an allelic exchange shuttle vector between *E. coli* and *Staphylococcal* species (Nakanishi, Oshida et al. 1986). The plasmid of FIG. 3 is constructed by inserting cDNA of a gene encoding a therapeutic protein into a restriction site of the MCS of pBT-2. The insert contains a coding sequence driven by a promoter. Such a promoter can be either constitutive or inducible. Examples of inducible promoters include those that are activated by chemical compounds such as alcohols, sugars, metals, or tetracycline, or by physical factors such as light or high temperatures.

Figure 5:
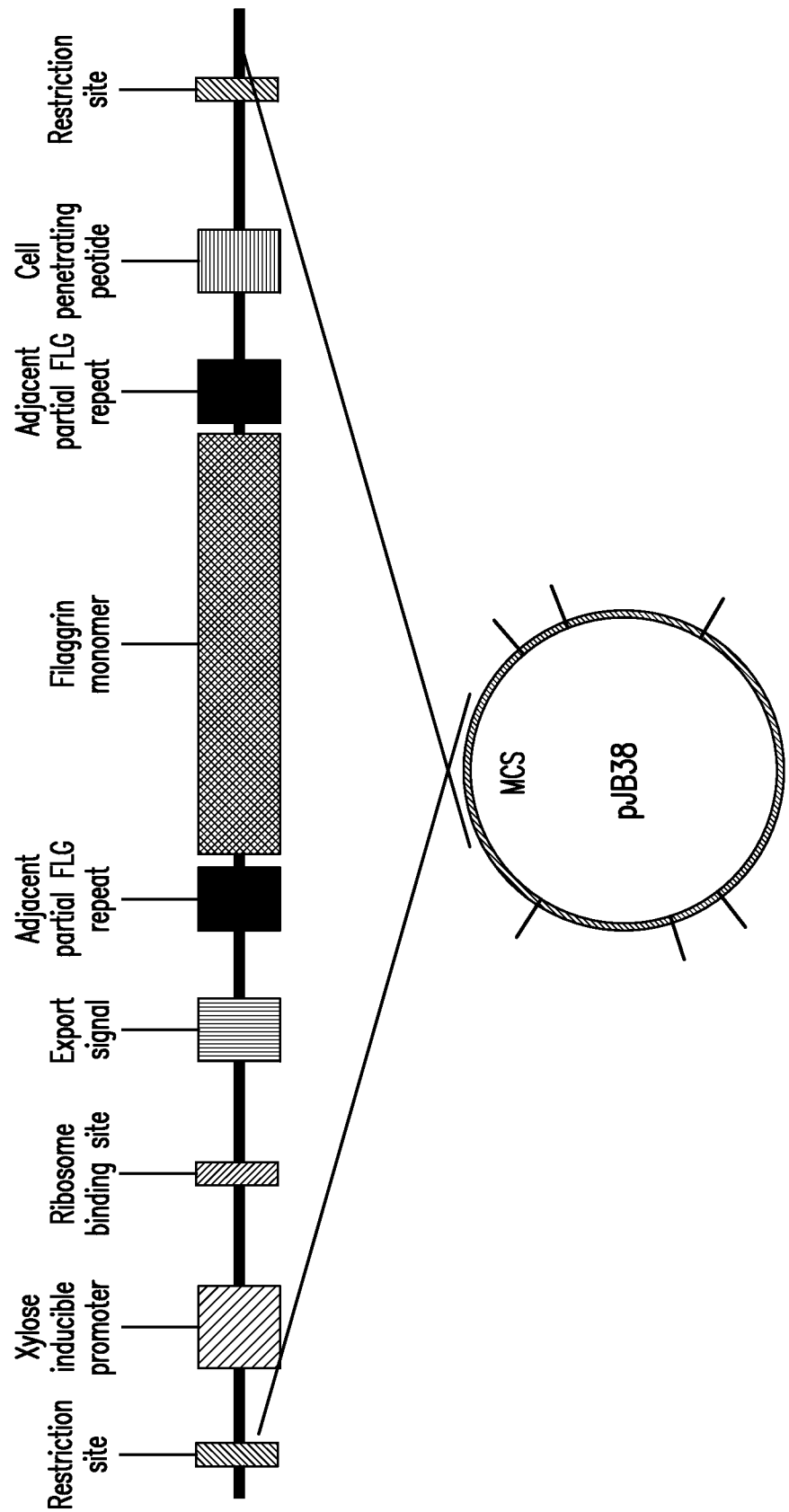
FIG. 5 depicts a vector design of the plasmid pJB38 (Cheung, A L., et al. (2004)). Restriction sites are built into the multiple cloning site (MCS) of the vector. Inserted into the MCS of the vector is a filaggrin expression vector with a xylose-inducible promoter, ribosome binding site, export signal (for example SecA export signal), partial FLG (filaggrin) repeats flanking the filaggrin monomer, and a cell penetrating signal. The insert of pAZT-01 was constructed and cloned into pJB38 by Bio Basic, Inc, (Markham, ON, Canada).

The genetic construct can be based on a plasmid vector pJB38, an allelic exchange shuttle vector between *E. coli* and *Staphylococcal* species. See (Cheung A L, et al. 2004). The mRNA sequence of human FLG has a Genebank accession No. NM_002016, and is reproduced above as SEQ. ID NO. 1. Plasmid pAZT-01 (FIG. 5) can be constructed by inserting part of the FLG cDNA into a restriction site of pJB38. The insert contains a coding sequence driven by a constitutive xylose promoter. The construct also encodes a secretion signal and a cell penetrating peptide, thus resulting in a filaggrin fusion protein.

6. Uses of Recombinant Bacterial Strain

It will be understood that the disorder to be treated can be any disorder associated with skin. In preferred embodiments the disorder is selected from the group comprising psoriasis, acne, atopic dermatitis, allergic contact dermatitis, epidermolytic hyperkeratosis, seborrheic dermatitis, eczema, dry skin, allergy, rashes, UV-irritated skin, detergent irritated skin (including irritation caused by enzymes and compounds used in washing detergents and sodium lauryl sulfate), thinning skin (e.g. skin from the elderly and children), bullous pemphigoid, pemphigus vulgaris, impetigo, vitiligio, baldness, and hirsutism.

Examples of proteins that can be administered according to the invention are mostly eukaryotic proteins. These can include but are not limited to single amino acids, small peptides, and large proteins. More particularly, genes encoding proteins that are useful in the invention as recombinant therapeutic proteins include, but are not limited to, the following genes. Members of the interleukin family of genes, including but not limited to IL-2, IL-3, IL-4, IL-5, IL-6, IL-7, IL-8, IL-9, IL-10, IL-11, IL-12, IL-13, IL-14 and IL-15 and genes encoding receptor antagonists thereof. Genes which encode hematopoietic growth factors, including but not limited to, erythropoietin, granulocyte colony stimulating factor, granulocyte macrophage colony stimulating factor, macrophage colony stimulating factor, stem cell factor, leukemia inhibitory factor and thrombopoietin are also contemplated in the invention. Genes encoding neurotropic factors are also contemplated, including but not limited to, nerve growth factor, brain derived neurotropic factor and ciliary neurotropic factor. In addition, genes which encode interferons, including but not limited to IFN-alpha, IFN-beta and IFN-gamma are included. Further contemplated in the invention are genes encoding chemokines such as the C—C family and the C—X—C family of cytokines, genes encoding hormones, such as proinsulin and growth hormone, and genes encoding thrombolytic enzymes, including tissue plasminogen activator, streptokinase, urokinase or other enzymes such as trypsin inhibitor. The invention further includes genes which encode tissue repair factors, growth and regulatory factors such as, but not limited to, oncostatine M, platelet-derived growth factors, fibroblast growth factors, epidermal growth factor, hepatocyte growth factor, bone morphogenic proteins, insulin-like growth factors, calcitonin and transforming growth factor alpha and beta. Further contemplated genes include genes encoding structural proteins such as filaggrin, actin, collagen, fibrillin, elastin, or scleroprotein.

Formulations

It will be further apparent that the formulation for use according to the present invention can comprise any pharmaceutically effective amount of the recombinant bacteria to produce a therapeutically effective amount of the desired polypeptide, for example, at least about 0.01%, about 0.05%, about 0.1%, about 0.2%, about 0.3%, about 0.4%, about 0.5%, about 0.6%, about 0.7%, about 0.8%, about 0.9%, about 1.0%, about 1.5%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 20.0%, about 25.0%, about 30.0%, about 35.0%, about 40.0%, about 45.0%, about 50.0% or more by weight of recombinant bacteria, the upper limit of which is about 90.0% by weight of recombinant bacteria.

In an alternative embodiment the formulation for use according to the present invention can comprise, for example, at least about 0.01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to about 5%, or more by weight of recombinant bacteria.

The topical formulation for use in the present invention can be in any form suitable for application to the body surface, such as a cream, lotion, sprays, solution, gel, ointment, paste, plaster, paint, bioadhesive, suspensions, emulsions, or the like, and/or can be prepared so as to contain liposomes, micelles, and/or microspheres. Such a formulation can be used in combination with an occlusive overlayer so that moisture evaporating from the body surface is maintained within the formulation upon application to the body surface and thereafter. The formulation can include a living cell culture composition and can comprise at least one engineered bacterial strain that produces a recombinant polypeptide. This engineered living cell culture composition can deliver the polypeptide directly to the skin for treating or preventing abnormal skin conditions.

Topical formulations include those in which any other active ingredient(s) is (are) dissolved or dispersed in a dermatological vehicle known in the art (e.g. aqueous or non-aqueous gels, ointments, water-in-oil or oil-in-water emulsions). Constituents of such vehicles can comprise water, aqueous buffer solutions, non-aqueous solvents (such as ethanol, isopropanol, benzyl alcohol, 2-(2-ethoxyethoxy) ethanol, propylene glycol, propylene glycol monolaurate, glycofurol or glycerol), oils (e.g. a mineral oil such as a liquid paraffin, natural or synthetic triglycerides such as Miglyol™, or silicone oils such as dimethicone). Depending, inter alia, upon the nature of the formulation as well as its intended use and site of application, the dermatological vehicle employed can contain one or more components (for example, when the formulation is an aqueous gel, components in addition to water) selected from the following list: a solubilizing agent or solvent (e.g. a β-cyclodextrin, such as hydroxypropyl β-cyclodextrin, or an alcohol or polyol such as ethanol, propylene glycol or glycerol); a thickening agent (e.g. hydroxyethylcellulose, hydroxypropylcellulose, carboxymethylcellulose or carbomer); a gelling agent (e.g. a polyoxyethylene-polyoxypropylene copolymer); a preservative (e.g. benzyl alcohol, benzalkonium chloride, chlorhexidine, chlorbutol, a benzoate, potassium sorbate or EDTA or salt thereof); and pH buffering agent(s) (such as a mixture of dihydrogen phosphate and hydrogen phosphate salts, or a mixture of citric acid and a hydrogen phosphate salt).

A pharmaceutically acceptable carrier can also be incorporated in the formulation of the present invention and can be any carrier conventionally used in the art. Examples thereof include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such carriers. The term "pharmaceutically acceptable" or "pharmaceutically acceptable carrier" is used herein to refer to a compound or composition that can be incorporated into a pharmaceutical formulation without causing undesirable biological effects or unwanted interaction with other components of the formulation. "Carriers" or "vehicles" as used herein refer to carrier materials suitable for incorporation in a topically applied composition. Carriers and vehicles useful herein include any such materials known in the art, which are non-toxic and do not interact with other components of the formulation in which it is contained in a deleterious manner. The term "aqueous" refers to a formulation that contains water or that becomes water-containing following application to the skin or mucosal tissue.

A film former, when it dries, forms a protective film over the site of application. The film inhibits removal of the active ingredient and keeps it in contact with the site being treated. An example of a film former that is suitable for use in this invention is Flexible Collodion, USP. As described in Remington: The Science and Practice of Pharmacy, 19th Ed. (Easton, Pa.: Mack Publishing Co., 1995), at page 1530, collodions are ethyl ether/ethanol solutions containing pyroxylin (a nitrocellulose) that evaporate to leave a film of pyroxylin. A film former can act additionally as a carrier. Solutions that dry to form a film are sometimes referred to as paints. Creams, as is well known in the arts of pharmaceutical formulation, are viscous liquids or semisolid emulsions, either oil-in-water or water-in-oil.

Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Lotions are preparations to be applied to the skin surface without friction, and are typically liquid or semiliquid preparations in which particles, including the active agent, are present in a water or alcohol base. Lotions are usually suspensions of solids, and preferably, comprise a liquid oily emulsion of the oil-in-water type. Lotions are preferred formulations herein for treating large body areas, because of the ease of applying a more fluid composition. It is generally necessary that the insoluble matter in a lotion be finely divided.

Lotions will typically contain suspending agents to produce better dispersions as well as compounds useful for localizing and holding the active agent in contact with the skin, e.g., methylcellulose, sodium carboxymethyl-cellulose, or the like.

Solutions are homogeneous mixtures prepared by dissolving one or more chemical substances (solutes) in a liquid such that the molecules of the dissolved substance are dispersed among those of the solvent. The solution can contain other pharmaceutically or cosmetically acceptable chemicals to buffer, stabilize or preserve the solute. Common examples of solvents used in preparing solutions are ethanol, water, propylene glycol or any other acceptable vehicles. As is of course well known, gels are semisolid, suspension-type systems. Single-phase gels contain organic macromolecules distributed substantially uniformly throughout the carrier liquid, which is typically aqueous, but also, preferably, contain an alcohol, and, optionally, an oil.

Preferred "organic macromolecules," i.e., gelling agents, are cross-linked acrylic acid polymers such as the "carbomer" family of polymers, e.g., carboxypolyalkylenes that can be obtained commercially under the Carbopol trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof. Ointments, as also well known in the art, are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, nonirritating, and nonsensitizing. As explained in Remington: The Science and Practice of Pharmacy, 19th Ed. (Easton. Pa.: Mack Publishing Co., 1995), at pages 1399-1404, ointment bases can be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum.

Emulsion ointment bases are either water-in-oil (W/O) emulsions or oil-in-water (O/W) emulsions, and include, for example, acetyl alcohol, glyceryl monostearate, lanolin, and stearic acid. Preferred water-soluble ointment bases are prepared from polyethylene glycols of varying molecular weight; see Remington: The Science and Practice of Pharmacy for further information.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Enhancers are those lipophilic co-enhancers typically referred to as "plasticizing" enhancers, i.e., enhancers that have a molecular weight in the range of about 150 to 1000, an aqueous solubility of less than about 1 wt. %, preferably less than about 0.5 wt. %, and most preferably less than about 0.2 wt. %. The Hildebrand solubility parameter 6 of plasticizing enhancers is in the range of about 2.5 to about 10, preferably in the range of about 5 to about 10. Preferred lipophilic enhancers are fatty esters, fatty alcohols, and fatty ethers. Examples of specific and most preferred fatty acid esters include methyl laurate, ethyl oleate, propylene glycol monolaurate, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, preferably a $C_2$-$C_4$ alkane diol or triol, are substituted with one or two fatty ether substituents.

Additional permeation enhancers will be known to those of ordinary skill in the art of topical drug delivery, and/or are described in the pertinent texts and literature. See, e.g., Percutaneous Penetration Enhancers, eds. Smith et al. (CRC Press, 1995)(incorporated herein by reference).

Various other additives can be included in the compositions of the present invention in addition to those identified above. These include, but are not limited to, antioxidants, astringents, perfumes, preservatives, emollients, pigments, dyes, humectants, propellants, and sunscreen agents, as well as other classes of materials whose presence can be pharmaceutically or otherwise desirable. Typical examples of optional additives for inclusion in the formulations of the invention are as follows: preservatives such as sorbate; solvents such as isopropanol and propylene glycol; astringents such as menthol and ethanol; emollients such as polyalkylene methyl glucosides; humectants such as glycerine; emulsifiers such as glycerol stearate, PEG-100 stearate, polyglyceryl-3 hydroxylauryl ether, and polysorbate 60; sorbitol and other polyhydroxyalcohols such as polyethylene glycol; sunscreen agents such as octyl methoxyl cinnamate (available commercially as Parsol MCX) and butyl methoxy benzoylmethane (available under the tradename Parsol 1789); antioxidants such as ascorbic acid (vitamin C), a-tocopherol (Vitamin E), β-tocopherol, γ-tocopherol, Δ-tocopherol, ε-tocopherol, $\zeta_1$-tocopherol, $\zeta_2$-tocopherol, η-tocopherol, and retinol (vitamin A); essential oils, ceramides, essential fatty acids, mineral oils, vegetable oils (e.g., soya bean oil, palm oil, liquid fraction of shea butter, sunflower oil), animal oils (e.g., perhydrosqualene), synthetic oils, silicone oils or waxes (e.g., cyclomethicone and dimethicone), fluorinated oils (generally perfluoropolyethers), fatty alcohols (e.g., cetyl alcohol), and waxes (e.g., beeswax, carnauba wax, and paraffin wax); skin-feel modifiers; and thickeners and structurants such as swelling clays and cross-linked carboxypolyalkylenes that can be obtained commercially under the Carbopol trademark. Other additives include beneficial agents such as those materials that condition the skin (particularly, the upper layers of the skin in the stratum corneum) and keep it soft by retarding the decrease of its water content and/or protect the skin. Such conditioners and moisturizing agents include, by way of example, pyrrolidine carboxylic acid and amino acids; organic antimicrobial agents such as 2,4,4'-trichloro-2-hydroxy diphenyl ether (triclosan) and benzoic acid; anti-inflammatory agents such as acetylsalicylic acid and glycyrrhetinic acid; anti-seborrhoeic agents such as retinoic acid; vasodilators such as nicotinic acid; inhibitors of melanogenesis such as kojic acid; and mixtures thereof. Further additional active agents including, for example, alpha hydroxyacids, alpha ketoacids, polymeric hydroxyacids, moisturizers, collagen, marine extract, and antioxidants such as ascorbic acid (Vitamin C), a-tocopherol (Vitamin E), β-tocopherol, γ-tocopherol, Δ-tocopherol, ε-tocopherol, ζ-tocopherol, $\zeta_2$-tocopherol. η-tocopherol, and retinol (Vitamin A), and/or pharmaceutically acceptable salts, esters, amides, or other derivatives thereof. A preferred tocopherol compound is a-tocopherol. Additional agents include those that are capable of improving oxygen supply in skin tissue, as described, for example, in Gross, et al, WO 94/00098 and Gross, et al, WO 94/00109, both assigned to Lancaster Group AG (incorporated herein by reference). Sunscreens and UV absorbing compounds can also be included. Non-limiting examples of such sunscreens and UV absorbing compounds include aminobenzoic acid (PABA), avobenzone, cinoxate, dioxybenzone, homosalate, menthyl anthranilate, oxtocrylene, octyl methoxycinnamate, octyl salicylate, oxybenzone, padimate O, phenylbenzimidazole sulfonic acid, sulisobenzone, titanium dioxide, trolamine salicylate, zinc oxide, ensulizole, meradimate, octinoxate, octisalate, and octocrylene. See Title 21. Chapter 1. Subchapter D. Part 352. "Sunscreen drug products for over-the-counter human use" incorporated herein in its entirety.

Other embodiments can include a variety of non-carcinogenic, non-irritating healing materials that facilitate treatment with the formulations of the invention. Such healing materials can include nutrients, minerals, vitamins, electrolytes, enzymes, herbs, plant extracts, glandular or animal extracts, or safe therapeutic agents that can be added to the formulation to facilitate the healing of dermal disorders.

The amounts of these various additives are those conventionally used in the cosmetics field, and range, for example, from about 0.01% to about 20% of the total weight of the topical formulation.

The formulations of the invention can also include conventional additives such as opacifiers, fragrance, colorant, stabilizers, surfactants, and the like. In certain embodiments, other agents can also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof. In other embodiments, other agents can also be added, such as repressors and inducers. i.e., to inhibit (i.e. glycose) or induce (i.e. xylose) the production of the polypeptide of interest. Such additives can be employed provided they are compatible with and do not interfere with the function of the formulations.

The formulations can also contain irritation-mitigating additives to minimize or eliminate the possibility of skin irritation or skin damage resulting from the chemical entity to be administered, or other components of the composition.

Suitable irritation-mitigating additives include, for example: a-tocopherol; monoamine oxidase inhibitors, particularly phenyl alcohols such as 2-phenyl-1-ethanol; glycerin; salicylates; ascorbates; ionophores such as monensin; amphiphilic amines; ammonium chloride; N-acetylcysteine; capsaicin; and chloroquine. The irritation-mitigating additive, if present, can be incorporated into the compositions at a concentration effective to mitigate irritation or skin damage, typically representing not more than about 20 wt. %, more typically not more than about 5 wt. %, of the formulation.

Further suitable pharmacologically active agents that can be incorporated into the present formulations in certain embodiments and thus topically applied along with the active agent include, but are not limited to, the following: agents that improve or eradicate pigmented or non-pigmented age spots, keratoses, and wrinkles; antimicrobial agents; antibacterial agents; antipruritic and antixerotic agents; anti-inflammatory agents; local anesthetics and analgesics; corticosteroids; retinoids; vitamins; hormones; and antimetabolites.

Some examples of topical pharmacologically active agents include acyclovir, amphotericins, chlorhexidine, clotrimazole, ketoconazole, econazole, miconazole, metronidazole, minocycline, nystatin, neomycin, kanamycin, phenytoin, para-amino benzoic acid esters, octyl methoxycinnamate, octyl salicylate, oxybenzone, dioxybenzone, tocopherol, tocopheryl acetate, selenium sulfide, zinc pyrithione, diphenhydramine, pramoxine, lidocaine, procaine, erythromycin, tetracycline, clindamycin, crotamiton, hydroquinone and its monomethyl and benzyl ethers, naproxen, ibuprofen, cromolyn, retinol, retinyl palmitate, retinyl acetate, coal tar, griseofulvin, estradiol, hydrocortisone, hydrocortisone 21-acetate, hydrocortisone 17-valerate, hydrocortisone 17-butyrate, progesterone, betamethasone valerate, betamethasone dipropionate, triamcinolone acetonide, fluocinonide, clobetasol propionate, minoxidil, dipyridamole, diphenylhydantoin, benzoyl peroxide, and 5-fluorouracil.

A cream, lotion, gel, ointment, paste or the like can be spread on the affected surface and gently rubbed in. A solution can be applied in the same way, but more typically will be applied with a dropper, swab, or the like, and carefully applied to the affected areas.

The application regimen will depend on a number of factors that can readily be determined, such as the severity of the condition and its responsiveness to initial treatment, but will normally involve one or more applications per day on an ongoing basis. One of ordinary skill can readily determine the optimum amount of the formulation to be administered, administration methodologies and repetition rates. In general, it is contemplated that the formulations of the invention will be applied in the range of once or twice weekly up to once or twice daily.

As described herein, the bacteria species selected for the composition is transformed using known recombinant techniques to express a compound of interest.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

Example 1 *Staphylococcus epidermidis* Expressing the Element Filaggrin Using Vector pAZT-01

A. Bacteria

Bacteria of the *Staphylococcus aureus* RN4220 strain were used in preparation of the vector (Kreiswirth, B N., et al. 1983). A stock solution of the strain was stored in −20° C. in 50% glycerol in brain heart fusion broth (BHI).

Bacteria of the *Staphylococcus epidermidis* strain ATCC12228 were used (Zhang, Y Q., et al. 2003). A stock solution of the strain was stored in −20° C. in 50% glycerol in brain heart fusion broth (BHI). Bacteria were cultured in brain heart fusion broth (BHI). After 16 hours of incubation, bacteria were harvested by centrifugation and 10-fold concentrated in brain heart fusion broth (BHI) at $2 \times 10^9$ bacteria/100 μl. A stock preparation of the bacteria was prepared by inoculating 5 mL broth with cells from the slant. The cells were grown overnight at 30° C. Then 3 mL fully grown culture was added to 1 ml 60% glycerol and stored at −80° C.

B. Genomic Integration into the Vector

Plasmid AZT-01 consists of shuttle vector pJB38 with a filaggrin expression insert (FIG. 5) (Cheung, A L., et al. 2004). The insert into pJB38 contains the complete operon for a filaggrin DNA sequence (Genbank accession no. NM_002016), a xylose-inducible promoter and was used in the production of the compound of interest. The pJB38-FLG vector (FIG. 5) was constructed and cloned by Bio Basic. Inc. (Markman, ON, Canada).

C. Transformation

A vector harboring the filaggrin sequence, or any vector constructed for the purpose of therapeutic treatment of abnormal human skin was transformed into the *S. epidermidis* strain, according to the following protocol, including the following steps: preparation of *S. aureus* bacterial cells, transformation of *S. aureus*, isolation of plasmid DNA from *S. aureus*, preparation of *S. epidermidis* bacterial cells, transformation of *S. epidermidis*, growth of bacteria, and storage of transformed bacteria. Alternative intermediate strains can also be used for transformation and isolation of plasmid DNA in preparation for transformation into *S. epidermidis*. These strains include but are not limited to *S. aureus* and *E. coli* strains, including those deficient in methylation.

Preparation and transformation of *S. aureus*: Preparation of the cells: *S. aureus* RN4220 cells were made electrocompetent by growing 50 ml culture overnight in BHI medium at 37° C. then inoculating 100 ml fresh BHI medium with 10 ml of overnight culture. When $OD_{600}$ reached 0.2-0.3, cells were pelleted, and resuspended with 1× volume of 4° C. 10% sucrose. This process was repeated 3×, then the cells were resuspended with 0.1× volume of 4° C. 10% sucrose, pelleted, and resuspended with 1 ml of 10% sucrose.

For transformation of RN4220, 200-500 mg of pAZT-01 was mixed with electrocompetent cells previously prepared and transformed using electroporation at room temperature at 2.5 kV using the MicroPulser Electroporator (Bio-Rad. Hercules, Calif.). Transformed cells were plated at 28° C. overnight on selective BHI medium, grown overnight in selective BHI medium and then used to isolate DNA.

Preparation and transformation of *S. epidermidis*: Electrocompetent *S. epidermidis* ATCC12228 were made using the following methods. First, 50 ml overnight culture of ATCC12228 from a −80° C. stock were grown at 37° C. in B2 medium (1.0% tryptone, 2.5% yeast extract, 0.5% glucose, 2.5% NaCl, 0.1% $K_2PO_4$, pH to 7.5). 10 ml of overnight culture were diluted into fresh pre-warmed B2 media and shaken until $OD_{600}$ reached 0.5-0.6, and were then pelleted from 10 min at 4° C. Next, cells were washed with 1, ½, ⅟20, and ⅟50 volumes of cold 10% glycerol, pelleting at 4° C. between washes. The final pellet was resuspended in 700 ul of cold 10% glycerol.

Electrocompetent ATCC12228 were transformed with pAZT-01, isolated from *S. aureus*, using electroporation at 2.5 kV, 25 uF, 100Ω. (normal reading is 4.5-5 msec using the Micropulser Electroporator (Bio-Rad. Hercules, Calif.)). Cells were then plated at 28° C. on selective BHI medium.

Transformation of the bacteria can also be performed via alternative methods of transformation including but not limited to alternative intermediate strains, bacteriophage transduction, and heat shock.

D. Induction of Protein Expression

Filaggrin expression was induced in ATCC12228 transformed with pAZT-01 in the following manner. First, 5 ml of an overnight culture at 28° C. of transformed ATCC12228 in selective BHI medium was taken to inoculate 100 ml of fresh BHI with antibiotic. The cells were grown until $OD_{600}$ reached 0.5-0.65, then the cells were induced using a final concentration of 1.5% xylose for 4.5 hours.

E. Analysis of Protein Expression and Secretion

For analysis cells were fractionated and analyzed via SDS-PAGE electrophoresis and western blotting. Bacterial cells from un-induced samples and induced samples were pelleted and lysed with CelLytic B Cell Lysis Reagent (Sigma-Aldrich, St. Louis, Mo.). The supernatant from the induced sample was also collected and concentrated. Samples were resuspended in a reduced sample buffer and then electrophoresed on a 4-15% Tris gel with Tris-HCL running buffer. Following electrophoresis, the gel was transferred to a PVDF membrane, and sequentially probed with a primary goat monoclonal antibody against filaggrin (sc-25897, Santa Cruz Biotechnology, Inc). A horseradish peroxidase-conjugated donkey anti-goal antibody (sc-2020) was then probed and the secondary antibodies were detected through autoradiography (Syngene GeneGnome Bio Imaging System) using enhanced chemiluminescence substrate (SuperSignal West Pico. Thermo Scientific).

Analysis of the supernatant and cell lysate demonstrates the successful expression and secretion of the therapeutic polypeptide upon transformation with plasmid containing protein of interest, followed by induction of protein expression.

Detection of protein expression and secretion is also possible using alternative methods and the current example should not be construed as a limitation to the present invention.

F. Treatment of Human Subjects with Foregoing Composition

Approximately $1 \times 10^9$ colony forming units (CFU) of *S. epidermidis* containing pAZT-01 can be added to a pharmaceutically acceptable carrier. The foregoing composition is useful for treating or preventing abnormal skin conditions in a subject in need thereof, e.g., a human subject having an abnormal skin condition such as eczema. The composition can be applied at least once per day, up to for example about 3 to 4 times per day, or as needed or prescribed. The composition can be used for as long as needed to ensure treatment of the condition or to continue to prevent the condition. The duration of treatment can vary from about 1 day up to about 10 to 14 days or longer. In certain instances, long term or chronic treatment can be administered.

Example 2 *Staphylococcus epidermidis* Colonizing Epidermal Layer and Expressing GFP A. Bacteria Bacteria of the *Escherichia coli* strains DH5α and DC10B were used in plasmid construction and preparation (Sambrook, J., et al. 1989; Monk, I., et al. 2012). Bacteria of the *Staphylococcus epidermidis* ATCC12228 strain were used for heterologous expression of GFP in the murine colonization and expression studies. A stock solution of the strain was stored in −20° C. in 50% glycerol in brain heart fusion broth (BHI). Bacteria were cultured in brain heart fusion broth (BHI). After 16 hours of incubation, bacteria were harvested by centrifugation and 10-fold concentrated in BHI at $2 \times 10^9$ bacteria/100 μl. A stock preparation of the bacteria was prepared by inoculating 5 mL broth with cells from the slant. The cells were grown overnight at 30° C. Then 3 mL fully grown culture was added to 1 ml 60% glycerol and stored at −80° C.

B. Vector

Plasmid pCM11 consists of shuttle vector with a sGFP expression insert (Lauderdale et al. 2010).

C. Transformation

A vector harboring the GFP sequence (e.g. pCM11 (Lauderdale et al. 2010)), or any vector constructed for the purpose of heterologous expression was transformed into the *S. epidermidis* strain ATCC12228, according to the following protocol, including the following steps: transformation into DH5a, isolation of plasmid DNA from DH5α, transformation of DC10B, isolation of plasmid DNA from DC10B, preparation and transformation of *S. epidermidis*, growth and application of transformed *S. epidermidis*.

*E. coli* DH5α was transformed with pCM11 using the heat shock method and plated on selective LB (Luria Broth) overnight at 37° C. Plasmid DNA was purified from 37° C. overnight cultures with selective LB media from DH5α transformants using Zymo Research Plasmid Miniprep Kit (Irvine, Calif.). Next, 200-500 ng pCM11 DNA was used to transform DC10B using electroporation at room temperature at 2.5 kV using the MicroPulser Electroporator (Bio-Rad, Hercules, Calif.). The transformed cells were plated overnight at 37° C. and then DNA was purified using the said method.

Next, electrocompetent *S. epidermidis* ATCC12228 were made using the following methods. First, 50 ml overnight culture of ATCC12228 were grown at 37° C. in B2 medium (1.0% tryptone, 2.5% yeast extract, 0.5% glucose, 2.5% NaCl, 0.1% $K_2PO_4$, pH to 7.5). 10 ml of overnight culture were diluted into fresh pre-warmed B2 media and shaken until $OD_{600}$ reached 0.5-0.6, and were then pelleted from 10 min at 4° C. Next, cells were washed with 1, 2, ½₀, and ⅟₅₀ volumes of cold 10% glycerol, pelleting at 4° C. between washes. The final pellet was resuspended in 700 ul of cold 10% glycerol. Electrocompetent ATCC12228 were transformed with pCM11, isolated from DC10B, using electroporation at 2.5 kV using the Micropulser Electroporator (Bio-Rad, Hercules, Calif.). Cells were then plated at 37° C. on selective BHI medium.

Figure 6B:
In FIG. 6B, S. epidermidis is transformed with pCM11 containing the GFP insert, which is in turn expressed, as demonstrated by the fluorescence. These images confirm the transformation of S. epidermidis and the expression of pCM11 within that strain, as indicated by the GFP fluorescence.
Figure 6A:
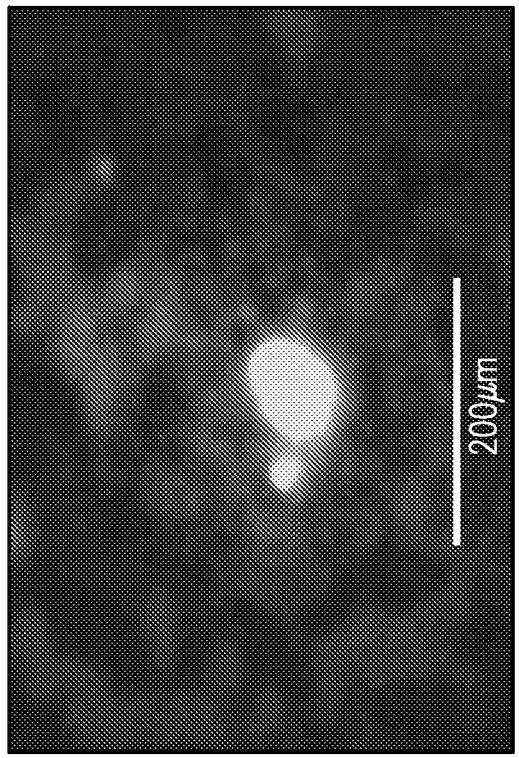
FIG. 6 depicts the transformation of S. epidermidis ATCC12228 with pCM11 containing a GFP (green fluorescent protein) expression platform as verified by fluorescence microscopy. Plasmid pCM11 (which contains a GFP expression platform) was used to transform E. coli DH5α cells using a heat shock method. Plasmid pCM11 isolated from E. coli DH5α was then used for transformation of E. coli DC10B using electroporation. Plasmid pCM11 was then isolated from E. coli DC10B and used to transform S. epidermidis using electroporation. As a control, FIG. 6A demonstrates the inherent fluorescence of S. epidermidis, confirming that the strain has minimal to no inherent fluorescence by itself prior to transformation with a GFP expressing plasmid.

Transformation and expression of the GFP insert was confirmed using microscopy as seen by the fluorescence of transformed *S. epidermidis* ATCC12228 in FIG. 6.

D. Murine Studies with ATCC12228 Transformed with pCM11

In order to visualize colonization of the ATCC12228 onto mouse skin, mice were treated with GFP-expressing ATCC12228 (ATCC12228 transformed with pCM11). A small cohort of mice (n=5) were clipped to remove hair and treated on dorsal skin with *S. epidermidis* ATCC12228 expressing GFP in pCM11. Approximately $1 \times 10^9$ CFUs of *S. epidermidis* were applied with a cotton wool tipped stick. After initiation of treatment, the mice were monitored for signs of *S. epidermidis* colonization.

Sections of skin were taken from skin post mortem for imaging studies. Sections were imaged using fluorescent microscopy (FIG. 7) including staining with DAPI and an anti-GFP monoclonal antibody (FIG. 8). Additional images were visualized using two-photon microscopy (FIG. 8).

Figures 7A, 7B:
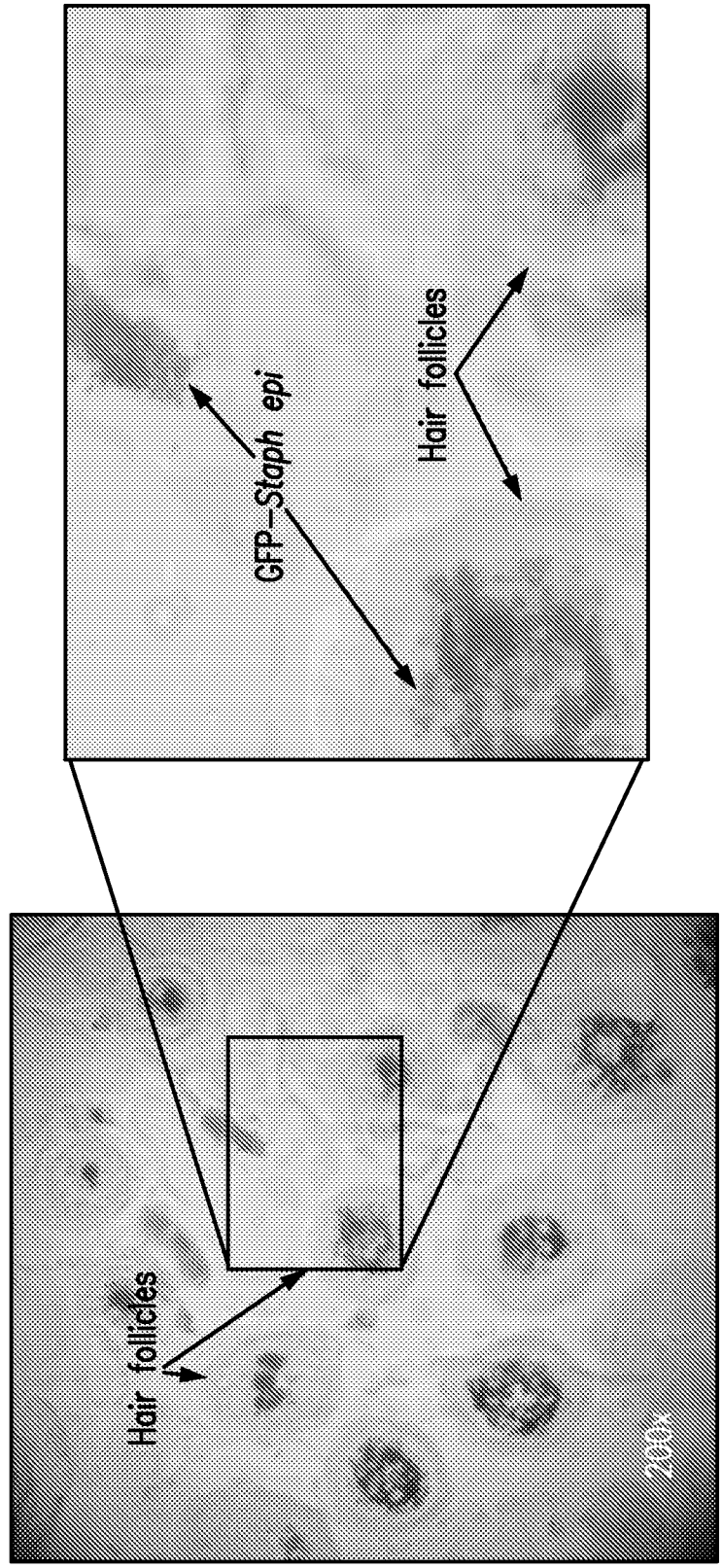
FIG. 7 depicts S. epidermidis ATCC12228 transformed with pCM11 containing the GFP (green fluorescent protein) insert, which was in turn applied on the dorsal skin of mice for three days. Sections of the skin were then taken postmortem for light microscopy (FIGS. 7A & 7B). Sections shown here were stained using Malachite Green stain and visualized at 200× (FIG. 7A) and further expansion (FIG. 7B). This figure demonstrates the colonization of *S. epidermidis* on the mouse skin after three days. (*Staph epi* refers to *Staphylococcus epidermidis*).

FIG. 7 depicts *S. epidermidis* ATCC12228 transformed with pCM11 containing the GFP insert, which was in turn applied on the dorsal skin of mice for three days. Sections of the skin were then taken post-mortem for light microscopy (FIGS. 7A & 7B). Sections shown here were stained using Malachite Green stain and visualized at 200× (FIG. 7A), and further expansion in FIG. 7B. This figure demonstrates the colonization of *S. epidermidis* on the mouse skin after three days.

FIG. 8 depicts *S. epidermidis* ATCC12228 transformed with pCM11 containing the GFP insert, which was in turn applied on the dorsal skin of mice for three days. Sections of the skin were then taken post-mortem for light microscopy (FIGS. 8A & 8B). FIG. 8A shows fluorescence of GFP indicating not only that *S. epidermidis* colonizes the skin after three days, but also that expression of GFP is maintained at that time. FIG. 8A shows fluorescence from GFP while FIG. 8B shows a section of skin stained with both DAPI (4',6-diamidino-2-phenylindole) and an anti-GFP monoclonal antibody. FIG. 8C demonstrates a section of the skin visualized using two-photon microscopy. This image demonstrates the extent of *S. epidermidis* colonization and GFP expression, as indicated by the fluorescence.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

INCORPORATION BY REFERENCE

The entire disclosure of each of the patent documents, including patent application documents, scientific articles, governmental reports, websites, and other references referred to herein is incorporated by reference herein in its entirety for all purposes. In case of a conflict in terminology, the present specification controls.

All sequence listings, or Seq. ID. Numbers, disclosed herein are incorporated herein in their entirety.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the methods and compositions of the present invention, where the term comprises is used with respect to the recited steps or components, it is also contemplated that the methods and compositions consist essentially of, or consist of, the recited steps or components. Further, it should be understood that the order of steps or order for performing certain actions is immaterial so long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

REFERENCES

The following references, to the extent that they provide exemplary procedural or other details supplementary to those set forth herein, are specifically incorporated herein by reference.

Armengot-Carbo, M. et al. (2014) "The role of filaggrin in the skin barrier and disease development." *Actas Dermosifiliogr* March; 106 (2):86-95.

Brachkova, M. I., P. Marques, J. Rocha, B. Sepodes, M. A. Duarte and J. F. Pinto (2011). "Alginate films containing *Lactobacillus plantarum* as wound dressing for prevention of burn infection." *J Hosp Infect* 79(4): 375-377.

Brown, S J., & McLean, W H. (2012) *J. Invest. Dermatol.* 132, 751-62

Chen, Y E., & Tsao, H. (2013) *J. Am. Acad. Dermatol.* 69, 143-155

Cheung A L, et al. (2004) "Regulation of virulence determinants in vitro and in vivo in *Staphylococcus aureus*." FEMS *Immunological Medical Microbiology* 40(1):1-9

"DNA Recombination." *Methods in Molecular Biology* 745 (XIV): 1-565.

Gross, et al., WO 94/00098 assigned to Lancaster Group AG
Gross, et al., WO 94/00109 assigned to Lancaster Group AG
Gueniche, A., P. Bastien, J. M. Ovigne, M. Kermici, G. Courchay, V. Chevalier, L. Breton and I. Castiel-Higounenc (2010). "*Bifidobacterium longum* lysate, a new ingredient for reactive skin." *Exp Dermatol* 19(8): 1-8.

Jeong J G et al. (2011). A Tat-grafted anti-nucleic acid antibody acquires nuclear-localization property and a preference for TAR RNA. *Biochem Biophys Res Commun*. March 18; 406(3):403-7.

Kreiswirth, B N., et al. (1983). The toxic shock syndrome exotoxin structural gene is not detectably transmitted by a prophage. Nature 305:709-712.

Lauderdale, et al. (2010). Biofilm dispersal of community-associated methicillin-resistant *Staphylococcus aureus* on orthopedic implant material. *J. Orthop. Research.* 28:55-61

Lee, S H., Jeong, S K. and Ahn, S K. (2006). "An update of the defensive barrier function of skin." *Yonsei Med J* 47(3): 293-306.

Lin, Y T., Wang, C T., and Chiang, B L. (2007). "Role of bacterial pathogens in atopic dermatitis." *Clin Rev Allergy Immunol* 33(3): 167-177.

Ma, J., et al. (2014) Cell-penetrating peptides mediated protein cross-membrane delivery and its use in bacterial vector vaccine. *Fish & Shellfish Immunology* 39 8-16

McAleer, M A., & Irvine, A D. (2013) *J. Allergy Clin. Immunol.* 131, 280-91.

Monk, I., et al. (2012) Direct transformation to manipulate genetically *Staphylococcus aureus* and *Staphylococcus epidermidis*. mBio.

Muizzuddin, N., Maher, W., Sullivan, M., Schnittger, S., and Mammone, T. (2012). "Physiological effect of a probiotic on skin." *J Cosmet Sci* 63(6): 385-395.

Nakanishi, N., T. Oshida, S. Yano, K. Takeda, T. Yamaguchi and Y. Ito (1986). "Construction and characterization of new cloning vectors derived from *Streptomyces griseobrunneus* plasmid pBT1 and containing amikacin and sulfomycin resistance genes." *Plasmid* 15(3): 217-229.

Nakatsuji, T. and R. L. Gallo (2014). "Dermatological therapy by topical application of non-pathogenic bacteria." *J Invest Dermatol* 134(1): 11-14.

Oehike J et al. (1998). Cellular uptake of an alpha-helical amphipathic model peptide with the potential to deliver polar compounds into the cell interior non-endocytically. *Biochim Biophys Acta*. November 11; 1414(1-2):127-39.

Ostenson C G et al. (1997). Galparan: a powerful insulin-releasing chimeric peptide acting at a novel site. *Endocrinology*. August; 138(8):3308-13.

Otsuka, A., et al. (2014) *J. Allergy Clin. Immunol.* 133, 139-46.e1-10 (2014).

Peral, M. C., M. A. Martinez and J. C. Valdez (2009). "Bacteriotherapy with *Lactobacillus plantarum* in burns." *Int Wound J* 6(1): 73-81.

Peral, M. C., M. M. Rachid, N. M. Gobbato, M. A. Huaman Martinez and J. C. Valdez (2010). "Interleukin-8 production by polymorphonuclear leukocytes from patients with chronic infected leg ulcers treated with *Lactobacillus plantarum*." *Clin Microbiol Infect* 16(3): 281-286

Powers, M E., et al. (2011). *J Bacteriol.*, 193:340-348

Proksch, E., J. M. Brandner and J. M. Jensen (2008). "The skin: an indispensable barrier." *Exp Dermatol* 17(12): 1063-1072

Remington: The Science and Practice of Pharmacy, 19$^{th}$ edition. Easton, Pa.: Mack Publishing Co., 1995

Sambrook J, et al. (1989). *Molecular Cloning: A Laboratory Manual*. Cold Spring Harbor Laboratory Press, New York.

Sambrook, J F., and Russell, D W., ed. (2001). Molecular Cloning: A Laboratory Manual, 3rd ed., Vols 1, 2 and 3. Cold Spring Harbor Laboratory Press Simonen, M. and I. Palva (1993). "Protein secretion in *Bacillus* species." *Microbiol Rev* 57(1): 109-137

Smith, E W., & Maibach, H I., (1995) Percutaneous Penetration Enhancers, CRC Press ISBN 9780849321528

Stout, T E., et al. (2014) *J Invest Dermatol*. 134, 423-9

The Science and Practice of Pharmacy (1995), 19th Ed. Easton, Pa.: Mack Publishing Co.

Volz, T., Y. Skabytska, E. Guenova, K. M. Chen, J. S. Frick, C. J. Kirschning, S. Kaesler, M. Rocken and T. Biedermann (2014). "Nonpathogenic bacteria alleviating atopic dermatitis inflammation induce IL-10-producing dendritic cells and regulatory Tr1 cells." *J Invest Dermatol* 134(1): 96-104

Webb, T R., & Hsu, C P S. U.S. Pat. No. 4,659,774 assigned to American Hoechst Corporation Wyman T B, et al. (1997) Design, synthesis, and characterization of a cationic peptide that binds to nucleic acids and permeabilizes bilayers. *Biochemistry*. March 11; 36(10): 3008-17

Zhang, Y Q., et al. (2003). Genome-based analysis of virulence genes in a non-biofilm-forming *Staphylococcus epidermidis* strain (ATCC12228). *Molecular Microbiology* 49(6), 1577-1593

---

What is claimed is:

1. A pharmaceutical composition for treating an abnormal skin condition in a human in need thereof, comprising (a) a cell culture composition comprising a bacterial strain selected from *Bifidobacterium, Brevibacterium, Propionibacterium, Lactococcus, Streptococcus, Staphylococcus, Lactobacillus, Enterococcus, Pediococcus, Leuconostoc,* or *Oenococcus*, and mixtures thereof, wherein the cell culture composition is a living cell culture composition, and wherein the cell culture composition comprises at least one engineered bacterial strain that produces a therapeutically effective amount of a recombinant polypeptide for treating the abnormal skin condition and (b) a pharmaceutically acceptable carrier.

2. A composition according to claim 1 wherein said composition comprises a bacterial strain containing human target DNA recombined with bacterial DNA.

3. A composition according to 1, wherein the composition comprises an engineered strain of *Staphylococcus epidermidis*.

4. A composition according to claim 1, wherein the pharmaceutically acceptable carrier comprises 0% water to no more than about 90% water.

5. A composition according to claim 1, wherein the pharmaceutically acceptable carrier is selected from an aqueous solution, an emulsion, a cream, a lotion, a gel, or an ointment.

6. A pharmaceutical composition for treating an abnormal skin condition in a human in need thereof, comprising (I) a cell culture composition comprising a bacterial strain selected from *Bifidobacterium, Brevibacterium, Propionibacterium, Lactococcus, Streptococcus, Staphylococcus, Lactobacillus, Enterococcus, Pediococcus, Leuconostoc,* or *Oenococcus*, and mixtures thereof, wherein the cell culture composition is a living cell culture composition, and wherein the cell culture composition comprises at least one engineered bacterial strain that produces a therapeutically effective amount of a recombinant polypeptide comprising (a) a filaggrin amino acid sequence, (b) a secretion signal, and (c) a cell penetrating peptide and (II) a pharmaceutically acceptable carrier, for treating the abnormal skin condition.

7. A composition according to claim 6 wherein said composition comprises a bacterial strain containing human target DNA recombined with bacterial DNA.

8. A pharmaceutical composition according to 6, wherein the cell culture composition comprises *Staphylococcus epidermidis*.

9. A pharmaceutical composition according to claim 6, wherein the filaggrin amino acid sequence comprises a sequence selected from SEQ ID NO 1, SEQ ID NO 5, SEQ ID NO 6, SEQ ID NO 7, SEQ ID NO 8, SEQ ID NO 9, SEQ ID NO 10, SEQ ID NO 12, SEQ ID NO 13, SEQ ID NO 14, SEQ ID NO 15, SEQ ID NO 16, or SEQ ID NO 17, and combinations thereof.

10. A pharmaceutical composition according to claim 6, wherein the filaggrin amino acid sequence comprises SEQ ID NO 1.

11. A pharmaceutical composition according to claim 6, wherein the filaggrin amino acid sequence has at least about 75% homology to SEQ ID NO 1.

12. A pharmaceutical composition according to claim 6, wherein the filaggrin amino acid sequence has at least about 80% homology to SEQ ID NO 1.

13. A pharmaceutical composition according to claim 6, wherein the filaggrin amino acid sequence has at least about 85% homology to SEQ ID NO 1.

14. A pharmaceutical composition according to claim 6, wherein the filaggrin amino acid sequence has at least about 90% homology to SEQ ID NO 1.

15. A pharmaceutical composition according to claim 6, wherein the filaggrin amino acid sequence has at least about 95% homology to SEQ ID NO 1.

16. A composition according to claim 6, wherein the pharmaceutically acceptable carrier comprises 0% water to no more than about 90% water.

17. A composition according to claim 6, wherein the pharmaceutically acceptable carrier is selected from an aqueous solution, an emulsion, a cream, a lotion, a gel, or an ointment.

* * * * *